US008614021B2

(12) United States Patent
Bazan et al.

(10) Patent No.: US 8,614,021 B2
(45) Date of Patent: Dec. 24, 2013

(54) AGENTS FOR ENHANCED CHARGE TRANSPORT ACROSS MICROBIAL MEMBRANES

(75) Inventors: Guillermo C. Bazan, Goleta, CA (US); Logan E. Garner, Goleta, CA (US); James J. Sumner, Ellicott City, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/158,296

(22) Filed: Jun. 10, 2011

(65) Prior Publication Data
US 2012/0264649 A1    Oct. 18, 2012

Related U.S. Application Data

(60) Provisional application No. 61/353,618, filed on Jun. 10, 2010.

(51) Int. Cl.
*H01M 8/16*    (2006.01)

(52) U.S. Cl.
USPC ......................................................... 429/401

(58) Field of Classification Search
USPC .................... 435/4; 506/15; 429/2
See application file for complete search history.

(56) References Cited

PUBLICATIONS

Du et al., "A state of the art review on microbial fuel cells: A promising technology for wastewater treatment and bioenergy," Biotechnology Advances 2007, 25:464-482.*

Choi et al., "Dynamic Behaviors of Redox Mediators within the Hydrophobic Layers as an Important Factor for Effective Microbial Fuel Cell Operation," Bull. Korean Chem. Soc. 2003, 24:437-440.*
Woo et al., "Solvent Effects on the Two-Photon Absorption of Distyrylbenzene Chromophores," J. Am. Chem. Soc. 2005, 127:14721-14729.*
STN public record of the compound with CAS Registry No. 159440-54-7 (Entered STN on Dec. 8, 1994).*
Hernandez et al., "Extracellular electron transfer," Cell. Mol. Life Sci. 2001, 58:1562-1571.*
Chikindas et al., "Pediocin PA-1, a Bacteriocin from Pediococcus acidilactici PAC1.0, Forms Hydrophilic Pores in the Cytoplasmic Membrane of Target Cells," Appl. Environ. Microbiol. 1993, 59(11):3577-3584.*
Holmes et al., "Microarray and genetic analysis of electron transfer to electrodes in Geobacter sulfurreducens," Environ. Microbiol. 2006, 8(10):1805-1815.*
Izallalen et al., "Geobacter sulfurreducens strain engineered for increased rates of respiration," Metabolic Engineering 2008, 10:267-275.*
Johnson et al., "Enhancement of Survival and Electricity Production in an Engineered Bacterium by Light-Driven Proton Pumping," Appl. Environ. Microbiol. 2010, 76(13):4123-4129.*

(Continued)

*Primary Examiner* — Samuel Woolwine
*Assistant Examiner* — Kaijiang Zhang
(74) *Attorney, Agent, or Firm* — Eric B. Compton

(57) ABSTRACT

The invention provides molecules useful for enhancing charge transport across membranes, such as electron transport across membranes, and methods of using such molecules, for example in improving the performance of a microbial fuel cell or in staining microbes for observation. The amphiphilic molecule comprises a conjugated core with hydrophilic groups on either end. The amphiphilic molecule inserts into the membrane of a microbe and facilitates charge transfer across the membrane of the microbe.

34 Claims, 11 Drawing Sheets

A.

B.    DMPC

(56) References Cited

PUBLICATIONS

Liang Research Group [online] [retrieved on Jun. 23, 2013] retrieved from http://cfm.mines.edu/research_2.html (4 pages).*

Lovley, "Bug juice: harvesting electricity with microorganisms," Nat. Rev. Microbiol. 2006, 4(7):497-508.*

Martinez et al., "Proteorhodopsin photosystem gene expression enables photophosphorylation in a heterologous host," PNAS 2007, 104:5590-5595.*

Robinson et al. Electron Transfer across Vesicle Bilayers. Chem. Soc. Rev. 20:49-94 (1991).*

Winum et al. Rigid Push-Pull Oligo(p-phenylene) Rods: Depolarization of bilayer membranes with negative membrane potential. J. Am. Chem. Soc. 121:7961-7961 (1999).*

Zhou et al. "End-Only" functionalized oligo(phenylene ethynylene)s: synthesis, photophysical and biocidal activity. The Journal of Physical Chemistry Letters. 1:3207-3212 (2010).*

Alferov et al. Electrical communication of cytochrome enriched *Escherichia coli* JM109 cells with graphite electrodes. Electrochimica Acta 54:4979-4984 (2009).*

Fuhrhop et al. Bolaform amphiphiles with a rigid hydrophobic bixin core in surface monolayers and lipid membranes. Langmuir 6:497-505 (1990).*

Schaetzle et al. Bacteria and yeasts as catalysts in microbial fuel cells: electron transfer from micro-organisms to electrodes for green electricity. Energy & Environmental Science 1:607-620 (2008).*

Porat et al. The unusual transmembrane electron transporter DsbD and its homologues: a bacterial family of disulfide reductases. Research in Microbiology 155:617-622 (2004).*

* cited by examiner

A.

B. DMPC

AGENTS FOR ENHANCED CHARGE TRANSPORT ACROSS MICROBIAL MEMBRANES

CROSS-REFERENCE TO RELATED APPLICATIONS

This application claims priority benefit of U.S. Provisional Patent Application No. 61/353,618, filed Jun. 10, 2010. The entire contents of that patent application are hereby incorporated by reference herein.

STATEMENT REGARDING FEDERALLY SPONSORED RESEARCH OR DEVELOPMENT

This invention was made with United States Government support under grants DAAD-19-03-D-0004 from the Army Research Office, FA9550-08-1-0248 from the Air Force Research Laboratory, and CMMI-0730689 from the National Science Foundation. The Government has certain rights in this invention.

BACKGROUND OF THE INVENTION

Microbial fuel cells (MFCs) convert chemical energy into electrical energy by the action of microbes on substrates such as glucose. Metabolism of glucose in living organisms can be divided into two separate chemical half-reactions. The first half-reaction is the oxidation of glucose to produce carbon dioxide, protons, and electrons:

$$C_6H_{12}O_6 + 6H_2O \rightarrow 6CO_2 + 24H^+ + 24e^-$$

and the second half-reaction is the reduction of oxygen to form water:

$$6O_2 + 24H^+ + 24e^- \rightarrow 12H_2O.$$

When the oxidation half-reaction and reduction half-reaction are combined, the overall reaction for metabolism of glucose is:

$$C_6H_{12}O_6 + 6O_2 \rightarrow 6CO_2 + 6H_2O.$$

The energy released in this reaction is used in living organisms to generate ATP, which serves as an energy carrier in cells to drive biochemical reactions. The energy is harnessed by coupling the generation of protons and electrons to enzymes that generate ATP.

If these electrons and protons are diverted from ATP generation in the cell, they can be used to power a fuel cell. FIG. 9 shows an example of a microbial fuel cell. The electrons generated by the microbes in the "microbe compartment" (the anode compartment, containing the anode and analyte) are collected by the anode and pass through an electrical connection to the cathode. The protons generated pass through a cation-permeable membrane (e.g., a Nafion membrane as in FIG. 9). Typically, oxygen is used as the final electron acceptor; as oxygen is reduced at the cathode, it combines with the protons passing from the analyte into the catholyte to form $H_2O$. As the electrons pass through the electrical connection between the anode and cathode, they can do work, and thus the microbial fuel cell (MFC) generates useful electricity from the oxidation of glucose.

Microbial fuel cells can, in theory, use any resource for fuel that can be digested and metabolized by microbes. Accordingly MFCs have enormous potential as alternative energy sources, such as in the use of biomass to generate electricity. The performance of MFCs will require improvements, however, before practical use can be made of MFCs.

Extracting the protons and electrons from the microbes is often done by means of a mediator, such as thionine, methylene blue, or methyl viologen. The mediator diffuses into the microbial cell, is reduced by the electrons generated during oxidation of glucose, diffuses out of the microbial cell, and is oxidized at the anode. The mediator can continue to act as a shuttle for electrons. However, the kinetics of diffusion can limit the kinetics of the reaction, and the redox potential of the mediator can constrain the voltage generated.

Mediator-less microbial fuel cells have been developed, where microbes can transfer electrons directly to the anode without the need of a mediator molecule. However, microorganisms capable of transferring electrons directly to an electrode are relatively uncommon.

The instant invention describes microbial fuel cells with enhanced performance characteristics, as well as compounds that are useful for enhancing MFC performance, and methods for enhancing MFC performance. The compounds and methods disclose allow microbes to transfer electrons to electrodes in a microbial fuel cell without the need for a mediator to diffuse into and out of the microbes, by inserting compounds of appropriate structure into the microbial membrane and facilitating transfer of electrons across the cell membrane.

In a more general sense, the invention describes methods for enhancing charge transfer (such as electron transfer) from a microorganism, in order to increase the rate of transmembrane charge transfer from the microorganism, and/or in order to increase the electromotive force (EMF) of transmembrane charge transfer from the microorganism

BRIEF SUMMARY OF THE INVENTION

In one embodiment, the invention embraces a method of increasing the rate of transmembrane charge transfer from a microorganism and/or increasing the electromotive force of transmembrane charge transfer from a microorganism, by adding an amount of charge-transfer agent sufficient to increase the rate of transmembrane charge transfer from the microorganism and/or sufficient to increase the electromotive force of transmembrane charge transfer from the microorganism. In one embodiment, the charge-transfer agent is not endogenous to the microorganism. In another embodiment, the charge-transfer agent is a deficient endogenous charge-transfer agent. In one embodiment, the charge-transfer agent is an electron-transfer agent.

The invention also embraces a method of increasing the rate of transmembrane charge transfer from a microorganism and/or increasing the electromotive force of transmembrane charge transfer from a microorganism, comprising adding an charge-transfer agent, such as an electron-transfer agent, to the lipid bilayer of the microbes, in an amount sufficient to increase the rate of transmembrane charge transfer from the microorganism and/or sufficient to increase the electromotive force of transmembrane charge transfer from the microorganism. In one embodiment, the charge-transfer agent, such as an electron-transfer agent, is an electronically delocalized molecule intercalated in the cell membrane of the microorganism. In another embodiment, the charge-transfer agent, such as an electron-transfer agent, has a first region which is hydrophilic and which is in contact with the external environment of the microorganism and/or the hydrophilic portion of the cell membrane of the microorganism facing the external environment, a second region of electronic delocalization in contact with the hydrophobic portion of the cell membrane of the microorganism, and a third region which is hydrophilic and which is in contact with the cytosol of the microorganism and/or the hydrophilic portion of the cell membrane of the microorganism facing the cytosol.

In one embodiment of the method, the charge-transfer agent is an electron-transfer agent of the form:

where $R_e$ and $R_f$ can be the same or different and are groups containing a hydrophilic moiety, and Pi is a molecule with a delocalized π-electron system.

In one embodiment of the method of increasing the rate of transmembrane charge transfer from a microorganism and/or increasing the electromotive force of transmembrane charge transfer from a microorganism, the charge-transfer agent is an electron transfer agent of the formula:

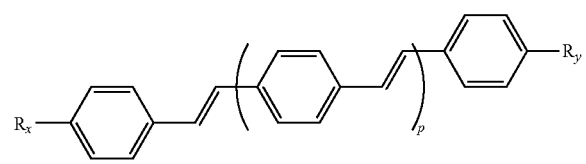

where p is an integer from 0 to 5, inclusive, $R_x$ is of the formula —N($R_1$)($R_2$) and $R_y$ is of the formula —N($R_3$)($R_4$), wherein $R_1$, $R_2$, $R_3$, and $R_4$ are each independently selected from the group consisting of

where each L is independently a linker group containing at least one carbon atom, and each $R_h$ is independently a hydrophilic group, such as a charged or polar functional group. In another embodiment, p is an integer from 0 to 4, inclusive. In another embodiment, p is an integer from 1 to 4, inclusive. In another embodiment, p is an integer from 1 to 3, inclusive. In another embodiment, p is selected from the integers 1 and 2. In another embodiment, p is 1. In another embodiment, p is 2.

In some embodiments, each L is independently selected from branched or linear, saturated or unsaturated, substituted or unsubstituted alkyl or heteroalkyl chains containing at least one carbon atom, and optionally incorporating one or more aryl or heteroaryl groups within the chain. In other embodiments, each L is independently selected from $C_1$-$C_{12}$ alkyl, $C_2$-$C_{12}$ alkenyl, $C_2$-$C_{12}$ alkynyl, $C_2$-$C_{12}$ unsaturated hydrocarbyl, $C_1$-$C_{12}$ alkyl-$C_6$-$C_{10}$ aryl-$C_1$-$C_{12}$ alkyl, or $C_1$-$C_{12}$ alkyl-$C_4$-$C_{10}$ heteroaryl-$C_1$-$C_{12}$ alkyl. In other embodiments, each L is independently substituted with $C_1$-$C_{12}$ alkyl, $C_2$-$C_{12}$ alkenyl, $C_2$-$C_{12}$ alkynyl, $C_1$-$C_{12}$ alkyl-$C_6$-$C_{10}$ aryl-$C_1$-$C_{12}$ alkyl, $C_1$-$C_{12}$ alkyl-$C_4$-$C_{10}$ heteroaryl-$C_1$-$C_{12}$ alkyl, hydroxyl, —O—$C_1$-$C_{12}$ alkyl, —$C_1$-$C_{12}$-alkyl-OH, fluoro, chloro, bromo, iodo, cyano, oxo, thiol, thioalkyl, carboxylic acid, carboxylic ester, amine, or amide groups.

In some embodiments, each $R_h$ is independently selected from the group consisting of: —N$^+$(R')(R")(R'")

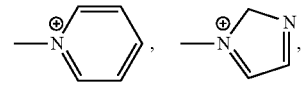

—SO$_3^-$, —CO$^{2-}$, —PO$_3^{2-}$, —PO$_3$H$^-$, —PO$_3$H$_2$, —PO$_4^{2-}$, —PO$_4^-$, and —PO$_4$H$_2$, where R', R", and R'" are independently selected from ($C_1$-$C_{12}$ alkyl), and where the groups optionally additionally comprise one or more counterions. In one embodiment, the counterions are halide ions. In another embodiment, the counterions are iodide ions.

In some embodiments, $R_x$ and $R_y$ are independently selected from groups of the form:

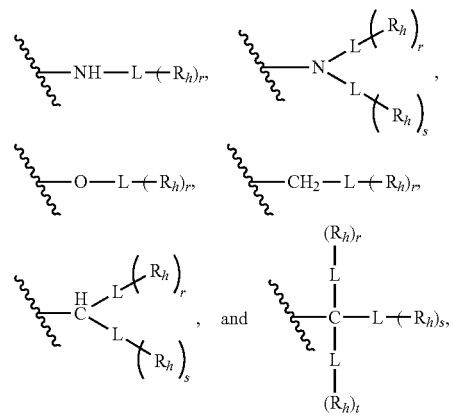

where each L and each $R_h$ can be selected from any of the definitions above. The subscripts r, s, and t can independently be 0, 1, 2, or 3, with the proviso that at least one $R_h$ is present in the $R_x$ or $R_y$ group (that is, r, when alone, must be at least 1; r+s, when t is absent, must be at least 1; or r+s+t must be at least 1).

In one embodiment of the method of increasing the rate of transmembrane charge transfer from a microorganism and/or increasing the electromotive force of transmembrane charge transfer from a microorganism, the charge-transfer agent is an electron transfer agent of the formula:

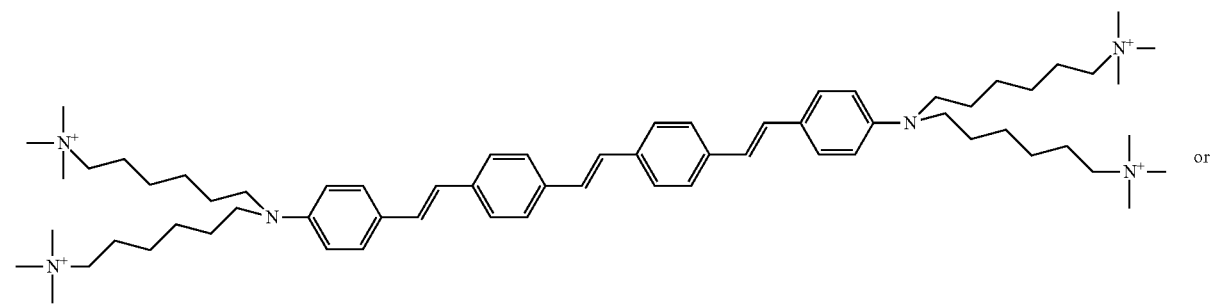

or

-continued

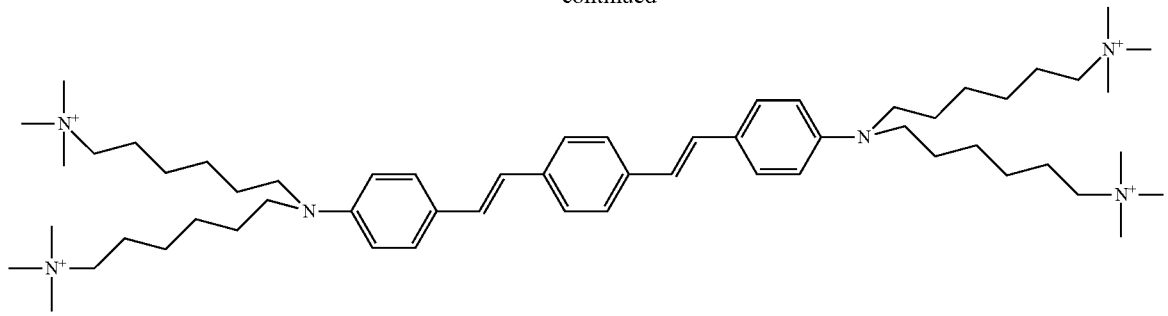

In one embodiment, the agent includes one or more counterions. In further embodiments, the one or more counterions are halide ions. In further embodiments, the one or more counterions are iodide ions.

In one embodiment of the method of increasing the rate of transmembrane charge transfer from a microorganism and/or increasing the electromotive force of transmembrane charge transfer from a microorganism, the charge-transfer agent is an electron transfer agent selected from the group consisting of:

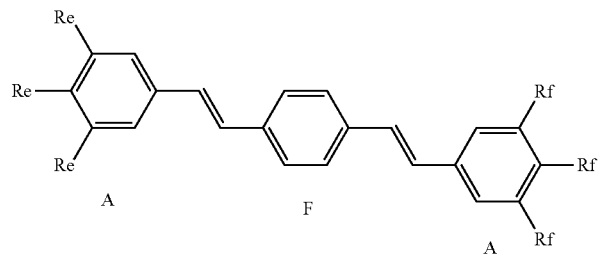

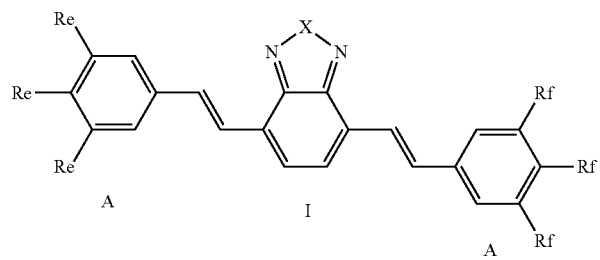

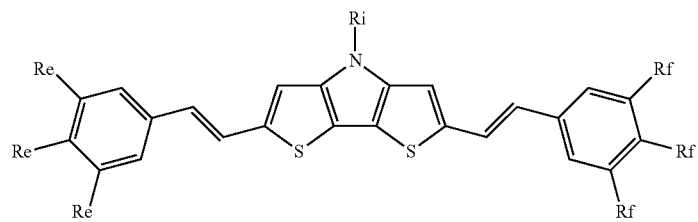

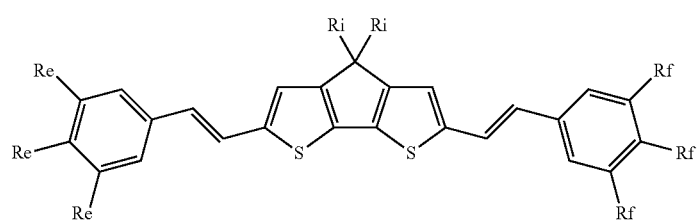

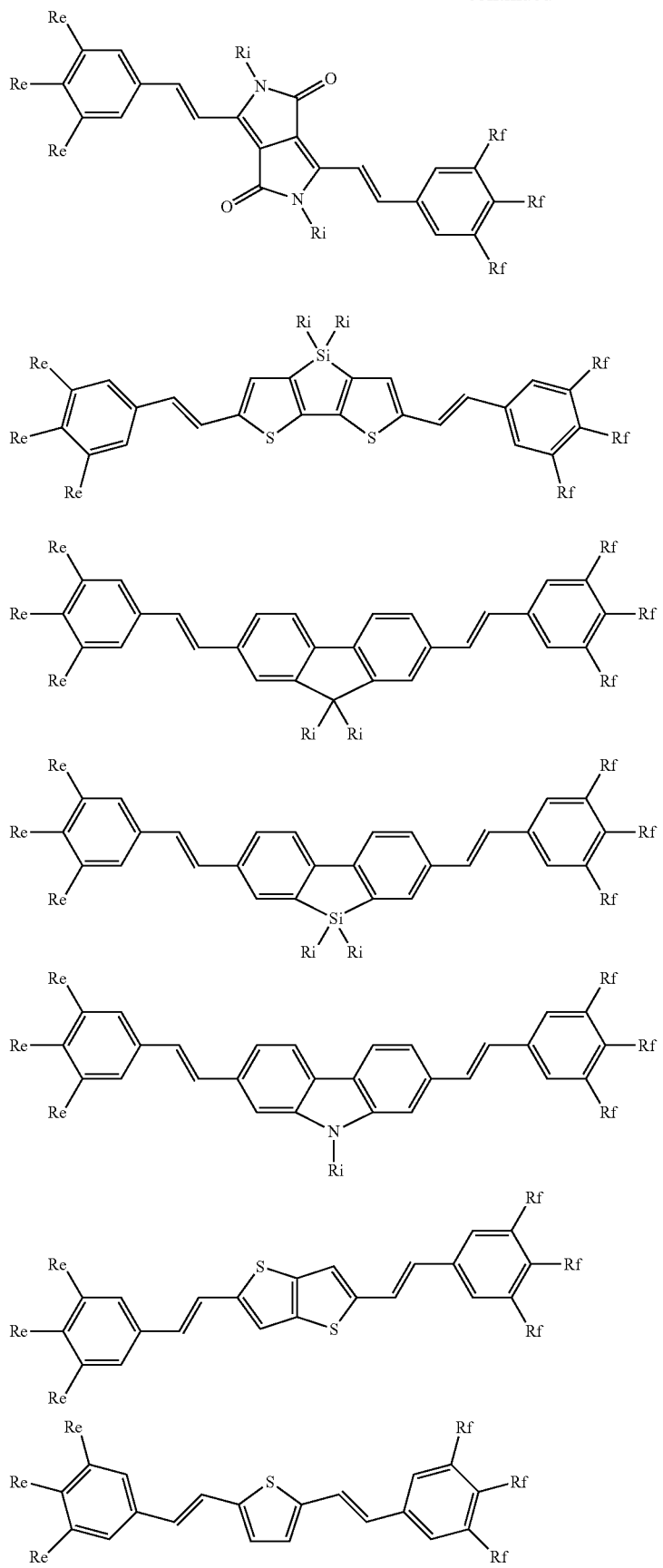

-continued
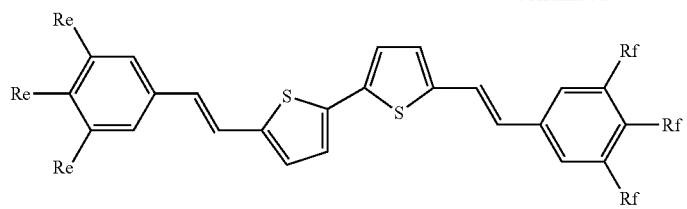
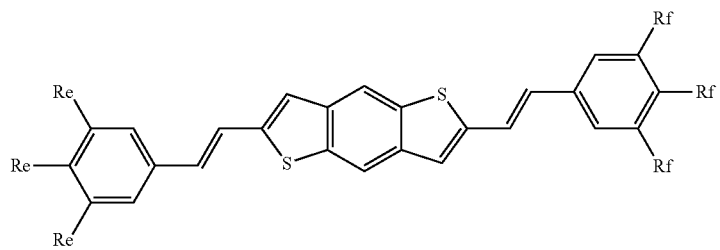
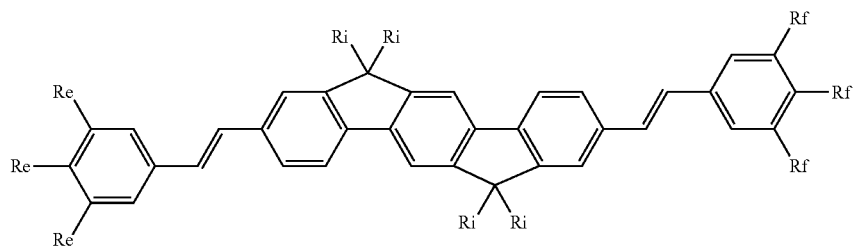
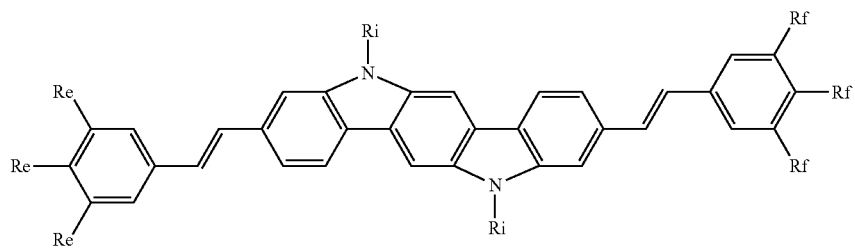
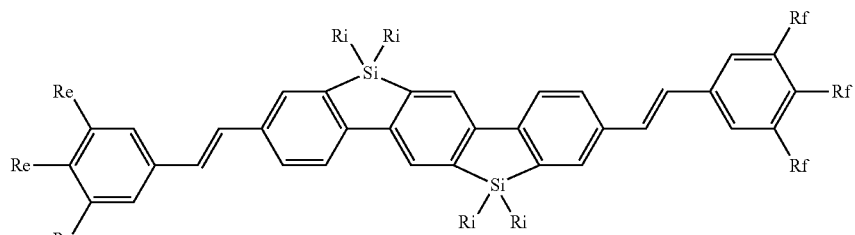
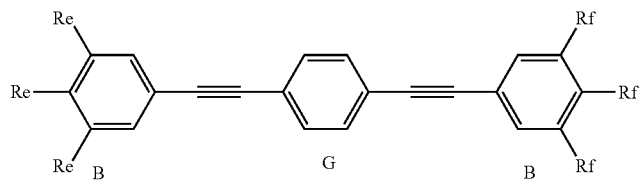
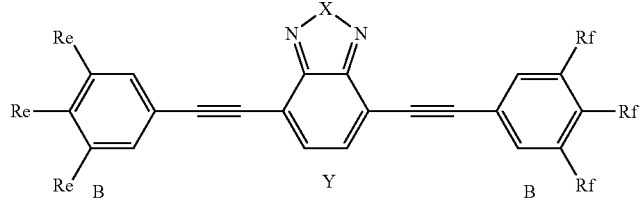

-continued
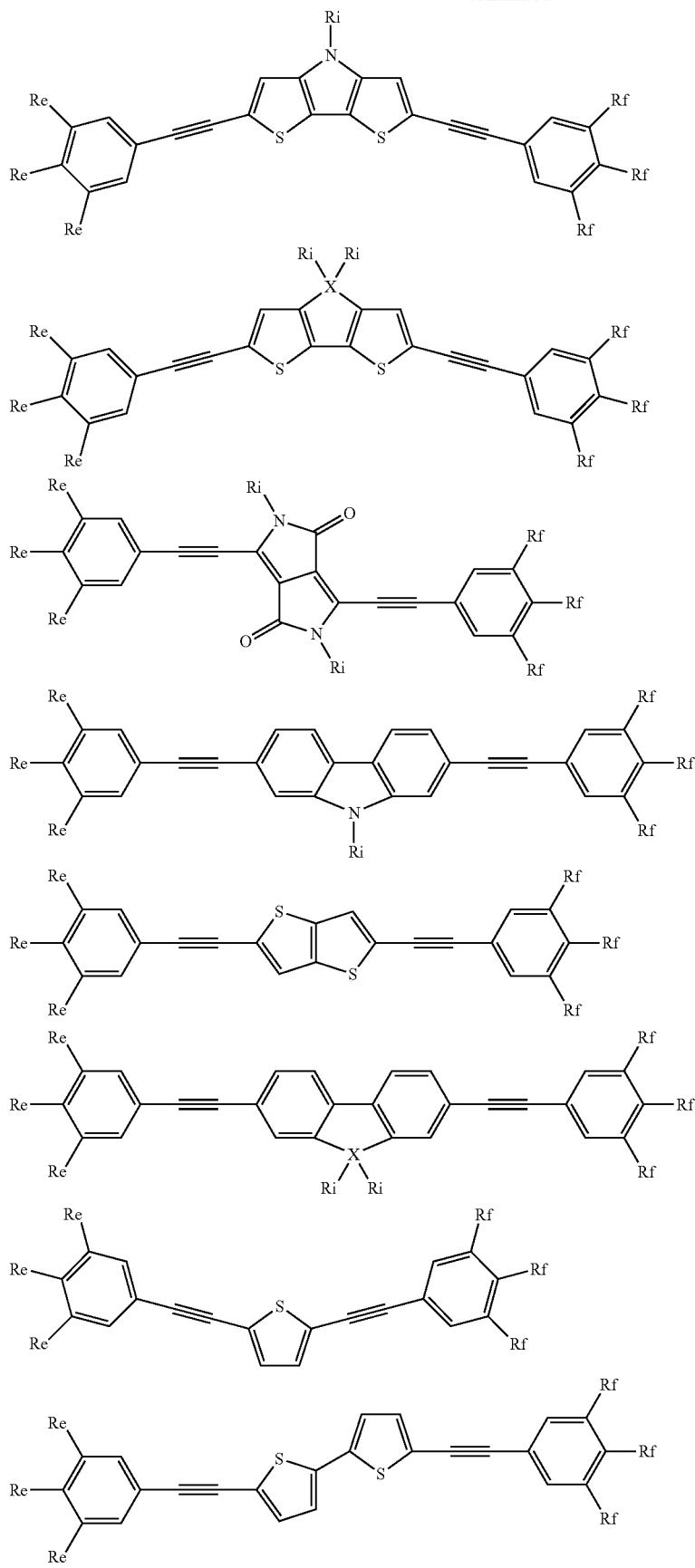

-continued
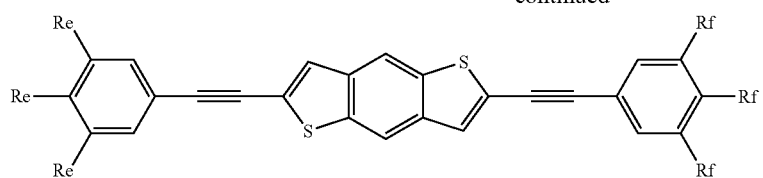
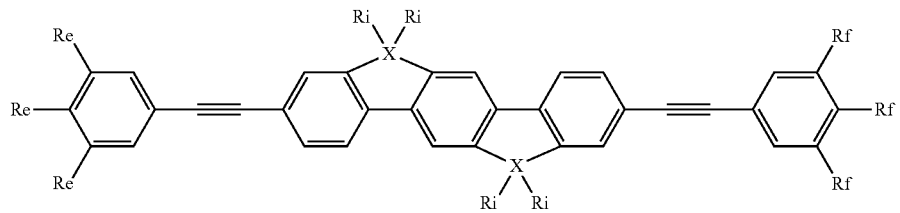
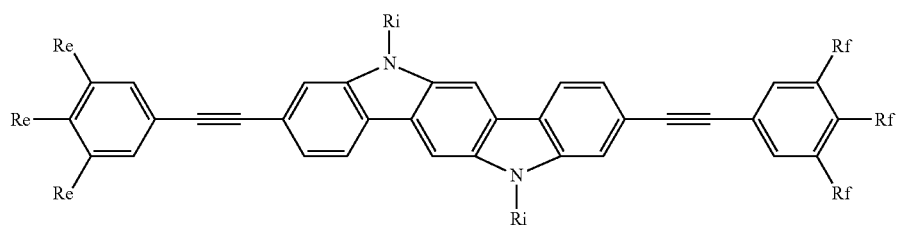
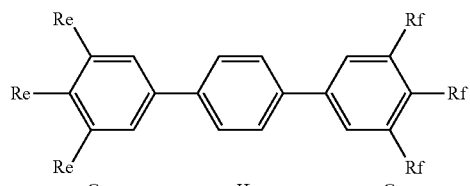
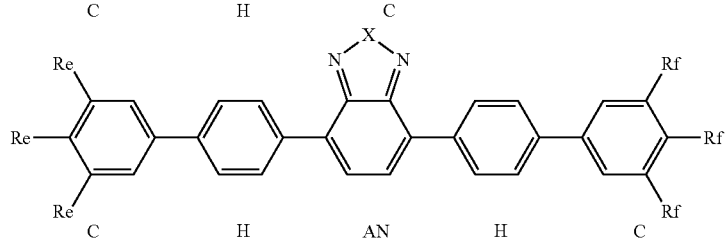
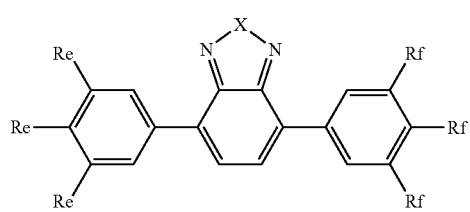
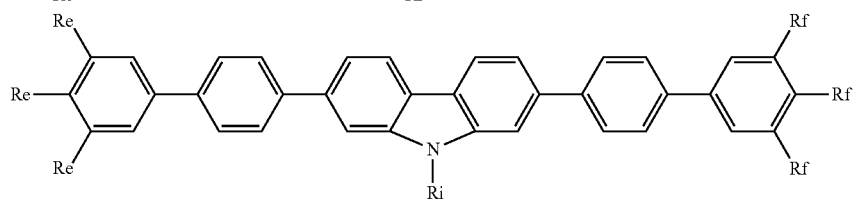
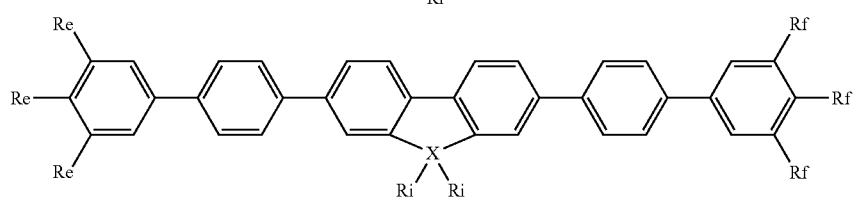

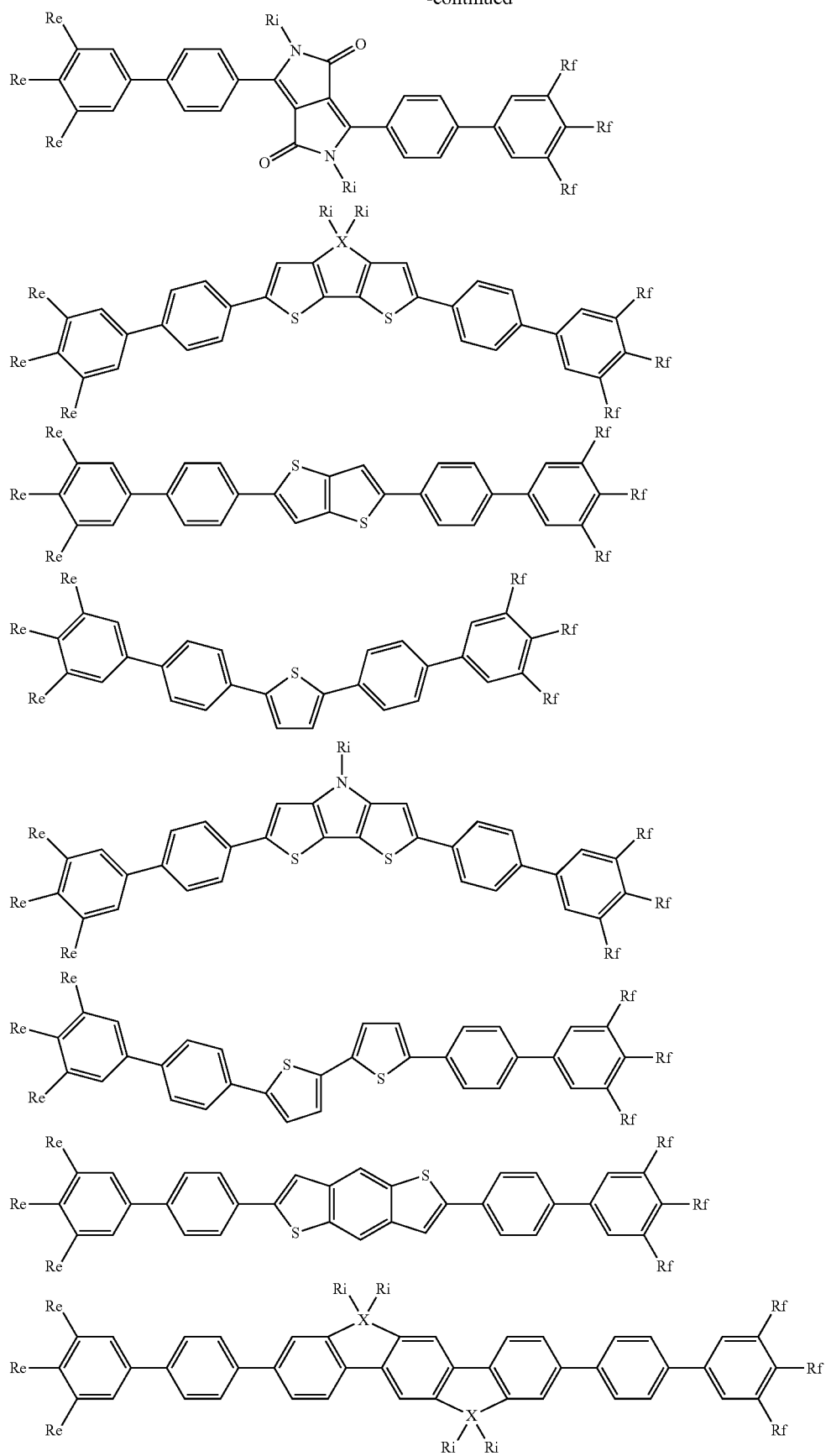

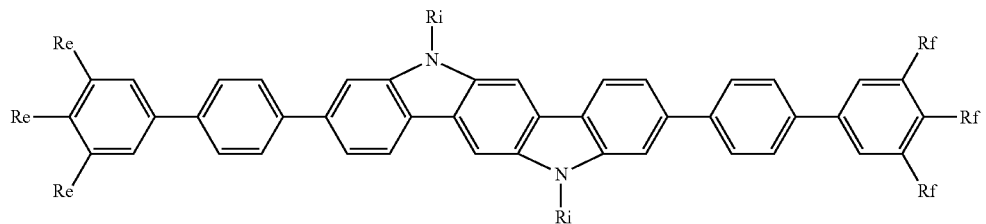
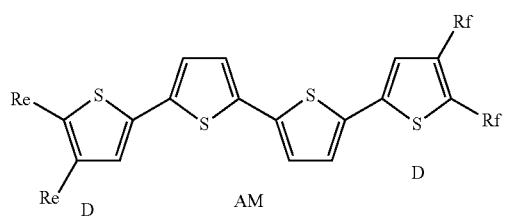
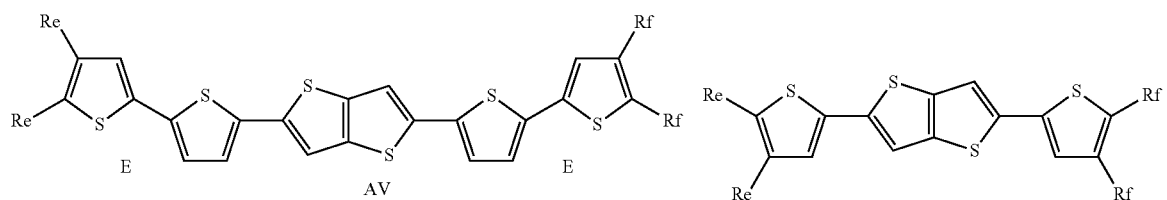
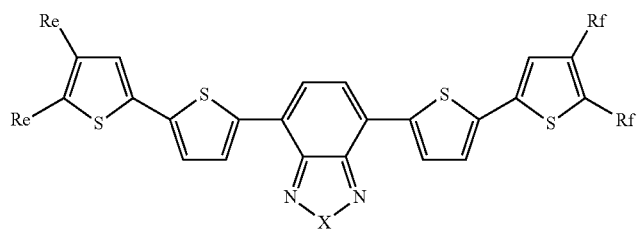
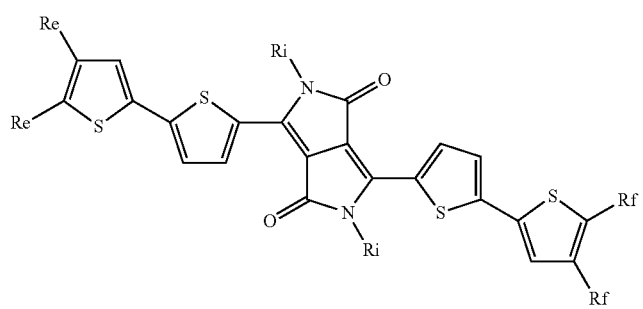
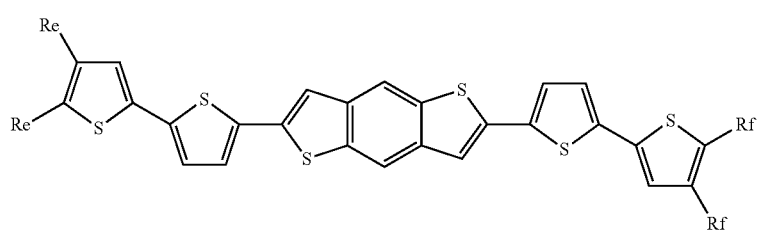
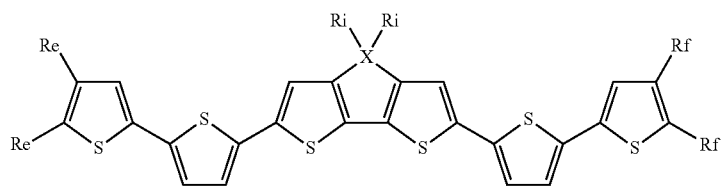

-continued

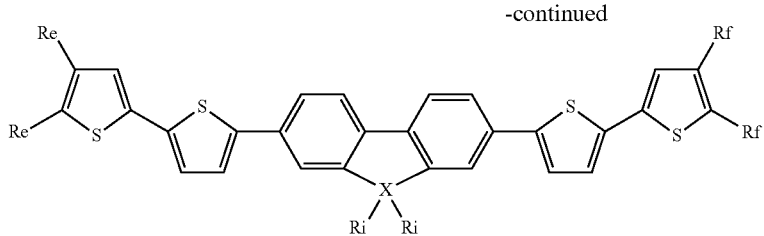

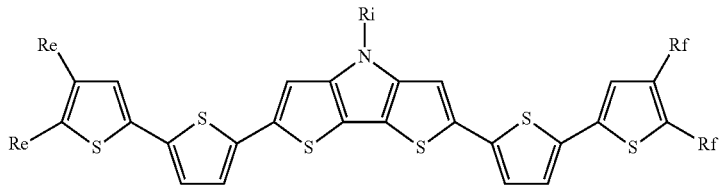

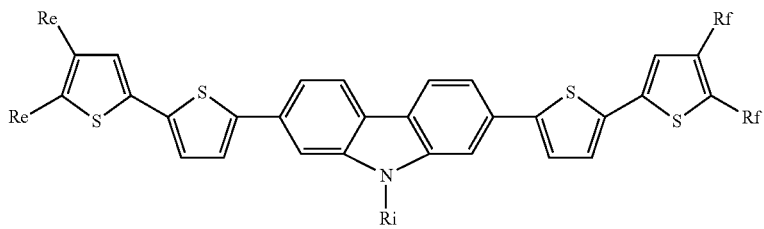

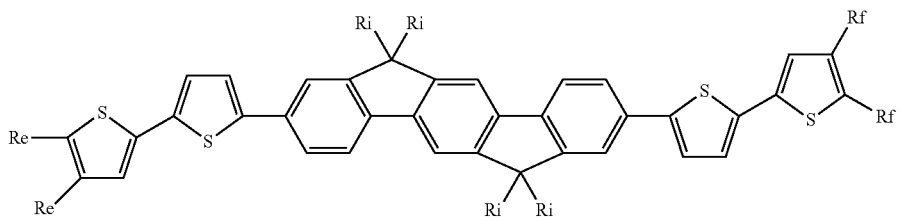

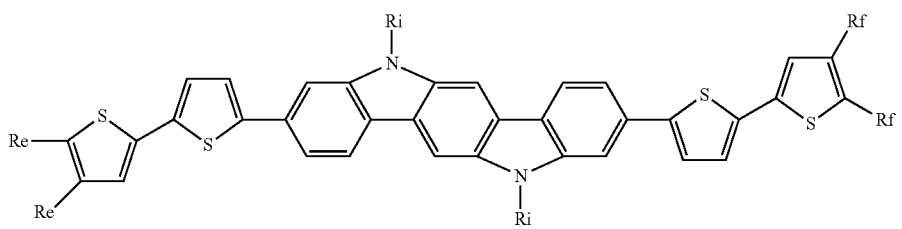

and where each Ri is independently selected from the group comprising —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aryl, F, Cl, Br, I, and —CN; and X is selected from O, S, or Se;

where at least one $R_e$ and at least one $R_f$ are each independently selected from the group consisting of -L-$R_h$ where each L is independently a linker group containing at least one carbon atom, and each $R_h$ is a independently hydrophilic group, such as a charged or polar functional group; and each remaining $R_e$ and each remaining $R_f$ is independently selected from the group consisting of —H, —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aryl, F, Cl, Br, I, and —CN.

In some embodiments, each L is independently selected from branched or linear, saturated or unsaturated, substituted or unsubstituted alkyl or heteroalkyl chains containing at least one carbon atom, and optionally incorporating one or more aryl or heteroaryl groups within the chain. In other embodiments, each L is independently selected from $C_1$-$C_{12}$ alkyl, $C_2$-$C_{12}$ alkenyl, $C_2$-$C_{12}$ alkynyl, $C_2$-$C_{12}$ unsaturated hydrocarbyl, $C_1$-$C_{12}$ alkyl-$C_6$-$C_{10}$ aryl-$C_1$-$C_{12}$ alkyl, or $C_1$-$C_{12}$ alkyl-$C_4$-$C_{10}$ heteroaryl-$C_1$-$C_{12}$ alkyl. In other embodiments, each L is independently substituted with $C_1$-$C_{12}$ alkyl, $C_2$-$C_{12}$ alkenyl, $C_2$-$C_{12}$ alkynyl, $C_1$-$C_{12}$ alkyl-$C_6$-$C_{10}$ aryl-$C_1$-$C_{12}$ alkyl, $C_1$-$C_{12}$ alkyl-$C_4$-$C_{10}$ heteroaryl-$C_1$-$C_{12}$ alkyl, hydroxyl, —O—$C_1$-$C_{12}$ alkyl, —$C_1$-$C_{12}$-alkyl-OH, fluoro, chloro, bromo, iodo, cyano, oxo, thiol, thioalkyl, carboxylic acid, carboxylic ester, amine, or amide groups.

In some embodiments, each $R_h$ is independently selected from the group consisting of: —$N^+(R')(R'')(R''')$,

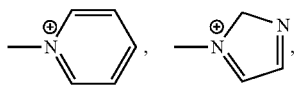

—$SO_3^-$, —$CO^{2-}$, —$PO_3^{2-}$, —$PO_3H^-$, —$PO_3H_2$, —$PO_4^{2-}$, —$PO_4H^-$, and —$PO_4H_2$, where R', R", and R''' are independently selected from ($C_1$-$C_{12}$ alkyl), and where the groups optionally additionally comprise one or more counterions. In one embodiment, the counterions are halide ions. In another embodiment, the counterions are iodide ions.

In some embodiments, the at least one $R_e$ and at least one $R_f$ are independently selected from groups of the form:

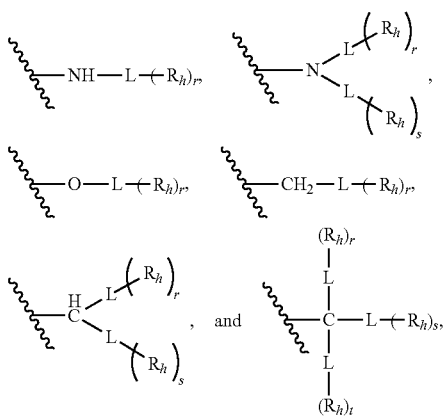

where each L and each $R_h$ can be selected from any of the definitions above. The subscripts r, s, and t can independently be 0, 1, 2, or 3, with the proviso that at least one $R_h$ is present in the $R_e$ or $R_f$ group (that is, r, when alone, must be at least 1; r+s, when t is absent, must be at least 1; or r+s+t must be at least 1). Multiple $R_h$ groups can be present on a single L group due to multiple substitution of $R_h$ groups at a single atom, or substitution of $R_h$ groups on different atoms. For example, when L is a branched C8 alkyl of the form

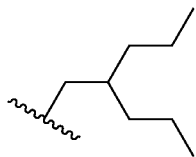

-L-($R_h$), can be of the form

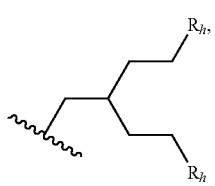

where r=2.

In one embodiment, the invention provides compounds and methods for enhancing the performance of microbial fuel cells. In another embodiment, the invention provides microbial fuel cells enhanced using the compounds and methods disclosed herein. In another embodiment, the invention provides microbial fuel cells enhanced by adding an amount of charge-transfer agent sufficient to increase the current and/or voltage of the microbial fuel cell. In one embodiment, the charge-transfer agent is not endogenous to the microorganism. In another embodiment, the charge-transfer agent is a deficient endogenous charge-transfer agent. In one embodiment, the charge-transfer agent is an electron-transfer agent.

In one embodiment, the invention embraces a microbial fuel cell, comprising an anode compartment comprising an anode in contact with a microbe-containing analyte; a cathode compartment comprising a cathode in contact with a catholyte; a cation-permeable membrane separating the anode compartment and the cathode compartment; and an electrical connection between the anode and the cathode; wherein the microbes in the microbe-containing analyte comprise a non-endogenous charge-transfer agent in their outer membranes. In one embodiment, the charge-transfer agent is a non-endogenous charge transfer agent. In one embodiment, the charge-transfer agent is a deficient endogenous charge transfer agent. In another embodiment, the charge-transfer agent is an electron-transfer agent.

In one embodiment of the microbial fuel cell, the electron-transfer agent is of the form:

$R_e$-Pi-$R_f$ where $R_e$ and $R_f$ can be the same or different and are groups containing a hydrophilic moiety, and Pi is a molecule with a delocalized π-electron system.

In one embodiment of the microbial fuel cell, the electron transfer agent is of the formula:

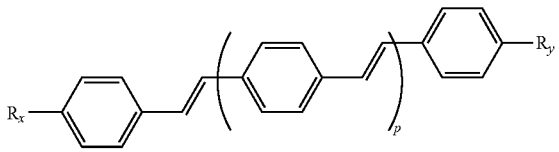

where p is an integer from 0 to 5, inclusive, $R_x$ is of the formula —$N(R_1)(R_2)$ and $R_y$ is of the formula —$N(R_3)(R_4)$, wherein $R_1$, $R_2$, $R_3$, and $R_4$ are each independently selected from the group consisting of -L-$R_h$ where each L is independently a linker group containing at least one carbon atom, and each $R_h$ is independently a hydrophilic group, such as a charged or polar functional group. In another embodiment, p is an integer from 0 to 4, inclusive. In another embodiment, p is an integer from 1 to 4, inclusive. In another embodiment, p is an integer from 1 to 3, inclusive. In another embodiment, p is selected from the integers 1 and 2. In another embodiment, p is 1. In another embodiment, p is 2.

In some embodiments, each L is independently selected from branched or linear, saturated or unsaturated, substituted or unsubstituted alkyl or heteroalkyl chains containing at least one carbon atom, and optionally incorporating one or more aryl or heteroaryl groups within the chain. In other embodiments, each L is independently selected from $C_1$-$C_{12}$ alkyl, $C_2$-$C_{12}$ alkenyl, $C_2$-$C_{12}$ alkynyl, $C_2$-$C_{12}$ unsaturated hydrocarbyl, $C_1$-$C_{12}$ alkyl-$C_6$-$C_{10}$ aryl-$C_1$-$C_{12}$ alkyl, or $C_1$-$C_{12}$ alkyl-$C_4$-$C_{10}$ heteroaryl-$C_1$-$C_{12}$ alkyl. In other embodiments, each L is independently substituted with $C_1$-$C_{12}$ alkyl, $C_2$-$C_{12}$ alkenyl, $C_2$-$C_{12}$ alkynyl, $C_1$-$C_{12}$ alkyl-$C_6$-$C_{10}$ aryl-$C_1$-$C_{12}$ alkyl, $C_1$-$C_{12}$ alkyl-$C_4$-$C_{10}$ heteroaryl-$C_1$-$C_{12}$ alkyl, hydroxyl, —O—$C_1$-$C_{12}$ alkyl, —$C_1$-$C_{12}$-alkyl-OH, fluoro, chloro, bromo, iodo, cyano, oxo, thiol, thioalkyl, carboxylic acid, carboxylic ester, amine, or amide groups.

In some embodiments, each $R_h$ is independently selected from the group consisting of: —$N^+(R')(R'')(R''')$,

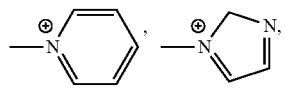

—$SO_3^-$, —$CO_2^{2-}$, —$PO_3^{2-}$, —$PO_3H^-$, —$PO_3H_2$, —$PO_4^{2-}$, —$PO_4H^-$, and —$PO_4H_2$, where R', R", and R''' are independently selected from ($C_1$-$C_{12}$ alkyl), and where the groups optionally additionally comprise one or more counterions. In one embodiment, the counterions are halide ions. In another embodiment, the counterions are iodide ions.

In some embodiments, $R_x$ and $R_y$ are independently selected from groups of the form:

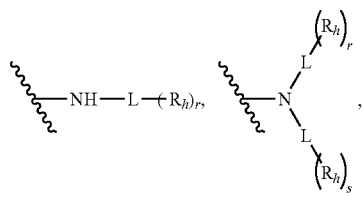

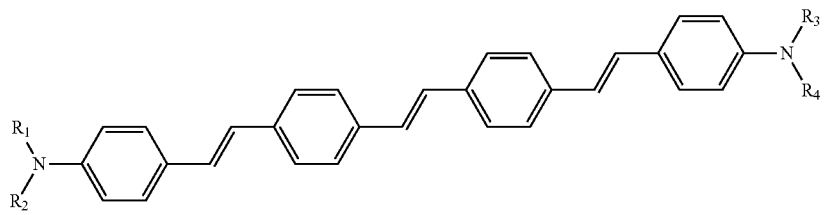

where each L and each $R_h$ can be selected from any of the definitions above. The subscripts r, s, and t can independently be 0, 1, 2, or 3, with the proviso that at least one $R_h$ is present in the $R_x$ or $R_y$ group (that is, r, when alone, must be at least 1; r+s, when t is absent, must be at least 1; or r+s+t must be at least 1).

In one embodiment, the agent includes one or more counterions. In further embodiments, the one or more counterions are halide ions. In further embodiments, the one or more counterions are iodide ions.

In one embodiment of the microbial fuel cell, the electron transfer agent is of the formula:

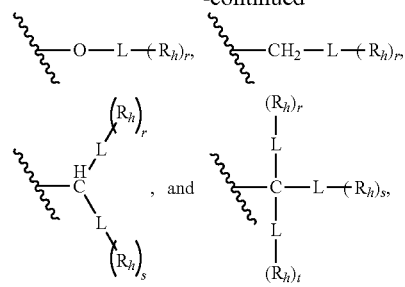

wherein $R_1$, $R_2$, $R_3$, and $R_4$ are selected from any of the definitions above. In one embodiment, the agent includes one or more counterions. In further embodiments, the one or more counterions are halide ions. In further embodiments, the one or more counterions are iodide ions.

In one embodiment of the microbial fuel cell, the electron transfer agent is of the formula:

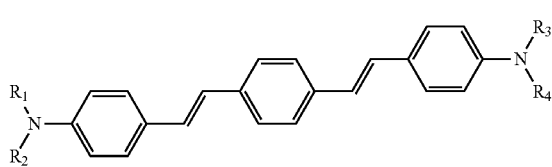

wherein $R_1$, $R_2$, $R_3$, and $R_4$ are selected from any of the definitions above. In one embodiment, the agent includes one or more counterions. In further embodiments, the one or more counterions are halide ions. In further embodiments, the one or more counterions are iodide ions.

In one embodiment of the microbial fuel cell, the electron transfer agent is of the formula:

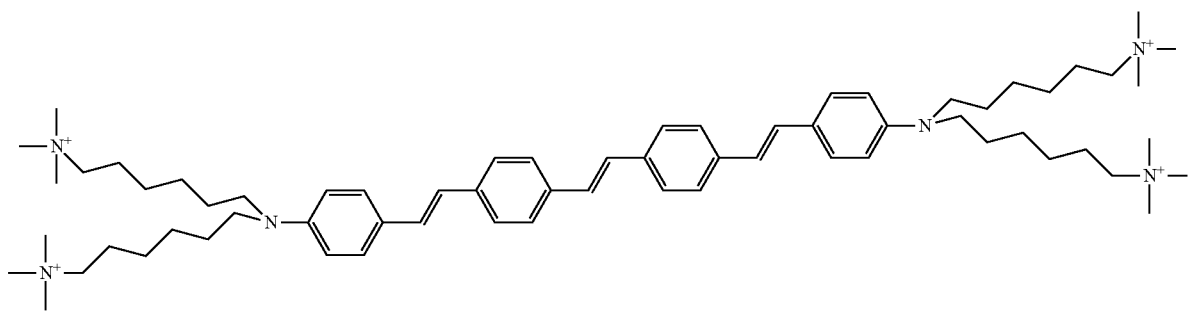

In one embodiment, the agent includes one or more counterions. In further embodiments, the one or more counterions are halide ions. In further embodiments, the one or more counterions are iodide ions.

In one embodiment of the microbial fuel cell, the electron transfer agent is of the formula:

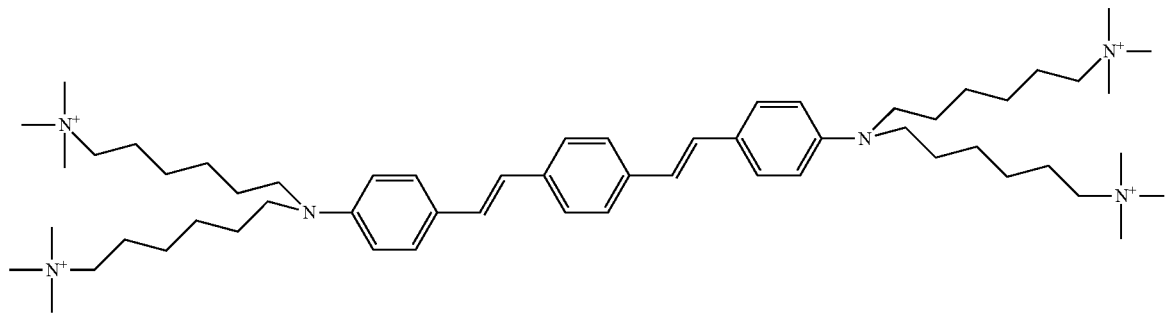

In one embodiment, the agent includes one or more counterions. In further embodiments, the one or more counterions are halide ions. In further embodiments, the one or more counterions are iodide ions.

In one embodiment of the microbial fuel cell, the electron transfer agent is selected from the group consisting of:

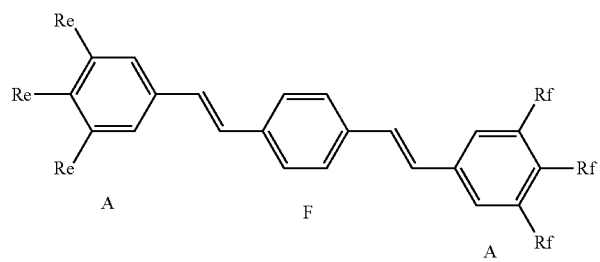

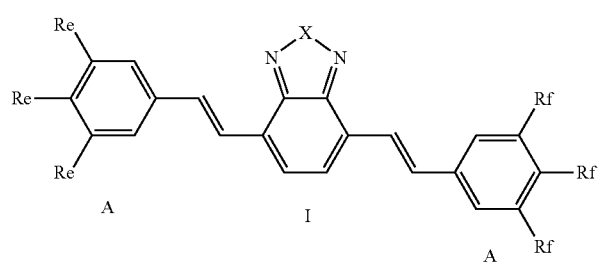

-continued
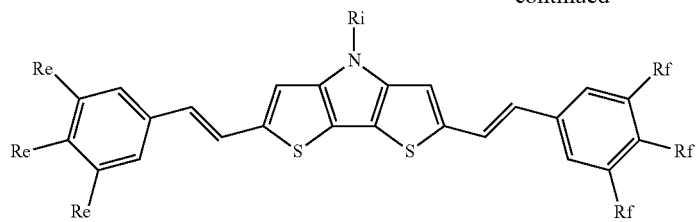
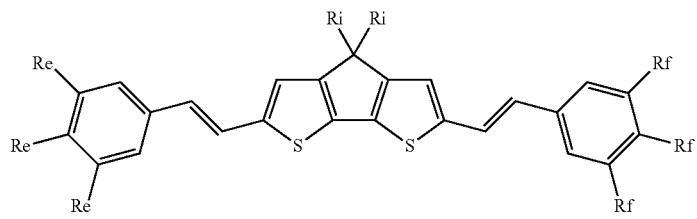
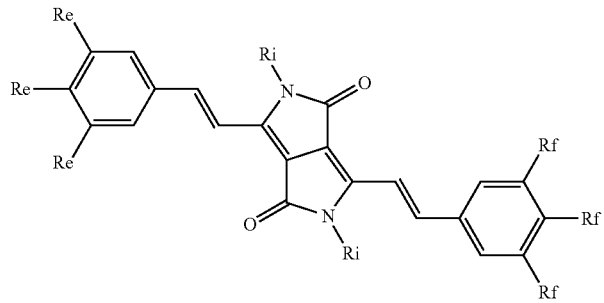
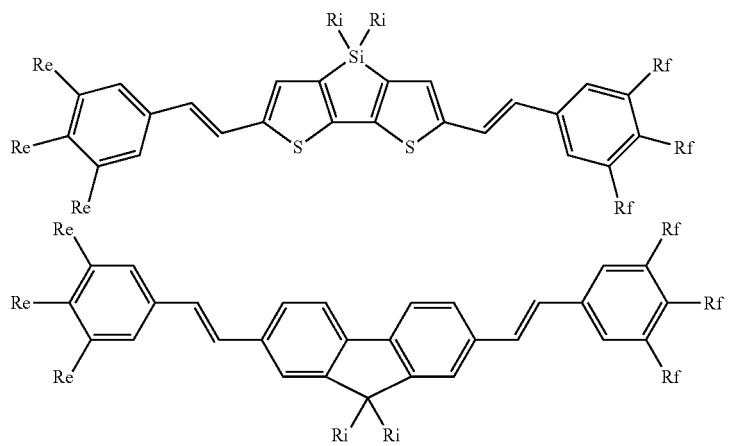
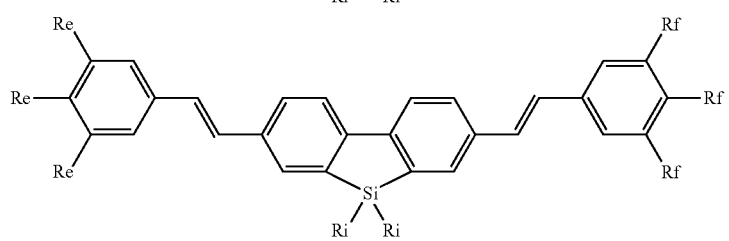
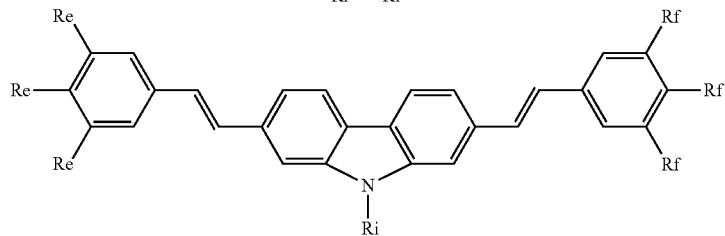

-continued
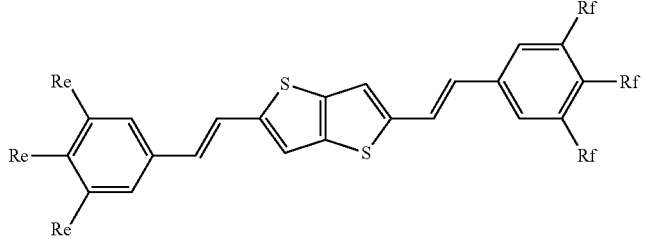
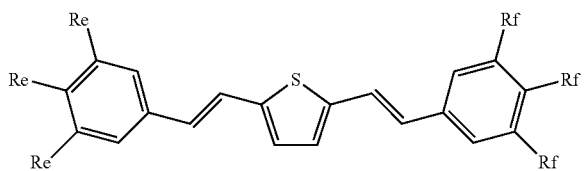
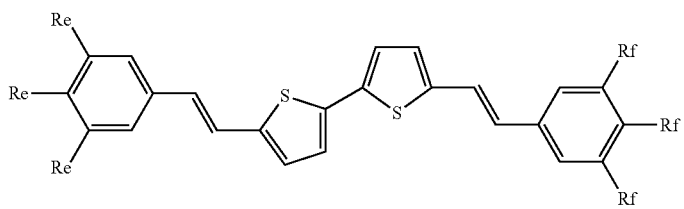
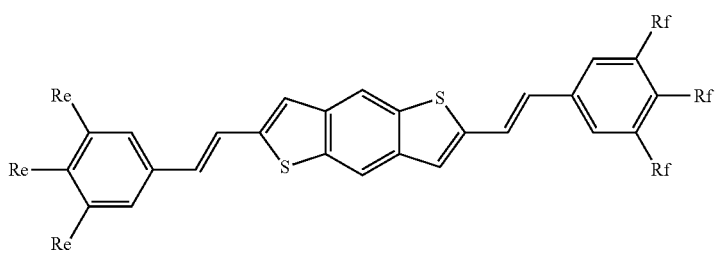
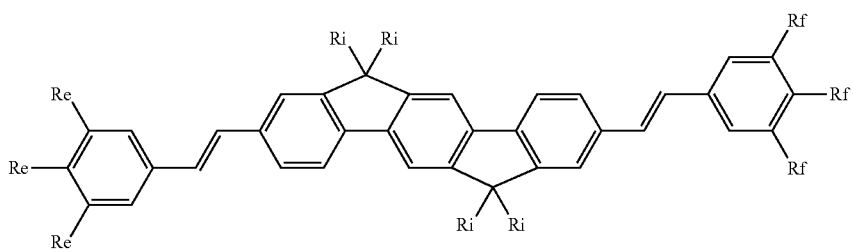
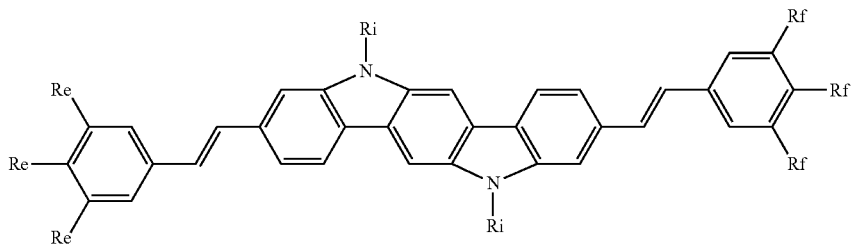
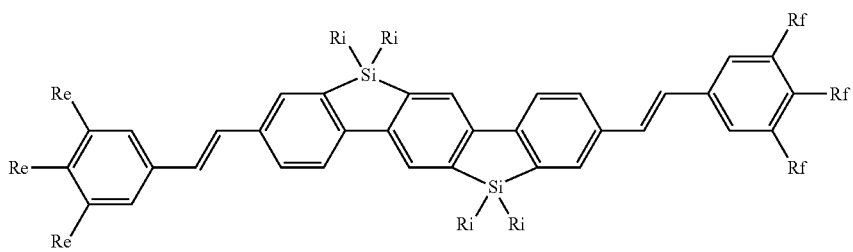

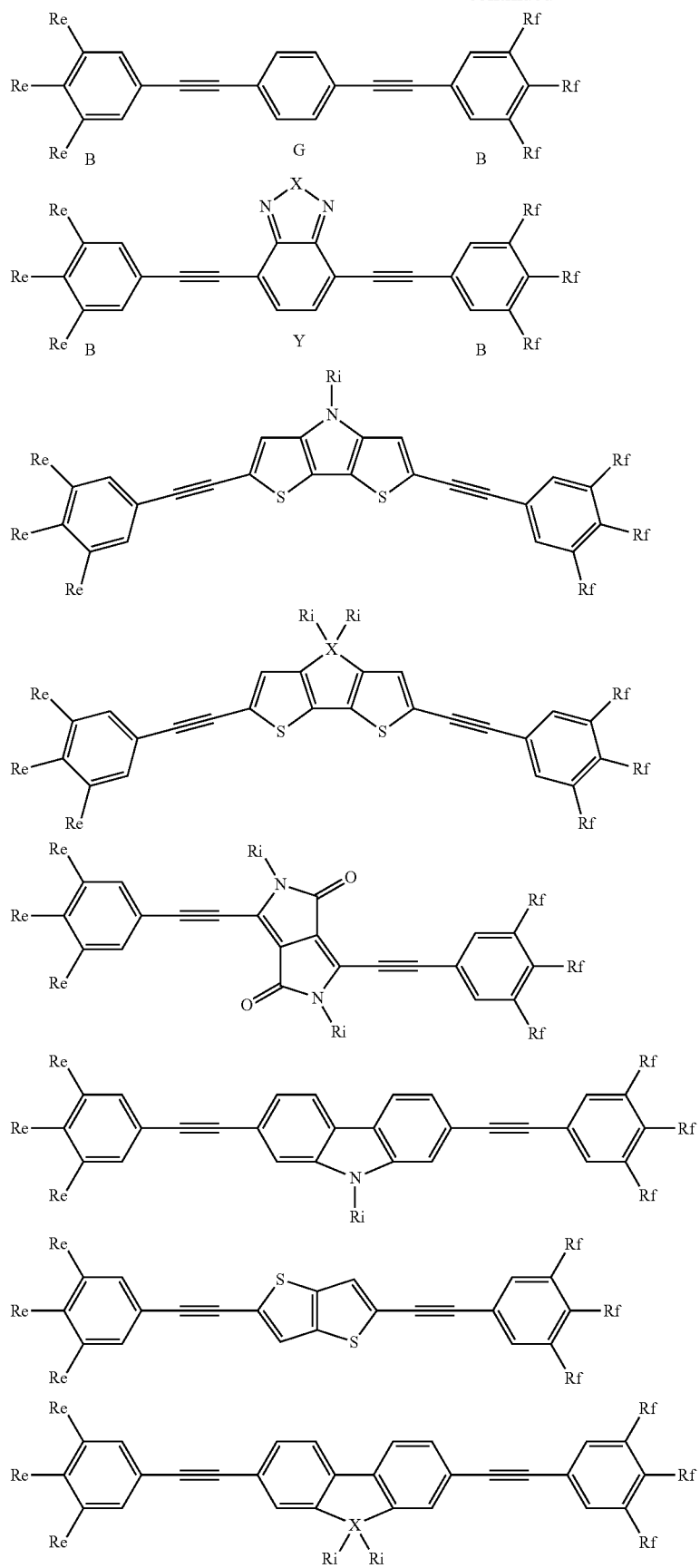

-continued
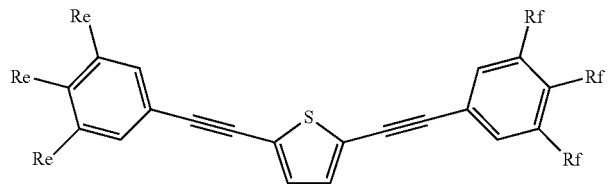
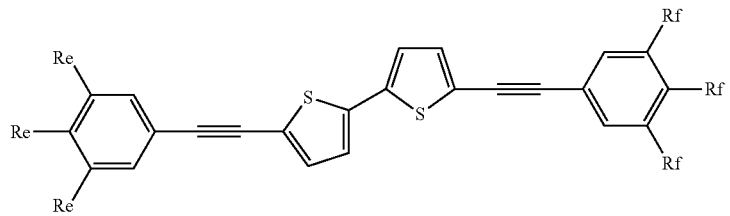
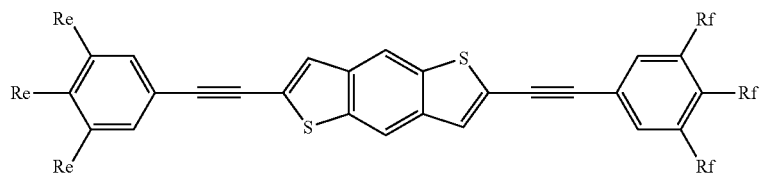
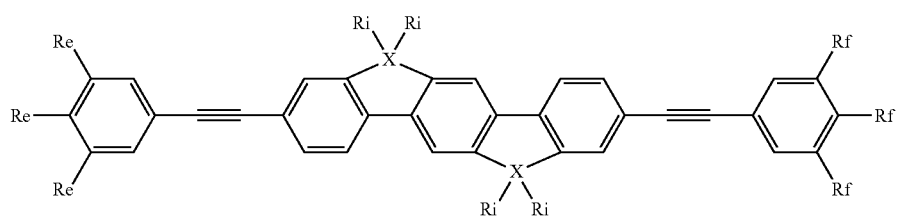
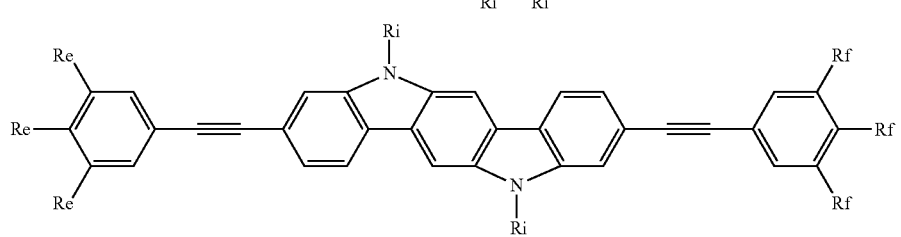
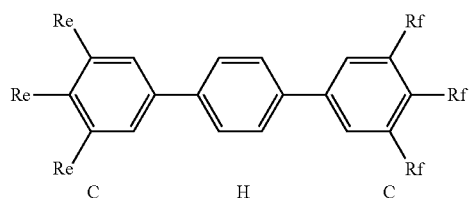
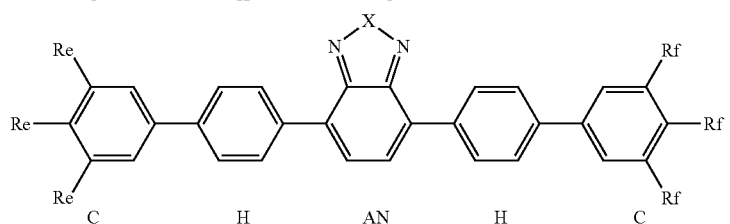
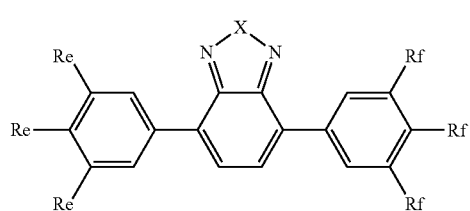

-continued
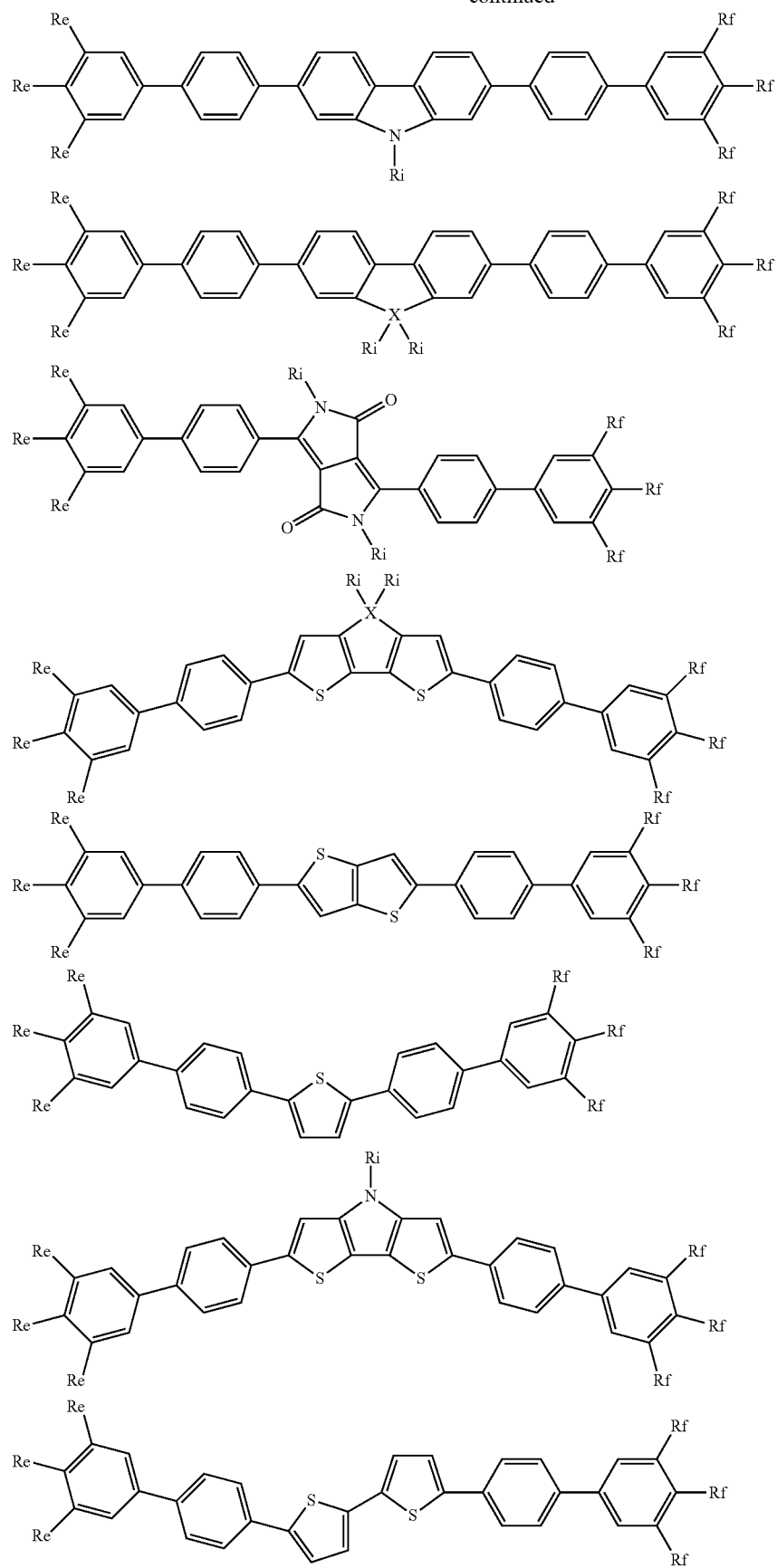

-continued
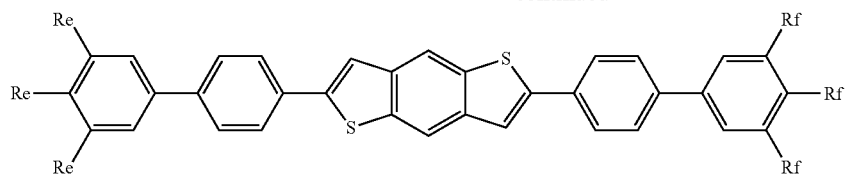
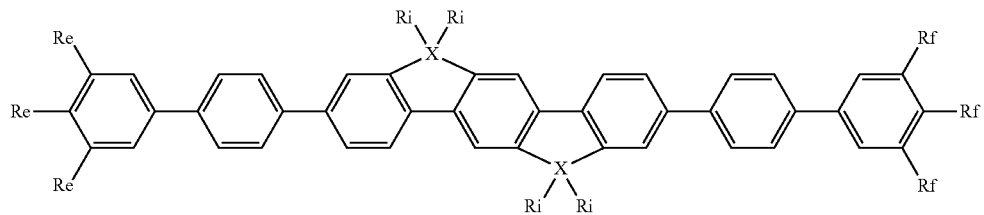
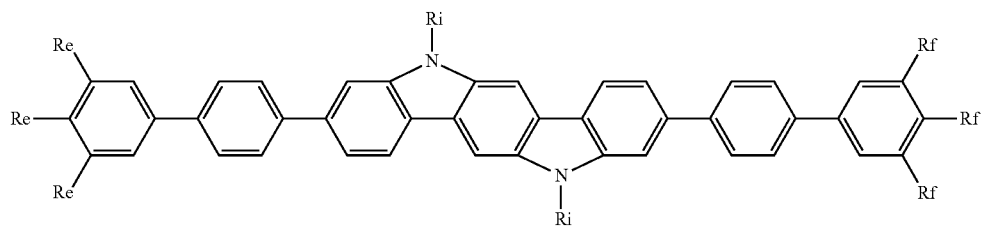
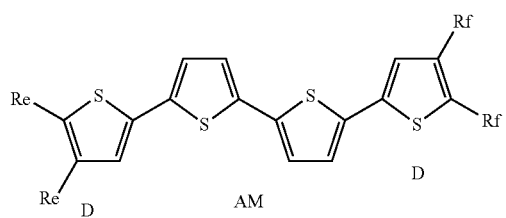
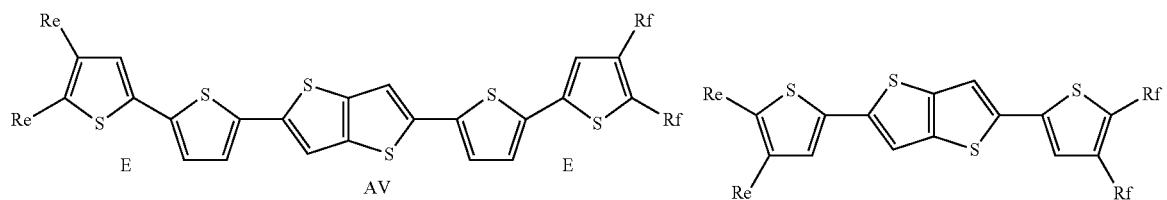
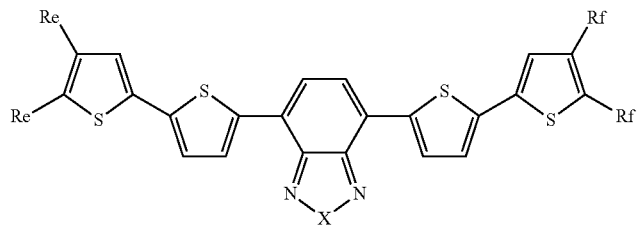
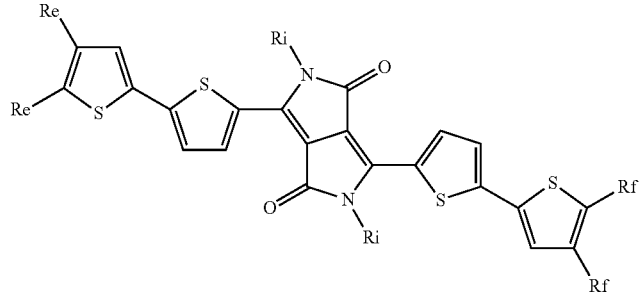

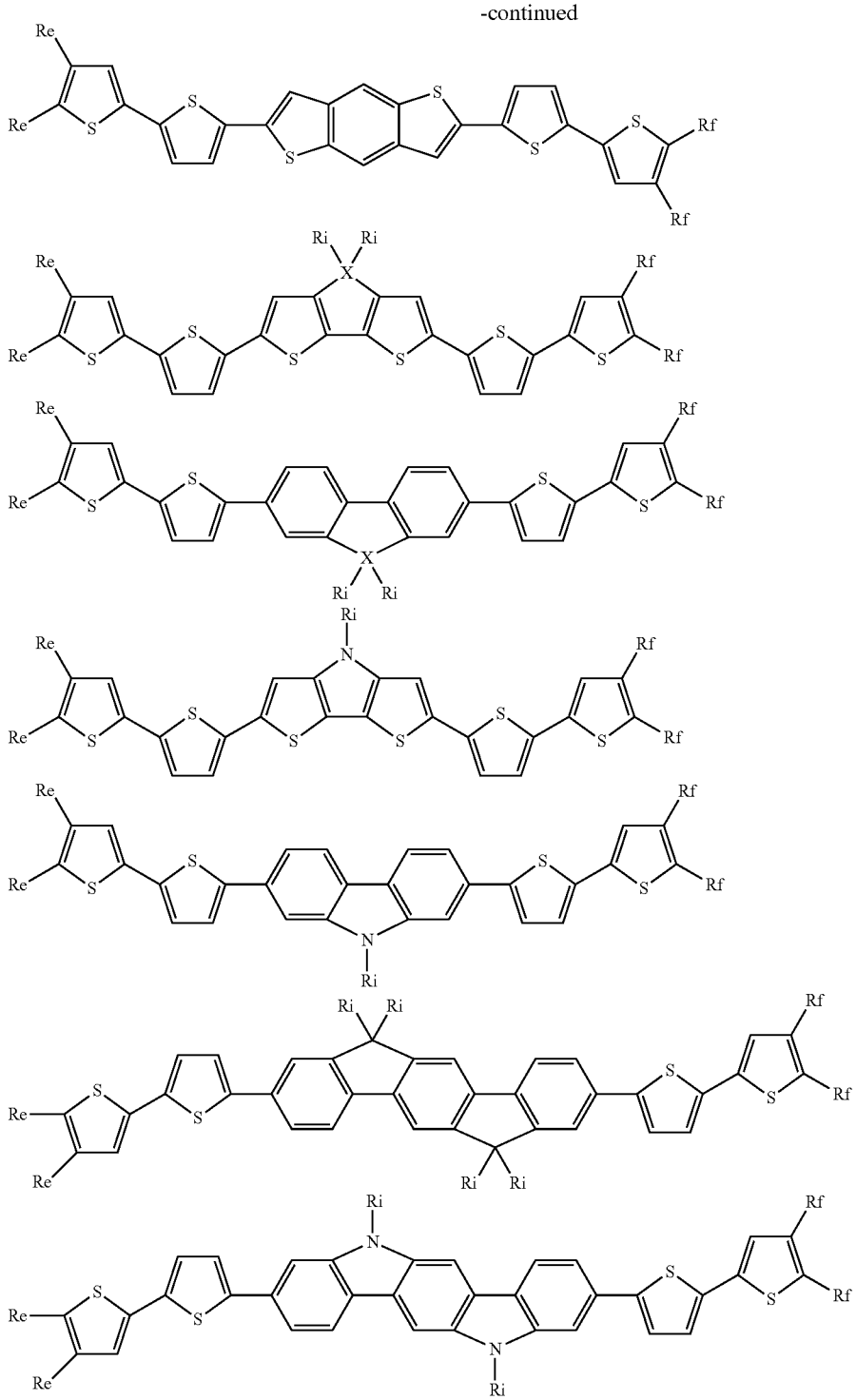

where each Ri is independently selected from the group comprising —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aryl, F, Cl, Br, I, and —CN; and X is selected from O, S, or Se;

where at least one $R_e$ and at least one $R_f$ are each independently selected from the group consisting of -L-$R_h$, where each L is independently a linker group containing at least one carbon atom, and each $R_h$ is a independently hydrophilic group, such as a charged or polar functional group; and each remaining $R_e$ and each remaining $R_f$ is independently selected from the group consisting of —H, —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aryl, F, Cl, Br, I, and —CN.

In some embodiments, each L is independently selected from branched or linear, saturated or unsaturated, substituted or unsubstituted alkyl or heteroalkyl chains containing at least one carbon atom, and optionally incorporating one or more aryl or heteroaryl groups within the chain. In other embodiments, each L is independently selected from $C_1$-$C_{12}$ alkyl, $C_2$-$C_{12}$ alkenyl, $C_2$-$C_{12}$ alkynyl, $C_2$-$C_{12}$ unsaturated hydrocarbyl, $C_1$-$C_{12}$ alkyl-$C_6$-$C_{10}$ aryl-$C_1$-$C_{12}$ alkyl, or $C_1$-$C_{12}$ alkyl-$C_4$-$C_{10}$ heteroaryl-$C_1$-$C_{12}$ alkyl. In other embodiments, each L is independently substituted with $C_1$-$C_{12}$ alkyl, $C_2$-$C_{12}$ alkenyl, $C_2$-$C_{12}$ alkynyl, $C_1$-$C_{12}$ alkyl-$C_6$-$C_{10}$ aryl-$C_1$-$C_{12}$ alkyl, $C_1$-$C_{12}$ alkyl-$C_4$-$C_{10}$ heteroaryl-$C_1$-$C_{12}$ alkyl, hydroxyl, —O—$C_1$-$C_{12}$ alkyl, —$C_1$-$C_{12}$-alkyl-OH, fluoro, chloro, bromo, iodo, cyano, oxo, thiol, thioalkyl, carboxylic acid, carboxylic ester, amine, or amide groups.

In some embodiments, each $R_h$ is independently selected from the group consisting of: —$N^+(R')(R'')(R''')$,

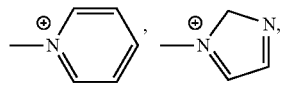

—$SO_3^-$, —$CO^{2-}$, —$PO_3^{2-}$, —$PO_3H^-$, —$PO_3H_2$, —$PO_4^{2-}$, —$PO_4H^-$, and —$PO_4H_2$, where R', R", and R''' are independently selected from ($C_1$-$C_{12}$ alkyl), and where the groups optionally additionally comprise one or more counterions. In one embodiment, the counterions are halide ions. In another embodiment, the counterions are iodide ions.

In some embodiments, the at least one $R_e$ and at least one $R_f$ are independently selected from groups of the form:

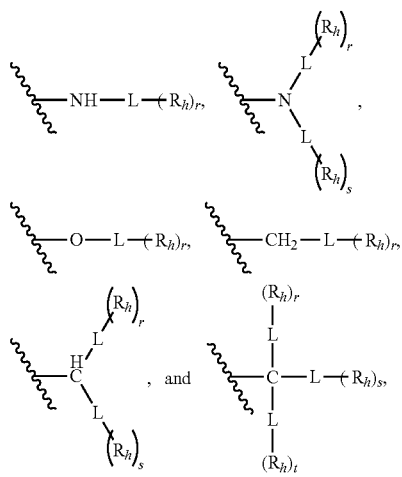

where each L and each $R_h$ can be selected from any of the definitions above. The subscripts r, s, and t can independently be 0, 1, 2, or 3, with the proviso that at least one $R_h$ is present in the $R_e$ or $R_f$ group (that is, r, when alone, must be at least 1; r+s, when t is absent, must be at least 1; or r+s+t must be at least 1). Multiple $R_h$ groups can be present on a single L group due to multiple substitution of $R_h$ groups at a single atom, or substitution of $R_h$ groups on different atoms. For example, when L is a branched C8 alkyl of the form

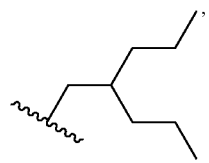 [SMILES: *CC(CCC)CCC]

-L-($R_h$)$_r$ can be of the form

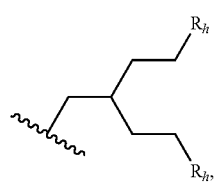

where r=2.

The invention also embraces a method of enhancing the performance of a microbial fuel cell, comprising adding an electron-transfer agent to the lipid bilayer of the microbes.

In one embodiment of the method, the electron-transfer agent is of the form:

$R_e$-Pi-$R_f$ where $R_e$ and $R_f$ can be the same or different and are groups containing a hydrophilic moiety, and Pi is a molecule with a delocalized π-electron system.

In one embodiment of the method of enhancing the performance of a microbial fuel cell, the electron transfer agent is of the formula:

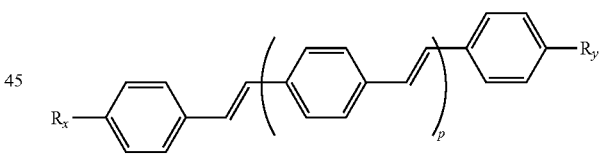

where p is an integer from 0 to 5, inclusive, $R_x$ is of the formula —$N(R_1)(R_2)$ and $R_y$ is of the formula —$N(R_3)(R_4)$, wherein each $R_1$, $R_2$, $R_3$ and $R_4$ is independently selected from the group consisting of

-L-$R_h$ where each L is independently a linker group containing at least one carbon atom, and each $R_h$ is independently a hydrophilic group.

In some embodiments, each L is independently selected from branched or linear, saturated or unsaturated, substituted or unsubstituted alkyl or heteroalkyl chains containing at least one carbon atom, and optionally incorporating one or more aryl or heteroaryl groups within the chain. In other embodiments, each L is independently selected from $C_1$-$C_{12}$ alkyl, $C_2$-$C_{12}$ alkenyl, $C_2$-$C_{12}$ alkynyl, $C_2$-$C_{12}$ unsaturated hydrocarbyl, $C_1$-$C_{12}$ alkyl-$C_6$-$C_{10}$ aryl-$C_1$-$C_{12}$ alkyl, or $C_1$-$C_{12}$ alkyl-$C_4$-$C_{10}$ heteroaryl-$C_1$-$C_{12}$ alkyl. In other embodiments, each L is independently substituted with $C_1$-$C_{12}$ alkyl, $C_2$-$C_{12}$ alkenyl, $C_2$-$C_{12}$ alkynyl, $C_1$-$C_{12}$ alkyl-$C_6$-$C_{10}$ aryl-$C_1$-$C_{12}$ alkyl, $C_1$-$C_{12}$ alkyl-$C_4$-$C_{10}$ heteroaryl-$C_1$-$C_{12}$ alkyl, hydroxyl, —O—$C_1$-$C_{12}$ alkyl, —$C_1$-$C_{12}$-alkyl-OH, fluoro, chloro, bromo, iodo, cyano, oxo, thiol, thioalkyl, carboxylic acid, carboxylic ester, amine, or amide groups.

In some embodiments, each $R_h$ is independently selected from the group consisting of: —$N^+(R')(R'')(R''')$,

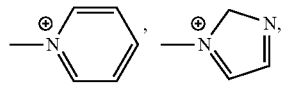

—$SO_3^-$, —$CO^{2-}$, —$PO_3^{2-}$, —$PO_3H^-$, —$PO_3H_2$, —$PO_4$, —$PO_4H^-$, and —$PO_4H_2$, where R', R", and R'" are independently selected from ($C_1$-$C_{12}$ alkyl), and where the groups optionally additionally comprise one or more counterions. In one embodiment, the counterions are halide ions. In another embodiment, the counterions are iodide ions.

In some embodiments, the at least one $R_e$ and at least one $R_f$ are independently selected from groups of the form:

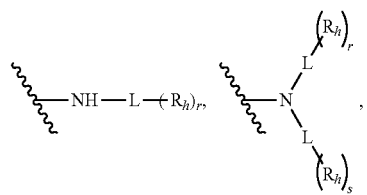

where each L and each $R_h$ can be selected from any of the definitions above. The subscripts r and s can independently be 0, 1, 2, or 3, with the proviso that at least one $R_h$ is present in the $R_1$, $R_2$, $R_3$, or $R_4$ group (that is, r, when alone, must be at least 1; or r+s must be at least 1).

In another embodiment, p is an integer from 0 to 4, inclusive. In another embodiment, p is an integer from 1 to 4, inclusive. In another embodiment, p is an integer from 1 to 3, inclusive. In another embodiment, p is selected from the integers 1 and 2. In another embodiment, p is 1. In another embodiment, p is 2.

In one embodiment of the method of enhancing the performance of a microbial fuel cell, the electron transfer agent is of the formula:

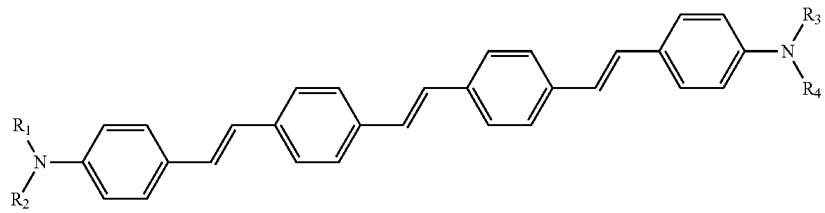

40 wherein $R_1$, $R_2$, $R_3$, and $R_4$ are selected from any of the definitions above.

In one embodiment of the method of enhancing the performance of a microbial fuel cell, the electron transfer agent is of the formula:

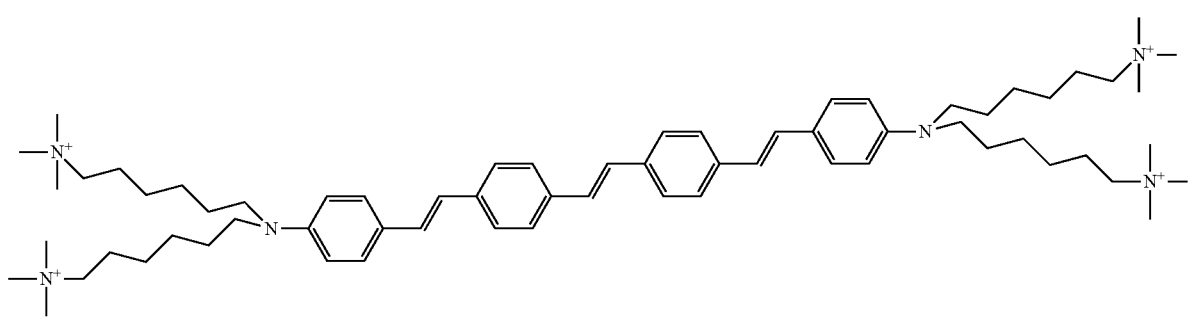

In one embodiment, the agent includes one or more counterions. In further embodiments, the one or more counterions are halide ions. In further embodiments, the one or more counterions are iodide ions.

In one embodiment of the method of enhancing the performance of a microbial fuel cell, the electron transfer agent is of the formula:

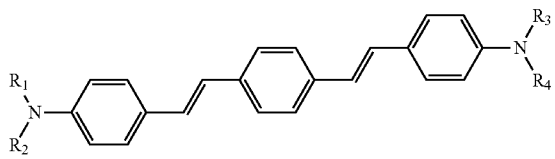

wherein $R_1$, $R_2$, $R_3$, and $R_4$ are selected from any of the definitions above. In one embodiment, the agent includes one or more counterions. In further embodiments, the one or more counterions are halide ions. In further embodiments, the one or more counterions are iodide ions.

In one embodiment of the method of enhancing the performance of a microbial fuel cell, the electron transfer agent is of the formula:

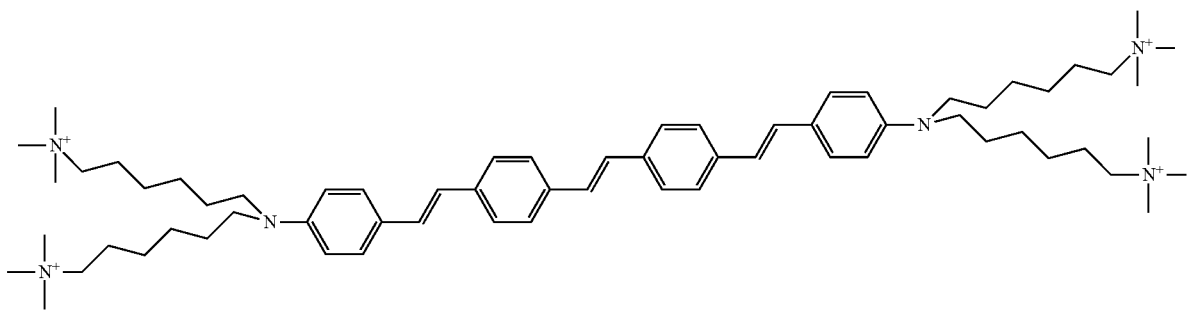

In one embodiment, the agent includes one or more counterions. In further embodiments, the one or more counterions are halide ions. In further embodiments, the one or more counterions are iodide ions.

In one embodiment of the method of enhancing the performance of a microbial fuel cell, the electron transfer agent is selected from the group consisting of:

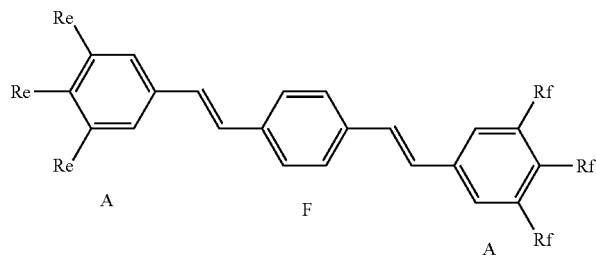

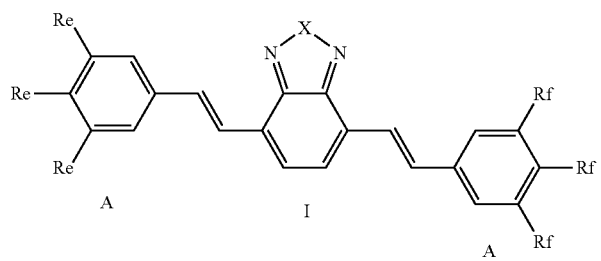

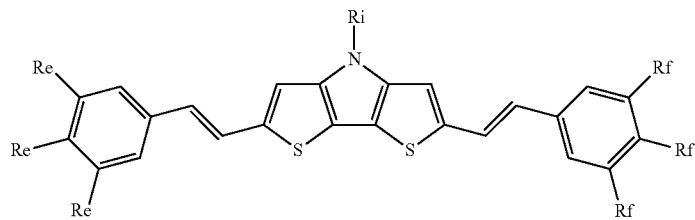

-continued
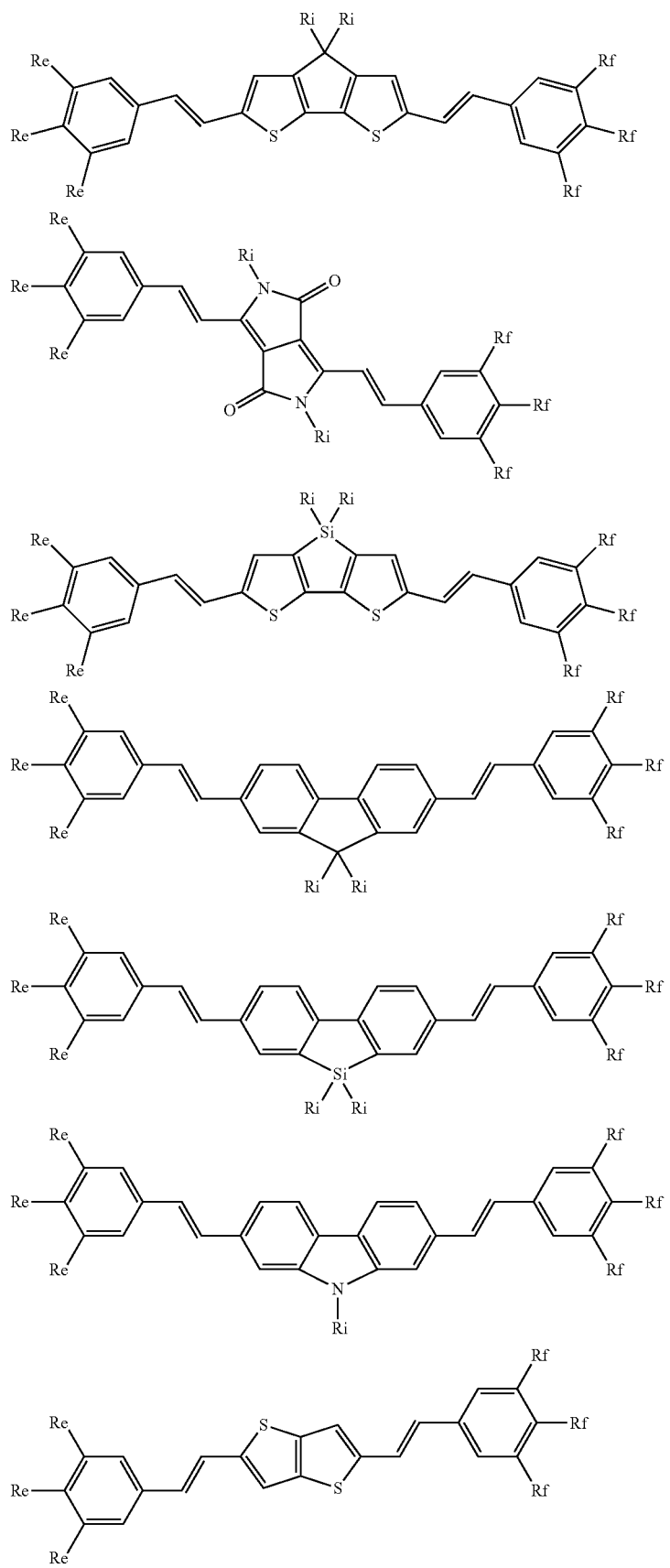

-continued
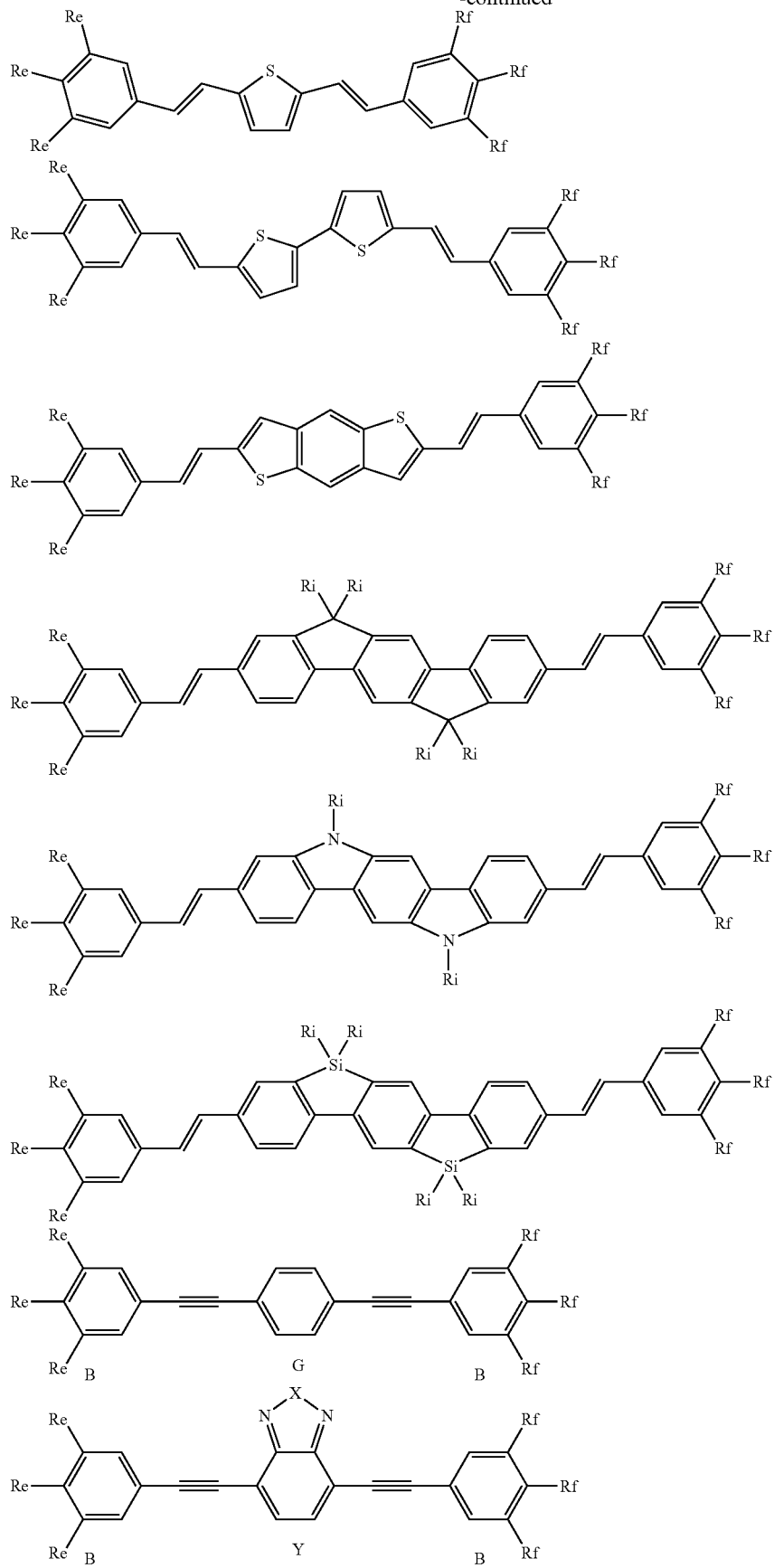

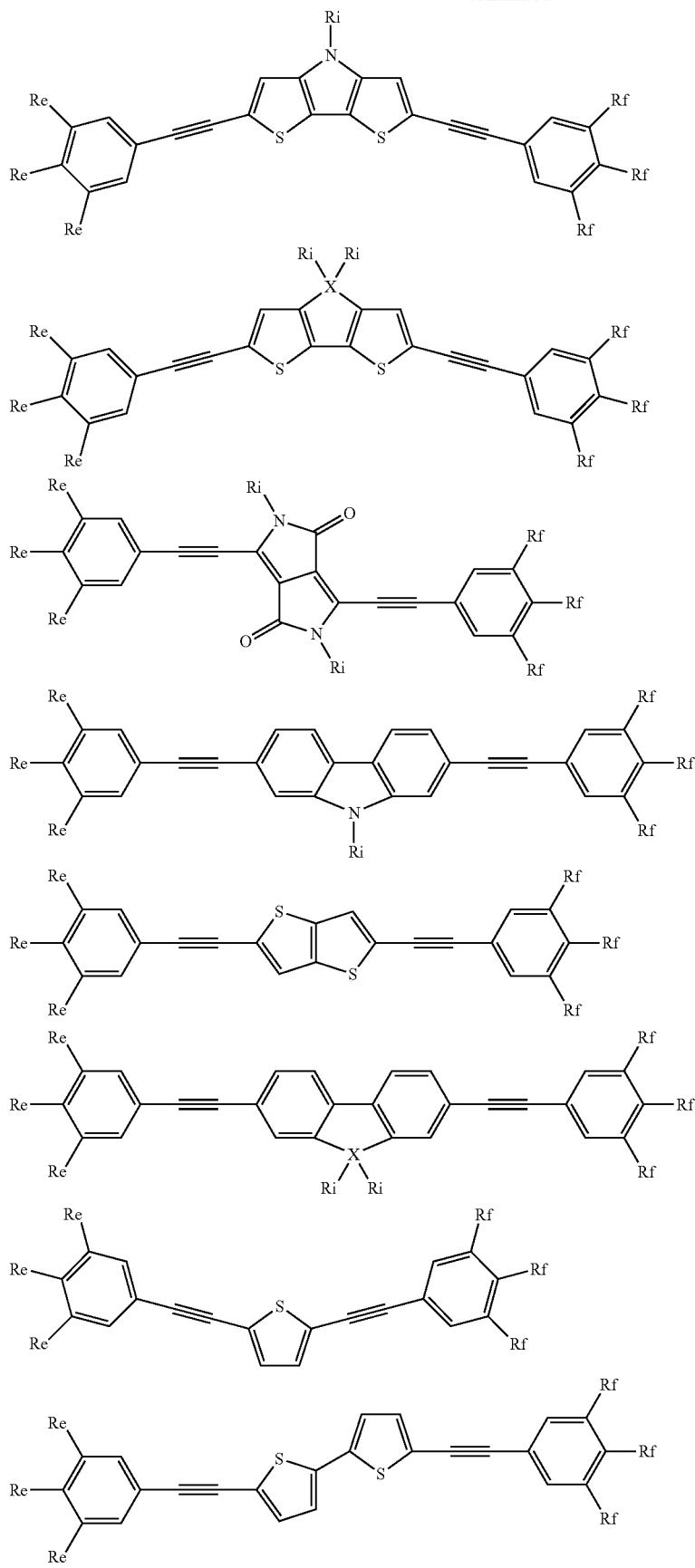

-continued
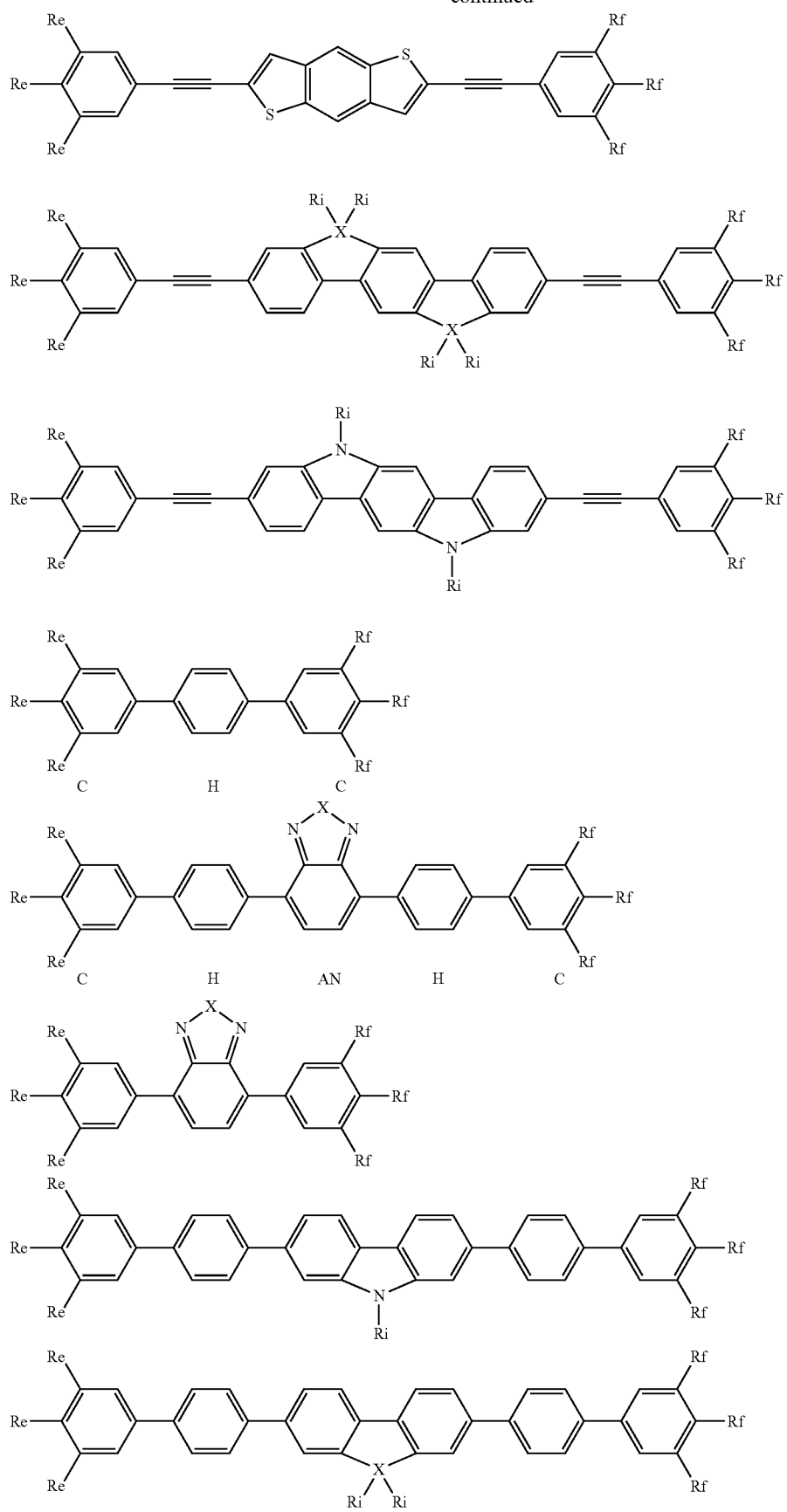

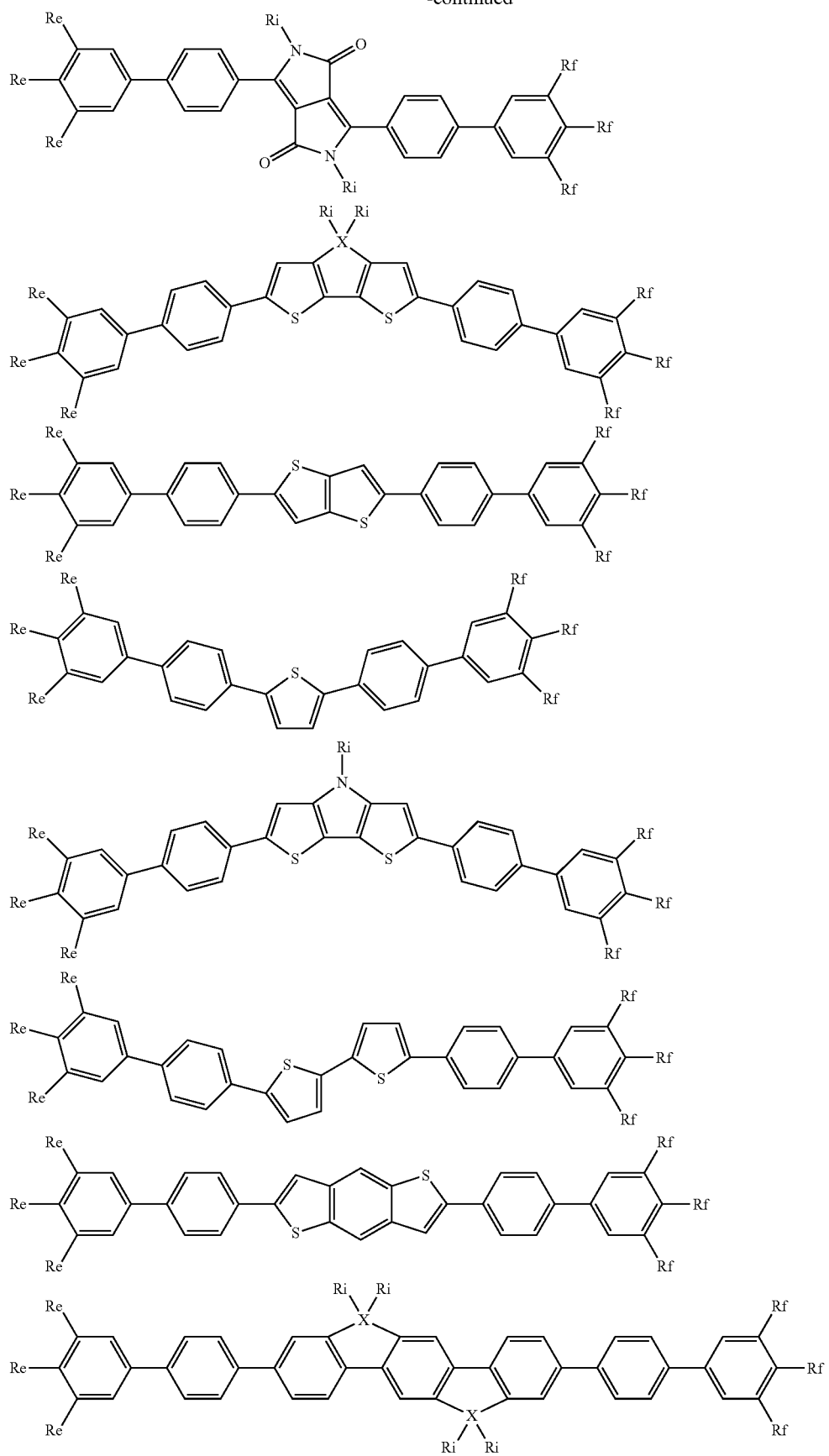

-continued
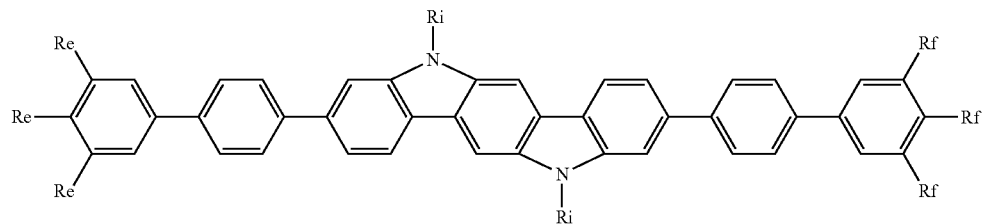
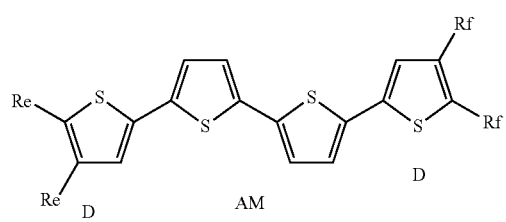
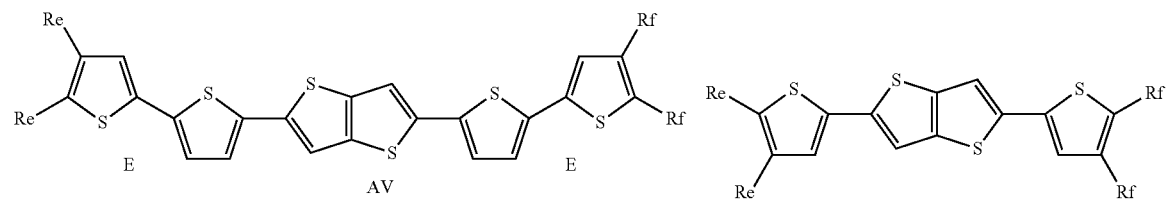
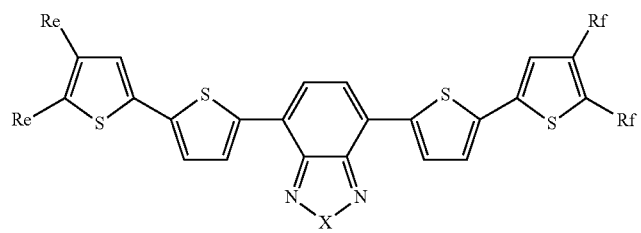
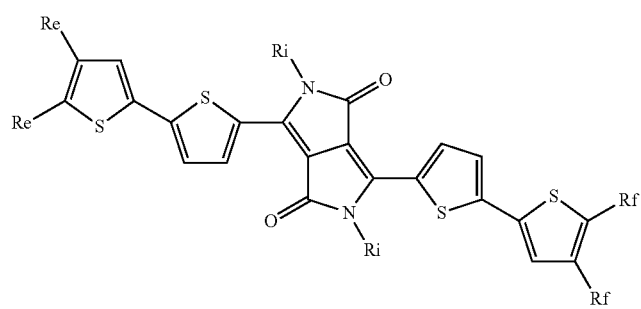
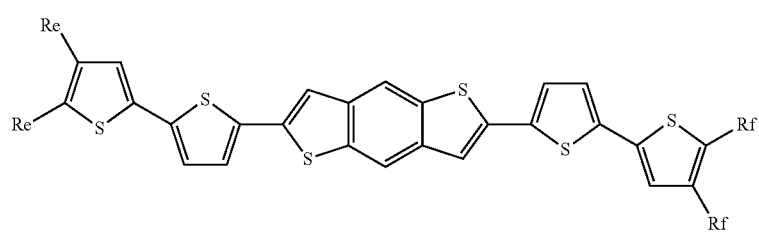
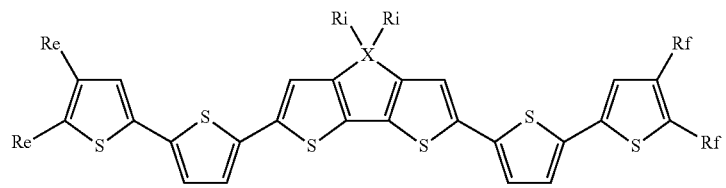

-continued

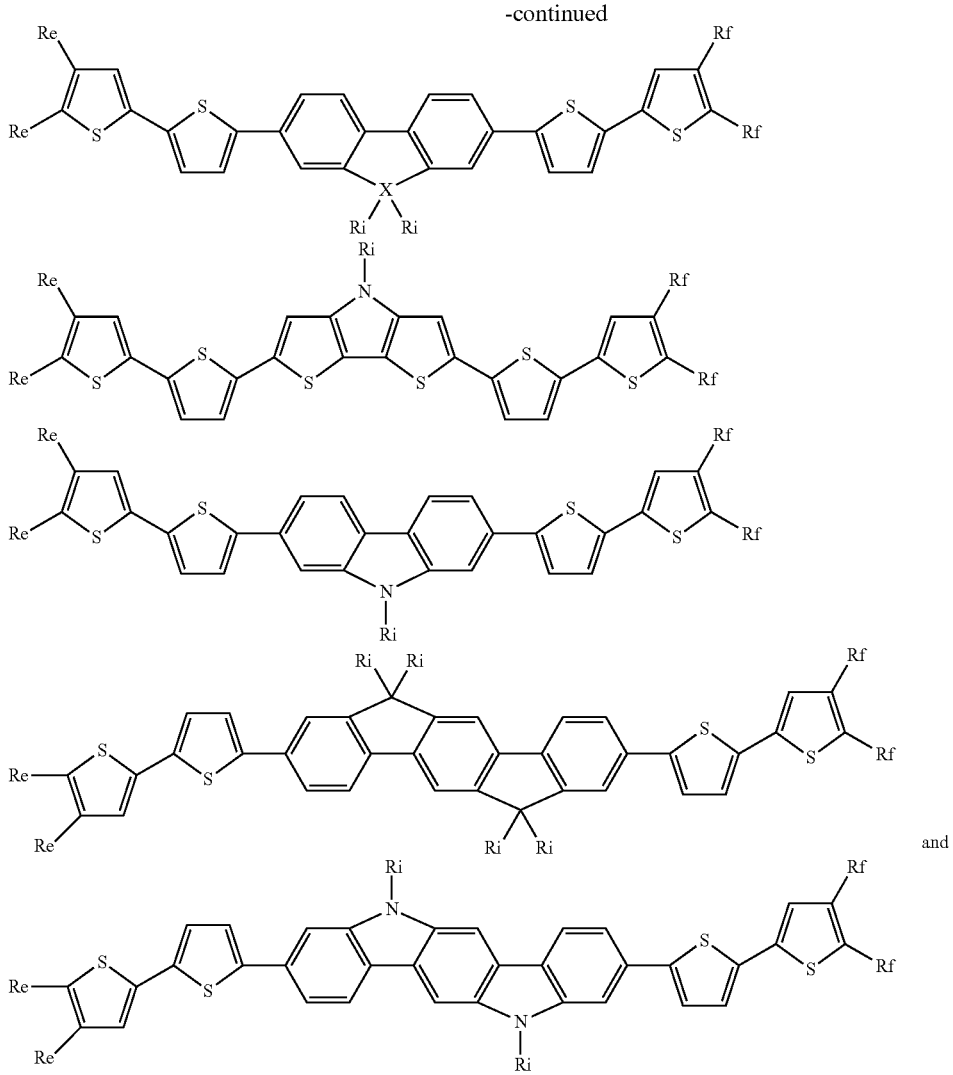

where each Ri is independently selected from the group comprising —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aryl, F, Cl, Br, I, and —CN; and X is selected from O, S, or Se;

where at least one $R_e$ and at least one $R_f$ are each independently selected from the group consisting of -L-$R_h$ where each L is independently a linker group containing at least one carbon atom, and each $R_h$ is a independently hydrophilic group, such as a charged or polar functional group; and each remaining $R_e$ and each remaining $R_f$ is independently selected from the group consisting of —H, —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aryl, F, Cl, Br, I, and —CN.

In some embodiments, each L is independently selected from branched or linear, saturated or unsaturated, substituted or unsubstituted alkyl or heteroalkyl chains containing at least one carbon atom, and optionally incorporating one or more aryl or heteroaryl groups within the chain. In other embodiments, each L is independently selected from $C_1$-$C_{12}$ alkyl, $C_2$-$C_{12}$ alkenyl, $C_2$-$C_{12}$ alkynyl, $C_2$-$C_{12}$ unsaturated hydrocarbyl, $C_1$-$C_{12}$ alkyl-$C_6$-$C_{10}$ aryl-$C_1$-$C_{12}$ alkyl, or $C_1$-$C_{12}$ alkyl-$C_4$-$C_{10}$ heteroaryl-$C_1$-$C_{12}$ alkyl. In other embodiments, each L is independently substituted with $C_1$-$C_{12}$ alkyl, $C_2$-$C_{12}$ alkenyl, $C_2$-$C_{12}$ alkynyl, $C_1$-$C_{12}$ alkyl-$C_6$-$C_{10}$ aryl-$C_1$-$C_{12}$ alkyl, $C_1$-$C_{12}$ alkyl-$C_4$-$C_{10}$ heteroaryl-$C_1$-$C_{12}$ alkyl, hydroxyl, —O—$C_1$-$C_{12}$ alkyl, —$C_1$-$C_{12}$-alkyl-OH, fluoro, chloro, bromo, iodo, cyano, oxo, thiol, thioalkyl, carboxylic acid, carboxylic ester, amine, or amide groups.

In some embodiments, each $R_h$ is independently selected from the group consisting of: —$N^+$(R')(R'')(R'''),

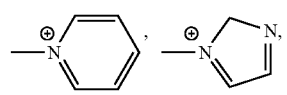

—$SO_3^-$, —$CO^{2-}$, —$PO_3^{2-}$, —$PO_3H^-$, —$PO_3H_2$, —$PO_4$, —$PO_4H^-$, and —$PO_4H_2$, where R', R'', and R''' are independently selected from ($C_1$-$C_{12}$ alkyl), and where the groups optionally additionally comprise one or more counterions. In one embodiment, the counterions are halide ions. In another embodiment, the counterions are iodide ions.

In some embodiments, the at least one $R_e$ and at least one $R_f$ are independently selected from groups of the form:

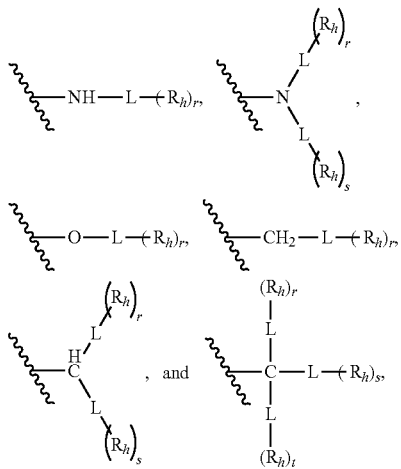

where each L and each $R_h$ can be selected from any of the definitions above. The subscripts r, s, and t can independently be 0, 1, 2, or 3, with the proviso that at least one $R_h$ is present in the $R_e$ or $R_f$ group (that is, r, when alone, must be at least 1; r+s, when t is absent, must be at least 1; or r+s+t must be at least 1). Multiple $R_h$ groups can be present on a single L group due to multiple substitution of $R_h$ groups at a single atom, or substitution of $R_h$ groups on different atoms. For example, when L is a branched C8 alkyl of the form

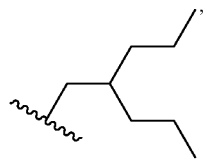 [SMILES: *CC(CCC)CCC]

$-L-(R_h)$, can be of the form

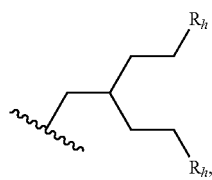

where r=2.

In another embodiment, the invention provides compounds and methods for detecting, imaging, labeling, identifying, or staining cells, by adding compounds to the membranes of the cells. In one embodiment, the added compound of the structure $R_e\text{-Pi-}R_f$ and said compound intercalates into or inserts into a cell membrane. The method further comprises illuminating the cells with light, such as ultraviolet or visible light, where said light is capable of being absorbed by the compound. The compound then emits light, such as fluorescent, phosphorescent, or scattered light. Detecting the emitted light, such as fluorescent emission, from the compound permits detection, imaging, or identification of the cells.

In one embodiment of the method for detecting, imaging, labeling, identifying, or staining cells, the compound is of the formula:

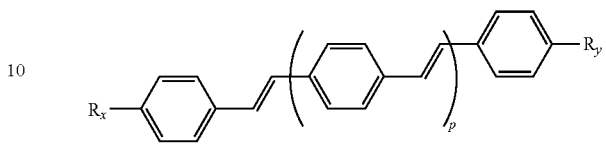

wherein $R_x$ and $R_y$ are groups containing a hydrophilic moiety, and p is an integer from 0 to 5, inclusive. In a further embodiment, $R_x$ is of the formula $-N(R_1)(R_2)$ and $R_y$ is of the formula $-N(R_3)(R_4)$, wherein each $R_1$, $R_2$, $R_3$ and $R_4$ is independently selected from the group consisting of $-L-R_h$ where each L is independently a linker group containing at least one carbon atom, and each $R_h$ is independently a hydrophilic group.

In some embodiments, each L is independently selected from branched or linear, saturated or unsaturated, substituted or unsubstituted alkyl or heteroalkyl chains containing at least one carbon atom, and optionally incorporating one or more aryl or heteroaryl groups within the chain. In other embodiments, each L is independently selected from $C_1$-$C_{12}$ alkyl, $C_2$-$C_{12}$ alkenyl, $C_2$-$C_{12}$ alkynyl, $C_2$-$C_{12}$ unsaturated hydrocarbyl, $C_1$-$C_{12}$ alkyl-$C_6$-$C_{10}$ aryl-$C_1$-$C_{12}$ alkyl, or $C_1$-$C_{12}$ alkyl-$C_4$-$C_{10}$ heteroaryl-$C_1$-$C_{12}$ alkyl. In other embodiments, each L is independently substituted with $C_1$-$C_{12}$ alkyl, $C_2$-$C_{12}$ alkenyl, $C_2$-$C_{12}$ alkynyl, $C_1$-$C_{12}$ alkyl-$C_6$-$C_{10}$ aryl-$C_1$-$C_{12}$ alkyl, $C_1$-$C_{12}$ alkyl-$C_4$-$C_{10}$ heteroaryl-$C_1$-$C_{12}$ alkyl, hydroxyl, $-O-C_1$-$C_{12}$ alkyl, $-C_1$-$C_{12}$-alkyl-OH, fluoro, chloro, bromo, iodo, cyano, oxo, thiol, thioalkyl, carboxylic acid, carboxylic ester, amine, or amide groups.

In some embodiments, each $R_h$ is independently selected from the group consisting of: $-N^+(R')(R'')(R''')$,

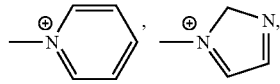

$-SO_3^-$, $-CO^{2-}$, $-PO_3^{2-}$, $-PO_3H^-$, $-PO_3H_2$, $-PO_4$, $-PO_4H^-$, and $-PO_4H_2$, where R', R'', and R''' are independently selected from ($C_1$-$C_{12}$ alkyl), and where the groups optionally additionally comprise one or more counterions. In one embodiment, the counterions are halide ions. In another embodiment, the counterions are iodide ions.

In another embodiment, p is an integer from 0 to 4, inclusive. In another embodiment, p is an integer from 1 to 4, inclusive. In another embodiment, p is an integer from 1 to 3, inclusive. In another embodiment, p is selected from the integers 1 and 2. In another embodiment, p is 1. In another embodiment, p is 2.

In another embodiment of the method for detecting, imaging, labeling, identifying, or staining cells, the compound is of the formula:

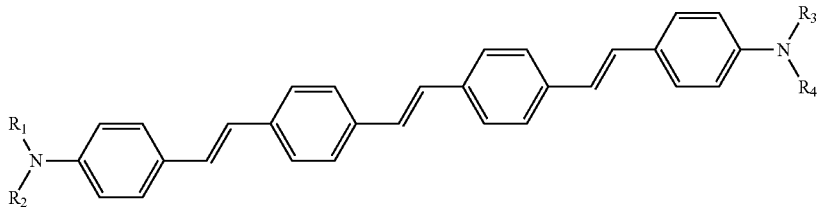

wherein $R_1$, $R_2$, $R_3$, and $R_4$ are selected from any of the definitions above.

In another embodiment of the method for detecting, imaging, labeling, identifying, or staining cells, the compound is of the formula:

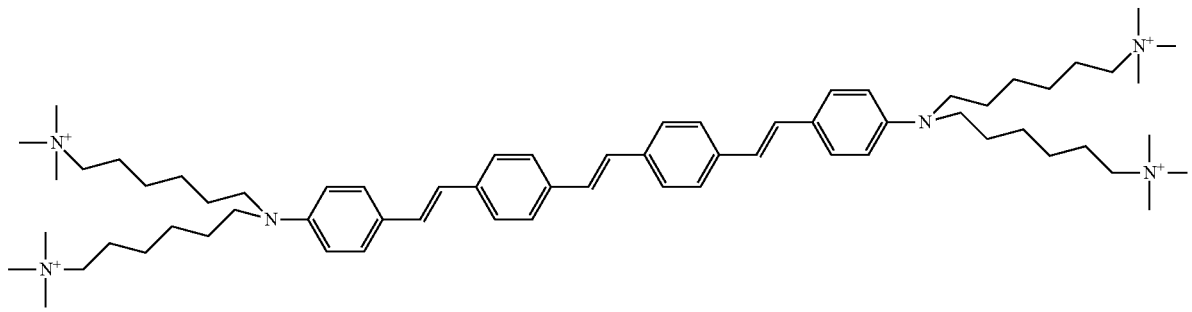

In one embodiment, the compound includes one or more counterions. In further embodiments, the one or more counterions are halide ions. In further embodiments, the one or more counterions are iodide ions.

In another embodiment of the method for detecting, imaging, labeling, identifying, or staining cells, the compound is of the formula:

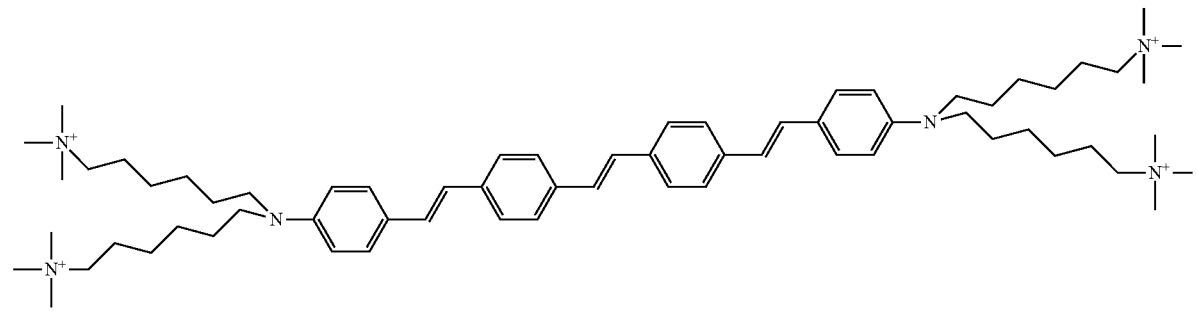

wherein $R_1$, $R_2$, $R_3$, and $R_4$ are selected from any of the definitions above. In one embodiment, the agent includes one or more counterions. In further embodiments, the one or more counterions are halide ions. In further embodiments, the one or more counterions are iodide ions.

In another embodiment of the method for detecting, imaging, labeling, identifying, or staining cells, the compound is of the formula:

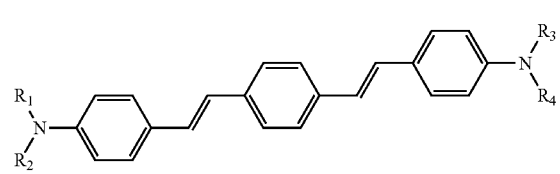

In one embodiment, the agent includes one or more counterions. In further embodiments, the one or more counterions are halide ions. In further embodiments, the one or more counterions are iodide ions.

In another embodiment of the method for detecting, imaging, labeling, identifying, or staining cells, the electron transfer agent is selected from the group consisting of:

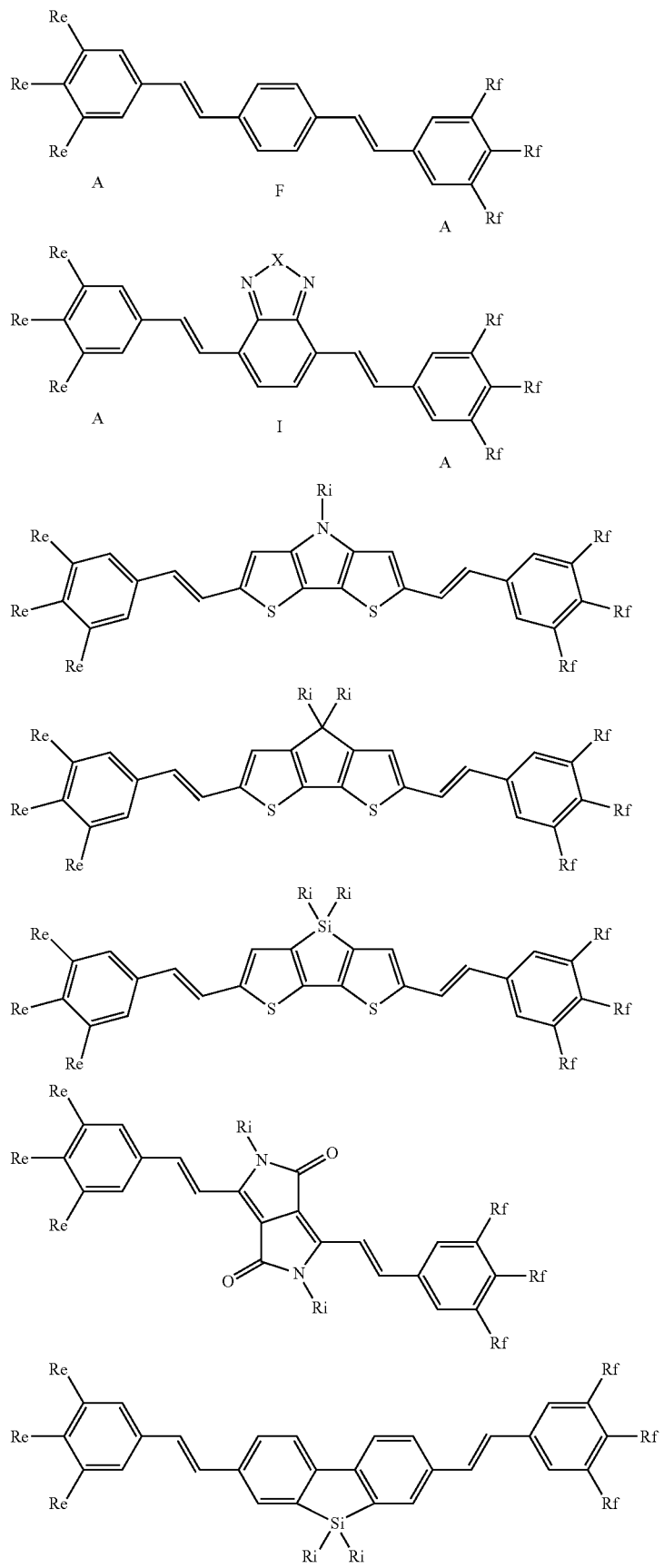

-continued
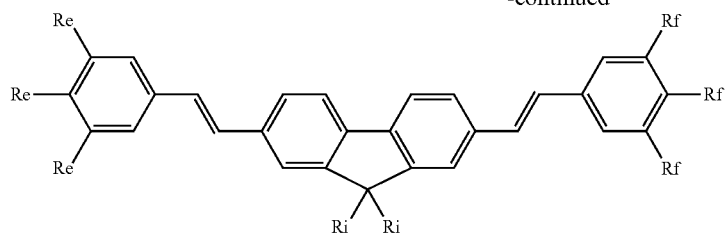
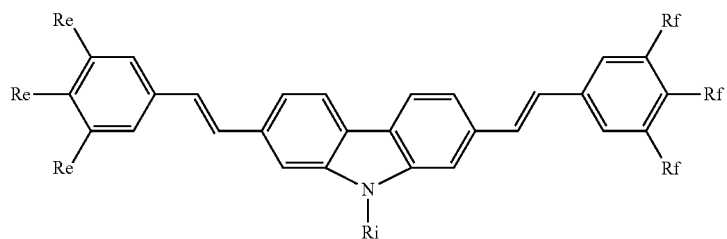
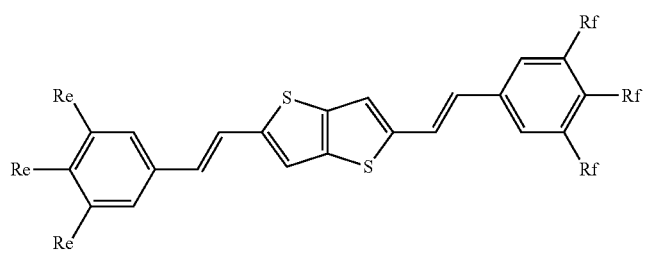
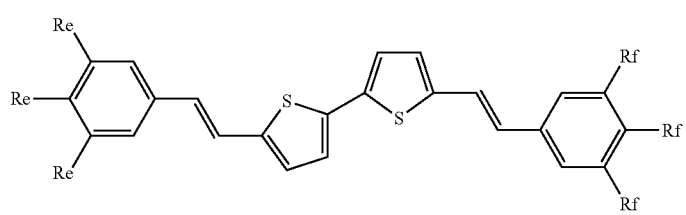
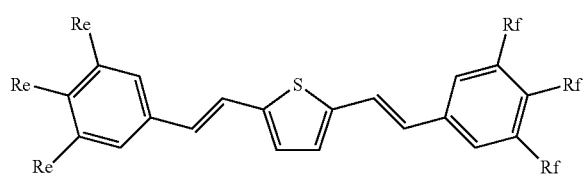
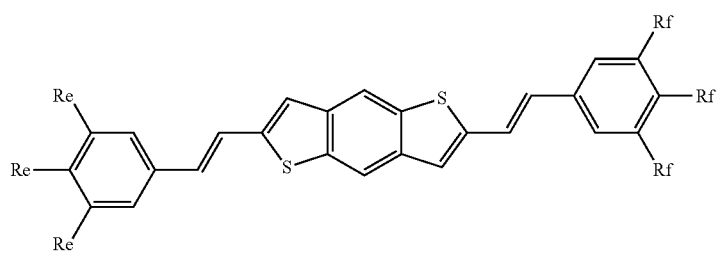
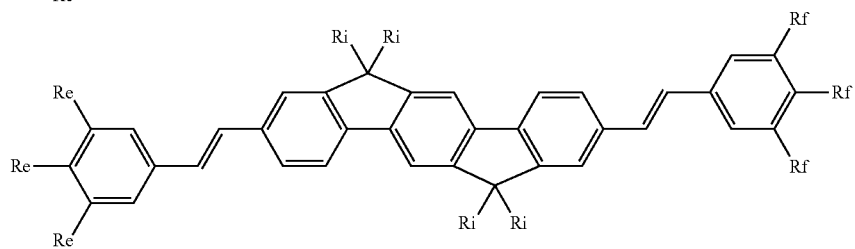

-continued
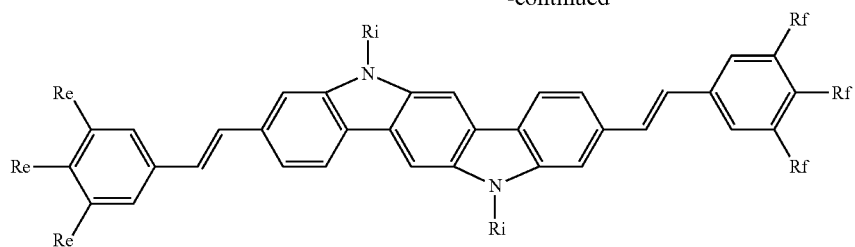
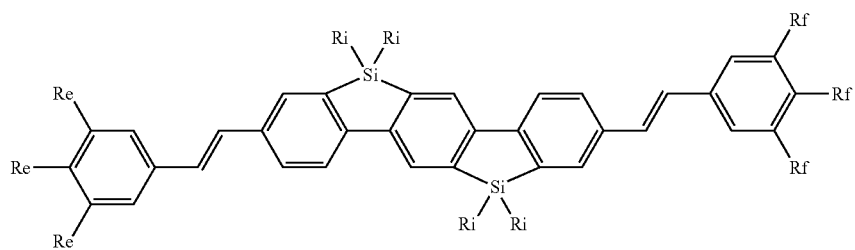
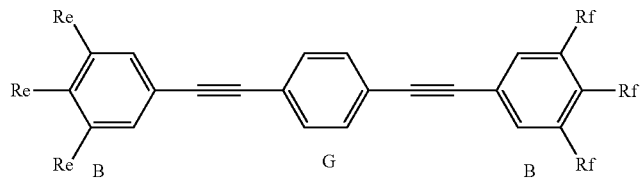
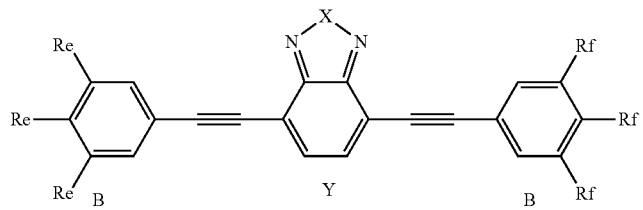
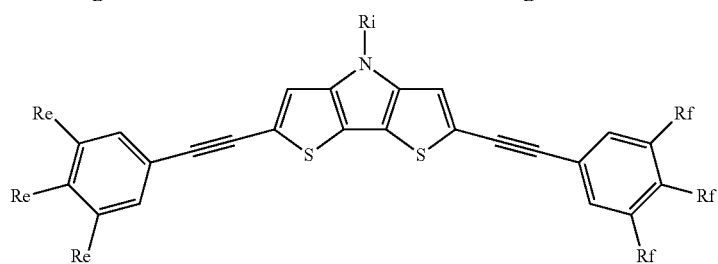
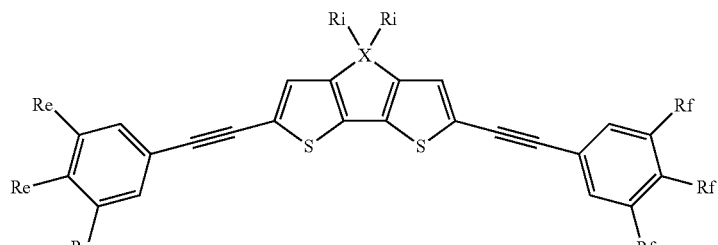
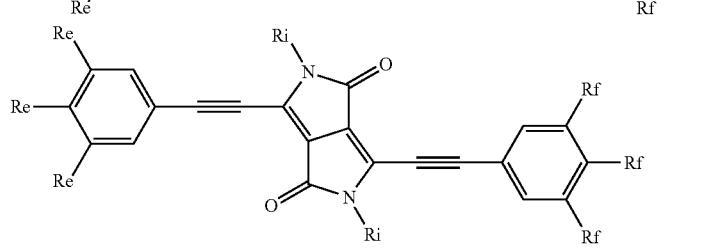

-continued
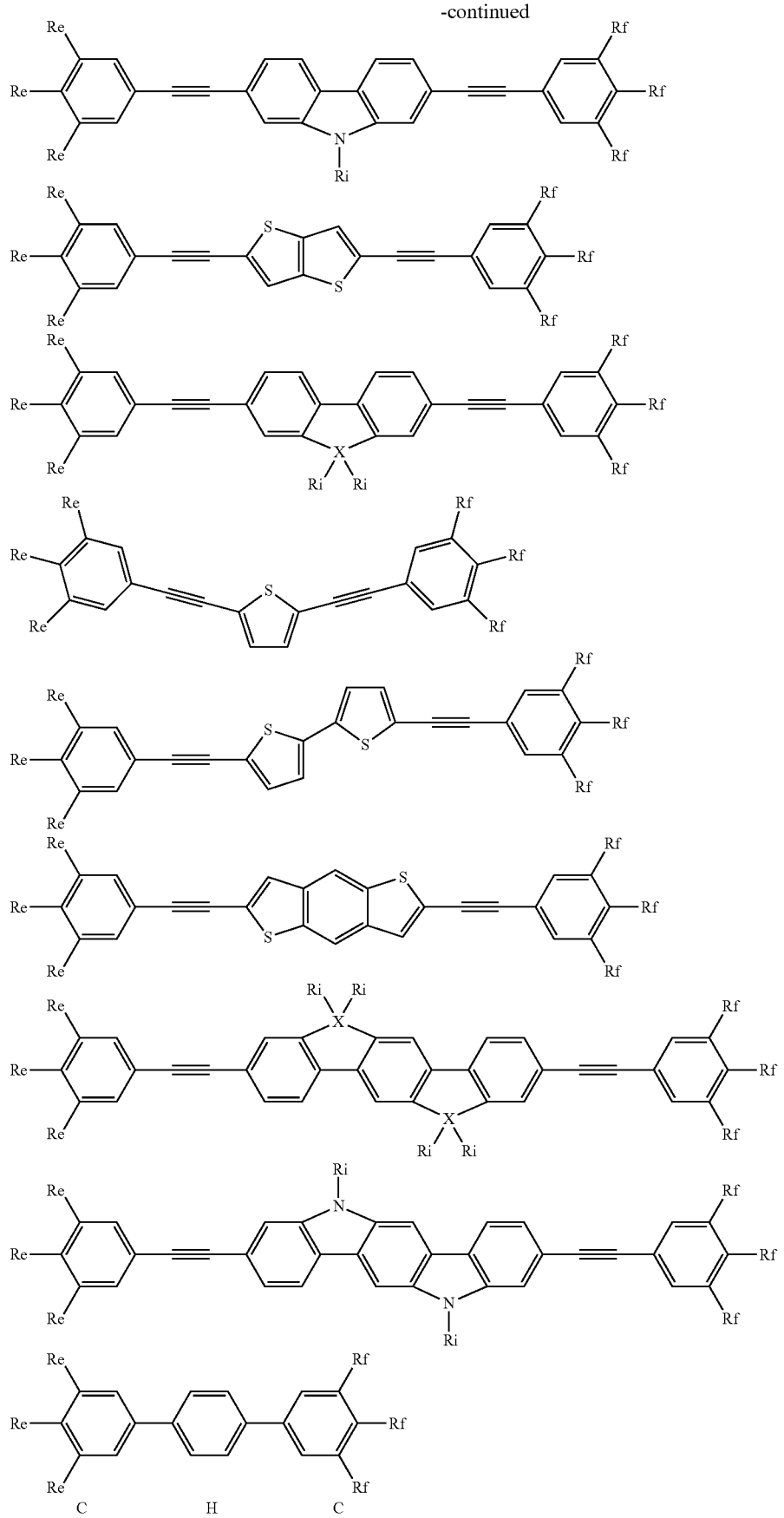

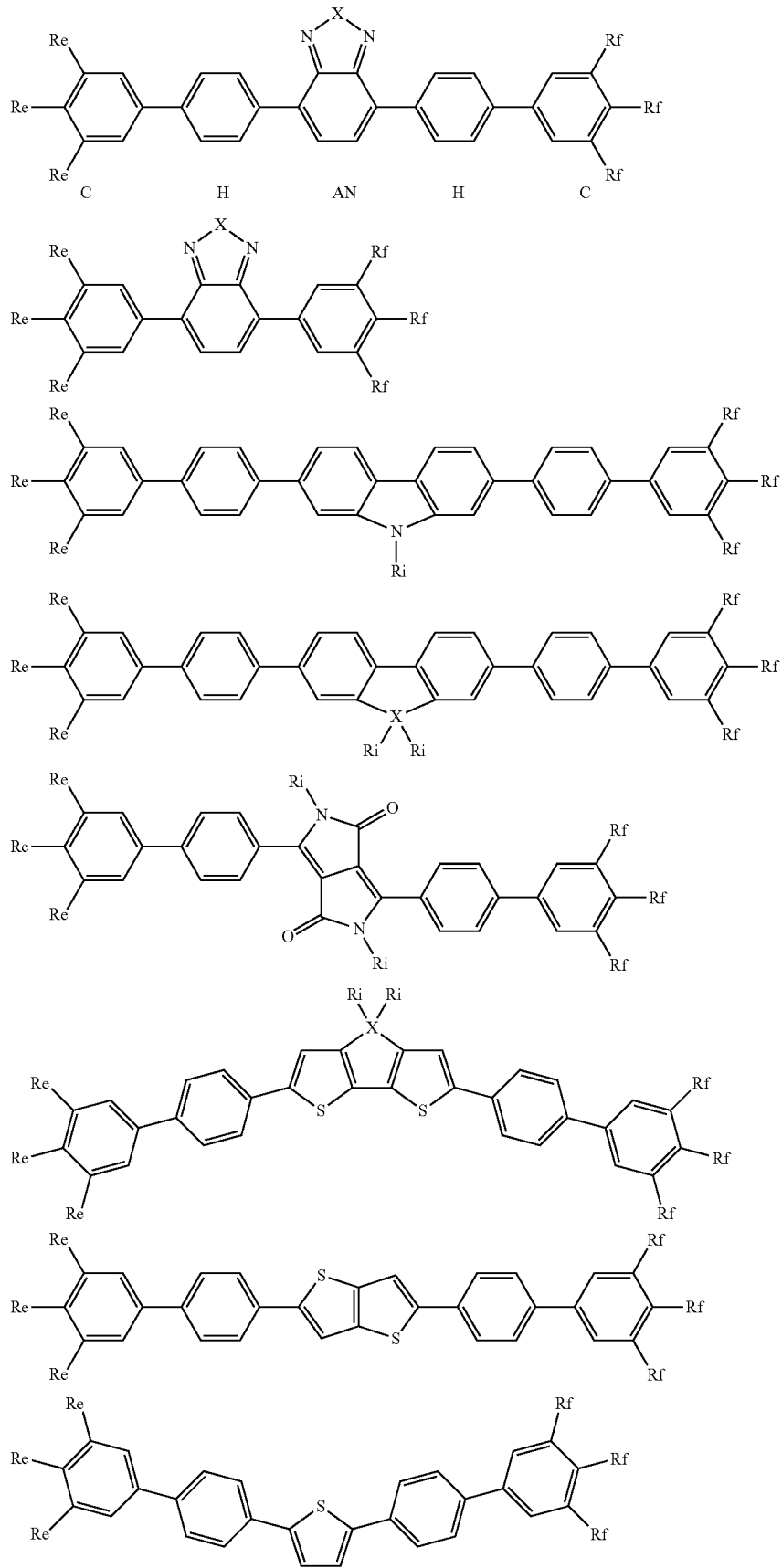

-continued
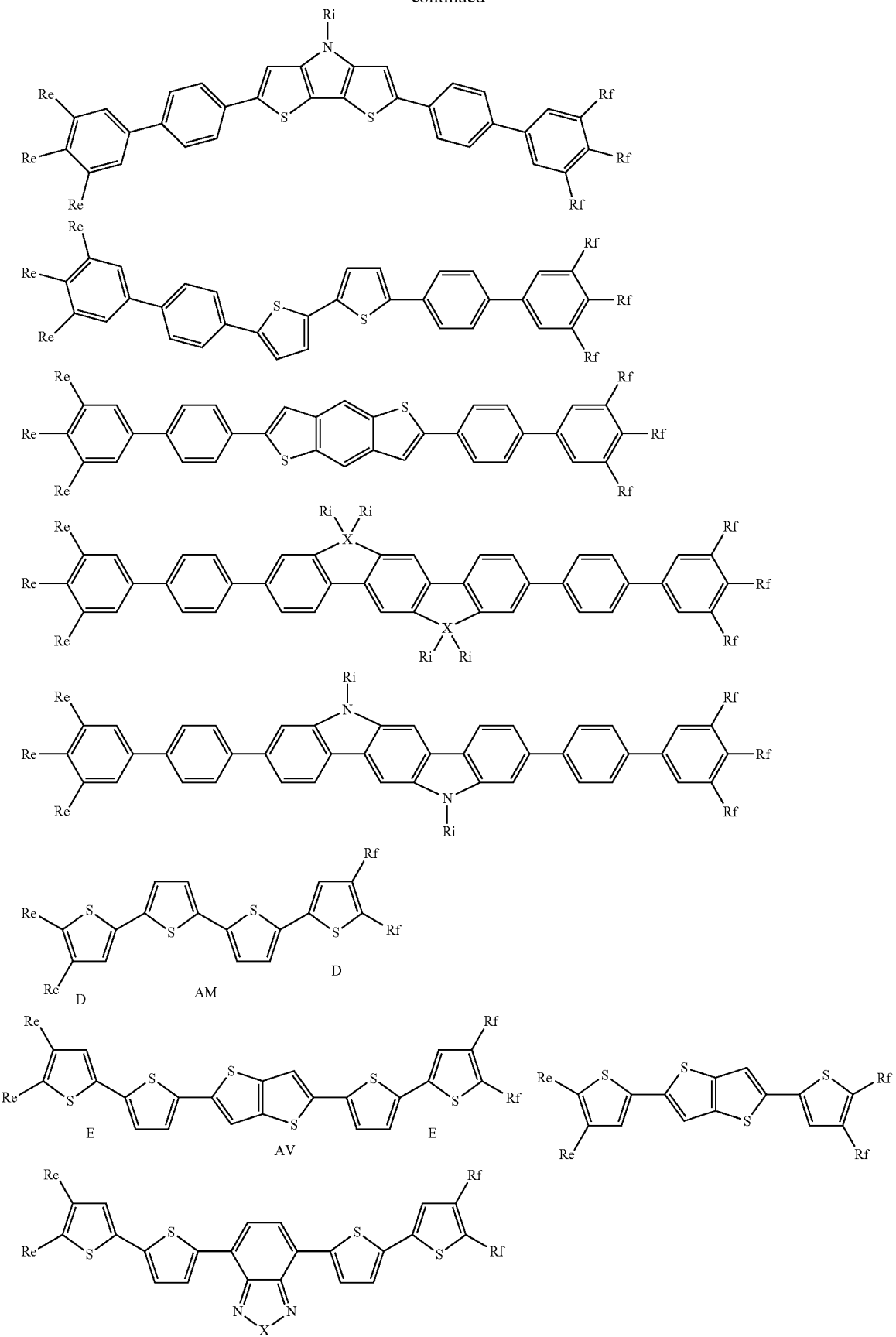

-continued
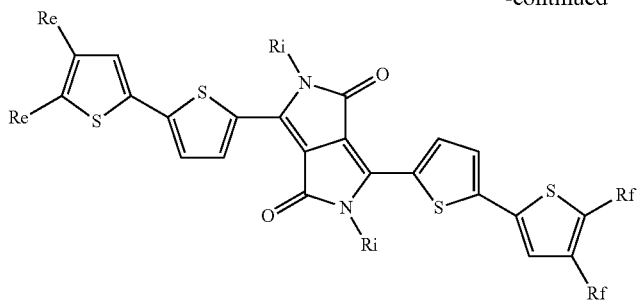
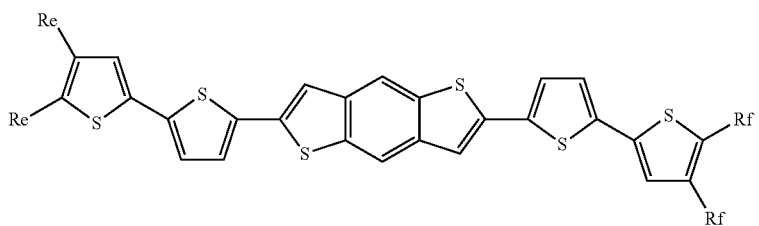
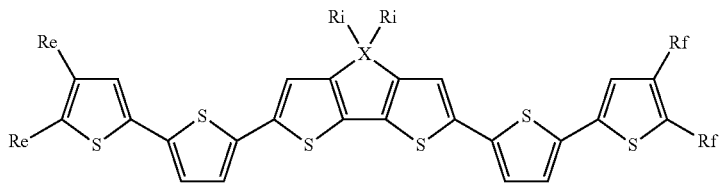
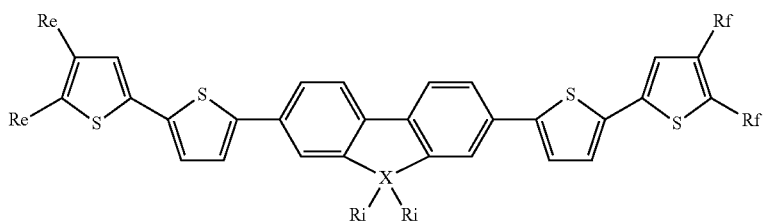
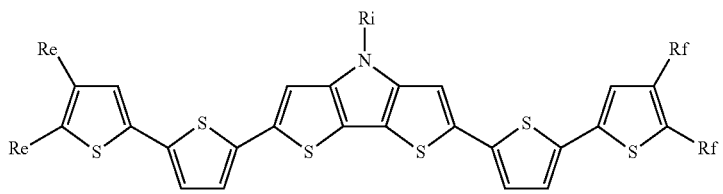
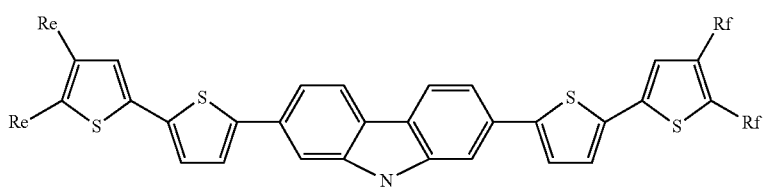
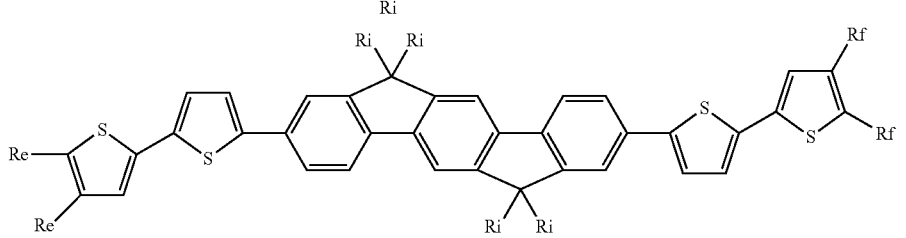
and -continued

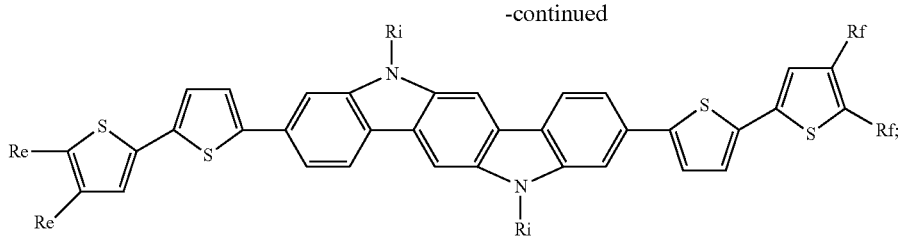

where each Ri is independently selected from the group comprising —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aryl, F, Cl, Br, I, and —CN; and X is selected from O, S, or Se;

where at least one $R_e$ and at least one $R_f$ are each independently selected from the group consisting of -L-$R_h$ where each L is independently a linker group containing at least one carbon atom, and each $R_h$ is a independently hydrophilic group, such as a charged or polar functional group; and each remaining $R_e$ and each remaining $R_f$ is independently selected from the group consisting of —H, —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aryl, F, Cl, Br, I, and —CN.

In some embodiments, each L is independently selected from branched or linear, saturated or unsaturated, substituted or unsubstituted alkyl or heteroalkyl chains containing at least one carbon atom, and optionally incorporating one or more aryl or heteroaryl groups within the chain. In other embodiments, each L is independently selected from $C_1$-$C_{12}$ alkyl, $C_2$-$C_{12}$ alkenyl, $C_2$-$C_{12}$ alkynyl, $C_2$-$C_{12}$ unsaturated hydrocarbyl, $C_1$-$C_{12}$ alkyl-$C_6$-$C_{10}$ aryl-$C_1$-$C_{12}$ alkyl, or $C_1$-$C_{12}$ alkyl-$C_4$-$C_{10}$ heteroaryl-$C_1$-$C_{12}$ alkyl. In other embodiments, each L is independently substituted with $C_1$-$C_{12}$ alkyl, $C_2$-$C_{12}$ alkenyl, $C_2$-$C_{12}$ alkynyl, $C_1$-$C_{12}$ alkyl-$C_6$-$C_{10}$ aryl-$C_1$-$C_{12}$ alkyl, $C_1$-$C_{12}$ alkyl-$C_4$-$C_{10}$ heteroaryl-$C_1$-$C_{12}$ alkyl, hydroxyl, —O—$C_1$-$C_{12}$ alkyl, —$C_1$-$C_{12}$-alkyl-OH, fluoro, chloro, bromo, iodo, cyano, oxo, thiol, thioalkyl, carboxylic acid, carboxylic ester, amine, or amide groups.

In some embodiments, each $R_h$ is independently selected from the group consisting of: —$N^+$(R')(R'')(R'''),

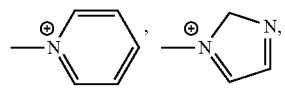

—$SO_3^-$, —$CO^{2-}$, —$PO_3^{2-}$, —$PO_3H^-$, —$PO_3H_2$, —$PO_4^{2-}$, —$PO_4H^-$, and —$PO_4H_2$, where R', R'', and R''' are independently selected from ($C_1$-$C_{12}$ alkyl), and where the groups optionally additionally comprise one or more counterions. In one embodiment, the counterions are halide ions. In another embodiment, the counterions are iodide ions.

In some embodiments, the at least one $R_e$ and at least one $R_f$ are independently selected from groups of the form:

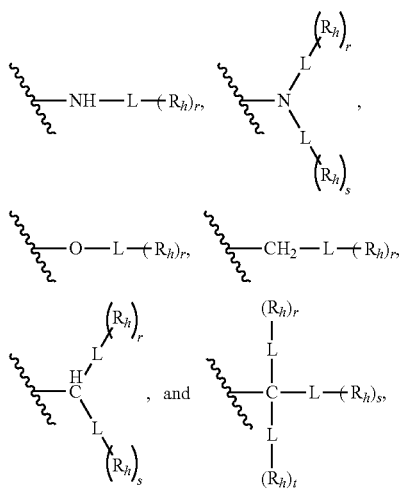

where each L and each $R_h$ can be selected from any of the definitions above. The subscripts r, s, and t can independently be 0, 1, 2, or 3, with the proviso that at least one $R_h$ is present in the $R_e$ or $R_f$ group (that is, r, when alone, must be at least 1; r+s, when t is absent, must be at least 1; or r+s+t must be at least 1). Multiple $R_h$ groups can be present on a single L group due to multiple substitution of $R_h$ groups at a single atom, or substitution of $R_h$ groups on different atoms. For example, when L is a branched C8 alkyl of the form

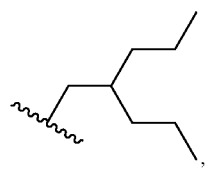 [SMILES: *CC(CCC)CCC]

-L-($R_h$), can be of the form

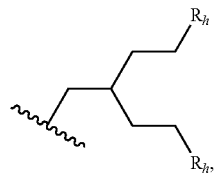

where r=2.

In another embodiment, the invention embraces a compound of the formula:

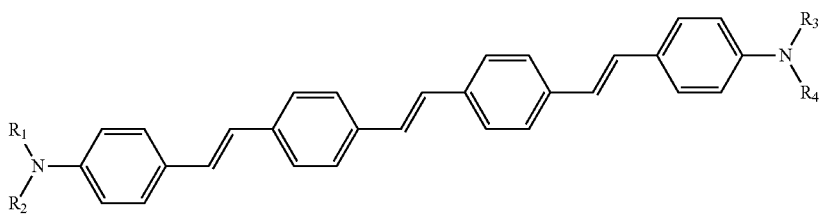

wherein $R_1$, $R_2$, $R_3$, and $R_4$ are independently selected from —($C_2$-$C_{12}$ alkylene)-$R_h$, where each $R_h$ is independently selected from the group consisting of: —$N^+(R')(R'')(R''')$,

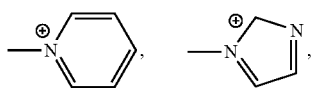

—$SO_3^-$, —$CO^{2-}$, —$PO_3$, —$PO_3H^-$, —$PO_3H_2$, —$PO_4^{2-}$, —$PO_4H^-$, and —$PO_4H_2$, where $R'$, $R''$, and $R'''$ are independently selected from ($C_1$-$C_{12}$ alkyl), and where the groups optionally additionally comprise one or more counterions. In one embodiment, $R_h$ is —$N^+(R')(R'')(R''')$, and $R'$, $R''$, and $R'''$ are independently selected from ($C_1$-$C_{12}$ alkyl). In one embodiment, $R_1$, $R_2$, $R_3$, and $R_4$ are —($C_6$-$C_{12}$—$N^+(R')(R'')(R''')$. In another embodiment, $R_1$, $R_2$, $R_3$, and $R_4$ are independently selected from —($C_2$-$C_{12}$ alkylene)-$N^+(CH_3)_3$. In another embodiment, $R_1$, $R_2$, $R_3$, and $R_4$ are —($C_6H_{12}$)—$N^+(CH_3)_3$. In another embodiment, the compound additionally comprises four counterions, such as halide ions, for example, iodide ions.

In one embodiment, the invention embraces a compound of the formula:

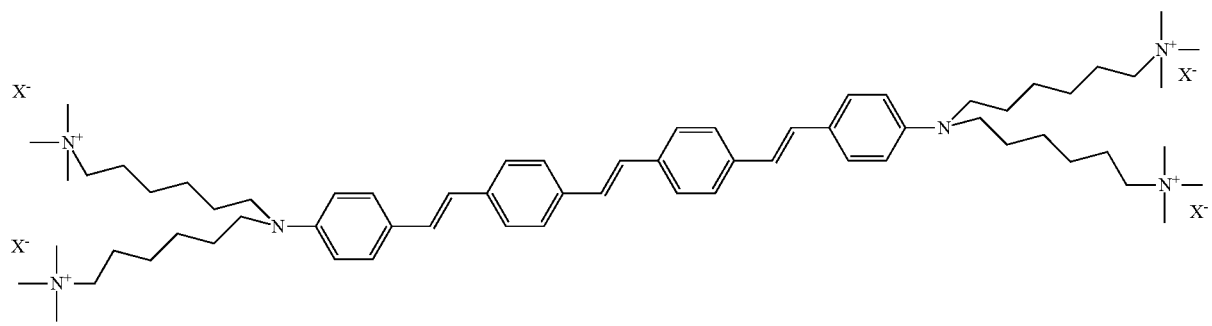

wherein each $X^-$ is a halide ion, such as iodide.

In another embodiment, the invention provides for a combinatorial library of conjugated electrolytes, wherein the combinatorial library comprises at least 10 molecules having a conjugated pi system formed by linking at least two conjugated segments selected from the following group:

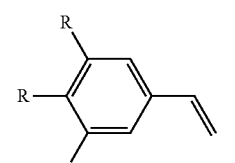  A

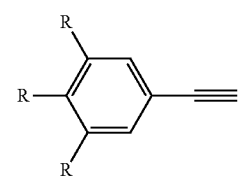  B

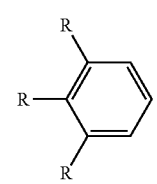  C

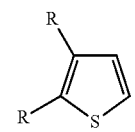  D

-continued

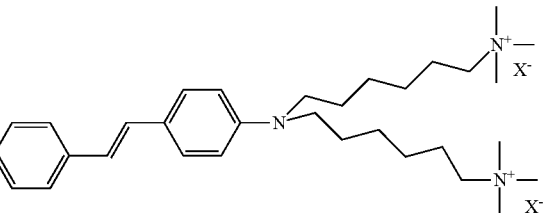  E

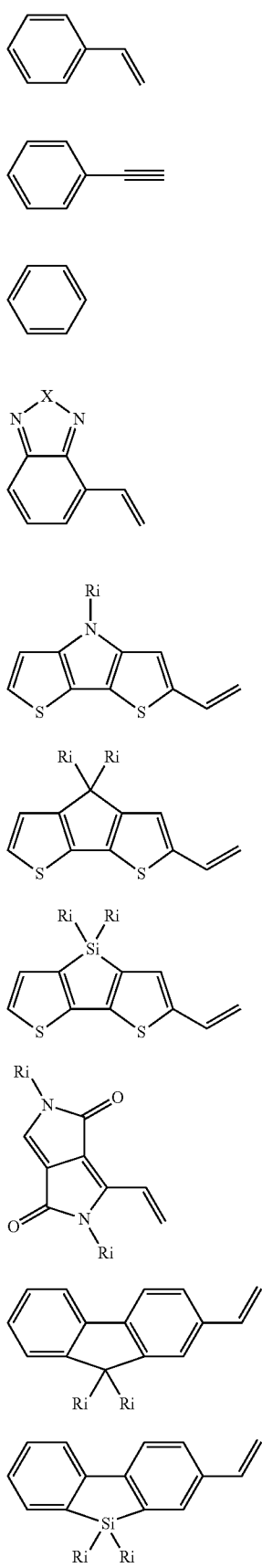
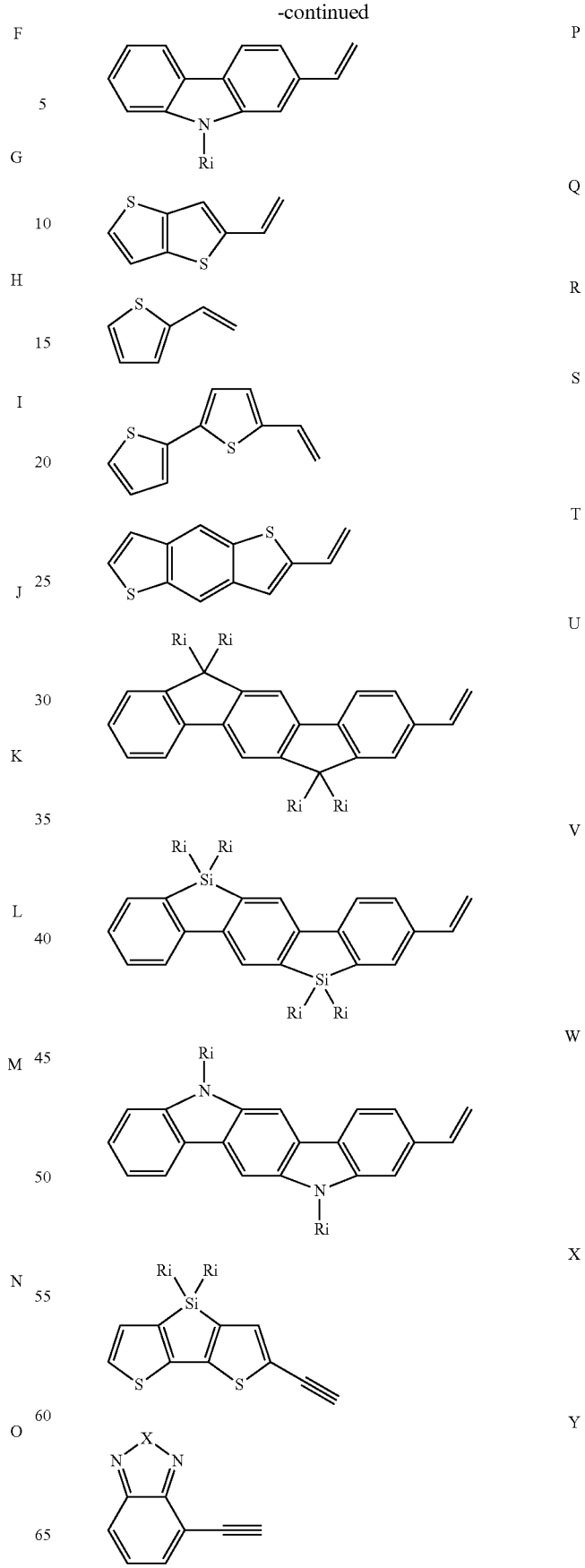

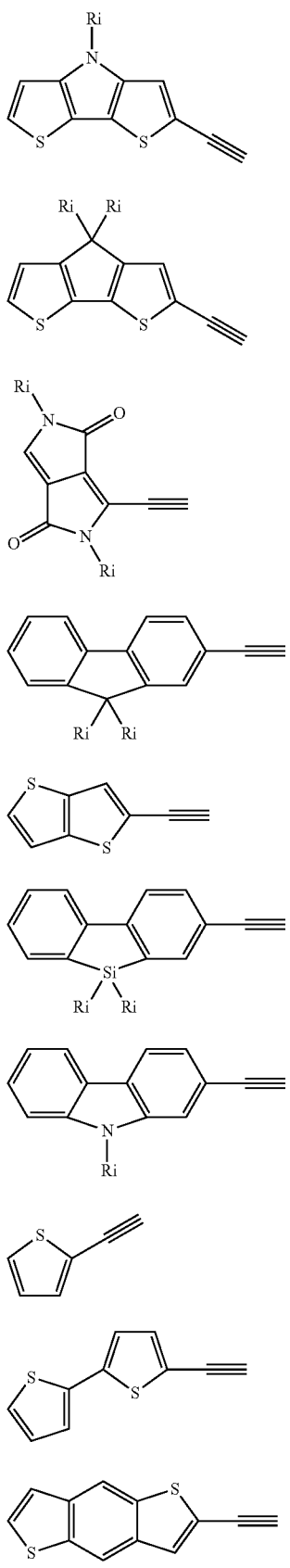
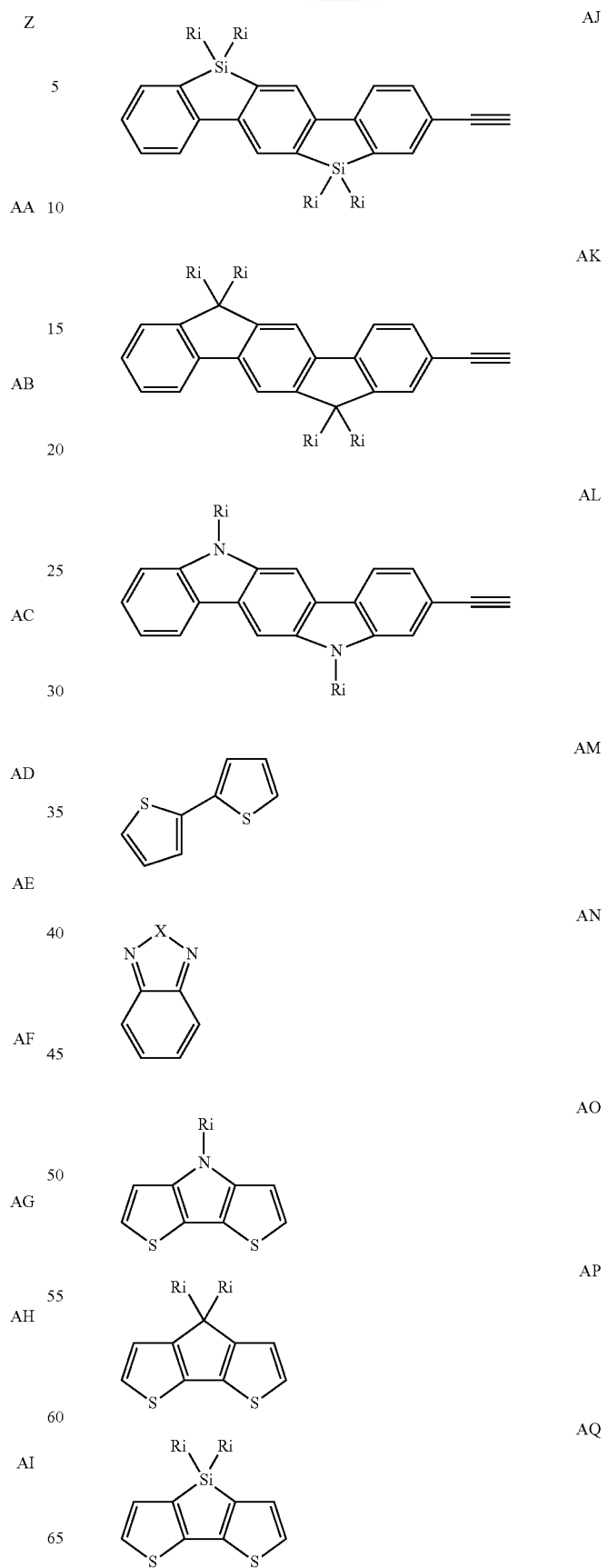

-continued

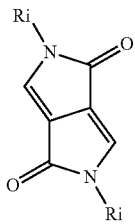
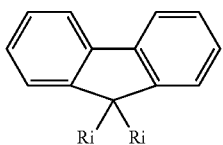
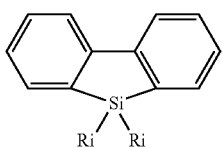
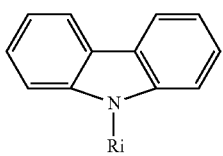
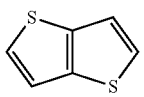
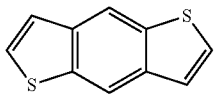
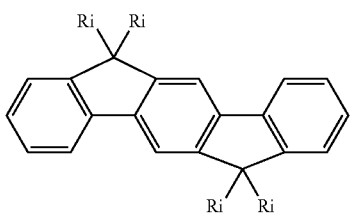
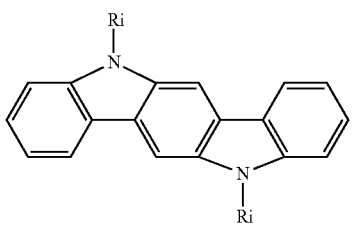

-continued

AR

BA
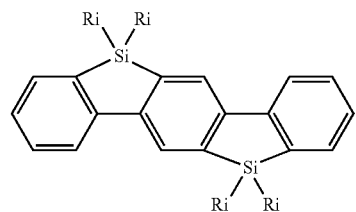

wherein the said segments have been linked together to form the conjugated pi system.

The invention further provides a method of making a combinatorial library of conjugated electrolytes comprising at least 10 molecules having a conjugated pi system formed by linking at least two conjugated segments selected from the following group:

A
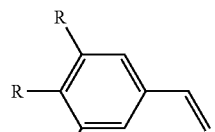

B
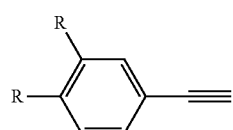

C
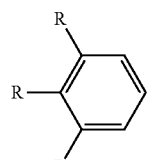

D
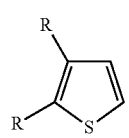

E
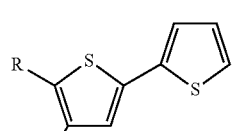

F
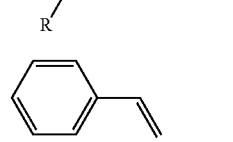

G
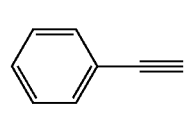

H
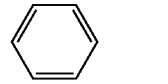

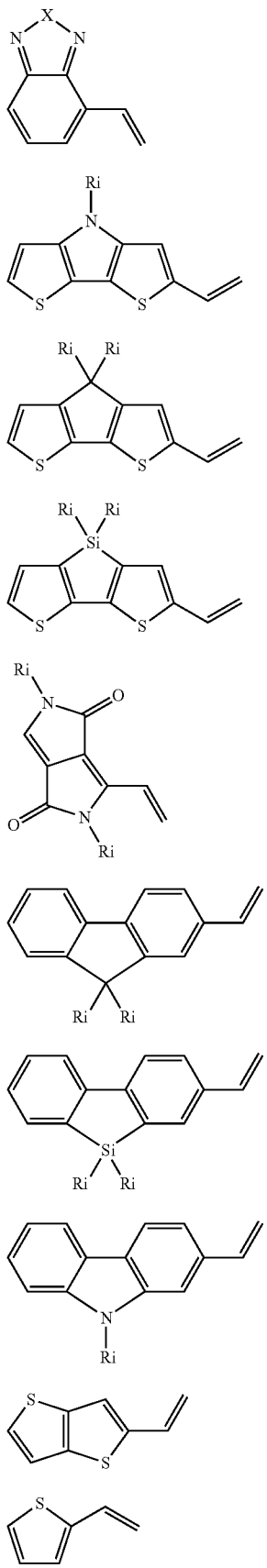
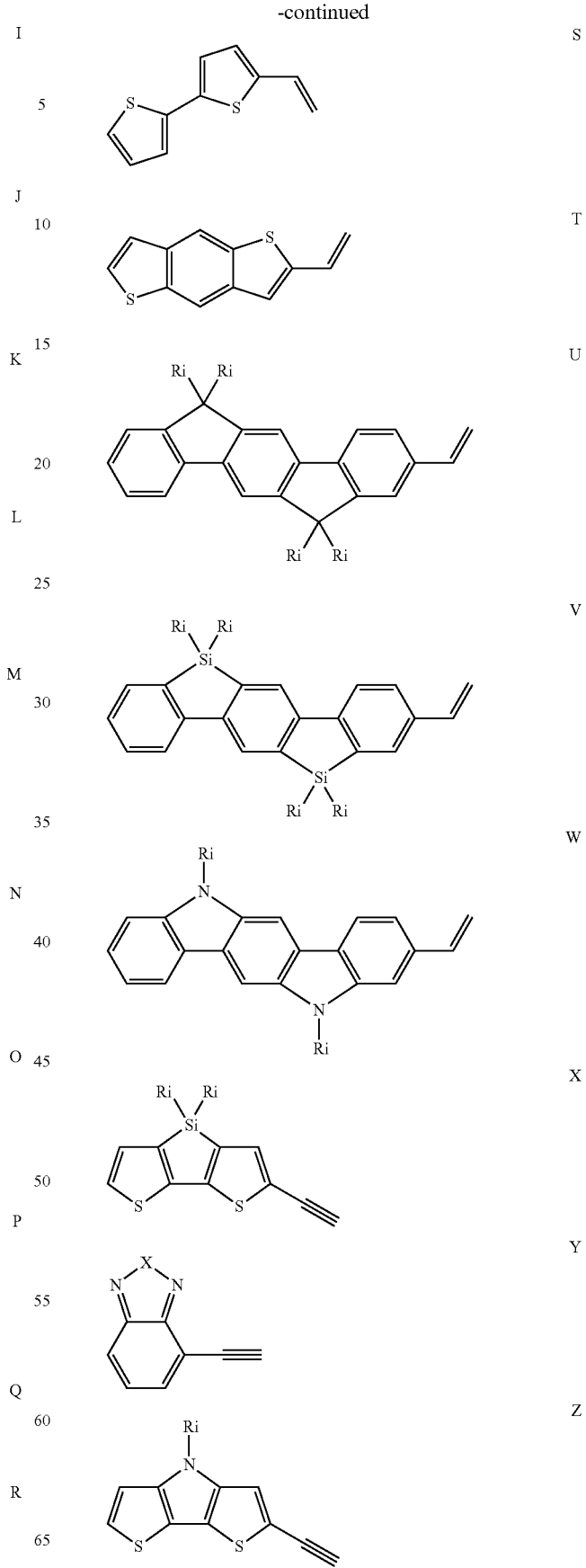

-continued
AA
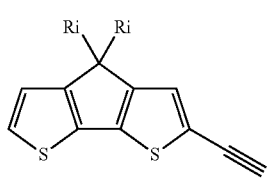
AB
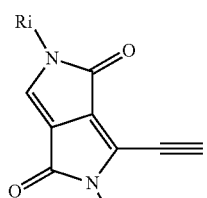
AC
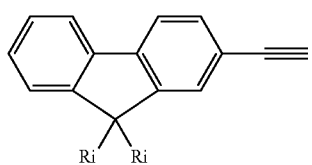
AD
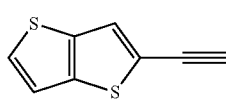
AE
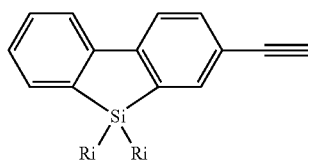
AF
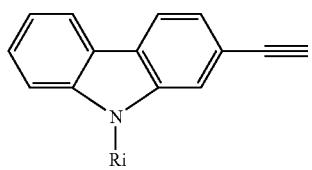
AG
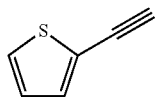
AH
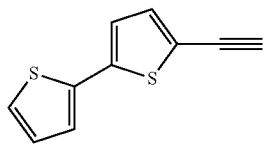
AI
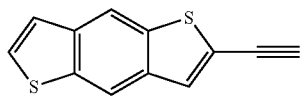
AJ
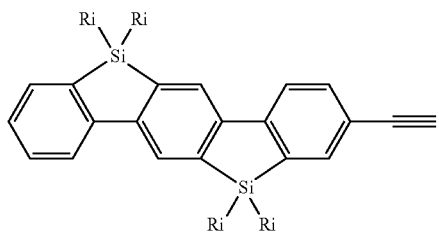
-continued
AK
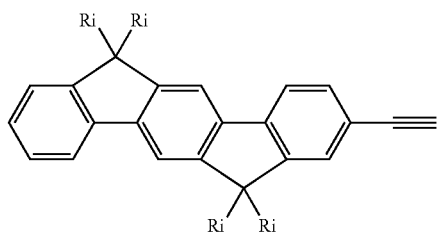
AL
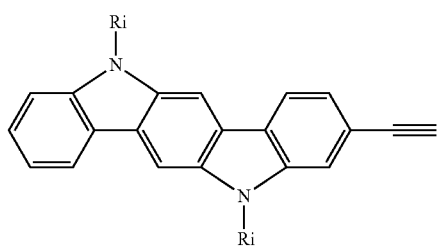
AM
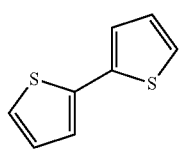
AN
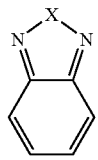
AO
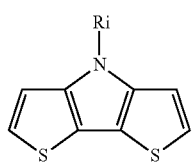
AP
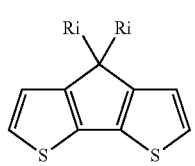
AQ
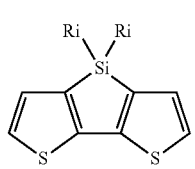
AR
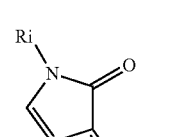
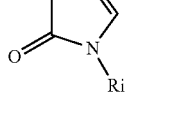

93
-continued

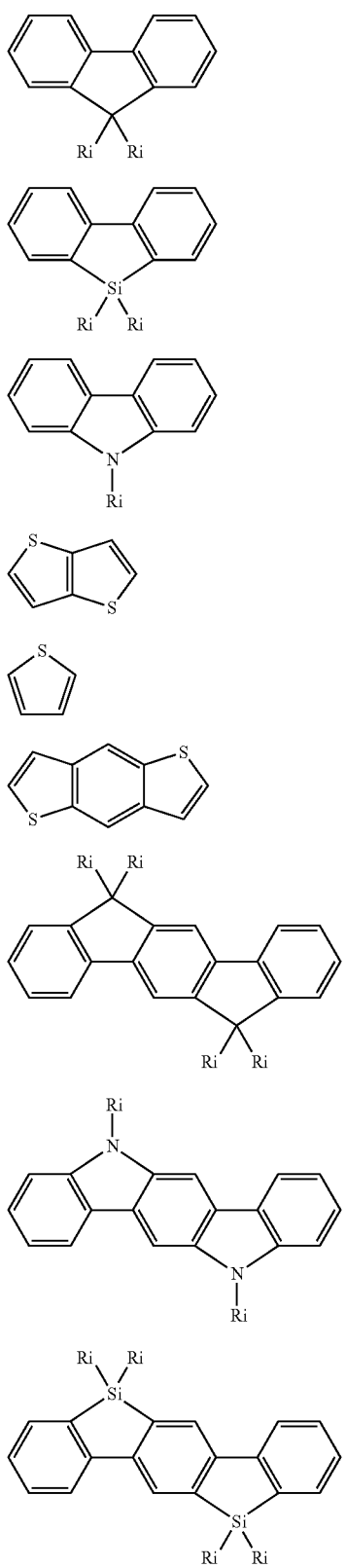

where the method comprises linking together the at least two conjugated segments to form a combined molecule having a conjugated pi system; and further comprises attaching two groups of the form $R_e$ and $R_f$ to opposite ends of the combined molecule to form a conjugated electrolyte, where the method is performed a sufficient number of times to provide at least ten distinct conjugated electrolytes.

DETAILED DESCRIPTION OF THE INVENTION

Definitions

Figure 1:
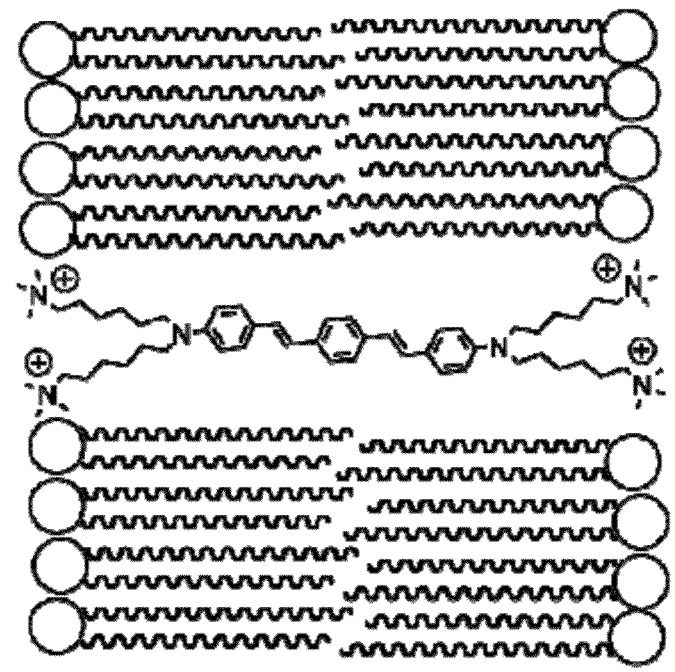
FIG. 1 is a cartoon representation of a DSBN+ modified lipid bilayer depicting the predicted orientation when intercalated within a phospholipid bilayer. The long molecular axis is normal to the plane of the membrane with the hydrophobic conjugated region within the non-polar inner membrane and the polar pendant group terminals oriented outward toward the polar aqueous environment on either side of the lipid bilayer.
Figure 1:
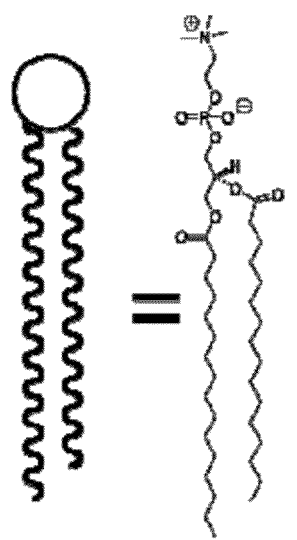

Definitions used herein are as follows:

"Alkyl" is intended to embrace a saturated linear, branched, cyclic, or a combination of linear and/or branched and/or cyclic hydrocarbon chain(s) and/or ring(s) having the number of carbons specified, or if no number of carbons is specified, having 1 to 12 carbon atoms. For example, groups embraced by "($C_1$-$C_{12}$)-alkyl" include, but are not limited to, methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl, or 2-ethylhexyl, where the point of attachment of the alkyl group to the remainder of the molecule can be at any chemically possible location.

"COE" refers to a conjugated oligoelectrolyte.

The "outer membrane" of a microbe refers to the cell membrane (plasma membrane) of the microbe, separating the contents of the cell from the exterior environment.

A transmembrane charge-transfer agent is an agent, such as a molecule, that facilitates transfer of charges across a membrane. The transmembrane charge-transfer agent is localized to the outer membrane of a microbe, by which is meant that the transmembrane charge-transfer agent primarily facilitates charge transfer across the membrane without the agent itself physically moving from inside the cell to outside the cell. In some embodiments, less than about 50%, less than about 40%, less than about 30%, less than about 20%, less than about 10%, less than about 5%, or less than about 1% of the charge transfer across the membrane occurs by the agent physically moving from inside the cell to outside the cell, while the remainder of the charge transfer across the membrane arises from mechanisms due to localization of the charge transfer agent in the membrane. Preferably, less than about 1% of the charge transfer across the membrane occurs by the agent physically moving from inside the cell to outside the cell, while about 99% or more of the charge transfer across the membrane arises from mechanisms due to localization of the charge transfer agent in the membrane. While not wishing to be constrained by theory, it is believed that the transmembrane charge transfer agents permit electrons to cross the outer membrane of the microbe via a tunneling mechanism. The charges can be electrons or ions. Charge-transfer agents that facilitate transfer of electrons are more specifically referred to as electron-transfer agents. "Non-endogenous charge-transfer agent" refers to a charge-transfer agent that does not occur naturally in the microbe in which the charge-transfer agent is employed (although it may occur naturally in other microbes or other organisms). Similarly, "non-endogenous electron-transfer agent" refers to an electron-transfer agent that does not occur naturally in the microbe in which the electron-transfer agent is employed (although it may occur naturally in other microbes or other organisms).

In other embodiments, deficient endogenous charge-transfer agents can be used. A "deficient endogenous charge-transfer agent" is a charge transfer agent that does occur naturally in the microbe in which the charge-transfer agent is employed, but in amounts that are not sufficient to have any significant effect (e.g., an effect equal to or greater than 5%) on current or voltage characteristics of the microbe, or on the current or voltage characteristics of a microbial fuel cell employing the microbe. In such instances, addition of further amounts of the deficient endogenous charge-transfer agent enhances the current and/or voltage characteristics of the microbe, or of a microbial fuel cell employing the microbe. Similarly, a "deficient endogenous electron-transfer agent" is an electron transfer agent that does occur naturally in the microbe in which the electron-transfer agent is employed, but in amounts that are not sufficient to have any significant effect (e.g., an effect equal to or greater than 5%) on current or voltage characteristics of the microbe, or of a microbial fuel cell employing the microbe.

A charged group can bear at least one net negative charge, at least one net positive charge, or can be zwitterionic (bearing both positive charges and an equal number of negative charges). A polar group is defined as a chemical group that can take part in hydrogen bonding (such as a hydroxyl group, —OH; an amine group, —NH$_2$; an amide group, —C(=O)—NH$_2$, an aldehyde, —C(=O)—H, etc.), or as a chemical group having a dipole moment of about 1 Debye or greater.

Conjugated Electrolytes and Conjugated Oligomers

Conjugated oligomers have been studied and used in solid-state electronic devices. Conjugated oligomers can be described by a select number of repeat units extracted from a polymer containing an electronically π-delocalized backbone. Homologous progressions of these molecules, and related systems with extended electronic delocalization, have been useful in fundamental studies with a focus on understanding how molecular connectivity influences optical and electronic properties, and in the development of emerging technologies (Martin, R. E.; Diederich, F. Angew. Chem. Int. Ed. 1999, 38, 1350-1377; Mullen, K., Wegner, G., Eds. Electronic Materials The Oligomer Approach; Wiley: Weinheim, 1998; Tour, J. M. Chem. Rev. 1996, 96, 537-553). One well-appreciated opportunity involves integration as the semiconducting component in field effect transistors (FETs) relevant for plastic electronics (Brédas, J.-L.; Beljonne, D.; Coropceanu, V.; Cornil, J. Chem. Rev. 2004, 104, 4971-5003; Facchetti, A. Materials Today. 2007, 10, 28-37; Facchetti, A.; Mushrush, M.; Yoon, M.-H.; Hutchison, G. R.; Ratner, M. A.; Marks, T. J. Am. Chem. Soc. 2004, 126, 13859-13874; Katz, H. E.; Bao, Z.; Gilat, S. L. Acc. Chem. Res. 2001, 34, 359-369; Murphy, A. R.; Fréchet, J. M. J. Chem. Rev. 2007, 107, 1066-1096; Yamishita, Y. Sci. Technol. Adv. Mater. 2009, 10, 1-9; Yasuda, T.; Ooi, H.; Morita, J.; Akama, Y.; Minoura, K.; Funahashi, M.; Shimomura, T.; Kato, T. Adv. Funct. Mater. 2009, 19, 411-419). A wide range of structural variations have been designed, developed and incorporated into FETs via different deposition methods (Bao, Z.; Rogers, J. A.; Katz, H. E. J. Mater. Chem. 1999, 9, 1895-1904; Briseno, A. L.; Roberts, M.; Ling, M.-M.; Moon, H.; Nemanick, E. J.; Bao, Z. J. Am. Chem. Soc. 2006, 128, 3880-3881; Chandekar, A.; Whitten, J. E. Appl. Phys. Lett. 2007, 91, 113103; Drolet, N.; Morin, J.-F.; Leclerc, N.; Wakim, S.; Tao, Y.; Leclerc, M. Adv. Funct. Mater. 2005, 15, 1671-1682; Geens, W.; Tsamouras, D.; Poortmans, J.; Hadziioannou, G. Synth. Met. 2001, 122, 191-194; Jurchescu, O. D.; Subramanian, S.; Kline, R. J.; Hudson, S. D.; Anthony, J. E.; Jackson, T. N.; Gundlach, D. J. Chem. Mater. 2008, 20, 6733-6737; Maulden, C. E.; Puntambekar, K.; Murphy, A. R.; Liao, F.; Subramanian, V.; Fréchet, J. M. J.; DeLongchamp, D. M.; Fischer, D. A.; Toney, M. F. Chem. Mater. 2009, 21, 1927-1938). The accumulated effort has yielded insight not only into device optimization but also on how weak intermolecular forces can be coordinated to yield desirable morphologies at interfaces and how intermolecular arrangements mediate charge carrier transport (Coropceanu, V.; Cornil, J.; de Silva, D. A.; Olivier, Y.; Silbey, R.; Brédas, J.-L. Chem. Rev. 2007, 107, 926-952; Fichou, D. J. Mater. Chem. 2000, 10, 571-588; Hutchison, G. R.; Ratner, M. A.; Marks, T. J. J. Am. Chem. Soc. 2005, 127, 16866-16881; Leclére, Ph.; Surin, M.; Viville, P.; Lazzaroni, R.; Kilbinger, A. F. M.; Henze, O.; Feast, W. J.; Cavallini, M.; Biscarini, F.; Schenning, A. P. H. J.; Meijer, E. W. Chem. Mater. 2004, 16, 4452-4466). More recently, thin films of conjugated oligomers bearing pendant groups with ionic functionalities, i.e. conjugated oligoelectrolytes (COEs), were demonstrated to be effective for reducing charge injection barriers at metal/organic interfaces (Yang, R.; Xu, Y.; Dang, X.-D.; Nguyen, T.-Q.; Cao, Y.; Bazan, G. C. J. Am. Chem. Soc. 2008, 130, 3282-3283). While more than one mechanism may be operating, for example ion motion and/or the formation of a spontaneously aligned dipole layer, the simplicity of incorporating COE injection layers via solution methods opens the opportunity to reduce the operating voltages of polymer-based light emitting diodes.

Several structural types of conjugated oligomers have also been used in molecular transconductance studies that assess charge transfer across a single or a few molecules. For instance, comparison of oligophenylenevinylene (OPV) and oligophenyleneethynylene (OPE) structures that span two gold contacts reveals better conductance across the OPV framework, relative to OPE (Huber, R.; González, M. T.; Wu, S.; Langer, M.; Grunder, S.; Horhoiu, V.; Mayor, M.; Bryce, M. R.; Wang, C.; Jitchati, R.; Schönenberger, C.; Calame, M. J. Am. Chem. Soc. 2008, 130, 1080-1084). Such experimental findings are corroborated by theoretical calculations and have revealed that structural parameters that affect HOMO-LUMO energy levels, such as planarity and bond length alternation, influence charge transport efficiency (Sachs, S. B.; Dudek, S. P.; Hsung, R. P.; Sita, L. R.; Smalley, J. F.; Newton, M. D.; Feldberg, S. W.; Chidsey, C. E. D. J. Am. Chem. Soc. 1997, 119, 10563-10564); (Kushmerick, J. G.; Pollack, S. K.; Yang, J. C.; Naciri, J.; Holt, D. B.; Ratner, M. A.; Shashidhar, R. Ann. N.Y. Acad. Sci. 2003, 1006, 277-290; Kushmerick, J. G.; Holt, D. B.; Pollack, S. K.; Ratner, M. A.; Yang, J. C.; Schull, T. L.; Naciri, J.; Moore, M. H.; Shashidhar, R. J. Am. Chem. Soc. 2002, 124, 10654-10655; Yin, X.; Liu, H.; Zhao, J. J. Chem. Phys. 2006, 125, 094711). Electrochemical measurements have also been used to demonstrate that OPVs of various lengths facilitate tunneling between a gold surface and a tethered redox species (Dudek, S. P.; Sikes, H. D.; Chidsey, C. E. D. J. Am. Chem. Soc. 2001, 123, 8033-8038; Sikes, H. D.; Smalley, J. F.; Dudek, S. P.; Cook, A. R.; Newton, M. D.; Chidsey, C. E. D.; Feldberg, S. W. Science. 2001, 291, 1519-1523). The work to date regarding single molecule transconductance has offered much insight into the factors that influence charge transport and has laid the foundation for the design and development of molecular wires that may play a role as charge transporting components in new technologies.

Oligomers broadly described by a D-π-D structure, where D is an electron donating group and it refers to a π-delocalized linker, have been immensely instructional for understanding and optimizing two photon absorption processes in organic materials. Some of these molecular systems have been utilized for three-dimensional fabrication (Zhou, W. H.; Kuebler, S. M.; Braun, K. L.; Yu, T. Y.; Cammack, J. K.; Ober, C. K.; Perry, J. W.; Marder, S. R. Science. 2002, 296, 1106-1109) and for two-photon microscopy of biological systems (So, P. T. C.; Dong, C. Y.; Masters, B. R.; Berland, K. M. Annu. Rev. Biomed. Eng. 2000, 02, 399), (Centonze, V. E.; White, J. G. Biophys. J. 1998, 75, 2015-2024; Periasamy, A.; Skoglund, P.; Noakes, C.; Keller, R. Microsc. Res. Technol. 1999, 47, 172-181; Zipfel, W. R.; Williams, R. M.; Webb, M. W. Nat. Biotechnol. 2003, 21, 1369-1377), (Xu, C.; Williams, R. M.; Zipfel, W.; Webb, M. W. Bioimaging. 1996, 4, 198-207). Molecules possessing D-π-D structures typically undergo intramolecular charge transfer excitation that results in large two-photon absorption cross sections (Albota, M.; Beljonne, D.; Brédas, J.-L.; Ehrlich, J. E.; Fu, J.-Y.; Heikal, A. A.; Hess, S. E.; Kogej, T.; Levin, M. D.; Marder, S. R.; McCord-Maughon, D.; Perry, J. W.; Röckel, H.; Rumi, M.; Subramaniam, G.; Webb, W. W.; Wu, X.-L.; Xu, C. *Science.* 1998, 281, 1653-1656). One specific example is the molecule 1,4-bis(4'-(N,N-bis(6"-(N,N,N-trimethylammonium)hexyl)amino)-styryl)benzene tetraiodide (DSBN+); the structure of which is shown in Scheme 1. This molecule incorporates charged groups that increase solubility in highly polar organic solvents and water. The distyrylbenzene (DSB) conjugated region is capped at each end with two nitrogen-bound, six carbon pendant groups containing terminal quaternary ammonium salts. By examination of optical properties in different solvents, and in combination with neutral derivatives, it is possible to examine how the dielectric constant of the medium perturbs linear and two-photon spectral responses (Woo, H. Y.; Liu, B.; Kohler, B.; Korystov, D.; Mikhailovsky, A.; Bazan, G. C. *J. Am. Chem. Soc.* 2005, 127, 14721-14729). These studies have highlighted the challenges in predicting a priori how the molecular features and the environment combine to yield different optical properties. It was also found that molecules such as DSBN+ display much larger emission quantum efficiencies and two-photon absorption cross-sections upon incorporation into micelles from an aqueous environment (Woo, H. Y.; Korystov, D.; Mikhailovsky, A.; Nguyen, T.-Q.; Bazan, G. C. *J. Am. Chem. Soc.* 2005, 127, 13794-13795). Association with the interior of the micelle is likely a consequence of the hydrophobic DSB framework.

where $R_e$ and $R_f$ can be the same or different and are groups containing a hydrophilic moiety, and Pi is a molecule with a delocalized π-electron system. The Pi moiety should extend over a substantial fraction of the distance of the lipid bilayer of the microbial cell.

The charge-transfer agents typically reside in the outer membrane, that is, they are intercalated or inserted in the cell membrane. The entire molecule can reside in the cell membrane, as illustrated, for example, in FIG. 1, or a part of the molecule can reside in the cell membrane while other parts of the molecule reside in the cytosol, the outer environment, or both the cytosol and the outer environment. The molecule may span part of the cell membrane (such as being contained entirely in the outer lemma or inner lemma of the lipid bilayer of the cell membrane), but preferably the molecule spans a majority of the width of the cell membrane when in extended conformation, such as at least about 60%, at least about 70%, at least about 80%, at least about 90%, or at least about 100% of the width of the cell membrane. The molecule can be longer than the cell membrane when fully extended, for example at least about 110%, at least about 120%, at least about 130%, at least about 140%, or at least about 150% of the width of the cell membrane.

The Pi moiety is a π-conjugated oligomer component with lengths in the range of about 1 nm to about 10 nm, or 2 nm to about 8 nm, or 3 nm to about 6 nm, that can be constructed by linking together unsaturated conjugated segments. The length of the Pi moiety, when fully extended, can be about 1 nm, about 2 nm, about 3 nm, about 4 nm, about 5 nm, about 6 nm, about 7 nm, about 8 nm, about 9 nm, or about 10 nm; or at least Scheme 1. Structure of OPV oligoelectrolytes.

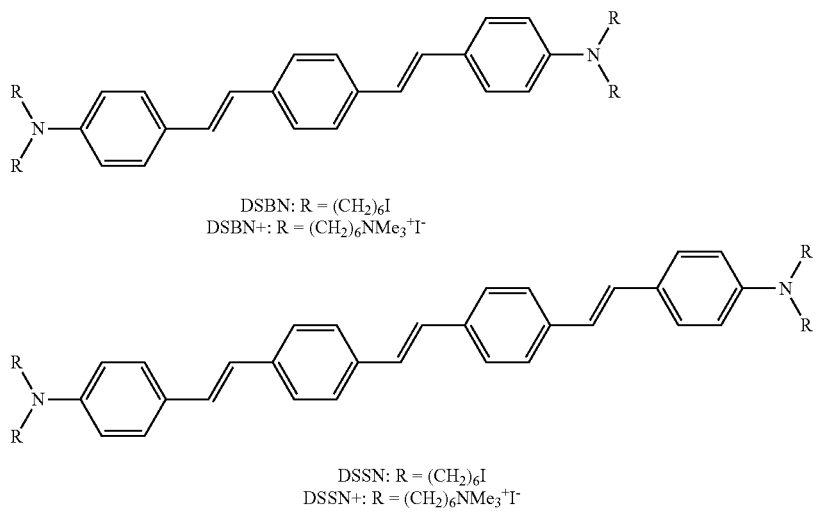

DSBN: R = (CH₂)₆I
DSBN+: R = (CH₂)₆NMe₃⁺I⁻

DSSN: R = (CH₂)₆I
DSSN+: R = (CH₂)₆NMe₃⁺I⁻

The instant invention takes advantage of the ability of these molecules to intercalate into lipid bilayer membranes in an ordered orientation. A schematic cartoon of the general concept is provided in FIG. 1. The dependence of optical features as a function of the medium provides a useful means of confirming the environment of the intercalated molecules.

Conjugated Molecules Useful in the Invention as Charge Transfer Agents

Molecules useful in the invention as charge-transfer (including electron-transfer) agents are conjugated electrolytes (COEs) of the form:

about 1 nm, at least about 2 nm, at least about 3 nm, at least about 4 nm, at least about 5 nm, at least about 6 nm, at least about 7 nm, at least about 8 nm, at least about 9 nm, or at least about 10 nm; or at most about 1 nm, at most about 2 nm, at most about 3 nm, at most about 4 nm, at most about 5 nm, at most about 6 nm, at most about 7 nm, at most about 8 nm, at most about 9 nm, or at most about 10 nm.

Examples of molecules useful as the Pi moiety are:
4,4'-distyryl stilbenes, e.g., 1,2-bis(4-stilbenzyl)ethenes such as 1,4-distyryl benzenes, such as

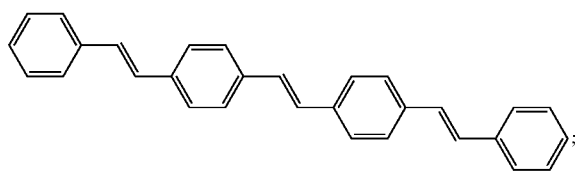 [SMILES: C(=C\c1ccc(/C=C/c2ccc(/C=C/c3ccccc3)cc2)cc1)/c1ccccc1]

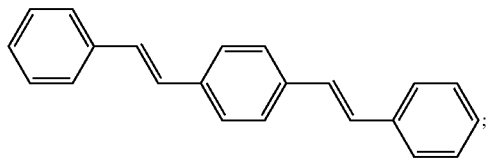 [SMILES: C(=C\c1ccc(/C=C/c2ccccc2)cc1)/c1ccccc1]

azobenzene-containing analogs of the distyryl stilbenes and distyryl benzenes, such as 1-phenyl-2-(4-(4-styrylstyryl)phenyl)diazene

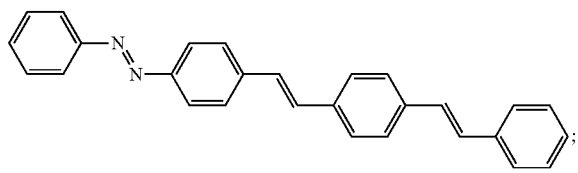 [SMILES: C(=C\c1ccc(/C=C/c2ccc(/N=N/c3ccccc3)cc2)cc1)/c1ccccc1]

1-phenyl-2-(4-styrylphenyl)diazene

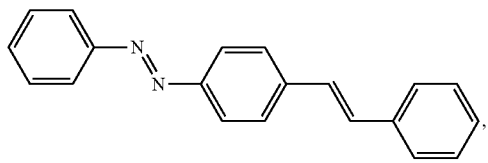 [SMILES: C(=C\c1ccc(/N=N/c2ccccc2)cc1)/c1ccccc1]

1,2-bis(4-(phenyldiazenyl)phenyl)ethane

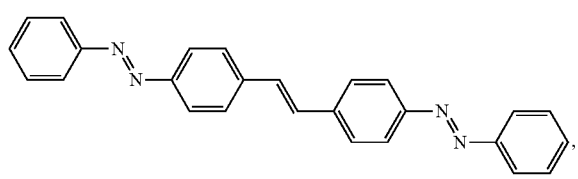 [SMILES: C(=C\c1ccc(/N=N/c2ccccc2)cc1)/c1ccc(/N=N/c2ccccc2)cc1]

and 1,2-bis(4-(phenyldiazenyl)phenyl)diazene

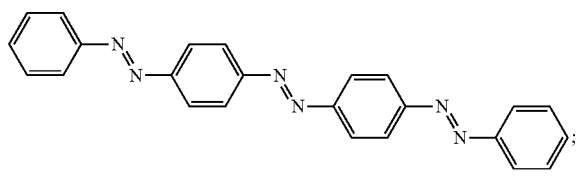 [SMILES: c1ccc(/N=N/c2ccc(/N=N/c3ccc(/N=N/c4ccccc4)cc3)cc2)cc1]

polyacenes, such as heptacene, octacene, nonacene

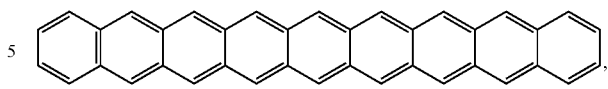

and decacene;
oligothiophenes such as 2,2':5',2'':5'',2''':5''',2''''-quinquethiophene

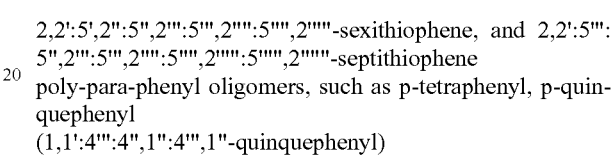

2,2':5',2'':5'',2''':5''',2'''':5'''',2'''''-sexithiophene, and 2,2':5'':5'',2''':5''',2'''':5'''',2''''':5''''',2''''''-septithiophene
poly-para-phenyl oligomers, such as p-tetraphenyl, p-quinquephenyl
(1,1':4'':4'',1''':4''',1''''-quinquephenyl)

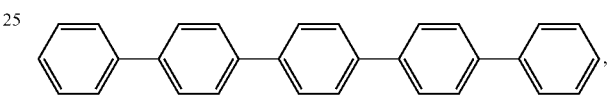

and p-sexiphenyl.

Additional Pi moieties can be obtained by combining segments such as the following fragments. The fragments are drawn as they appear once the desired Pi system has been constructed; reactive intermediates that can be used to obtain systems containing the following fragments are well-known in the art.

Fragments for Combination into Pi Systems

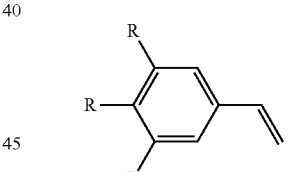

A

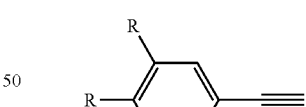

B

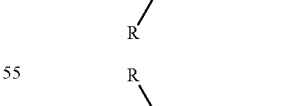

C

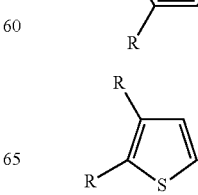

D

103
-continued
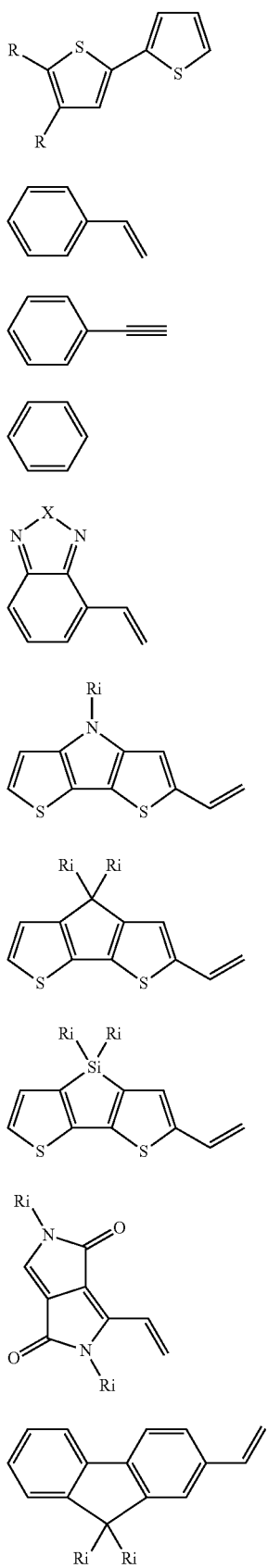
104
-continued
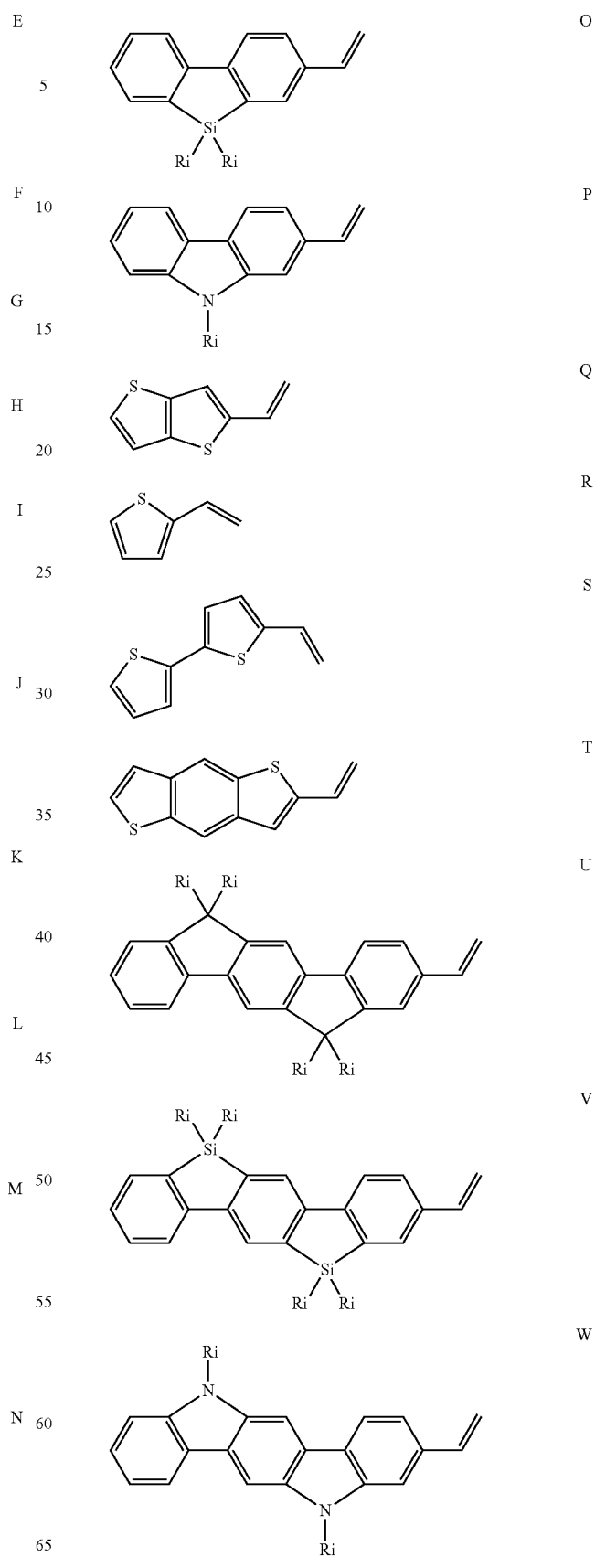

105
-continued
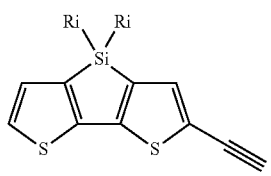
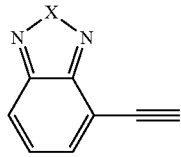
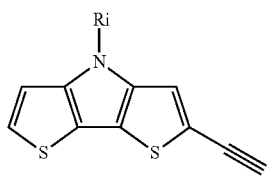
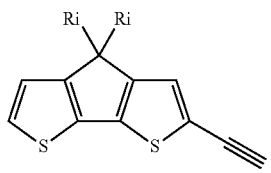
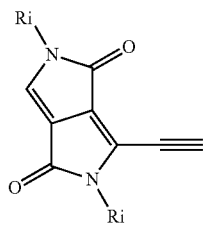
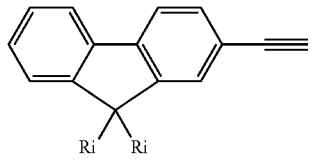
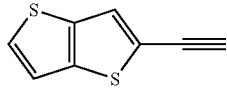
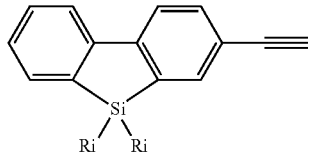
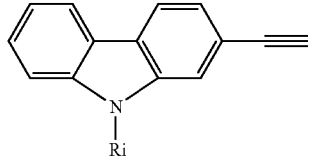
106
-continued
X
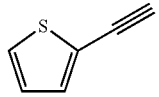
Y
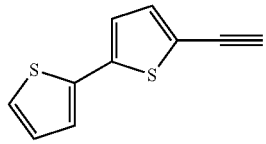
Z
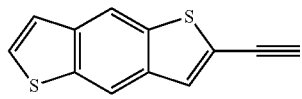
AA
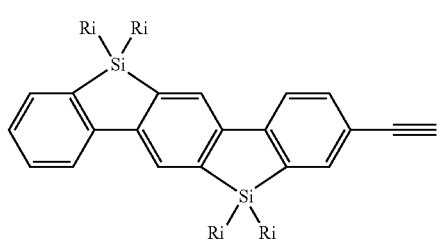
AB
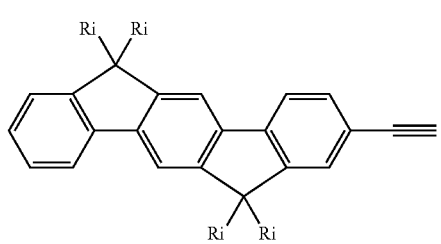
AC
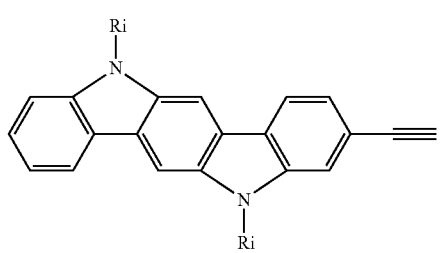
AD
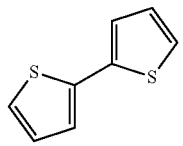
AE
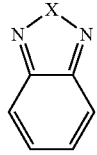
AF
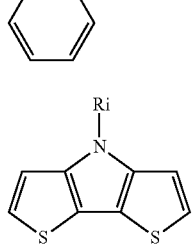
AG
AH
AI
AJ
AK
AL
AM
AN
AO

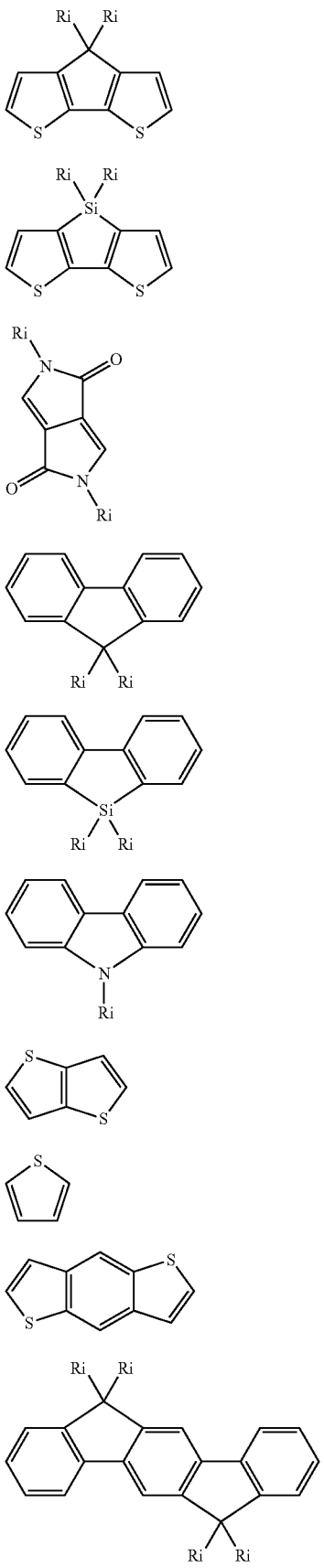

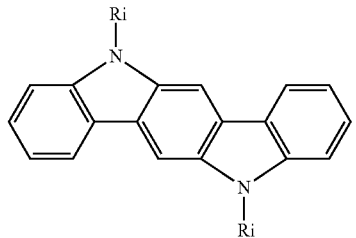

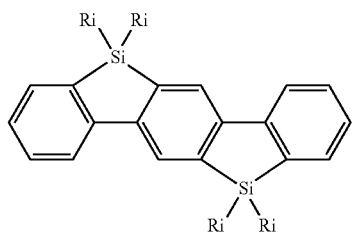

Segments A, B, C, D, and E are typical end caps of the conjugated regions of the COE oligomers. The groups labeled R are, independently, either a group of form $R_e$ or $R_f$, which are typical substituents required to modify solubility, another substituent, or a hydrogen or a non-entity. The number of R groups of form $R_e$ or $R_f$ depends upon the placement and chosen number of solubilizing groups (discussed in greater detail below in terms of $R_e$ and $R_f$). Segments F through BA are examples of repeat units that can be combined to create COEs for use in the invention. The repeat units can be unsubstituted, or can be substituted where chemically possible (by removing an H atom and replacing that valence with the desired substituent) at carbon, nitrogen, silicon or oxygen atoms with —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aromatic groups, halogens (F, Cl, Br, I), or other various functional groups (for example, cyano groups). Substitution is explicitly shown above for Ri groups on Si, N and bridgehead carbons of fluorenes etc. (e.g. AS), where each Ri can independently be selected from —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aromatic groups, halogens (F, Cl, Br, I), or other various functional groups (for example, cyano groups). X is selected from O, S, or Se.

Conjugated oligomers can be constructed using a single, multiple or a combination of these segments. Some examples of oligomers (Pi) that can be constructed using the segments are shown below. Note that segments are labeled by their corresponding letter in two oligomers of each oligomer type in order to illustrate the segment concept. For example, the first phenylvinylene segment listed below is a combination of an A unit, an F unit, and another A unit from the list of segments above.

Phenylvinylene-including conjugated electrolytes (PVs):
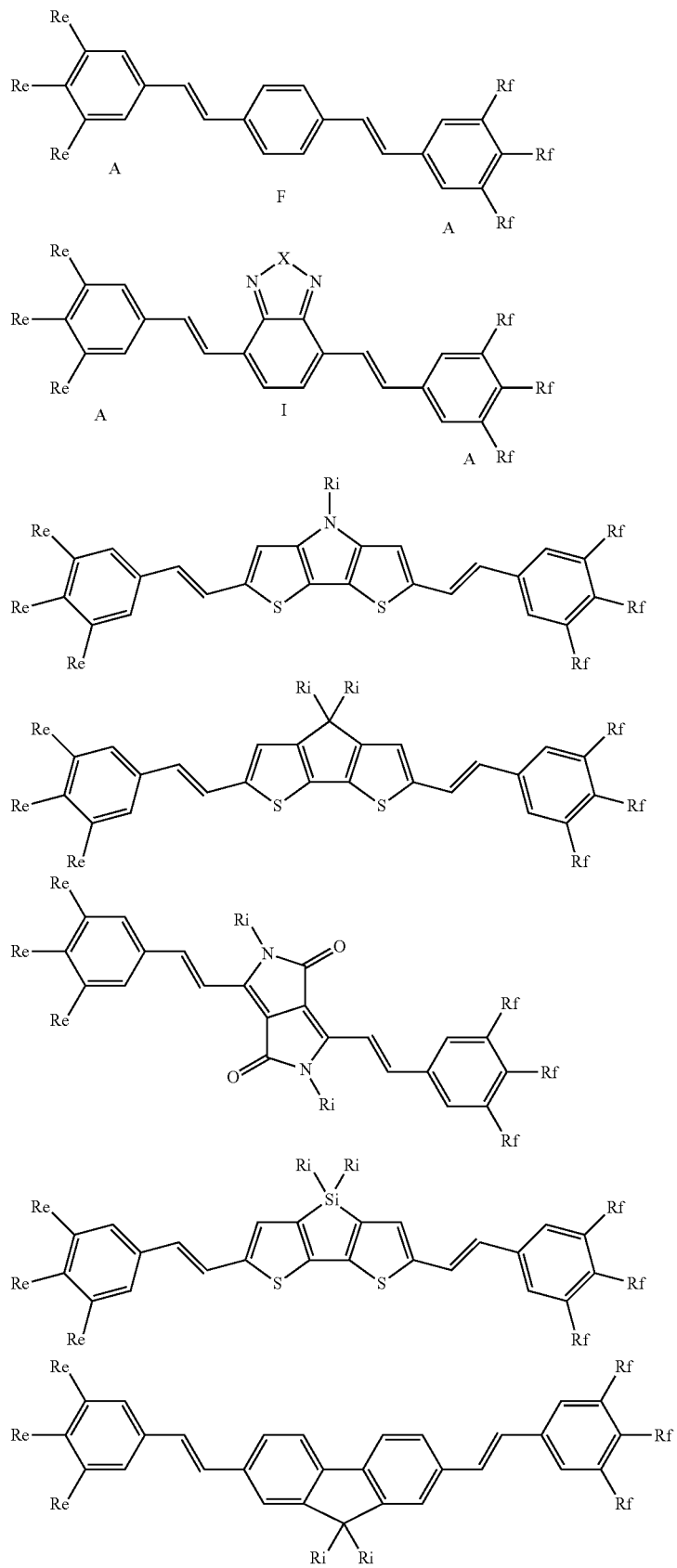

-continued
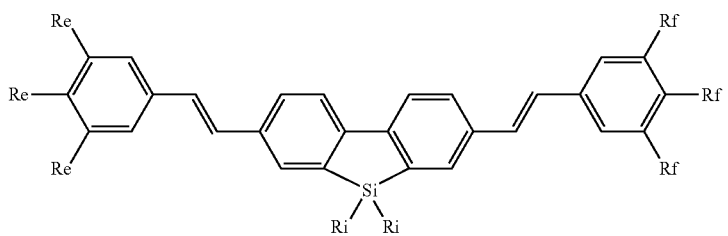
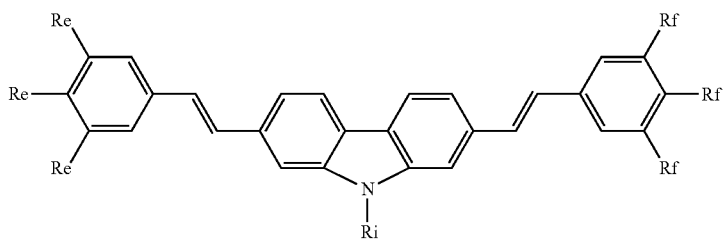
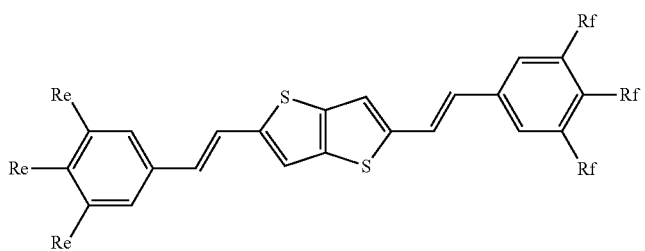
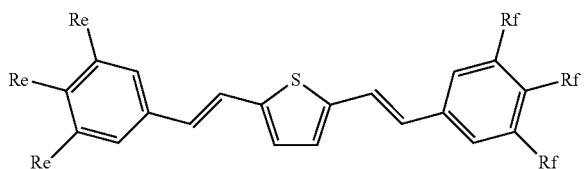
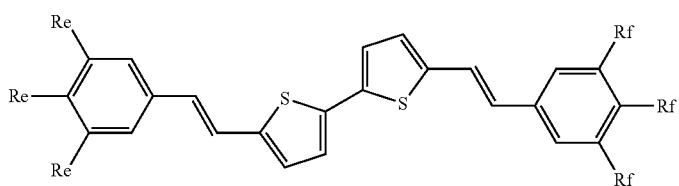
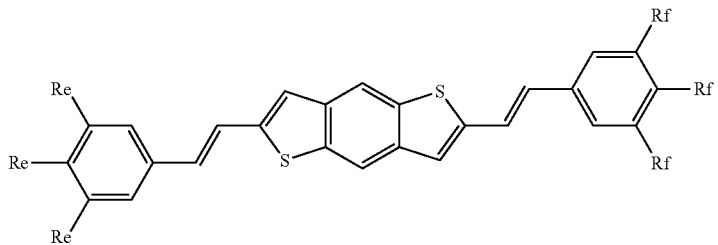
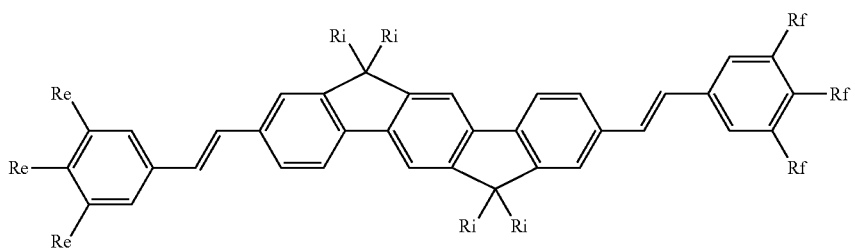

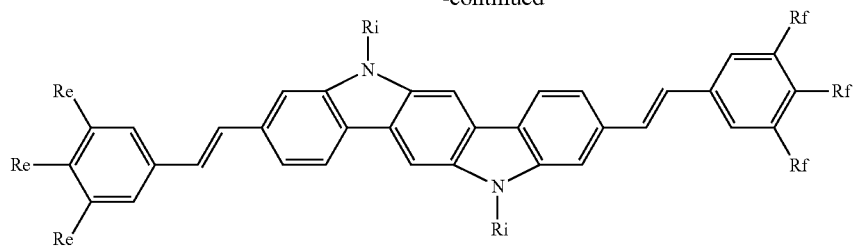
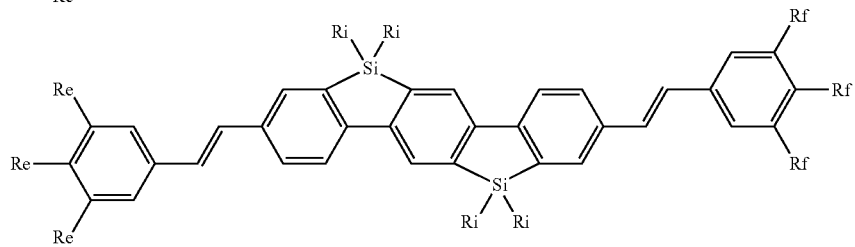
Phenylethynylene-containing conjugated electrolytes (PEs):
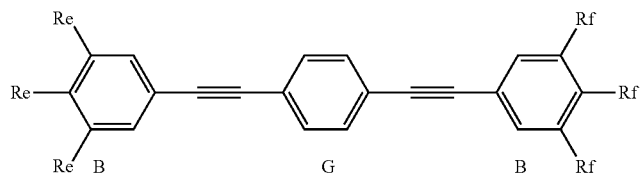
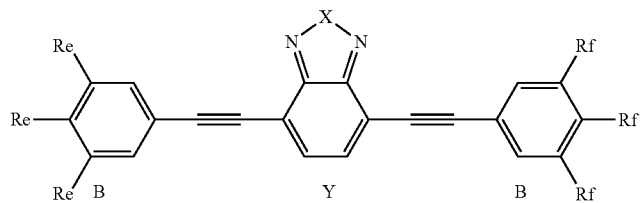
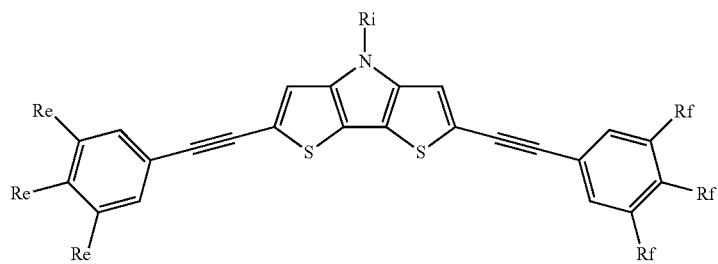
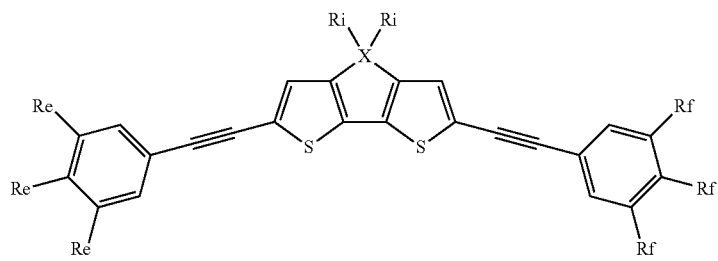

-continued
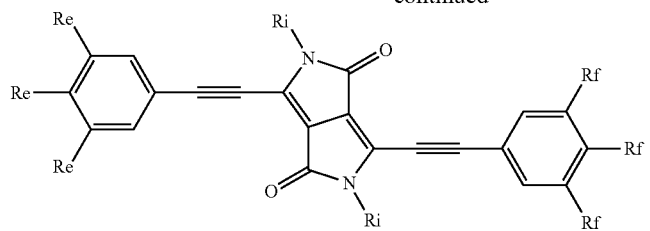
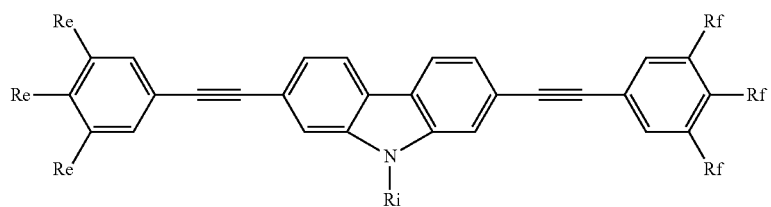
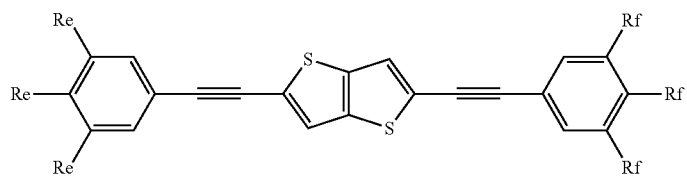
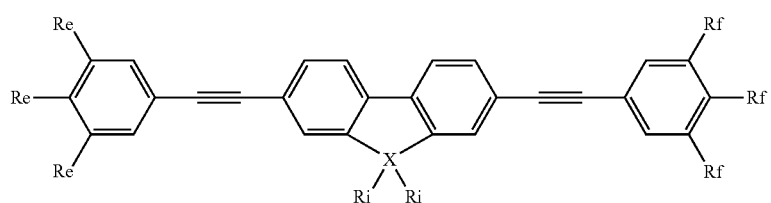
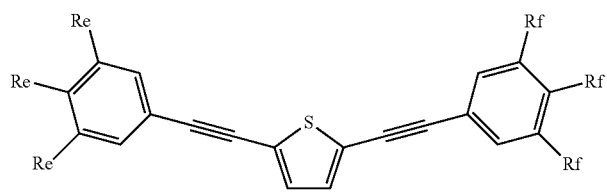
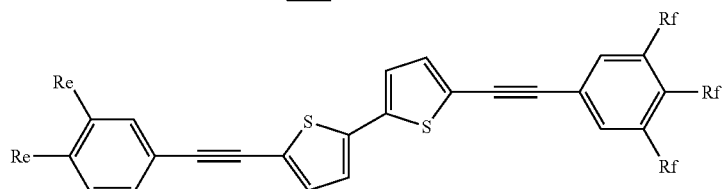
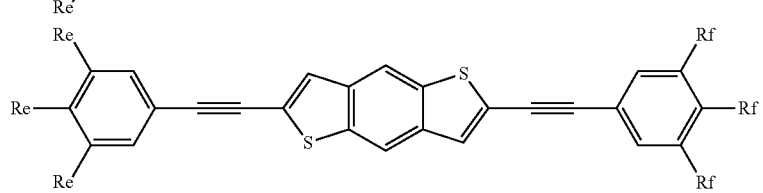
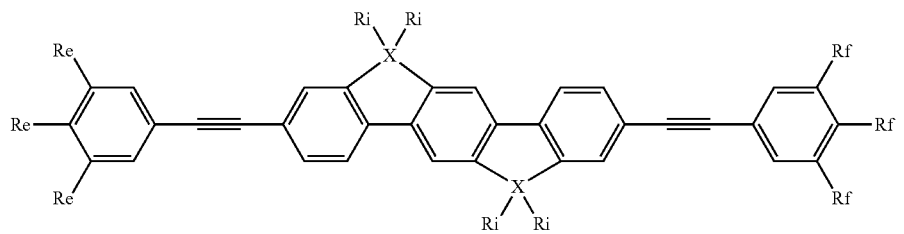

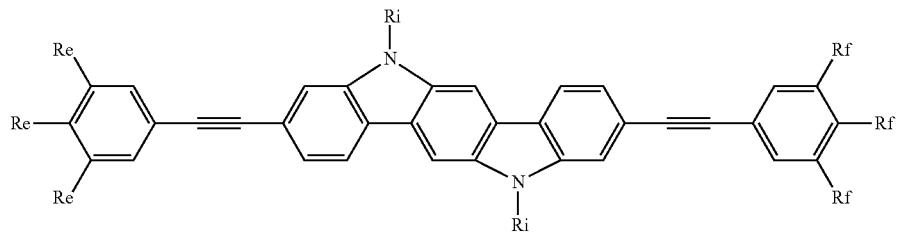
Polyphenylene-containing conjugated electrolytes (PPs):
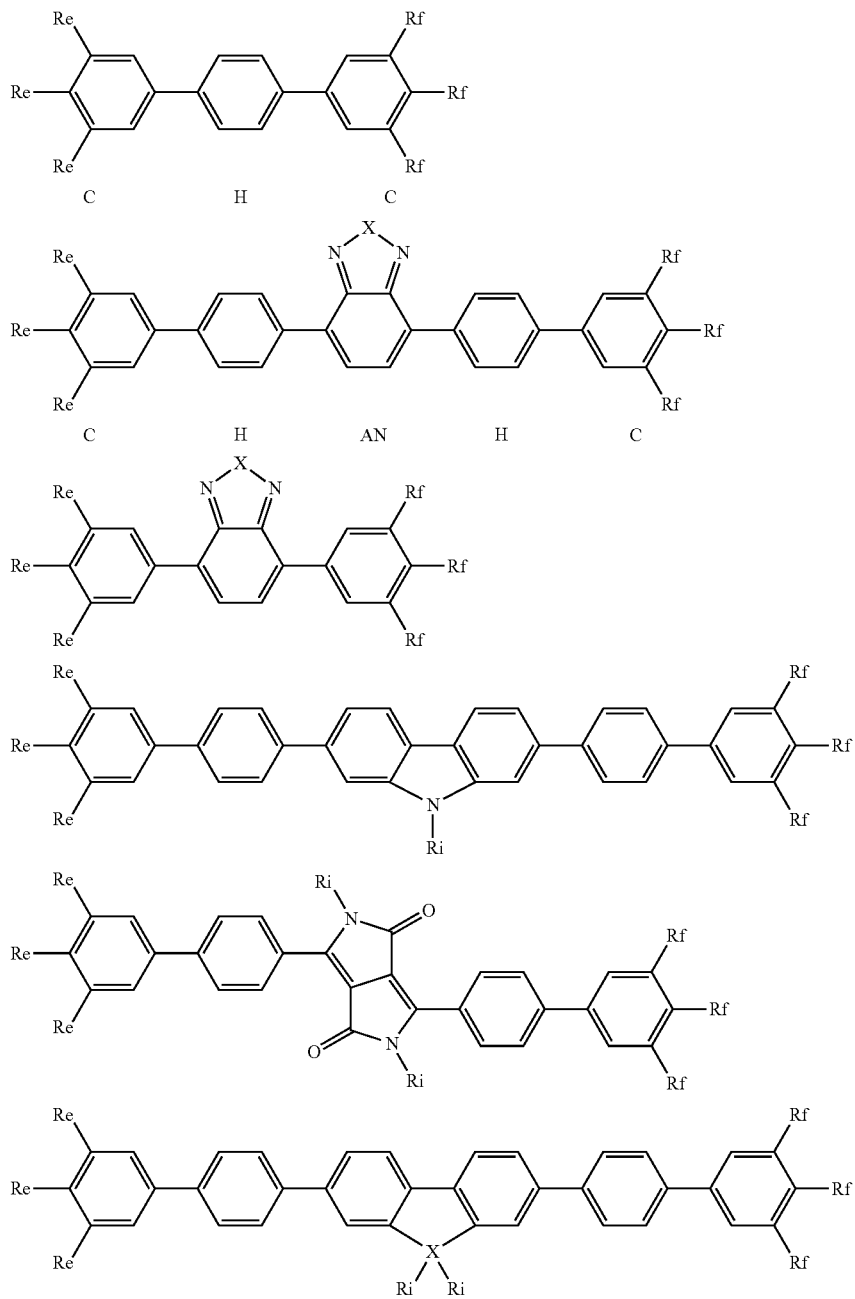

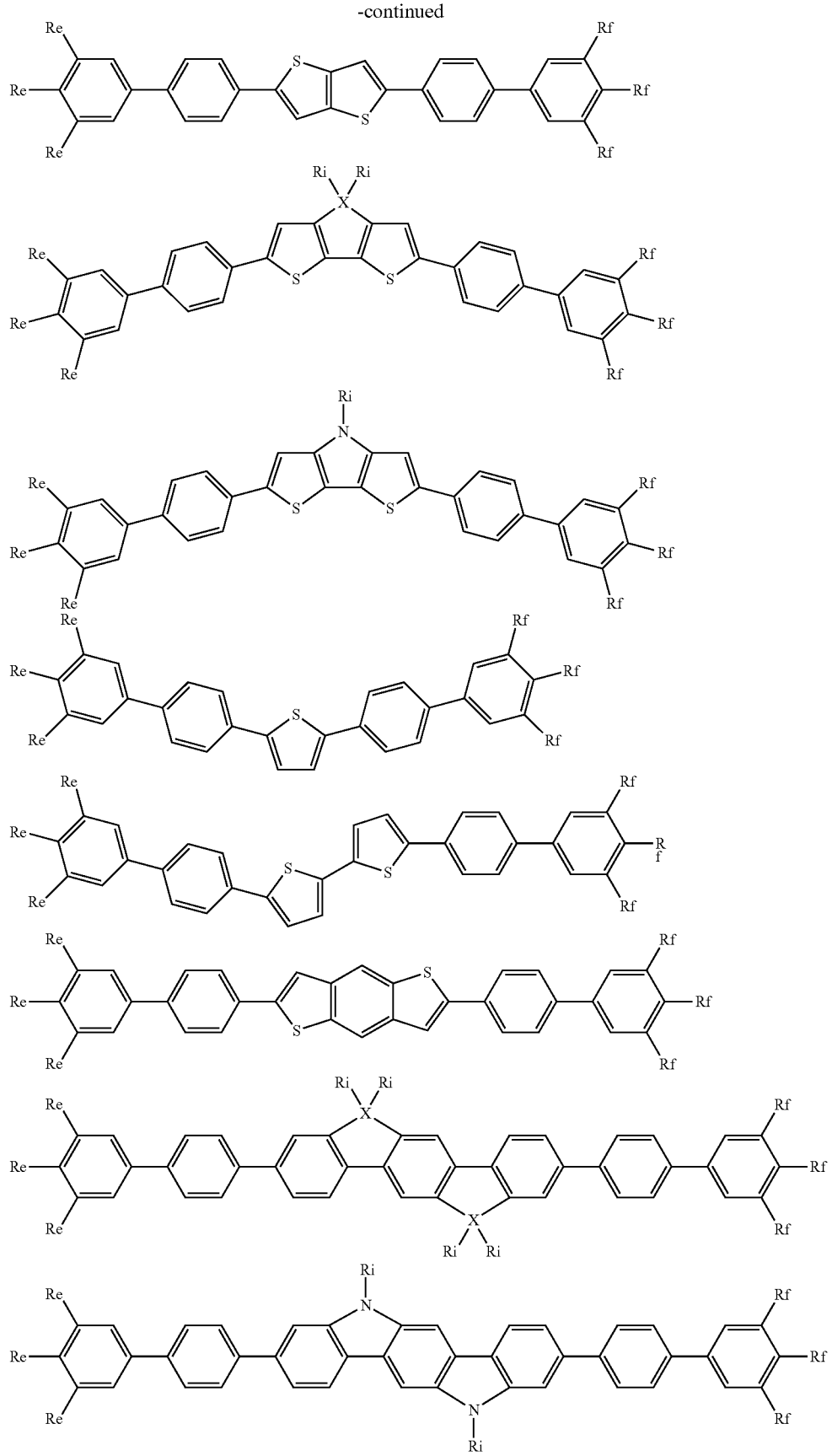

Thiophene-containing conjugated electrolytes:
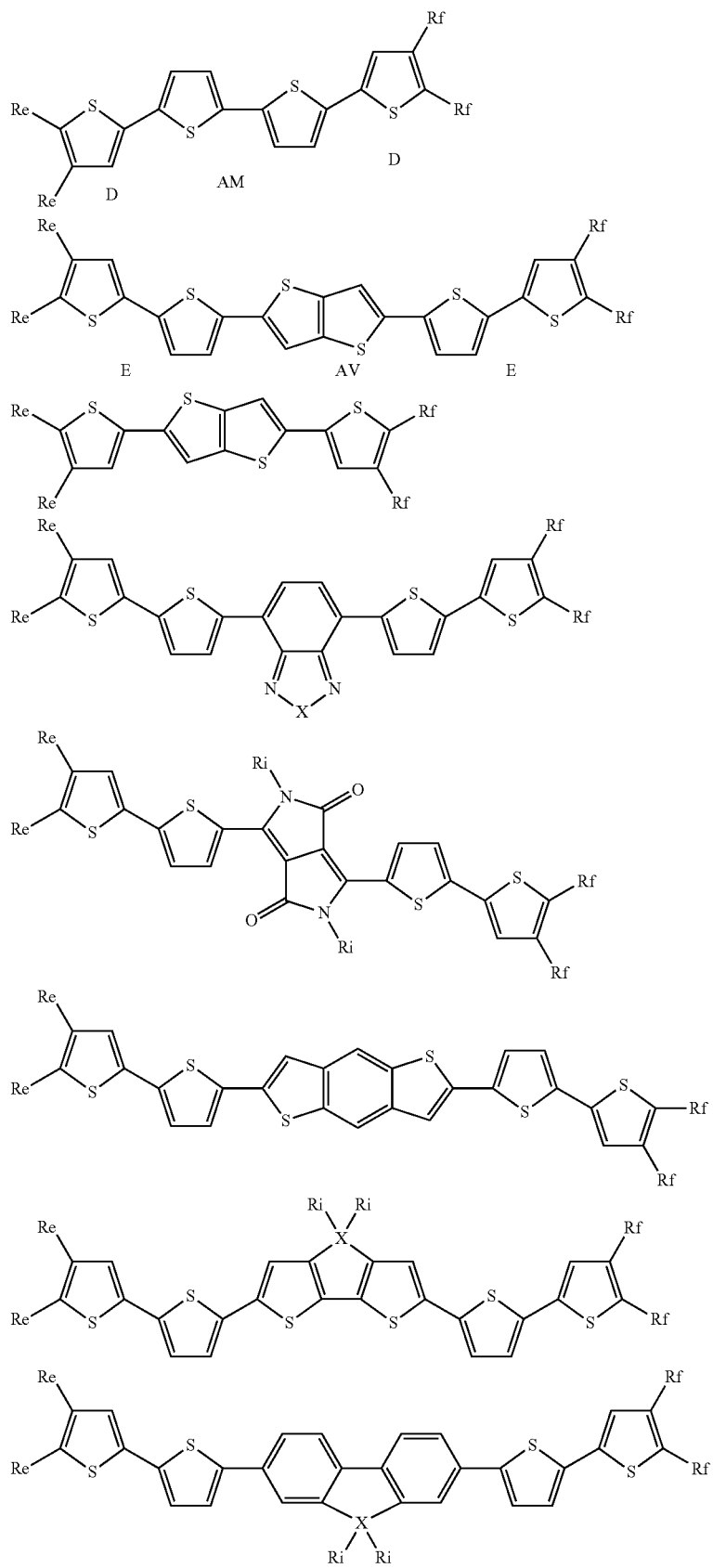

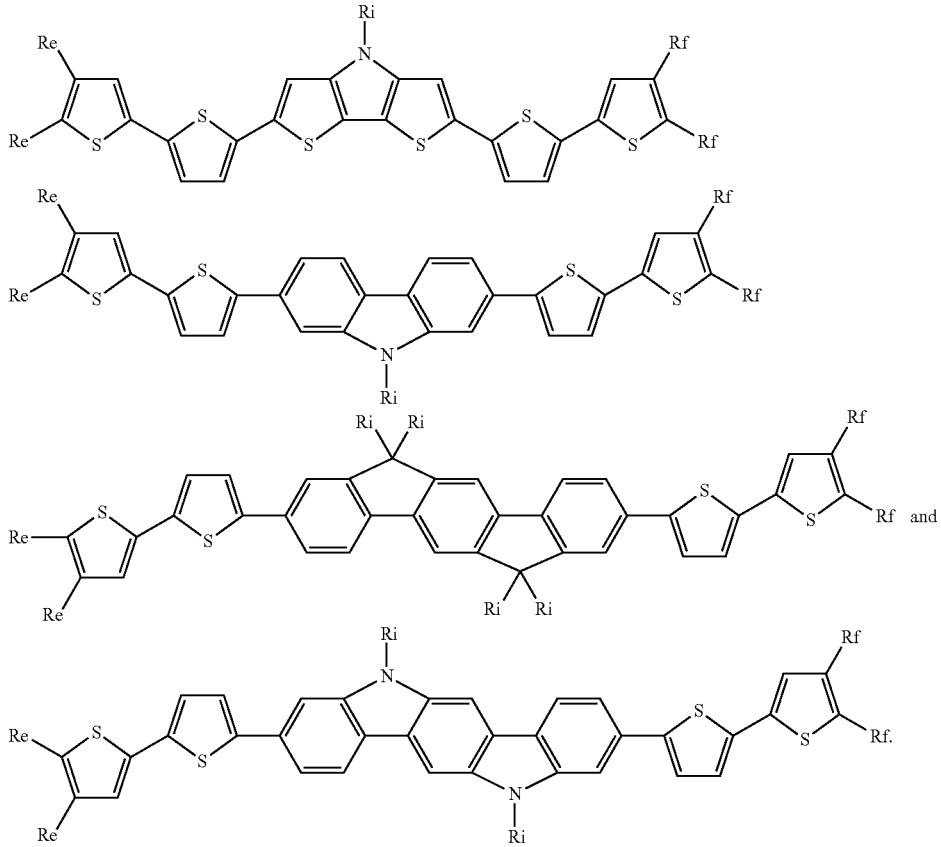

The segments and conjugated electrolytes are synthesized by methods known in the art. Descriptions of such synthetic methods can be found in, for example, Wang, S.; Bazan, G. C. *Chem. Commun.* 2004, 2508-2509; Stork, M.; Gaylord, B. S.; Heeger, A. J.; Bazan, G. C. *Adv. Mater.* 2002, 14, 361-366; Gaylord, B. S.; Wang, S.; Heeger, A. J.; Bazan, G. C. *J. Am. Chem. Soc.* 2001, 123, 6417-6418; Hong, J. W.; Gaylord, B. S.; Bazan, G. C. *J. Am. Chem. Soc.* 2002, 124, 11868-11869; Liu, B.; Gaylord, B. S.; Wang, S.; Bazan, G. C. *J. Am. Chem. Soc.* 2003, 125, 6705-6714; Herland, A.; Nilsson, K. P. R.; Olsson, J. D. M.; Hammarstrom, P.; Konradsson, P.; Inganas, O. *J. Am. Chem. Soc.* 2005, 127, 2317-2323; Woo, H. Y.; Hong, J. W.; Liu, B.; Mikhailovsky, A.; Korystov, D.; Bazan, G. C. *J. Am. Chem. Soc.* 2005, 127, 820-821; and Wang, S.; Hong, J. W.; Bazan, G. C. *Org. Lett.* 2005, 7, 1907-1910.

$R_e$ and $R_f$ are pendant groups bearing a hydrophilic functionality. The hydrophilicity of these groups maintain an amphiphilic structure for the membrane additive and ensure proper insertion and alignment in the microbial cell membrane. Hydrophilic end groups can include quaternary amines, primary, secondary and tertiary amines, amides, esters, and hydroxy groups. Other hydrophilic end groups can include carboxylic acids, and zwitterionic groups such as amino acids. These groups can incorporate saturated linear or branched alkyl chains ($C_1$-$C_{12}$ alkyl, $C_3$-$C_{12}$ alkyl, or $C_1$-$C_6$ alkyl) and can be linked to the conjugated Pi moiety via amino, alkoxy, and C—C linkages.

Examples of various $R_e$ and $R_f$ groups are shown below. The counter ion used can be any water stable ion compatible with the microbe of interest. Cationic counter-ions include, but are not limited to, inorganic cations such as sodium, potassium, calcium, magnesium, or lithium cations, and organic cations such as tetraethylammonium. Anionic counter-ions include, but are not limited to, inorganic cations such as chloride, bromide, iodide, or fluoride, and organic anions such as formate or acetate. It will be understood by the skilled artisan that, once in solution, counter-ions will often dissociate or exchange with other ions in solution. Thus, addition of a molecule in a certain form, such as a tetrabromide, is not intended to imply that the molecule will remain in the tetrabromide form once in solution.

Groups useful as the $R_e$ or $R_f$ moieties are independently selected from the group consisting of the form:

-L-$R_h$ where each L is independently a linker group containing at least one carbon atom, and each $R_h$ is a independently hydrophilic group, such as a charged or polar functional group; and each remaining $R_e$ and each remaining $R_f$ is independently selected from the group consisting of —H, —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aryl, F, Cl, Br, I, and —CN.

Each L can be independently selected from branched or linear, saturated or unsaturated, substituted or unsubstituted alkyl or heteroalkyl chains containing at least one carbon atom, and optionally incorporating one or more aryl or heteroaryl groups within the chain. For example, each L can be independently selected from $C_1$-$C_{12}$ alkyl, $C_2$-$C_{12}$ alkenyl, $C_2$-$C_{12}$ alkynyl, $C_2$-$C_{12}$ unsaturated hydrocarbyl, $C_1$-$C_{12}$ alkyl-$C_6$-$C_{10}$ aryl-$C_1$-$C_{12}$ alkyl, or $C_1$-$C_{12}$ alkyl-$C_4$-$C_{10}$ heteroaryl-$C_1$-$C_{12}$ alkyl. When substituted, each L can be independently substituted with $C_1$-$C_{12}$ alkyl, $C_2$-$C_{12}$ alkenyl, $C_2$-$C_{12}$ alkynyl, $C_1$-$C_{12}$ alkyl-$C_6$-$C_{10}$ aryl-$C_1$-$C_{12}$ alkyl, $C_1$-$C_{12}$ alkyl-$C_4$-$C_{10}$ heteroaryl-$C_1$-$C_{12}$ alkyl, hydroxyl, —O—$C_1$-$C_{12}$ alkyl, —$C_1$-$C_{12}$-alkyl-OH, fluoro, chloro, bromo, iodo, cyano, oxo, thiol, thioalkyl, carboxylic acid, carboxylic ester, amine, or amide groups.

The $R_h$ moiety can be independently selected from the group consisting of: —$N^+(R')(R'')(R''')$,

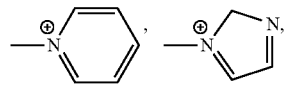

—$SO_3^-$, —$CO^{2-}$, —$PO_3^{2-}$, —$PO_3H^-$, —$PO_3H_2$, —$PO_4^{2-}$, —$PO_4H^-$, and —$PO_4H_2$, where R', R'', and R''' are independently selected from ($C_1$-$C_{12}$ alkyl), and where the groups optionally additionally comprise one or more counterions. The counterions can halide ions, such as iodide ions.

$R_e$ and $R_f$ can be, independently, of the form:

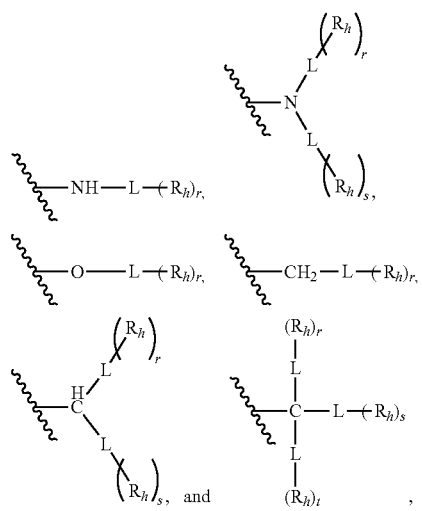

where each L and each $R_h$ can be selected from any of the definitions above. The subscripts r, s, and t can independently be 0, 1, 2, or 3, with the proviso that at least one $R_h$ is present in the $R_e$ or $R_f$ group (that is, r, when alone, must be at least 1; r+s, when t is absent, must be at least 1; or r+s+t must be at least 1). Multiple $R_h$ groups can be present on a single L group due to multiple substitution of $R_h$ groups at a single atom, or substitution of $R_h$ groups on different atoms. For example, when L is a branched C8 alkyl of the form

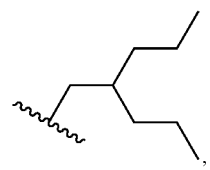

-L-($R_h$), can be of the form

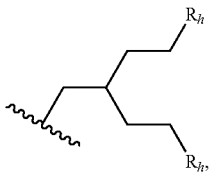

where r=2.

As noted above, descriptions of synthetic methodology useful for assembling segments, including segments having one or more $R_e$ or $R_f$ groups, can be found in, for example, Wang, S.; Bazan, G. C. *Chem. Commun.* 2004, 2508-2509; Stork, M.; Gaylord, B. S.; Heeger, A. J.; Bazan, G. C. *Adv. Mater.* 2002, 14, 361-366; Gaylord, B. S.; Wang, S.; Heeger, A. J.; Bazan, G. C. *J. Am. Chem. Soc.* 2001, 123, 6417-6418; Hong, J. W.; Gaylord, B. S.; Bazan, G. C. *J. Am. Chem. Soc.* 2002, 124, 11868-11869; Liu, B.; Gaylord, B. S.; Wang, S.; Bazan, G. C. *J. Am. Chem. Soc.* 2003, 125, 6705-6714; Herland, A.; Nilsson, K. P. R.; Olsson, J. D. M.; Hammarstrom, P.; Konradsson, P.; Inganas, O. *J. Am. Chem. Soc.* 2005, 127, 2317-2323; Woo, H. Y.; Hong, J. W.; Liu, B.; Mikhailovsky, A.; Korystov, D.; Bazan, G. C. *J. Am. Chem. Soc.* 2005, 127, 820-821; and Wang, S.; Hong, J. W.; Bazan, G. C. *Org. Lett.* 2005, 7, 1907-1910.

Microorganisms Useful in the Invention

Any microorganism which can be grown anaerobically can be utilized in the microbial fuel cells of the invention. The microorganism used can be a prokaryotic microbe or a eukaryotic microbe. The microorganism can be unicellular or multicellular, or may exist in both unicellular and multicellular forms. Yeast (such as baker's yeast), protists, and protozoans can be used, such as amoeba and paramecia. Mixotrophic algae can be used. Bacteria and archaea can also be used in the invention. Extremophiles can be used in the invention. Useful microorganisms include, but are not limited to, microbes from *Geobacter, Shewanella, Rhodoferax, Pseudomonas, Desulfito, Clostridium, Geothrix, Bacterodies, Escherichia,* and *Saccharomyces* genera, as well as environmental collections of mixed consortia.

Biological Fuels Useful in the Invention

Any fuel that can be processed by microorganisms to yield electrons can be used. Such fuels include, but are not limited to, sugars (for example, glucose, fructose, lactose, etc.), organic acids and metabolic intermediates (for example, lactate, acetate, etc.), biopolymers (for example, cellulose, chitosan, etc.) and mixed waste streams (for example, compost, wastewater, food wastes, etc.)

Applications of Charge-Transfer Agents

As noted above, the charge-transfer agents are useful as membrane additives to microorganisms for use in enhancing charge transfer from the microorganisms, for example for use in microbial fuel cells. The concentration of agent in the microbial medium required to produce the desired enhancement can be determined empirically, by adding the agent in different concentrations until the desired performance is attained or maximum enhancement is achieved. The empirical determination is performed by adding the agents to the analyte of the microbial fuel cell and measuring the relative performance of the agent-enhanced microbes versus the unenhanced microbes. The agents can be added in concentrations of about or at least about 1 nM, about or at least about 10 nM, about or at least about 25 nM, about or at least about 50 nM, about or at least about 100 nM, about or at least about 250 nM, about or at least about 500 nM, about or at least about 1 µM, about or at least about 10 µM, about or at least about 25

μM, about or at least about 50 μM, about or at least about 100 μM, about or at least about 250 μM, about or at least about 500 μM, about or at least about 1 mM, about or at least about 10 mM, about or at least about 25 mM, about or at least about 50 mM, about or at least about 100 mM, about or at least about 250 mM, about or at least about 500 mM, or about or at least about 1 M.

The agents are added in order to increase the rate of transmembrane charge transfer from the microorganism and/or to increase the electromotive force of transmembrane charge transfer from the microorganism. Thus in one embodiment, the invention embraces a method of increasing the rate of transmembrane charge transfer from a microorganism and/or increasing the electromotive force of transmembrane charge transfer from a microorganism, by adding an amount of charge-transfer agent sufficient to increase the rate of transmembrane charge transfer from the microorganism and/or sufficient to increase the electromotive force of transmembrane charge transfer from the microorganism.

The agents can be added in a concentration sufficient to increase the rate of transmembrane charge transfer from the microorganism by about or at least about 5%, about or at least about 10%, about or at least about 20%, about or at least about 25%, about or at least about 50%, about or at least about 75%, about or at least about 100%, about or at least about 150%, about or at least about 200%, about or at least about 250%, about or at least about 300%, about or at least about 400%, about or at least about 500%, or about or at least about 1000%. The agents can be added in a concentration sufficient to increase the electromotive force of transmembrane charge transfer from the microorganism by about or at least about 5%, about or at least about 10%, about or at least about 20%, about or at least about 25%, about or at least about 50%, about or at least about 75%, about or at least about 100%, about or at least about 150%, about or at least about 200%, about or at least about 250%, about or at least about 300%, about or at least about 400%, about or at least about 500%, or about or at least about 1000%. The agents can be added in a concentration sufficient to increase the rate and the electromotive force of transmembrane charge transfer from the microorganism by any combination of the foregoing parameters.

When the agents are used to enhance the operation of a microbial fuel cell, the agents can be added in a concentration sufficient to increase the current of the microbial fuel cell by about or at least about 5%, about or at least about 10%, about or at least about 20%, about or at least about 25%, about or at least about 50%, about or at least about 75%, about or at least about 100%, about or at least about 150%, about or at least about 200%, about or at least about 250%, about or at least about 300%, about or at least about 400%, about or at least about 500%, or about or at least about 1000%. The agents can be added in a concentration sufficient to increase the voltage of the microbial fuel cell by about or at least about 5%, about or at least about 10%, about or at least about 20%, about or at least about 25%, about or at least about 50%, about or at least about 75%, about or at least about 100%, about or at least about 150%, about or at least about 200%, about or at least about 250%, about or at least about 300%, about or at least about 400%, about or at least about 500%, or about or at least about 1000%. The agents can be added in a concentration sufficient to increase the current and the voltage of the microbial fuel cell by any combination of the foregoing parameters.

EXAMPLES

Materials

Starting materials were purchased from Aldrich, Fisher or Acros and used as received unless specified otherwise. Phosphorous oxychloride and HEPES buffer solution (1 M in water) were purchased from Fluka and used as received. p-tolualdehyde and vinylbenzyl chloride were purchased from Acros, dried over $CaH_2$, degassed and vacuum distilled prior to use. N,N-bis(6'-iodohexyl)-4-aminobenzaldehyde (4), 1,4-bis(4'-(N,N-bis(6"-iodohexyl)amino)styryl)benzene (DSBN), 1,4-bis(4'-(N,N-bis(6"-(N,N,N-trimethylammonium)hexyl)amino)-styryl)benzene tetraiodide (DSBN+) (see Woo, H. Y.; Liu, B.; Kohler, B.; Korystov, D.; Mikhailovsky, A.; Bazan, G. C. *J. Am. Chem. Soc.* 2005, 127, 14721-14729), and (E)-1,2-bis(4-(bromomethyl)phenyl) ethene (2A) (see Feast, W. J.; Lovenich, P. W.; Puschmann, H.; Taliani, C. *Chem. Commun.* 2001, 505-506) were prepared according to literature procedures and characterized by $^1H$ and $^{13}C$ NMR, mass spectrometry and elemental analysis.

Instrumentation.

Confocal images were collected using a Leica TCS SP high-resolution spectral confocal microscope equipped with a Millennia® series argon laser excitation source. UV/visible absorbance spectra were collected using either a Shimadzu UV-2401 PC or a Beckman-Coulter DU800. PL spectra were collected using a Photon Technology International spectrophotometer composed of a 814 Photomultiplier Detection System, a LPS-220B Lamp Power Supply and a Time Master Control Module. Cryo-TEM images were obtained using a FEI Tecnai G2 Sphera Microscope. Nuclear magnetic resonance spectra were collected on either a Varian UNITY INOVA 400/54 (1996) 400 MHz NMR spectrometer, a Bruker Avance500 500 MHz, a Bruker Avance200 200 MHz or a Bruker Avance II 800 MHz NMR spectrometer. Electrochemical measurements were made using a CH Instruments model CHI730B Electrochemical Analyzer employing CH instruments glassy carbon (working), Pt (counter) and Ag/AgCl (reference) electrodes. Instrumentation used to monitor MFC performance consisted of a series of leads that were wired such that any current generated by the fuel cells was passed through a 10 kΩ resistor and measured as a voltage that the custom software plots automatically as a function of time, collecting a reading every ten seconds. This instrumentation and software was designed and assembled/fabricated in house by James J. Sumner and coworkers at the US Army Research Labs, Adlephi, Md. Mass spectra were collected using either a Shimadzu GC-17A/QP-5000 EI GCMS, a VG70 Magnetic Sector FAB MS, or a PE Sciex QStar quadrupole/time-of-flight tandem mass spec ESI MS. CHN elemental analysis was performed on a Control Equipment Corp. model CEC 440HA organic element analyzer.

Example 1A

Preparation of (E)-1,2-bis(4-(chloromethyl)phenyl) ethene (2B)

A 100 mL 2-neck Schlenk flask was interfaced with a reflux condenser, placed under an inert atmosphere, and flame dried. This flask was charged with 50 mL of dried, degassed $CH_2Cl_2$ via cannula. In a glove box under nitrogen 40 mg of $2^{nd}$ generation Grubbs catalyst (1 mole % of 1 eq., 47 μmol) was sealed in a 25 mL Schlenk flask and removed from the glove box. This flask was interfaced with a Schlenk manifold and 20 mL of dry, degassed $CH_2Cl_2$ was added to the flask via cannula, yielding a dark red solution. This solution was then cannulated into the 100 mL reaction apparatus. A syringe was then used to load the reaction flask with 1.34 mL (2 eq., 4.7 mmol) of dry vinylbenzyl chloride. The solution was allowed to reflux under Ar at 50° C. for 24 hours. The reaction solution was then allowed to cool slowly and sit for ~2 hours. The product crystallized out of the reaction solution and the crude (off-white needle crystals) was collected via filtration and washed with cold hexanes. The pure product was afforded as a white solid in 80% yield following silica gel chromatography using a 2:1 ($CH_2Cl_2$: hexane) solvent system. $^1$H NMR (500 MHz, $CD_2Cl_2$): δ 7.57 (d, 4H), 7.42 (d, 4H), 7.17 (s, 2H), 4.65 (s, 4H). $^{13}$C (500 MHz, $CD_2Cl_2$): δ 137.46, 137.21, 129.15, 128.64, 126.92, 46.29. GCMS: 276 ($M^+$), 241 $(M-Cl)^+$, 206 $(M-2Cl)^+$, 103. Elemental Analysis (CHN) calculated: C, 69.33; H, 5.09; N, 0.0. Found: C, 69.50; H, 5.10; N, 0.239.

Example 1B

Preparation of (E)-4,4'-bis(diethylphosphonatemethyl)stilbene (E)-tetraethyl (4,4'-(ethene-1,2-diyl)bis (4,1-phenylene))bis(methylene)diphosphonate (3)

In a typical procedure 1 g 2A (1 eq., 2.73 mmol) or 1 g 2B (1 eq., 3.6 mmol) and 40 mL of neat triethylphosphite was combined in a 50-100 mL round bottom flask equipped with a reflux condenser. This solution was allowed to reflux at 120° C. for 24 hrs (rxn of 2A) or 48 hrs (rxn of 2B). Upon completion of the allotted time the reaction solution was allowed to cool and the off-white solid crude product was isolated via removal of excess $P(OEt)_3$ by vacuum distillation. Pure 3 was obtained as white crystals in 55% yield by recrystallization from toluene (reaction of 2A). In the case of the reaction of 2B a subsequent recrystallization is required to obtain pure 3 in 50% yield. $^1$H NMR (500 MHz, $CD_2Cl_2$): δ 7.47 (d, 4H), 7.28 (m, 4H), 7.1 (s, 2H), 4.0 (m, 8H), 3.11 (d, 4H), 1.25 (t, 12H). $^{13}$C (500 MHz, $CD_2Cl_2$): δ 136.02, 135.99, 131.61, 131.54, 130.22, 130.16, 128.09, 126.58, 126.56, 62.13, 62.08, 34.05, 32.95, 16.32, 16.27. ESI/TOF-MS: 503 $(M+Na)^+$, 743 $(2M+Na)^+$, 1463 $(3M+Na)^+$. Elemental Analysis (CHN) calculated: C, 59.99; H, 7.13; N, 0.0. Found: C, 59.80; H, 7.05; N, 0.12.

Example 1C

Preparation of 4,4'-bis(4'-(N,N-bis(6''-iodohexyl) amino)styryl)stilbene (DSSN)

In a typical procedure 0.449 g 3 (1 eq., 0.93 mmol) and 1.277 g 4 (2.5 eq., 2.4 mmol; see Scheme 2, below, for the structure of 4) were loaded into a 100 mL Schlenk flask and placed under an inert atmosphere. 50 mL of dry THF was added to the 100 mL flask followed by stirring until the solution was homogeneous. In a glove box under Ar, 0.21 g $NaO^tBu$ (2.3 eq., 2.2 mmol)) was sealed in a 25 mL Schlenk flask and removed from the glove box. This flask was interfaced with the Schlenk line and 20 mL of dry THF was added via cannula, dissolving the $NaO^tBu$. The $NaO^tBu$ solution was then cannulated into the reaction flask containing 3 and 4 under rigorous stirring. This results in a nearly immediate color change to bright orange followed by a gradual (over 5-20 min) transition to a light orange/yellow solution. The reaction was allowed to run at RT for 24 hours. At which time the THF was removed via rotary evaporation yielding the crude product as a yellow solid. The crude was re-dissolved in $CH_2Cl_2$, washed with water and brine and the organic phase was dried with $MgSO_4$. The $MgSO_4$ was removed via filtration and the crude was isolated following solvent removal by rotary evaporation. The pure product DSSN was afforded as a yellow/orange solid in 76% yield by silica gel chromatography using a 2:1 ($CH_2Cl_2$: hexanes) solvent system. $^1$H NMR (500 MHz, $CD_2Cl_2$): δ 7.50 (d, J=8.5 Hz, 4H), 7.47 (d, J=8.5 Hz, 4H), 7.37 (d, J=8.7 Hz, 4H), 7.12 (s, 2H), 7.05 (d, J=16.2 Hz, 2H), 6.9 (d, J=16.2 Hz, 2H), 6.63 (d, J=8.7 Hz, 4H), 3.3 (t, 8H), 3.23 (t, 8H), 1.85 (m, 8H), 1.60 (m, 8H), 1.44 (m, 8H), 1.36 (m, 8H). $^{13}$C (800 MHz, $CD_2Cl_2$): δ 147.88, 137.69, 135.77, 128.78, 127.79, 127.59, 126.75, 126.17, 124.47, 123.00, 111.72, 50.86, 33.61, 30.39, 30.39, 27.16, 26.07, 7.32. FAB-MS: 1254 ($M^+$). Elemental Analysis (CHN) calculated: C, 51.69; H, 5.62; N, 2.23. Found: C, 52.43; H, 5.90; N, 2.45.

Example 1D

Preparation of 4,4'-bis(4'-(N,N-bis(6''-(N,N,N-trimethylammonium)hexyl)amino)-styryl)stilbene tetraiodide (DSSN+)

In a typical procedure 0.55 g DSSN was loaded in a 500 mL round bottom flask and dissolved in THF (no BHT inhibitor). The flask was interfaced with a gas condenser and vacuum apparatus. The condenser cup was loaded with dry ice and acetone and the DSSN solution was cooled via dry ice acetone bath. The apparatus was placed under reduced pressure and an excess of $NMe_3$ was condensed into the THF solution. This solution was allowed to stir for 24 hours. The quaternization and resulting polarity change results in precipitation of a yellow solid from the THF solution. The excess $NMe_3$ and the THF was removed via reduced pressure distillation and the residual solid in the reaction flask was dissolved in methanol and a second excess of $NMe_3$ was condensed into the methanol solution followed by stirring for 24 hours at RT to assure full quaternization. The methanol and excess $NMe_3$ was removed via vacuum distillation and the crude product was then re-dissolved in methanol and precipitated with diethyl ether. The precipitate was collected via filtration and dried under vacuum yielding pure DSSN++ as a yellow/orange solid in 73% yield. $^1$H NMR (500 MHz, DMSO-$d_6$): δ 7.56 (d, J=8.0 Hz, 4H), 7.51 (d, J=8.0 Hz, 4H), 7.4 (d, J=8.0 Hz, 4H), 7.22 (s, 2H), 7.13 (d, J=16.5 Hz, 2H), 6.9 (d, J=16.2 Hz, 2H), 6.6 (d, J=7.7 Hz, 4H), 3.28 (m, 16H), 3.04 (s, 36H), 1.69 (m, 8H), 1.54 (m, 8H), 1.33 (m, 16H). $^{13}$C (500 MHz, DMSO-$d_6$): δ 147.93, 137.71, 135.93, 129.15, 128.35, 127.94, 127.72, 127.23, 126.60, 123.19, 112.08, 65.79, 52.69, 50.47, 27.12, 26.40, 26.21, 22.57. ESI/TOF-MS: 245 $(M-4I)^{4+}$, 369 $(M-3I)^{3+}$, 588, 618 $(M-2I)^{2+}$. Elemental Analysis (CHN) calculated: C, 53.16; H, 7.16; N, 5.64. Found: C, 53.62; H, 6.69; N, 5.16.

Example 1E

Preparation of Membrane Modified Vesicles

In order to prepare a typical membrane modified vesicle sample by sonication a methanolic DMPC solution containing a desired mol % DSBN+ was prepared (a typical solution is 1-5 mole % DSBN+ based on 50 micro-moles of DMPC). The methanol was slowly removed by argon flow while the solution was held at a constant 32-38° C. followed by vacuum oven drying at room temperature until dried to a constant weight. Next, enough $H_2O$ or pH 7 HEPES buffer was added to obtain a solution with a concentration of ~1-20 mg/mL depending upon application (imaging or photoluminescence measurement for example). This solution was then sonicated at 40-50° C. for 0.5-7 hours, typically until the solution had lost most of its turbidity. This generates multi-lamellar vesicles. Uni-lamellar vesicles with diameters of ~450 nm (with a somewhat broad size distribution based on cryo-TEM images) were formed as the resulting solution was filtered using 0.45 µm pore size syringe filters to yield a slightly turbid solution that must be further diluted to clarity with water or buffer in order to collect UV absorbance or photoluminescence spectra.

Example 2

Preparation of Supported Lipid Bilayer Membranes

Bilayer membranes supported on glassy carbon electrodes were prepared according to a modified literature procedure (Huang, W.; Zhang, Z.; Han, X.; Tang, J.; Wang, J.; Dong, S.; Wang, E. *Biophys. J.* 2002, 83, 3245-3255; Wu, Z.; Tang, J.; Cheng, Z.; Yang, X.; Wang, E. *Anal. Chem.* 2000, 72, 6030-6033). Five DMPC (2 mg/mL in methanol) membrane forming solutions were prepared: a solution containing only DMPC (control), two solutions containing 3 mol % oligoelectrolyte (DSSN+ and DSBN+, respectively), and a solution containing 3 mol % tridodecylamine (TDA). Electrode surface modification was performed by applying a constant 1.5 V bias for four minutes to a freshly polished glassy carbon electrode submerged in a 0.1 M aq. NaOH solution. Upon completion of this process the electrode was dried via argon steam followed by deposition of a 5 µL aliquot of the desired DMPC membrane forming solution to the electrode surface. The solvent was allowed to evaporate and electrode was immediately placed into phosphate buffer (pH 7.4) to allow the bilayer to assemble over a 0.5 hour time period. The working electrode containing the supported bilayer lipid membrane (sBLM) was then used directly.

Example 3

Cyclic Voltammetry Blocking Experiments

Cyclic voltammograms were collected at scan rates of 50-200 mV/sec using a standard three-electrode setup that employed a Pt wire counter electrode, a Ag/AgCl reference electrode and a glassy carbon working electrode (modified or unmodified). All runs were performed in aq. 0.5 M KCl electrolyte solution containing 1 mM potassium ferricyanide (the active redox and indicator species). Oxygen was removed from the system via bubbling Ar through the solution for several minutes prior to data collection. The working electrode was freshly polished between each run prior to voltammogram collection or sBLM formation followed by voltammogram collection. Data was collected within the range of 0-0.4 V potentials relative to Ag/AgCl.

Example 4

Cell Staining Procedure

Stock solutions of DSSN+ and DSBN+ (1-5 mM, typically 5 mL) were prepared in pH 7.3 phosphate buffer. Yeast cells were cultured in standard growth media or selective growth media. Cultures were never allowed to exceed an optical density of 6. In a typical cell staining run a 1 mL sample was transferred to 1.5 mL Eppendorf tube and the growth media was removed by centrifugation of cells followed by decanting of the growth media. The cells were then re-suspended in phosphate buffer and an appropriate volume of oligoelectrolyte stock solution was added to achieve a 10-100 µM concentration of DSSN+ or DSBN+. The cells were then shaken lightly for 10-180 min at room temperature. The cells can then be imaged directly or following buffer exchange via centrifugation and cell re-suspension. In an alternate procedure, as is the same staining (membrane incorporation) procedure performed with MFC inoculation samples, the cells are simply stained (by addition of COE stock solutions prepared in growth media to culture samples) and imaged directly in the original growth media. This can be done because no compounds within the media absorb or emit in a range which conflicts with the imaging parameters. Sample preparation is completed by depositing a ~3-6 µL aliquot of stained cell solution onto a traditional slide followed by a cover slip (in this case the slide is inverted and placed over a water or oil immersion objective interfaced with either a Nikon or Leica confocal fluorescence microscope).

Example 5

Microbial Fuel Cell Preparation and Assembly

Two-chamber MFCs were constructed in a similar fashion as previously described (Milliken, C. E.; May, H. D. *Appl. Microbiol. Biotechnol.* 2007, 73, 1180-1189; Sund, C. J.; Wong, M. S.; Sumner, J. J. *Biosens. Bioelectron.* 2009, 24, 3144-3147; Sund, C. J.; McMasters, S.; Crittenden, S. R.; Harrell, L. E.; Sumner, J. J. *Appl. Microbiol. Biotechnol.* 2007, 76, 561-568) with some modifications and pictured in FIG. 9. The anodes and cathodes consisted of carbon felt (100% Activated Carbon Fiber Filter, CarboPur Technologies, Montreal, Canada), ⅛ inch thick, cut to the dimensions of 5 cm by 1 cm. The carbon felts were attached to 0.25 mm diameter titanium wires (AlfaAesar, Ward Hill, Mass.) as electrical leads. A new piece of Nafion® 117 (DuPont, Wilmington, Del., USA) was used for each fuel cell. Anode wires were passed through silicone rubber septa used to seal the anode compartment following inoculation while the cathode compartment was covered with a loose-fitting glass vial. Each fuel cell compartment was filled with 20 ml of media and autoclaved. Inoculation of MFCs consisted of addition of 300 µL of stained (25 µM COE) or unstained yeast stock solution (O.D.=1.75). Methylene blue was added separately as a stock solution (0.1% by weight, 2.67 mM) for the positive control runs employing this mediator. MFCs were incubated in an aerobic 30° C. incubator and the potential across a 10 kΩ resistor was measured and recorded every 10 seconds via a DAQPad-6016 and a custom LabView® VI (National Instruments, Austin, Tex., USA).

Example 6

Confocal/Fluorescence Imaging

Samples were prepared by depositing an ~3-6 µL aliquot of multi-lamellar vesicle solution or stained cell solution onto a standard slide followed by placement of a cover slip. The slide was then inverted and placed cover slip down over either a 100× oil immersion objective or a 63× water immersion objective. Images of vesicles and cells were collected using either a Leica confocal microscope equipped with a 63× water immersion objective and a 488 nm Ar laser excitation source or a Nikon confocal microscope (used in epi-mode) equipped with a 100× oil immersion objective and a Hg lamp excitation source coupled to an excitation color filter that permits ~480-

500 nm excitation and a emission color filter that permits detection of radiation of wavelengths ≥500 nm.

Example 7

Molecular Orientation in Lipid Structures

In order to probe oligoelectrolyte molecular orientation a stationary multi-lamellar vesicle containing 3 mol % DSBN+ was imaged using a confocal microscope equipped with a 488 nm Ar laser excitation source. A 15 mg/mL vesicle sample was prepared via sonication for 3 hrs at 35-40° C. The multi-lamellar vesicle sample was then allowed to cool and 3 µL of this solution was placed on a traditional slide followed by a cover slip. The slide was then inverted and placed on the confocal microscope stage. The cover slip causes formation of a thin liquid layer in which vesicle motion is restricted and larger stationary vesicles can be found.

Example 8

Cryo-TEM Sample Preparation

Cryo-TEM samples were prepared by first depositing a 3.5 µL aliquot of the desired uni-lamellar vesicle solution onto an Electron Microscopy Sciences TEM grid (lacey/carbon film on 200 mesh copper grid) mounted within a FEI Vitrobot™ Mark IV automated vitrification instrument. Temperature and humidity of sample preparation were 22° C. and >90%, respectively. Vitrification is achieved by rapid plunge-freezing of the sample using liquid ethane as the cryogen. The grid was then handled exclusively under liq. $N_2$ and carefully loaded into the pre-cooled and prepared TEM where images could then be collected.

Example 9

Synthesis and Characterization

Compound DSBN+ was prepared as previously reported (Woo, H. Y.; Liu, B.; Kohler, B.; Korystov, D.; Mikhailovsky, A.; Bazan, G. C. *J. Am. Chem. Soc.* 2005, 127, 14721-14729). Scheme 2 shows the synthesis of DSSN+. This route is based upon the assembly of the desired end-capped π-system by coupling a bis(methylene)phosphonate (for example 3 in Scheme 2) with the amino functionalized benzaldehyde 4 via a trans-selective Horner-Wadsworth-Emmons reaction. Compound 3 may be accessed via two different pathways. The three-step pathway (Pathway 1, Scheme 2) begins with preparation of 1 in good yield via a McMurry coupling of p-tolualdehyde followed by a low-yielding (29%) Wohl-Ziegler radical bromination that affords 2A (Feast, W. J.; Lovenich, P. W.; Puschmann, H.; Taliani, C. *Chem. Commun.* 2001, 505-506). The desired bisphosphonate 3 can then be generated by an Arbuzov reaction. Alternatively, 3 can be prepared in two steps (Pathway 2, Scheme 2) beginning with the metathesis condensation of 4-vinylbenzylchloride to yield 2B, followed by an Arbuzov reaction. The second pathway removes one step, while effectively circumventing a low yielding radical bromination at the negligible cost of a slightly lower reaction yield (50% and 55% yield of 3 for the two and three step pathways, respectively). As stated above, a subsequent Horner-Wadsworth-Emmons reaction affords the neutral chromophore DSSN in reasonable yield (76%). Preparation of DSSN+(73% yield) was completed by quaternization of DSSN using trimethylamine.

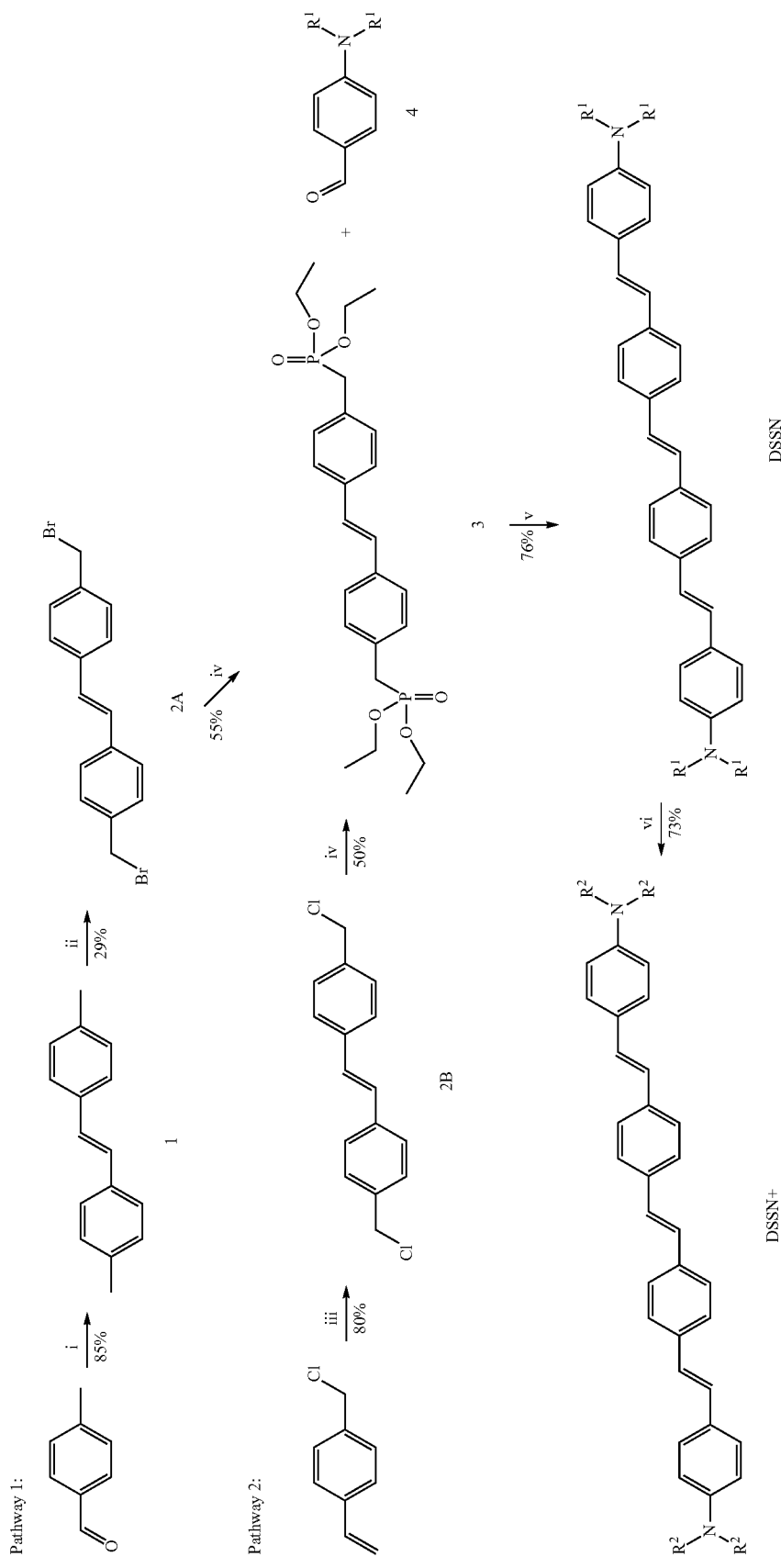

Each synthetic target and intermediate was characterized by $^1$H and $^{13}$C NMR spectroscopy, mass spectrometry and elemental analysis. Evidence indicating all-trans conformations of DSSN and DSSN+ was provided by $^1$H NMR spectroscopy. Signals corresponding to protons of the center vinylic linkage are observed as a singlet, indicating a high degree of molecular symmetry, while signals corresponding to protons of the outer vinylic linkages are observed as a doublet with a coupling constant indicative of a trans conformation (J=~16 Hz).

Example 10

Optical Characterization

Figure 2:
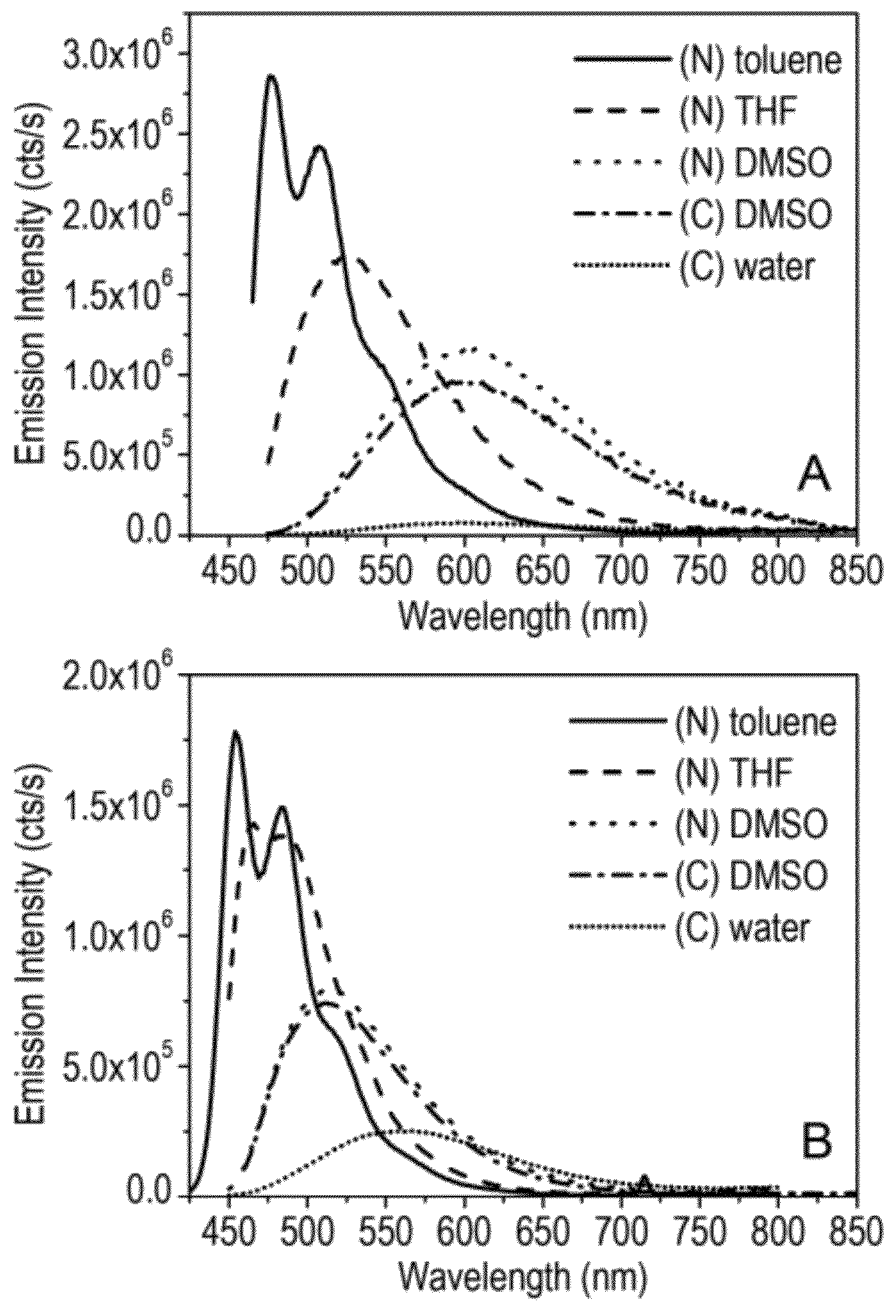
FIG. 2 shows photoluminescence (PL) spectra of 5-7 µM DSSN (A) and DSBN (B) in toluene (—), THF (- - -), and DMSO (·····) as well as DSSN+ (A) and DSBN+ (B) in DMSO (-·-·) and water (········). Peak areas shown are proportional to η values. General trends exhibited by both chromophores: $\lambda_{em}$ decreases and η increases with decreasing solvent polarity. Excitation wavelengths were chosen to match the optical density of the fluorescein reference sample. (N) indicates the neutral compounds, (C) indicates the charged compounds.

General photophysical and solvatochromatic features of the neutral (DSSN, DSBN) and charged (DSSN+, DSBN+) versions of each chromophore were probed by using UV-Vis absorption and photoluminescence (PL) spectroscopies. As expected, these structural analogs exhibit similar sensitivities to the polarity of the surrounding medium. Table 1 shows a summary and comparison of the spectral characteristics for the neutral and charged versions of each chromophore in solvents of varying polarities. FIG. 2 shows the corresponding PL spectra. General trends expressed by both structural analog pairs are as follows: absorbance maxima ($\lambda_{abs}$) occur in the 406-436 nm range and exhibit relatively small shifts in different solvents. Large hypsochromic shifts in PL maxima ($\lambda_{em}$) and increased quantum efficiencies ($\eta$) are observed as the solvent polarity decreases. Compared to the distyrylbenzene chromophore (DSBN and DSBN+) the distyrylstilbene counterpart (DSSN and DSSN+) has red shifted $\lambda_{abs}$ and $\lambda_{em}$ and a larger molar extinction coefficient ($\in_{max}$); consistent with its more extended conjugation length and greater size (Johnsen, M.; Paterson, M. J.; Arnbjerg, J.; Christiansen, O.; Nielsen, C. B.; Jorgensen, M.; Ogilby, P. R. Phys. Chem. Chem. Phys. 2008, 10, 1177-1191; Meier, H. Angew. Chem. Int. Ed. 2005, 44, 2482-2506; Narwark, O.; Gerhard, A.; Meskers, S. C. J.; Brocke, S.; Thorn-Csányi, E.; Bässler, H. Chem. Phys. 2003, 294, 17-30; Seixas de Melo, J.; Burrows, H. D.; Svensson, M.; Andersson, M. R.; Monkman, A. P. J. Chem. Phys. 2003, 118, 1550-1556). It is important to note that when comparing the solvatochromatic properties of a given neutral and charged chromophore pair that the difference in pendant group terminals (alkyliodide in DSSN and DSBN vs. trimethyl ammonium iodide in DSSN+ and DSBN+) has a negligible effect on the electronic structure of the chromophore (Woo, H. Y.; Liu, B.; Kohler, B.; Korystov, D.; Mikhailovsky, A.; Bazan, G. C. J. Am. Chem. Soc. 2005, 127, 14721-14729). This conclusion is supported by the nearly identical UV-Vis and PL features of each structural analog pair when dissolved in DMSO (Table 1, FIG. 2).

As seen in FIG. 2, the $\lambda_{em}$ values of each chromophore exhibit a ~110-120 nm hypsochromic shift as the solvent is shifted from polar ($\lambda_{em}$=594 and 566 nm in water for DSSN+ and DSBN+, respectively) to non-polar ($\lambda_{em}$=476 and 454 nm in toluene for DSSN and DSBN, respectively). This shift is accompanied by the appearance of vibronic structure (Pond, S. J. K.; Rumi, M.; Levin, M. D.; Parker, T. C.; Beljonne, D.; Day, M. W.; Bredas, J.-L.; Marder, S. R.; Perry, J. W. J. Phys. Chem. A. 2002, 106, 11470-11480; Renak, M. L.; Bartholomew, G. P.; Wang, S. J.; Ricatto, P. J.; Lachicotte, R. J.; Bazan, G. C. J. Am. Chem. Soc. 1999, 121, 7787-7799; Rumi, M.; Ehrlich, J. E.; Heikal, A. A.; Perry, J. W.; Barlow, S.; Hu, Z.; McCord-Maughon, D.; Parker, T. C.; Rockel, H.; Thayumanavan, S.; Marder, S. R.; Beljonne, D.; Bredas, J.-L. J. Am. Chem. Soc. 2000, 122, 9500-9510; Wang, S. J.; Oldham, W. J.; Hudack, R. A.; Bazan, G. C. J. Am. Chem. Soc. 2000, 122, 5695-5709). The $\eta$ values of each analog are similar for a given solvent, and are considerably greater in toluene (0.95 and 0.98 for DSSN and DSBN, respectively) than in water (0.06 and 0.33 for DSSN+ and DSBN+, respectively). FIG. 2 shows the PL spectra of DSSN/DSSN+(FIG. 2A) and DSBN/DSBN+ (FIG. 2B); peak areas are proportional to the magnitude of $\eta$ in Table 1. The difference in r values of DSSN+ and DSBN+ in water may be due to a greater degree of DSSN+ aggregation caused by its larger hydrophobic component, which may lead to increased self quenching (Gaylord, B. S.; Wang, S.; Heeger, A. J.; Bazan, G. C. J. Am. Chem. Soc. 2001, 123, 6417-6418), (Hsu, J.-H.; Fann, W. Chuang, K.-R.; Chen, S.-A. Proc. SPIE. 1997, 3145, 436-443; Je, J.; Kim, O.-K. Macromol. Symp. 2007, 249-250, 44-49).

TABLE 1

Summary of UV-Vis and PL Spectra

| | toluene | | THF | | DMSO | | water | |
|---|---|---|---|---|---|---|---|---|
| | $\lambda_{abs}$ ($\in_{max}$)$^a$ | $\lambda_{em}$ ($\eta$)$^b$ | $\lambda_{abs}$ ($\in_{max}$) | $\lambda_{em}$ ($\eta$) | $\lambda_{abs}$ ($\in_{max}$) | $\lambda_{em}$ ($\eta$) | $\lambda_{abs}$ ($\in_{max}$) | $\lambda_{em}$ ($\eta$) |
| DSSN | 425 (10.7) | 476 (0.95) | 426 (10.6) | 526 (0.89) | 436 (9.6) | 602 (0.73) | | |
| DSSN+ | | | | | 435 (9.8) | 596 (0.71) | 412 (6.6) | 594 (0.06) |
| DSBN | 410 (8.4) | 454 (0.98) | 410 (8.5) | 466 (0.92) | 419 (7.8)$^c$ | 516 (0.81) | | |
| DSBN+ | | | | | 419 (8.2) | 511 (0.86) | 406 (6.0) | 566 (0.33) |

$^a$Molar extinction coefficients ($\in_{max}$) were measured at $\lambda_{max}$ and are reported in units of Lmol$^{-1}$cm$^{-1}$ × 10$^{-4}$.
$^b$Quantum efficiency ($\eta$) values were measured relative to a fluorescein standard at pH 12.
$^c\in_{max}$ value abstracted from reference (Woo, H. Y.; Liu, B.; Kohler, B.; Korystov, D.; Mikhailovsky, A.; Bazan, G. C. J. Am. Chem. Soc. 2005, 127, 14721-14729).

Example 11

Incorporation of COEs into Lipid Bilayers

A model vesicle system was chosen to examine the incorporation of DSBN+ and DSSN+ into phospholipid bilayers, develop a characterization methodology, and ascertain molecular orientation. Vesicles are excellent model systems for membranes due to their ease of formation via self-assembly, structural integrity, large surface area, and high degree of order with respect to spherical shape and orientation of the molecular constituents (Marques, E. F. Langmuir. 2000, 16, 4798-4807; Robinson, J. N.; Cole-Hamilton, D. J. Chem. Soc. Rev. 1991, 20, 49-94). The specific lipids employed were 1,2-dimyristoyl-sn-glycero-3-phosphocholine (DMPC) and 1,2-dipalmitoyl-sn-glycero-3-phosphocholine (DPPC), the tails of which each contain 14 and 16 carbons, respectively.

These lipids were chosen due to ease of vesicle formation under the conditions employed in this study (Ref. 22; Knoll, W.; Ibel, K.; Sackmann, E. *Biochemistry.* 1981, 20, 6379-6383; Morigaki, K.; Walde, P. *Curr. Opin. Colloid Interface Sci.* 2007, 12, 75-80; Šegota, S.; Težak, Đ. *Adv. Colloid Interface Sci.* 2006, 121, 51-75; Singer, M. A.; Finegold, L.; Rochon, P.; Racey, T. J. *Chem. Phys. Lipids.* 1990, 54, 131-146; Woodle, M. C.; Papahadjopoulos, D. *Methods Enzymol.* 1989, 171, 193-217) and the tendency of phosphatidylcholine lipid bilayers to be tolerant of added components with respect to maintenance of their microheterogeneous structures (Steinberg-Yfrach, G.; Rigaud, J.-L.; Durantini, E. N.; Moore, A. L.; Gust, D.; Moore, T. A. *Nature.* 1998, 392, 479-482). Lipid bilayers composed of DMPC have thicknesses on the order of ~31-34 Å while DPPC lipid bilayers are slightly thicker (~34-37 Å) (Kučerka, N.; Uhríová, D.; Teixeira, J.; Balgavý, P. *Physica B: Condens. Matter.* 2004, 350, e639-e642; Lewis, B. A.; Engelman, D. M. *J. Mol. Biol.* 1983, 166, 211-217). The thickness of DMPC and DPPC bilayer membranes are close to the molecular lengths of DSBN+ and DSSN+ (~35-40 Å). Such similarities were anticipated to favor the type of membrane intercalation shown in FIG. 1.

Efforts to modify the vesicle membranes with DSBN+ and DSSN+ followed modified literature procedures (Lin, A. J.; Slack, N. L.; Ahmad, A.; George, C. X.; Samuel, C. E.; Safinya, C. R. *Biophys. J.* 2003, 84, 3307-3316). First, a lipid stock solution containing the desired fraction of either DSSN+ or DSBN+, typically 1-5 mol % relative to lipid, was prepared in methanol. This lipid/COE stock solution was then heated and held above the transition temperature of the lipid (23° C. and 41° C. for DMPC and DPPC, respectively) as the solvent was removed via Argon flushing, followed by vacuum drying to a constant weight. The resulting lipid/COE solid was then suspended in pH=7.3 HEPES buffer to the desired concentration (1-10 mg/mL). Multi-lamellar vesicles were then formed by self-assembly upon sonication of the resulting solution. Uni-lamellar vesicles were prepared by filtration (using 0.45 or 0.2 μm pore size syringe filters) or by extrusion (Olson, F.; Hunt, C. A.; Szoka, F. C.; Vail, W. J.; Papahadjopoulos, D. *Biochim. Biophys. Acta.* 1979, 557, 9-23; Socaciu, C.; Bojarski, P.; Aberle, L.; Diehl, H. A. *Biophys. Chem.* 2002, 99, 1-15; Szoka, F.; Olson, F.; Heath, T.; Vail, W.; Mayhew, E.; Papahadjopoulos, D. *Biochim. Biophys. Acta.* 1980, 601, 559-571).

Figure 3:
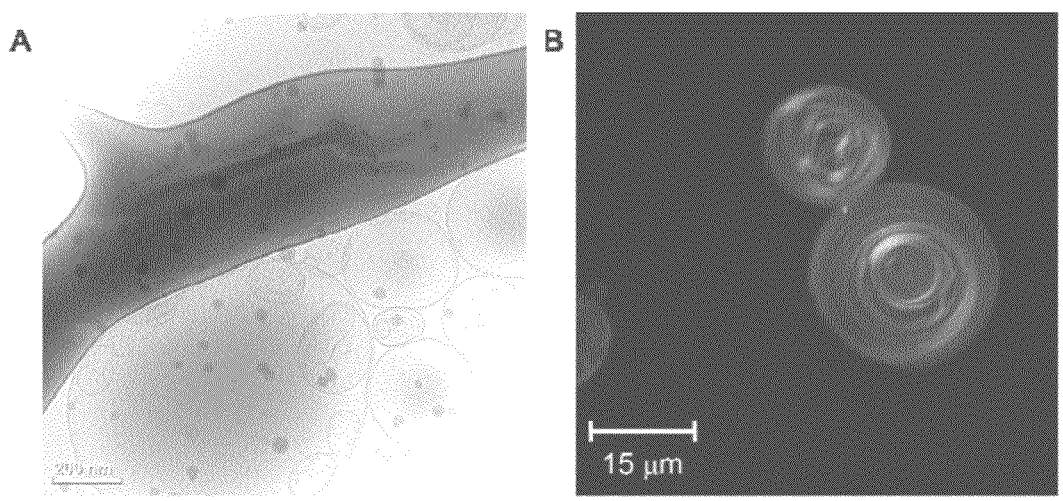
FIG. 3 shows (A) Cryo-TEM image of uni-lamellar DMPC vesicles modified with 5 mol % DSBN+ relative to lipid (16 mg/mL). (B) Confocal microscopy image of 5 mol % DSBN+/DMPC multi-lamellar vesicles (2 mg/mL) obtained following 488 nm excitation. Each image demonstrates successful vesicle formation as well as a maintained liposomal microstructure upon addition of DSBN+. The confocal microscopy image is generated by the fluorescence response of DSBN+ and demonstrates oligoelectrolyte association with lipid bilayers.

Confirmation of vesicle formation and that the microheterogeneous liposomal structure is maintained upon modification with DSBN+ or DSSN+ was provided by cryogenic transmission electron microscopy (cryo-TEM) and confocal microscopy. The cryo-TEM image of uni-lamellar DMPC vesicles containing membrane embedded DSBN+ shown in FIG. 3A demonstrates successful vesicle formation, as well as unperturbed liposomal microstructure. FIG. 3B is a confocal microscopy image of multi-lamellar DMPC vesicles prepared in the presence of DSBN+. The image was generated by DSBN+ fluorescence emission following excitation via at 488 nm. The layers that compose the vesicles can be seen, demonstrating that these oligoelectrolytes readily associate with the membranes. Subsequent characterization described in more detail below will demonstrate that, indeed, the chromophores span the width of the membranes.

Example 12

Optical Characterization of PV Oligoelectrolytes within Lipid Bilayers

Figure 4:
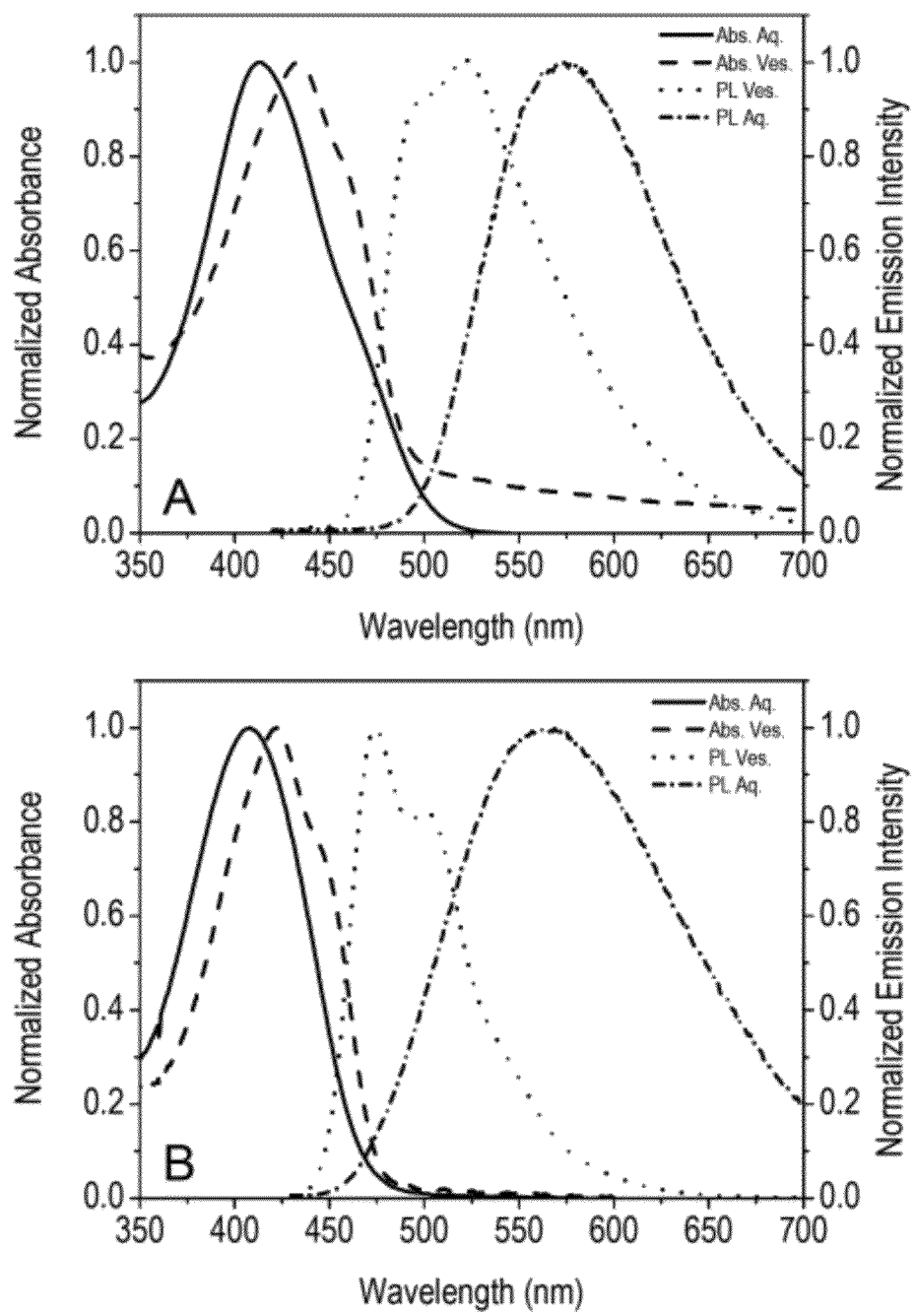
FIG. 4 shows normalized UV-Vis absorbance and PL spectra of (A) DSSN+ and (B) DSBN+ in pH 7.3 HEPES buffer (absorbance=—, emission=-·-·) and while embedded within DMPC vesicle membranes (absorbance=- - -, emission=·····). Both molecules exhibit an indicative red shift in $\lambda_{abs}$ (21 nm and 16 nm for DSSN+ and DSBN+, respectively) and a blue shift in $\lambda_{em}$ (62 nm and 92 nm for DSSN+ and DSBN+, respectively) due to the difference in environmental polarity between an aqueous solvent and the inner region of a lipid bilayer.

Several indicative changes in UV-Vis and PL properties of DSSN+ and DSBN+ are observed upon association with phospholipid bilayer membranes. A comparison of the UV-Vis and PL spectra of DSSN+ and DSBN+ in water and lipid bilayers is shown in FIG. 4; the corresponding summary of the data is provided in Table 2. Compared to the spectroscopic features of the chromophores in water, one observes a bathochromic shift in $\lambda_{abs}$ (21 nm and 16 nm for DSSN+ and DSBN+, respectively) and a large hypsochromic shift in $\lambda_{em}$ (62 nm and 92 nm for DSSN+ and DSBN+, respectively) when associated with the lipid bilayers. Each shift is accompanied by the appearance of vibronic structure. When compared to the emission features of each chromophore in toluene (FIG. 2), it can be seen that the emission of DSSN+ and DSBN+ with lipid bilayer membranes is consistent with a non-polar environment. The $\in_{max}$ and η values of DSSN+ and DSBN+ embedded in lipid bilayers (8.4 and 4.8 Lmol$^{-1}$cm$^{-1}$×10$^{-4}$ for $\in_{max}$, and 0.85 and 0.59 for η of DSSN+ and DSBN+, respectively) are greater than that of these chromophores in water (6.6 and 6.0 Lmol$^{-1}$ cm$^{-1}$×10$^{-4}$ for $\in_{max}$, and 0.06 and 0.33 for η of DSSN+ and DSBN+, respectively), with the exception of the $\in_{max}$ of DSBN+. These values are also approaching the characteristic values in toluene (10.7 and 8.4 Lmol$^{-1}$ cm$^{-1}$×10$^{-4}$ for $\in_{max}$, and 0.95 and 0.98 for i of DSSN and DSBN, respectively). The observed UV-Vis and PL features of DSSN+ and DSBN+ indicate that these chromophores are embedded within the lipid bilayers and experience the more hydrophobic interior environment of the membrane (Bose, D.; Ghosh, D.; Das, P.; Girigoswami, A.; Sarkar, D.; Chattopadhyay, N. *Chem. Phys. Lipids.* 2010, 163, 94-101).

TABLE 2

Comparison of UV-Vis absorbance and PL spectroscopy of DSSN+ and DSBN+ in water and lipid bilayers

| | water | | lipid bilayer | |
|---|---|---|---|---|
| | $\lambda_{abs}(\in_{max})^a$ | $\lambda_{em}(\eta)^b$ | $\lambda_{abs}(\in_{max})$ | $\lambda_{em}(\eta)$ |
| DSSN+ | 412 (6.6) | 594 (0.06) | 433 (8.4) | 532 (0.85) |
| DSBN+ | 406 (6.0) | 566 (0.33) | 422 (4.8) | 474 (0.59) |

$^a\in_{max}$ values are reported in units of Lmol$^{-1}$cm$^{-1}$ × 10$^{-4}$.
$^b$η values were obtained relative to a fluorescein standard at pH 12.

Figure 5:
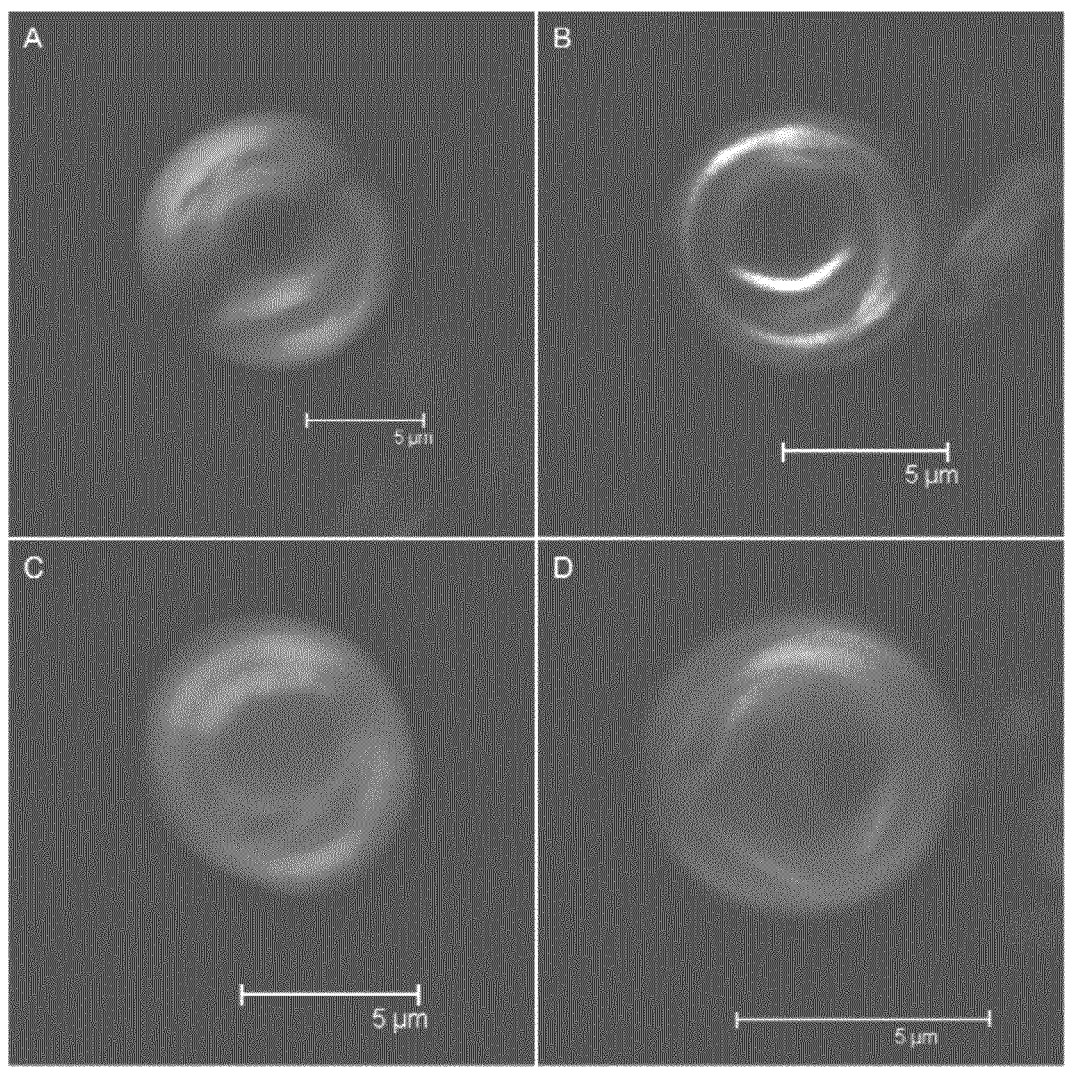
FIG. 5 shows confocal microscopy fluorescence images of a multi-lamellar vesicles containing 5 mol % oligoelectrolyte (10 mg/mL). (A) DMPC/DSBN+. (B) DPPC/DSBN+. (C) DMPC/DSSN+. (D) DPPC/DSSN+. Images were collected by excitation at 488 nm.

FIG. 5 displays four confocal microscopy images of modified multi-lamellar vesicles, each corresponding to one of the four lipid/oligoelectrolyte combinations (DMPC/DSBN+, DPPC/DSBN+, DMPC/DSSN+, and DPPC/DSSN+; each 5 mol % COE). These images, obtained following excitation of the chromophores, illustrate preferential accumulation inside the vesicle membranes. These images also suggest excellent structural diversity, i.e. the short/long COEs can both be incorporated into bilayers composed of lipids of varying tail lengths.

Oligoelectrolyte Molecular Orientation within Lipid Bilayers

Molecular orientations of DSBN+ and DSSN+ were probed via confocal microscopy by examination of the emission intensity profile of the COEs within stationary vesicles following excitation using a polarized source. Oligo(phenylenevinylenes) posses a primary transition dipole (μ) that is oriented along the long molecular axis (Gierschner, J.; Ehni, M.; Egalhaaf, H-J.; Medina, B. M.; Beljonne, D.; Benmansour, H.; Bazan, G. C. J. *Chem. Phys.* 2005, 123, 144914; Spano, F. C. *Chem. Phys. Lett.* 2000, 331, 7-13). The probability of generating an emissive excited state using a polarized excitation source depends on the orientation of μ with respect to the plane of polarization of the excitation light (Bur, A. J.; Roth, S. C.; Thomas, C. L. *Rev. Sci. Instrum.* 2000, 71, 1516-1523; Bur, A. J.; Lowry, R. E.; Roth, S. C.; Thomas, C. L.; Wang, F. W. *Macromolecules.* 1992, 25, 3503-3510). An immobilized membrane with DSBN+ or DSSN+ in the expected molecular orientation should exhibit regions with greater and less emission upon excitation with a polarized excitation source. This concept has been previously employed to investigate local order in smectic liquid crystals (Smalyukh, I. I.; Shiyanovskii, S. V.; Lavrentovich, O. D. *Chem. Phys. Lett.* 2001, 336, 88-96).

Figure 6:
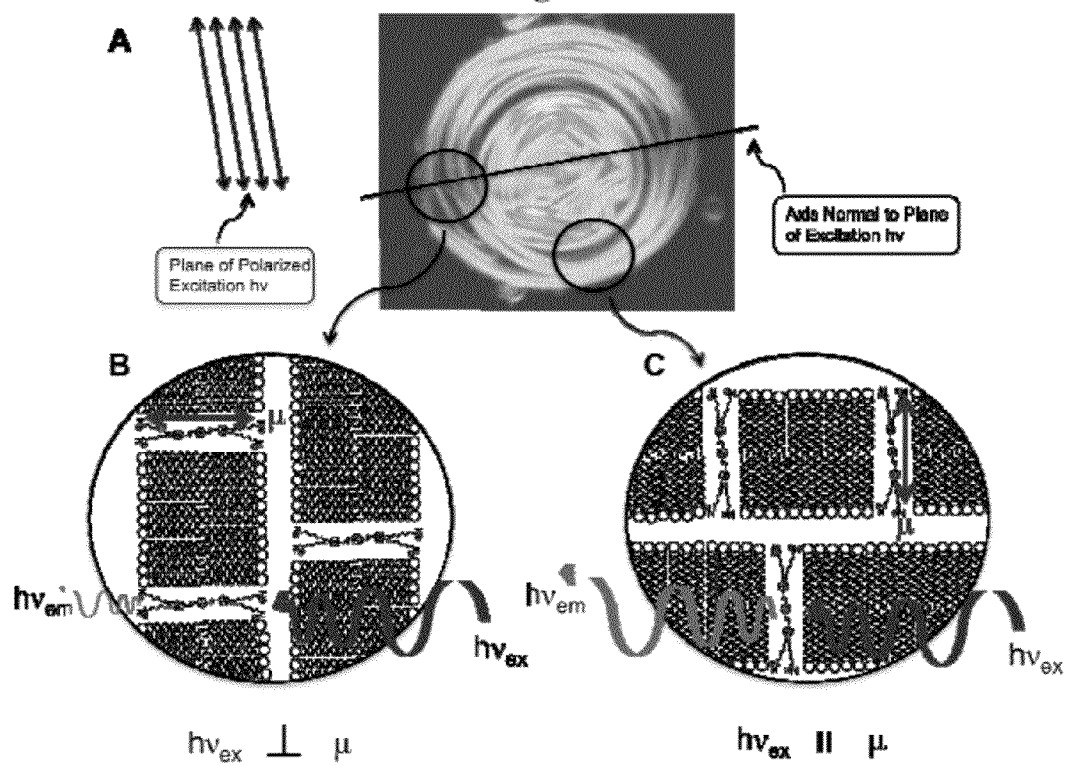
FIG. 6 shows (A) Image of a stationary multi-lamellar DMPC vesicle (diameter=~15 µm) containing 3 mol % DSBN+ that exhibits an equatorial extinction line (black line) perpendicular to the plane of the 488 nm Ar laser excitation light. (B) A closer view within the extinction line region in which DSBN+ molecules are oriented with their transition dipoles (arrow labeled µ) perpendicular to the plane of the excitation light (right arrow labeled $hv_{ex}$) resulting in attenuated emission (left arrow arrow labeled $hv_{em}$). (C) A closer view within the regions above and below the extinction line in which DSBN+ transition dipoles are oriented parallel to the plane polarized excitation light (right arrow labeled $hv_{ex}$) resulting in a greater number of excited states and stronger emission (left arrow arrow labeled $hv_{em}$).

FIG. 6A provides the confocal fluorescence image of a stationary vesicle obtained upon excitation of membrane-embedded DSBN+ with a polarized excitation source. The vesicle image contains an equatorial region (highlighted by a black line) with attenuated intensity perpendicular to the plane of the polarized light. These intensity distributions can be used to determine the preferred orientations of µ. Specifically, less intense emission is anticipated in regions where µ is perpendicular to the plane of polarized excitation light, as illustrated in FIG. 6B. Conversely, as shown in FIG. 6C, the alignment of chromophores such that µ is parallel to the plane of incident polarized light favors excitation, leading to greater emission intensity. In FIGS. 6B and 6C, the emission output is schematically represented by the size of the green arrows. The results indicate that DSBN+ and DSSN+ exist within lipid bilayers in an ordered orientation with the long axis perpendicular to the plane of the membrane. This molecular orientation is fully consistent with the integration of π-segments and polar groups as shown in FIG. 1.

Example 13

Transmembrane Electron Transport

OPVs within a saturated alkane thiol monolayer can facilitate charge tunneling from a metallic electrode to a tethered redox species (Dudek, S. P.; Sikes, H. D.; Chidsey, C. E. D. *J. Am. Chem. Soc.* 2001, 123, 8033-8038; Sikes, H. D.; Smalley, J. F.; Dudek, S. P.; Cook, A. R.; Newton, M. D.; Chidsey, C. E. D.; Feldberg, S. W. *Science.* 2001, 291, 1519-1523). A variation of this approach was used in which supported bilayer membranes (sBLM) containing DSSN+, DSBN+ and other control molecules were prepared on the surface of a glassy carbon electrode surface. The sBLM-modified electrodes were then employed in a series of 'blocking' experiments in which cyclic voltammetry was used to monitor the reversible oxidation of aqueous ferricyanide. The unmodified sBLM acts as an insulating layer between the working electrode and the solution containing ferricyanide thereby greatly suppressing the redox current (Wiegand, G.; Arribas-Layton, N.; Hillebrandt, H.; Sackmann, E.; Wagner, P. *J. Phys. Chem. B.* 2002, 106, 4245-4254; Żebrowska, A.; Krysiński, P.; Łotowski, Z. *Bioelectrochemistry.* 2002, 56, 179-184). DSBN+ and DSSN+ within an sBLM are oriented with their long axes perpendicular to the surface of the electrode, thus potentially forming a transmembrane molecular wire through which electrons tunnel to and from redox species at the water-membrane interface.

In these experiments, a bare glassy carbon electrode and glassy carbon electrodes supporting DMPC and DPPC BLMs containing no additional components, 2 mol % tridodecylamine (TDA), 2 mol % DSSN+ and 2 mol % DSBN+ (relative to lipid) were used to collect voltammograms in the presence of an aqueous 0.5 M KCl solution containing 2 mM ferricyanide. The surface of the electrode was pretreated, according to literature protocols, to promote bilayer formation (Huang, W.; Zhang, Z.; Han, X.; Tang, J.; Wang, J.; Dong, S.; Wang, E. *Biophys. J.* 2002, 83, 3245-3255; Wu, Z.; Tang, J.; Cheng, Z.; Yang, X.; Wang, E. *Anal. Chem.* 2000, 72, 6030-6033). Specifically, membranes were prepared by depositing 3 µL of a 2 mg/mL lipid stock solution containing either 0 or 2 mol % DSSN+, DSBN+ or TDA onto a surface modified electrode, followed by submerging into pH 7.4 phosphate buffer to allow sBLM formation. The sBLM containing TDA provides a control sample to examine whether additional membrane components and possible structural modifications increase electron transfer to redox species in solution.

Figure 7:
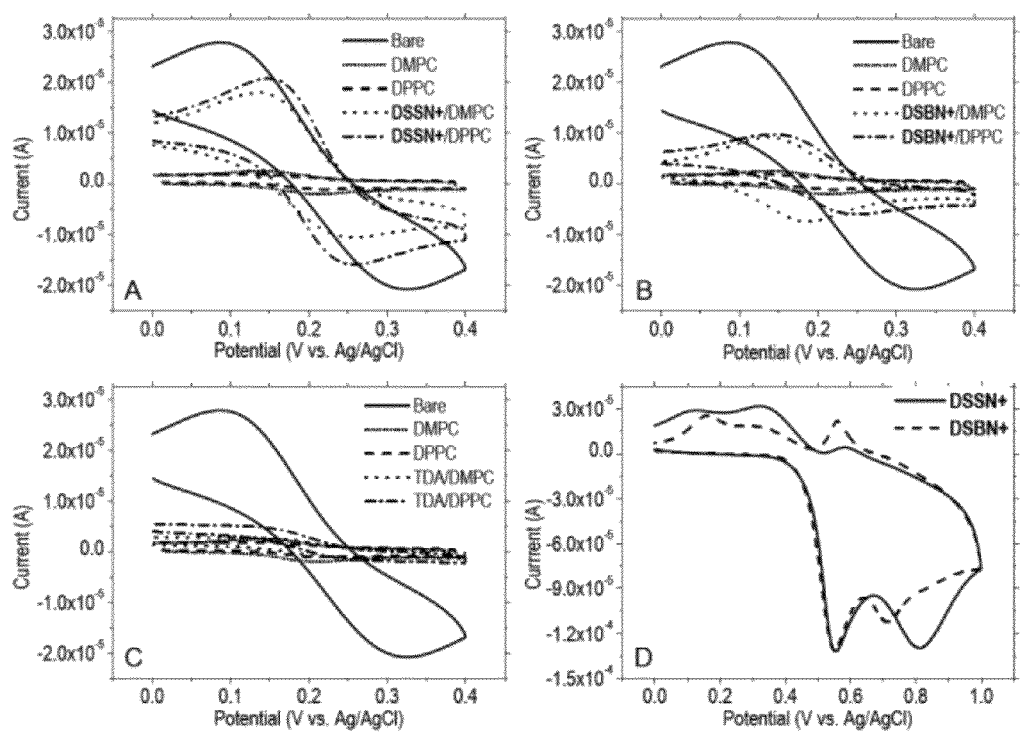
FIG. 7 shows (A-C) Results of the cyclic voltammetry blocking experiment that indicate that DSSN+ (A) and DSBN+ (B) facilitate transmembrane electron transport across insulating sBLMs from the glassy carbon electrode surface to aq. ferricyanide. The insulating effect can be seen by comparison of the prevalent reversible redox couple observed when a bare electrode is employed (A-C; —) that is absent in the traces obtained using electrodes supporting unmodified BLMs (A-C; ········· ; and - - - for DMPC and DPPC sBLMs, respectively). The facilitation of electron transport by DSSN+ and DSBN+ can be seen by the greater current observed when an electrode bearing a sBLM containing 2 mol % of DSSN+ or DSBN+ is employed ( ····· and –··– for modified DMPC and DPPC sBLMs, respectively). Little to no transmembrane electron transfer occurs across an sBLM containing 2 mol % TDA (C; ( ····· and –··– for modified DMPC and DPPC sBLMs). (D) Current/potential curves corresponding to DSSN+ and DSBN+ show an oxidation (~0.55 V vs. Ag/AgCl) above that of ferricyanide (~0.3 V vs. Ag/AgCl). This data suggests a charge tunneling process. All traces shown were obtained using a 200 mV/s scan rate.

FIG. 7 shows the results of the sBLM blocking experiments. The reversible ferricyanide oxidation ($E_{p(ox)}$=0.252 V vs. SCE) is observed in the voltammogram obtained by using a bare glassy carbon electrode (A-C, black curves). The insulating property of an unmodified sBML is confirmed by nearly featureless CV traces (FIG. 7A-C, blue and green curves). Similarly, the CV traces obtained employing an electrode supporting a BLM containing 2 mol % TDA is also featureless (FIG. 7C); evidence that the presence of this component does not perturb the bilayer structure.

CV traces corresponding to sBLMs modified with DSSN+ and DSBN+ (FIGS. 5A and 5B, purple and red for modified DMPC and DPPC sBLMs, respectively) display higher currents with respect to the control experiments, indicating that transmembrane electron transfer is facilitated. That observed oxidation occurs at $E_{p(ox)}$=~0.3 V vs. Ag/AgCl and $E_{p(red)}$=~0.1 V vs. Ag/AgCl (FIG. 5A-C), below the oxidation potential of DSSN+ and DSBN+ (FIG. 5D, $E_{ox}$=~0.55 V), suggests a transmembrane tunneling process. The ability of DSSN+ to better facilitate transmembrane electron transport can be seen by the greater current response corresponding to runs employing sBLMs containing DSSN+(FIG. 7A) instead of DSBN+ (FIG. 7B). This higher current may be attributed to the ability of DSSN+ to more completely span the membrane structure due to its more extended conjugation length.

The results obtained from the CV blocking experiments indicate that transmembrane charge transfer through insulating sBLMs is facilitated upon incorporation of DSSN+ and DSBN+. Furthermore, these COEs may act as 'molecular wire' tunneling pathways.

Example 14

Interaction with Living Systems

Figure 8:
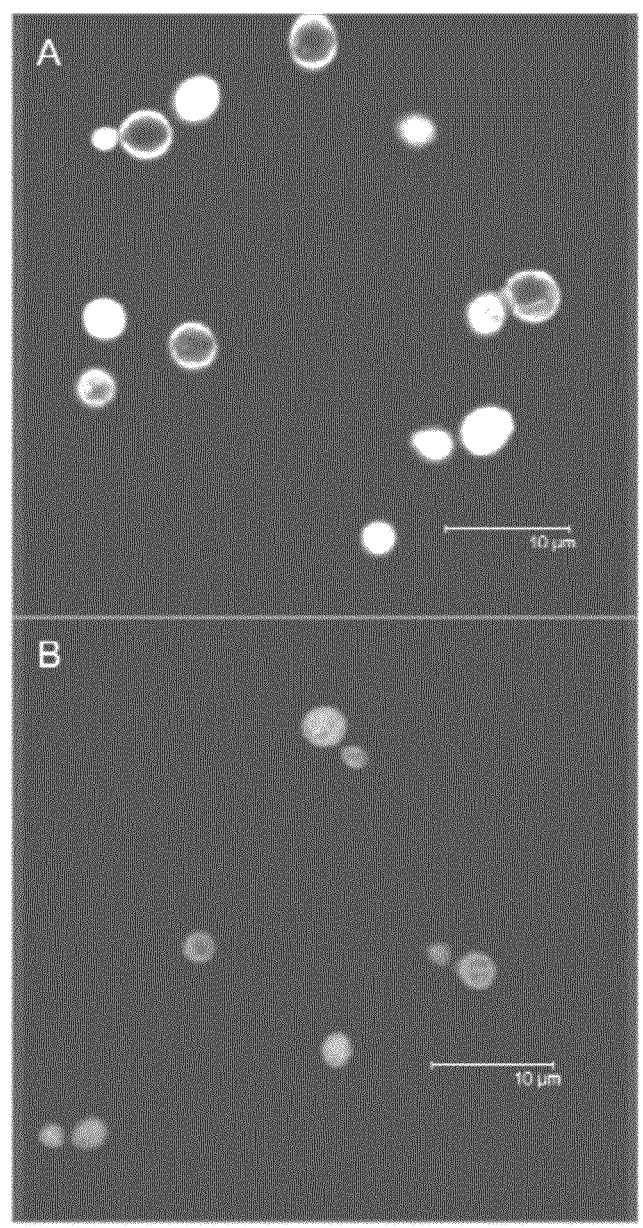
FIG. 8 shows confocal microscopy fluorescence images of Baker's yeast stained with 100 µM DSSN+ (A) and DSBN+ (B) upon excitation at 488 nm. It can be seen that these dyes readily interact with the membranes of living cells. Note that some cells (that are imaged in the focal plane) posses the equatorial extinction line that indicates an ordered molecular orientation within cell membranes.

FIG. 8 consists of two sets of confocal microscopy fluorescence images of Baker's yeast, each stained and imaged in a 100 µM solution of DSSN+ (FIG. 8A) or DSBN+ (FIG. 8B) after 1 hour of shaking without exchanging the staining media. These images illustrate the apparent preferential accumulation of the COEs within cell membranes, in agreement with other reports in which amphiphilic compounds are introduced to living systems (Reeve, J. E.; Collins, H. A.; Mey, K. D.; Kohl, M. M.; Thorley, K. J.; Paulsen, O.; Clays, K.; Anderson, H. L. *J. Am. Chem. Soc.* 2009, 131, 2758-2759). The lack of background fluorescence is attributed to the low η of these chromophores when in contact with water.

Example 15

COE Electron Transport Mediators in Yeast Microbial Fuel Cells

Microbial fuel cells (MFCs) function on the principle that electrons from the metabolic cycle of many anaerobic and facultative organisms known as exoelectrogens can be used to generate a useful electrical current (Logan, B. E. *Nature*

Figure 9:
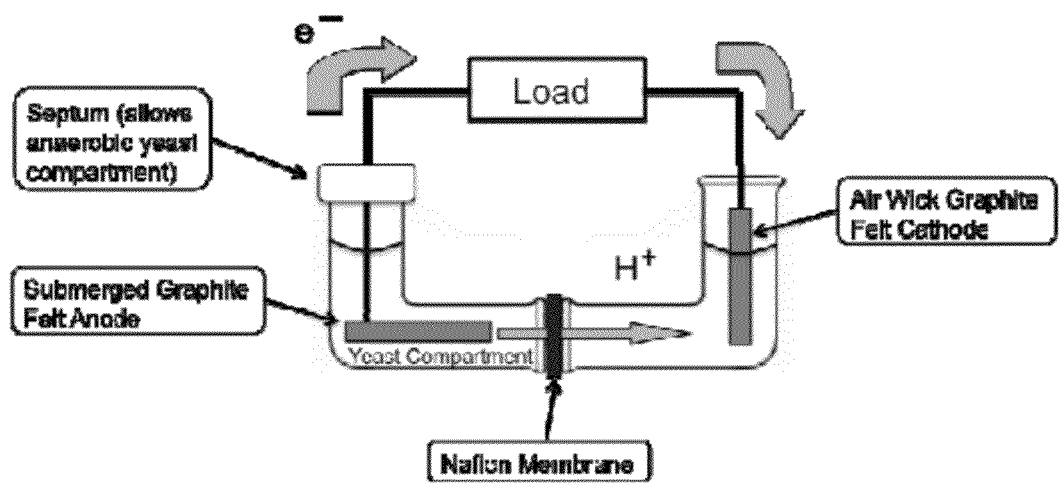
FIG. 9 is a schematic of the U-tube MFC design (see Milliken, C. E.; May, H. D. *Appl. Microbiol. Biotechnol.* 2007, 73, 1180-1189; Sund, C. J.; Wong, M. S.; Sumner, J. J. *Biosens. Bioelectron.* 2009, 24, 3144-3147; Sund, C. J.; McMasters, S.; Crittenden, S. R.; Harrell, L. E.; Sumner, J. J. *Appl. Microbiol. Biotechnol.* 2007, 76, 561-568) employed in this study. The MFC is composed of an anaerobic anode/yeast compartment that is separated by a proton permeable Nafion membrane from an aerobic cathode compartment.

*Reviews Microbiology.* 2009, 7, 375-381; Schaetzle, O.; Barriere, F.; Baronian, K. *Energy Environ. Sci.* 2008, 1, 607-620). Recent work has shown that a surprisingly large number of organisms exhibit exoelectrogenic character (Ref. 35; Logan, B. E.; Regan, J. M. *Trends in Microbiology.* 2006, 14, 512-518; Lovley, D. R. *Nature Reviews Microbiology.* 2006, 4, 497-508). Extracting energy from these organisms is typically achieved by using a strategy similar to that employed in a chemical fuel cell. Typically, a community of microorganisms populating a high surface area electrode in an anaerobic environment oxidizes biological fuels such as sugars in an anode compartment. This anode compartment is commonly separated from a cathode compartment by a proton exchange membrane that facilitates charge balance, much like a salt bridge in a galvanic cell. The cathode compartment is typically aerobic and is the site of oxygen reduction, which completes the oxidation-reduction reaction of the whole cell. Electrons gained from bio-fuel oxidation at the anode must flow through a desired pathway (the lead between the electrodes) in order to participate in oxygen reduction at the cathode, thus generating a usable potential (Ref. 35 (b) Walker, A. L.; Walker, C. W. Jr. *J. Power Sources.* 2006, 160, 123-129). A schematic of a U-tube type MFC that outlines the key compartments and components is shown in FIG. 9. Although the MFC concept is relatively simple, much remains poorly understood about the factors that influence their performance at the molecular, cellular, and device level (Logan, B. E.; Regan, J. M. *Environ. Sci. Technol.* 2006, 40, 5172-5180; Yazdi-Rismani, H.; Carver, S. M.; Christy, A. D.; Tuovinen, O. H. *J. Power Sources.* 2008, 180, 683-694; Zhao, F.; Slade, R. C. T.; Varcoe, J. L. *Chem. Soc. Rev.* 2009, 38, 1926-1939).

Some exoelectrogens are capable of direct electron transfer to an electrode while others require an electron transport mediator (Watanabe, K.; Manefield, M.; Lee, M.; Kouzuma, A. *Curr. Opin. Biotechnol.* 2009, 20, 633-641). Common mediators employed in bacterial and yeast fuel cells are diffusion based redox carriers that are membrane permeable, such as methylene blue and neutral red (Gunawarddena, A.; Fernando, S.; To, F. *Int. J. Mol. Sci.* 2008, 9, 1893-1907). These types of mediators may have undesirable features, such as cellular uptake that does not favor electron transfer, redox properties that are not compatible with target species and substrates (Wilkinson, S.; Klar, J.; Applegarth, S. *Electroanalysis.* 2006, 18, 2001-2007), and possible diffusion limited kinetics (Bullen, R. A.; Arnot, T. C.; Lakeman, J. B.; Walsh, F. C. *Biosens. Bioelectron.* 2006, 21, 2015-2045; Tones, C. I.; Marcus, A. K.; Lee, H.-S.; Parameswaran, P.; Krajmalnik-Brown, R.; Rittmann, B. E. *FEMS Microbiol. Rev.* 2010, 34, 3-17). It would thus be beneficial to modify microorganisms with structural features that enable transmembrane electron transport and that do not impede their metabolic function. The accumulated information on DSSN+ and DSBN+ argues that these molecular species display all the desirable features to accomplish this modification.

A U-tube type MFC (Milliken, C. E.; May, H. D. *Appl. Microbiol. Biotechnol.* 2007, 73, 1180-1189; Sund, C. J.; Wong, M. S.; Sumner, J. J. *Biosens. Bioelectron.* 2009, 24, 3144-3147; Sund, C. J.; McMasters, S.; Crittenden, S. R.; Harrell, L. E.; Sumner, J. J. *Appl. Microbiol. Biotechnol.* 2007, 76, 561-568) (FIG. 9) was employed to test and compare the performance of a series of yeast MFCs employing nM concentrations of DSSN+ and DSBN+ to the performance of a series of negative controls with no external mediator and a series of positive controls employing the common electron transport mediator methylene blue in $\mu$M concentrations. The details of MFC construction, preparation, and evaluation are discussed in detail in the section entitled "Microbial fuel cell preparation and assembly." MFC performance was evaluated in terms of voltage instead of current. Voltage readings were obtained as a function of current across a 10 k$\Omega$ resistor.

Figure 10:
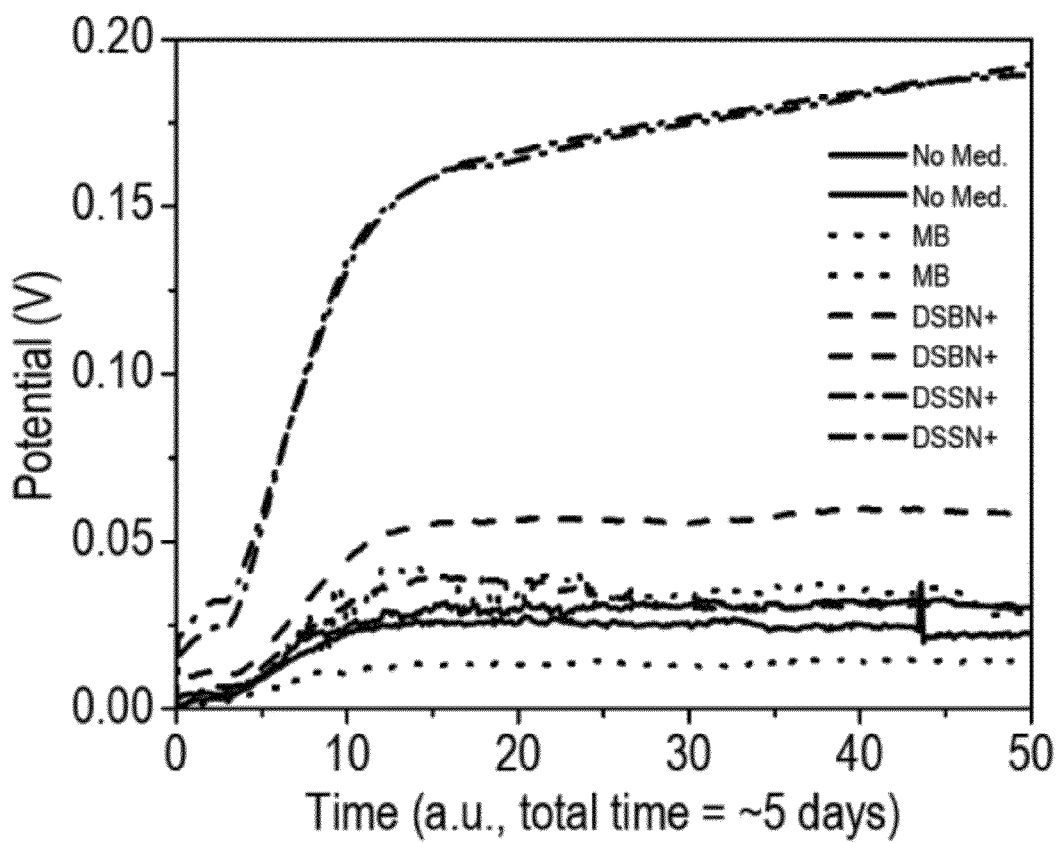
FIG. 10 shows plots of yeast MFC voltage production as a function of time for MFCs containing no mediator (—), 13 µM methylene blue ( ····· ) 190 nM DSBN+ ( - - - ), and 190 nM DSSN+( –··– ). Two separate sets of data are shown for each set of conditions. Voltage is measured as a function of current across a 10 kΩ resistor. Note the large increase in performance afforded by DSSN+ despite a concentration two orders of magnitude lower than that of the common diffusion-based electron transport mediator methylene blue.

FIG. 10 shows the relative performance of the tested MFCs. Maximum voltages ($V_{max}$) obtained for the mediatorless MFCs and those employing 13 $\mu$M methylene blue are ~25 mV (green) and ~40 mV (blue), respectively. MFCs employing the shorter oligoelectrolyte DSBN+ (190 nM) produce slightly greater voltages ($V_{max}$=~55 mV, orange plots). A notable increase in performance is afforded by the longer DSSN+ (190 nM), which resulted in a ~5 fold increase in voltage production ($V_{max}$=~200 mV) compared to methylene blue, despite being two orders of magnitude lower in concentration. Furthermore, the difference in performance between MFCs employing DSSN+ and DSBN+ is consistent with the difference in transmembrane electron transport properties observed in the cyclic voltammetry experiments.

Figure 11:
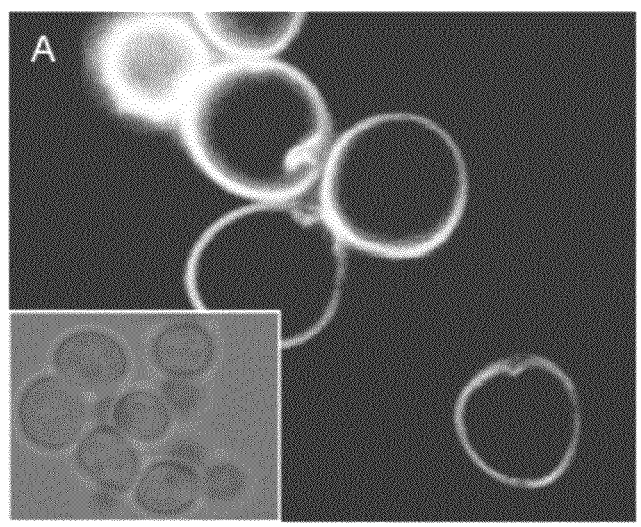
FIG. 11 shows (A) Epi-fluorescence image of yeast in growth media containing 25 µM DSSN+ prior to fuel cell inoculation. The yeast is stained such that the primarily cell membranes can be seen. Inset: example brightfield image of the sample prior to inoculation. (B) Epi-fluorescence image of yeast removed from the MFC on day 4 of operation. Although emission is not very intense these cells contain DSSN+ despite the large dilution upon inoculation (to a nM regime) and exponential increase in the number of total cells over the course of 4 days. Inset: Brightfield image that matches the day 4 epi-fluorescence image. Note: $\lambda_{ex}$=~480 nm provided by a Hg lamp and the proper filter. This excitation range is out of the range of absorbance of the fluorescent amino acids tryptophan, tyrosine and phenylalanine ($\lambda_{abs}$ (Trp, Tyr, Phe)=~220-320 nm), thus any observed emission is attributed to DSSN+.
Figure 11:
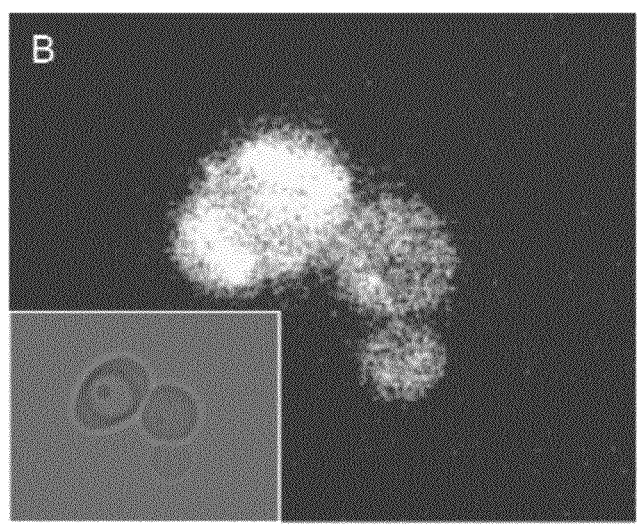

The ability of DSBN+ and DSSN+ to be passed on to or exist within cell membranes of subsequent yeast generations born over the course of MFC operation was also investigated. Aliquots of an MFC using the mediator DSSN+ were taken before MFC inoculation and after 4 days of MFC operation. Cells from each of these aliquots were imaged using a confocal microscope in epi-fluorescence mode and brightfield mode. FIG. 11A corresponds to the yeast sample containing 25 $\mu$M DSSN+ that was used to inoculate the MFC series corresponding to this mediator. This particular staining/cell membrane modification procedure consisted of light shaking for 3 hours in the presence of $\mu$M oligomer concentrations. The external cell membranes are observable due to emission of DSSN+. FIG. 11B is an epi-fluorescence and brightfield image (inset, lower left) of a small group of yeast cells removed from the same MFC on the fourth day of operation. These images were collected using the same setup as the images in FIG. 11A and demonstrate the presence of this mediator in later cell generations. The emission is much less intense, an effect that is not surprising considering the exponentially greater number of cells present after 4 days of cell reproduction. This result indicates that DSSN+ can be passed on to daughter cells either during budding reproduction (implying that some cellular uptake, into cytoplasm, occurs) and/or by an equilibrium between membrane embedded and aqueous DSSN+.

The disclosures of all publications, patents, patent applications and published patent applications referred to herein by an identifying citation are hereby incorporated herein by reference in their entireties.

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

What is claimed is:

1. A microbial fuel cell, comprising:
   an anode compartment comprising an anode in contact with a microbe-containing analyte;
   a cathode compartment comprising a cathode in contact with a catholyte;
   a cation-permeable membrane separating the anode compartment and the cathode compartment; and
   an electrical connection between the anode and the cathode;
   wherein the microbes in the microbe-containing analyte comprise a cell membrane formed of a lipid bilayer having a charge-transfer agent substantially residing therewithin so as to facilitate transmembrane electron transport, wherein the charge-transfer agent comprises: a first region which is hydrophilic, a second region of electronic delocalization, and a third region which is hydrophilic;

wherein the charge-transfer agent is of sufficient length such that the first region contacts with the external environment of the microbe and/or the hydrophilic portion of the cell membrane of the microbe facing the external environment, the second region contacts with the hydrophobic portion of the cell membrane of the microbe, and the third region contacts with the cytosol of the microbe and/or the hydrophilic portion of the cell membrane of the microbe facing the cytosol, respectively.

2. The microbial fuel cell of claim 1, wherein the lipid bilayer of the cell membrane of the microbes includes a hydrophobic conjugated inner region within the cell membrane and polar pendant group terminals oriented outwardly on either side of the lipid bilayer which define a plane the membrane, and a longitudinal axis of the charge-transfer agent orients substantially normal to the plane of the membrane lipid bilayer.

3. The microbial fuel cell of claim 1, wherein the charge-transfer agent spans at least about 60% to at least about 150% of the width of the cell membrane when in extended conformation.

4. The microbial fuel cell of claim 1, wherein the charge-transfer agent is an electron-transfer agent of the form:

where $R_e$ and $R_f$ can be the same or different and are groups containing a hydrophilic moiety, and Pi is a molecule with a delocalized π-electron system.

5. The microbial fuel cell of claim 4, wherein the Pi component of the electron-transfer agent ranges from about 1 nm to about 10 nm.

6. The microbial fuel cell of claim 4, wherein the electron transfer agent is selected from the group consisting of:

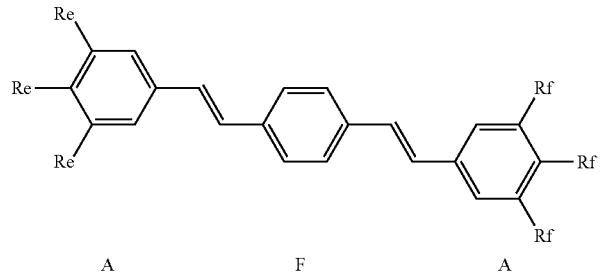

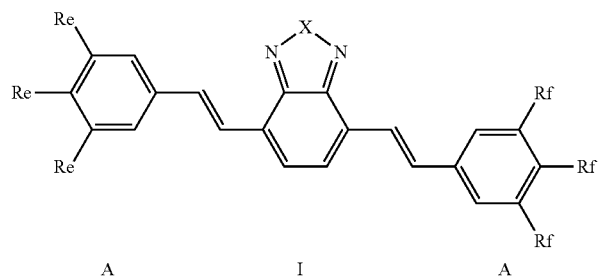

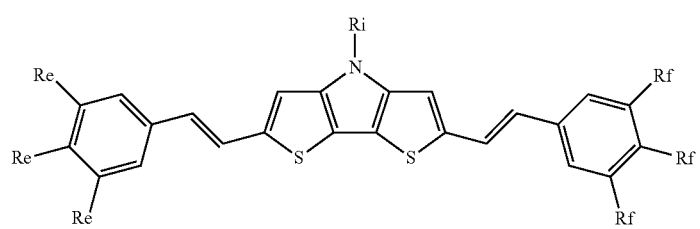

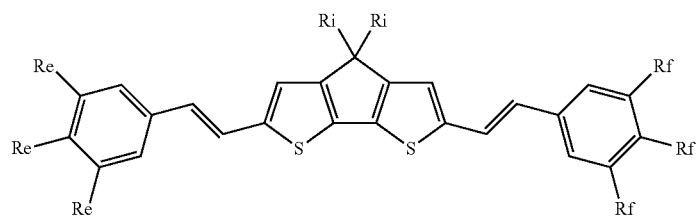

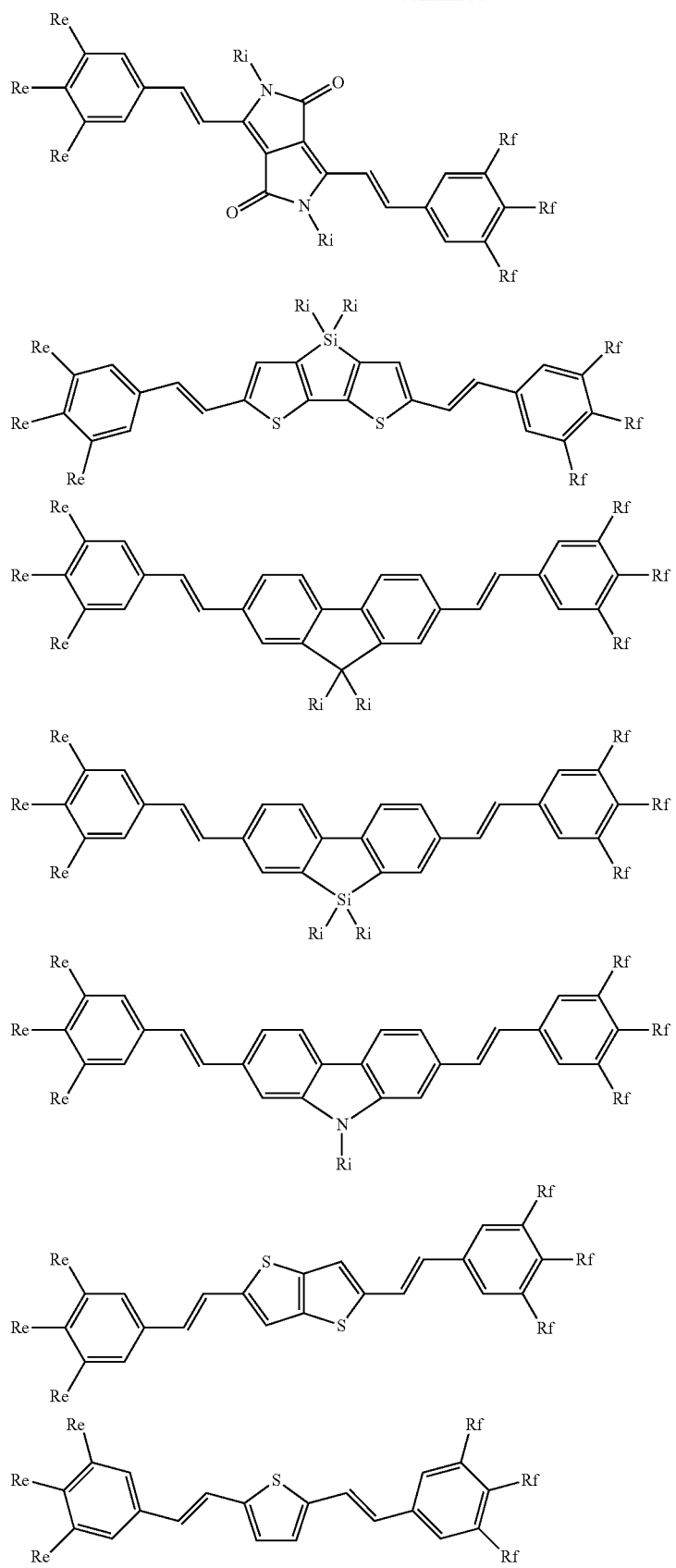

-continued
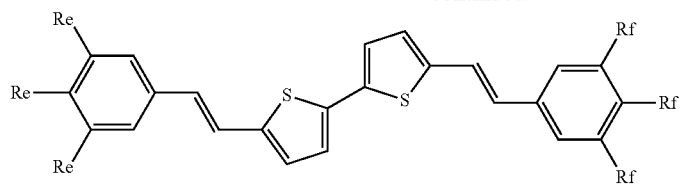
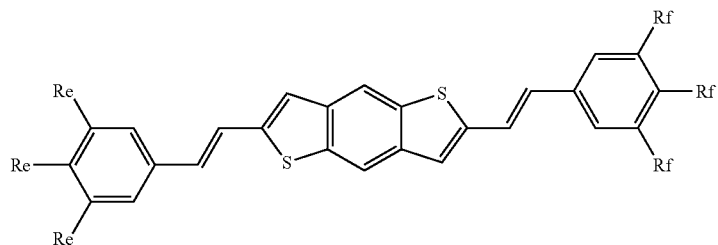
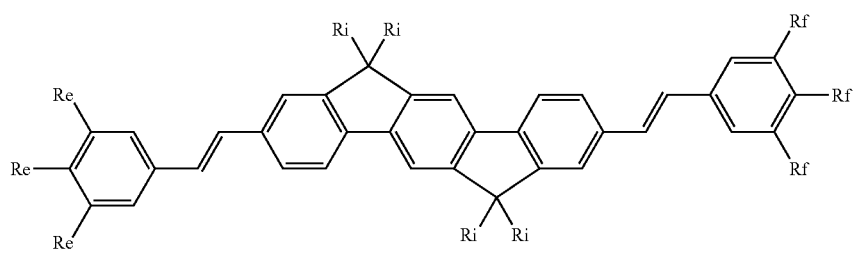
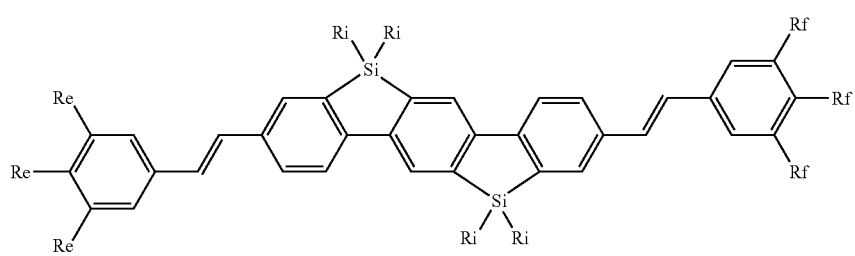
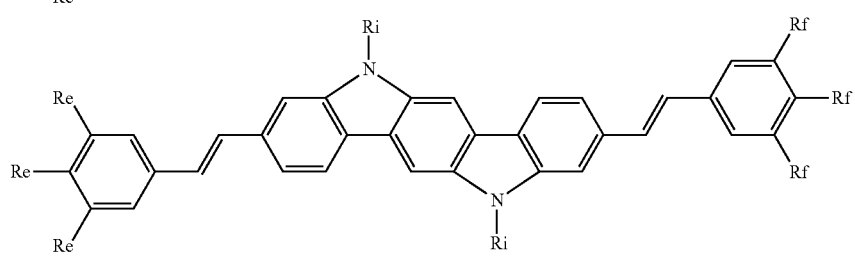
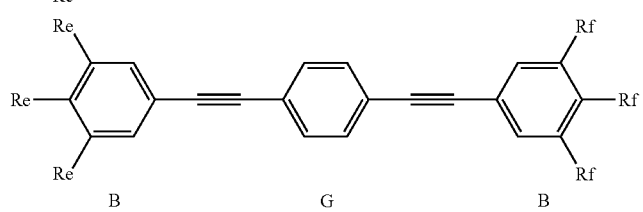
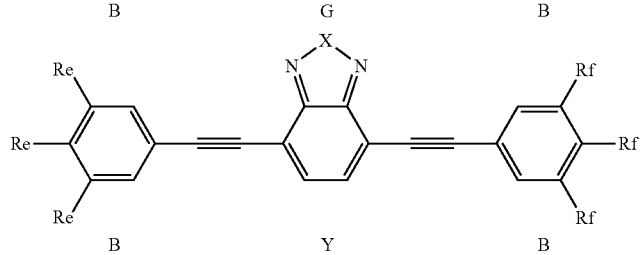

-continued
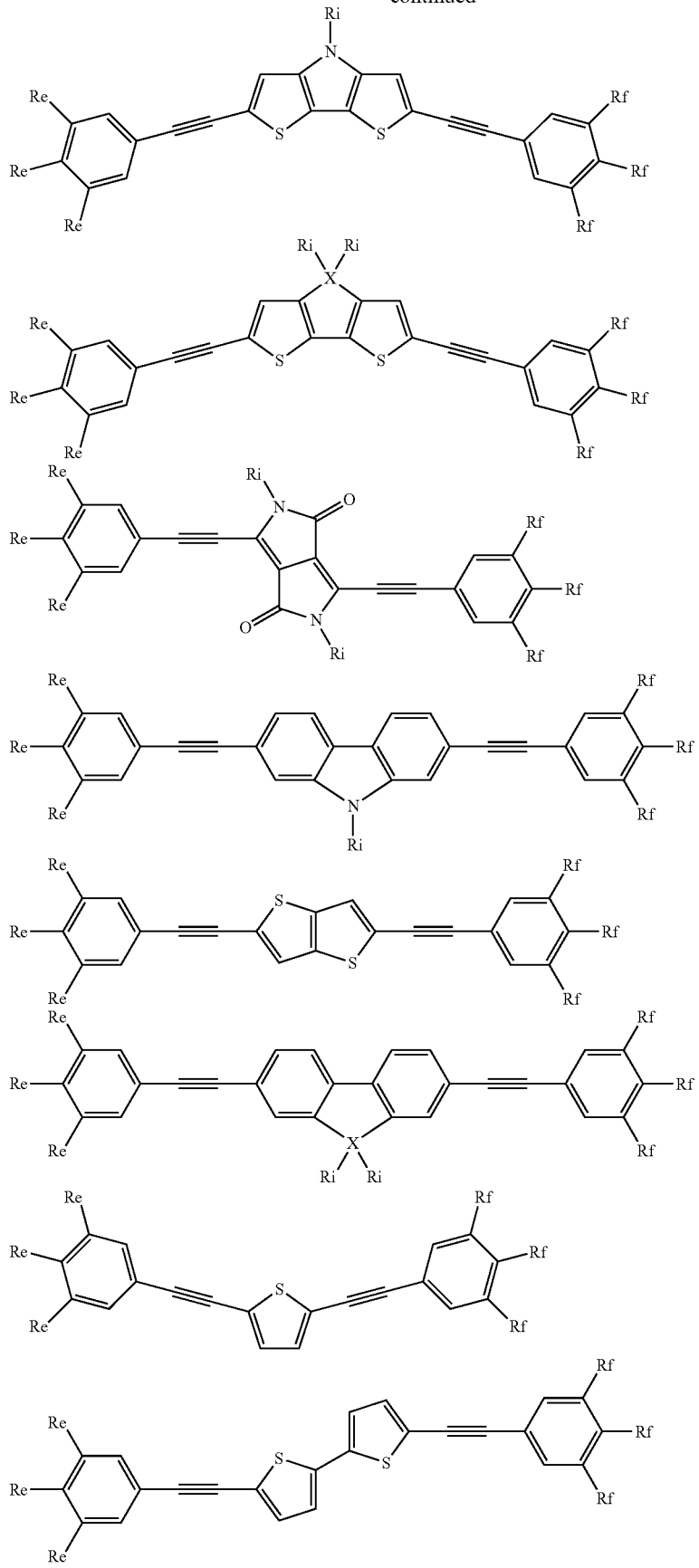

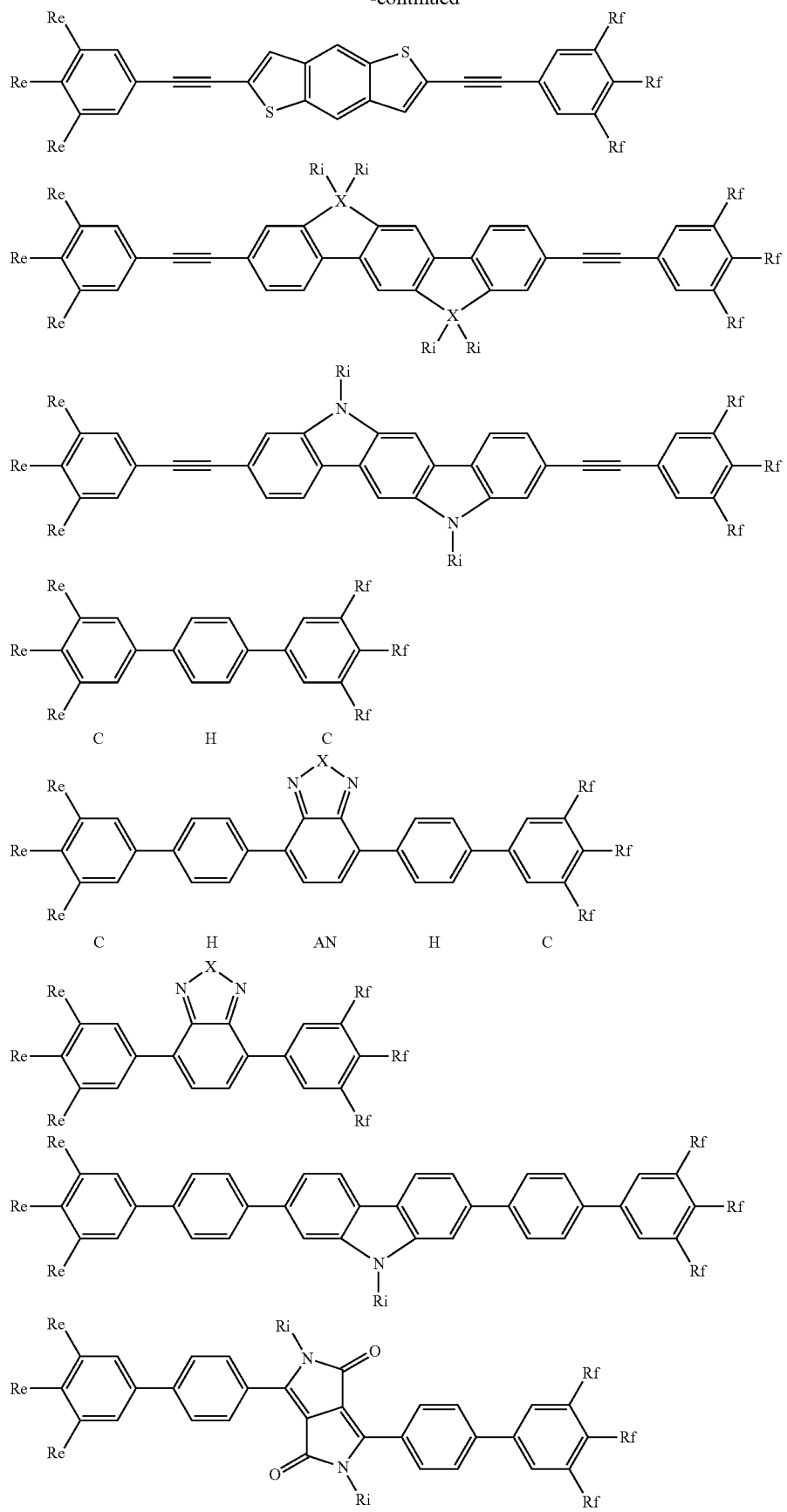

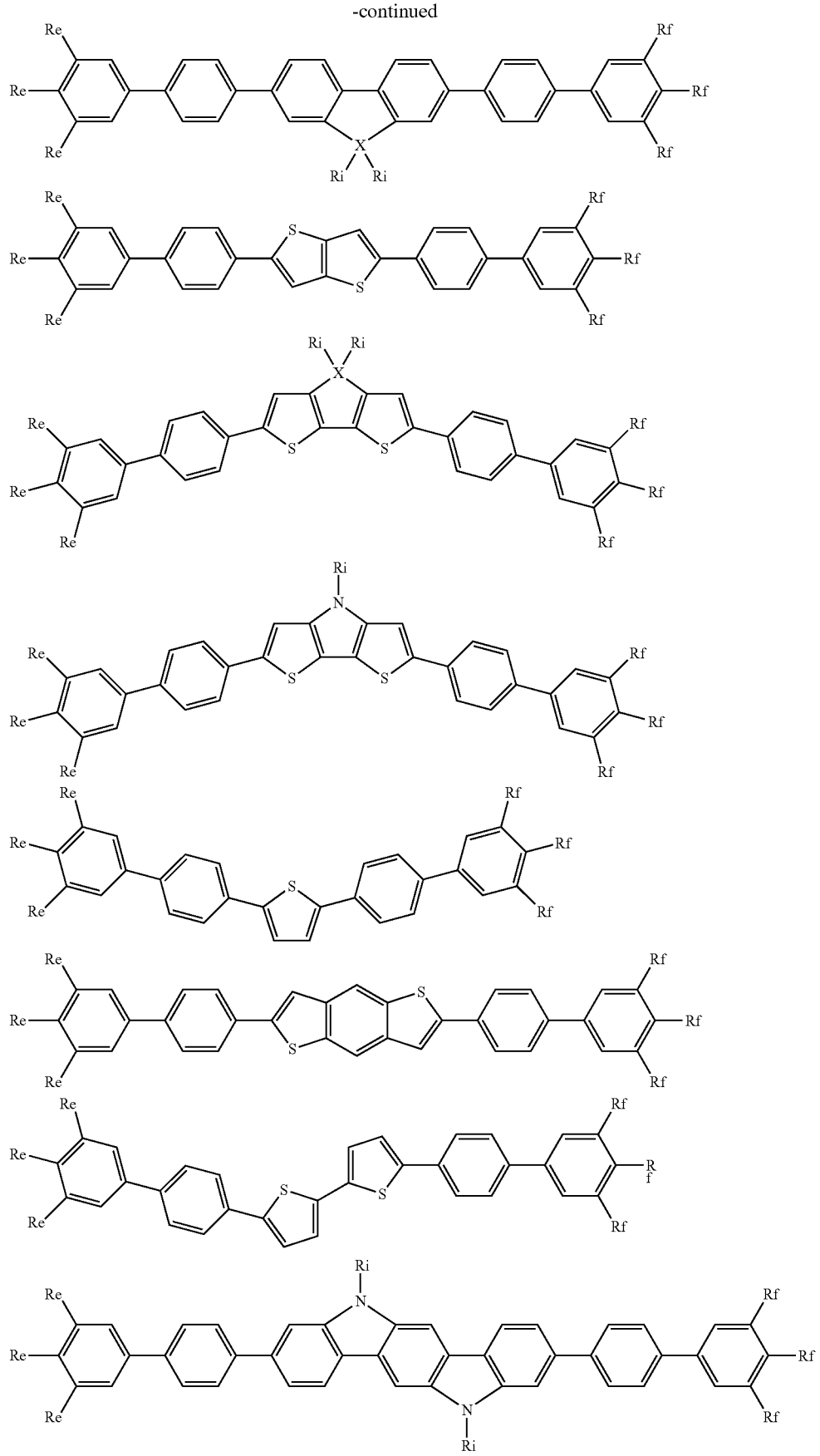

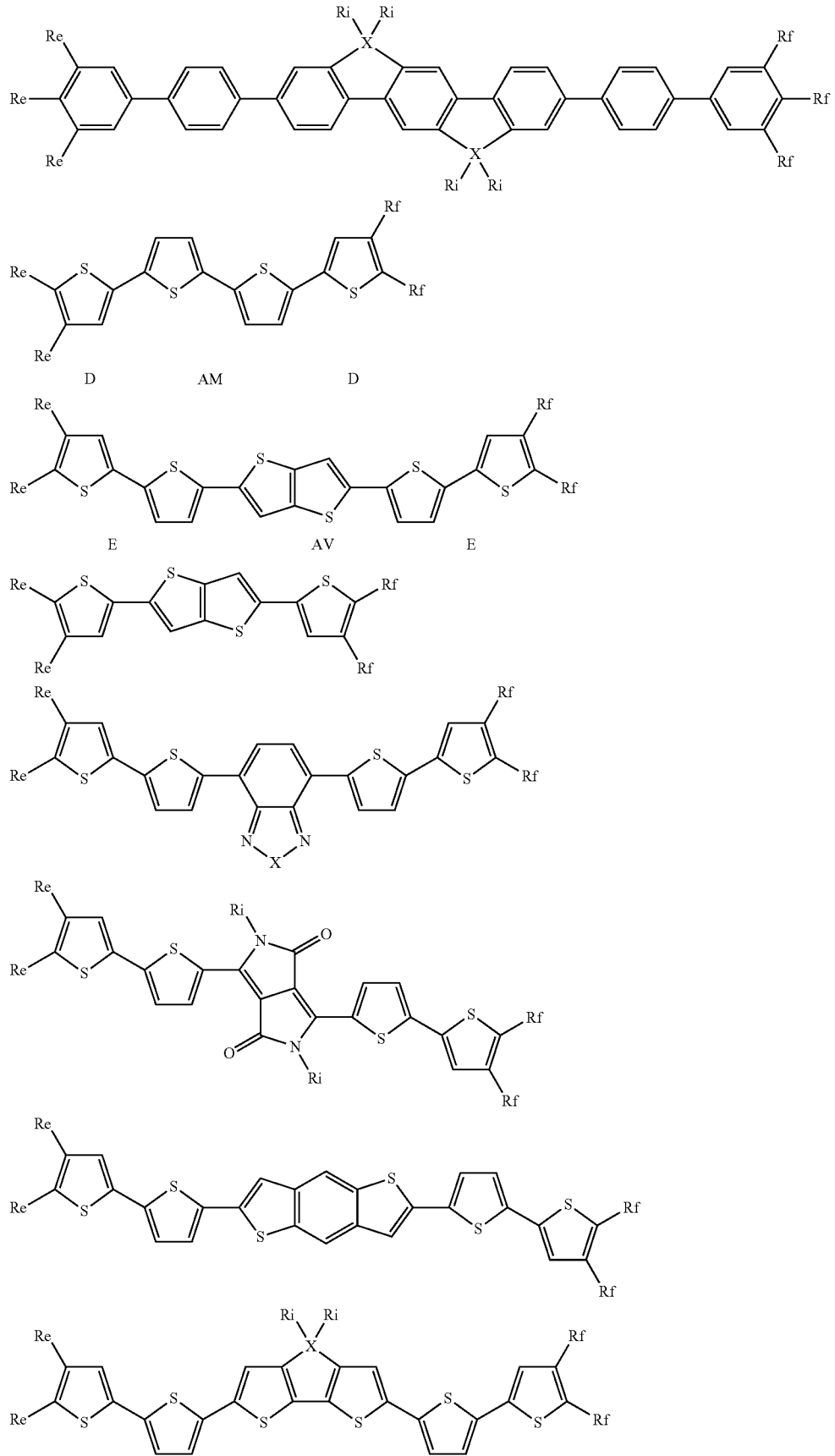

-continued

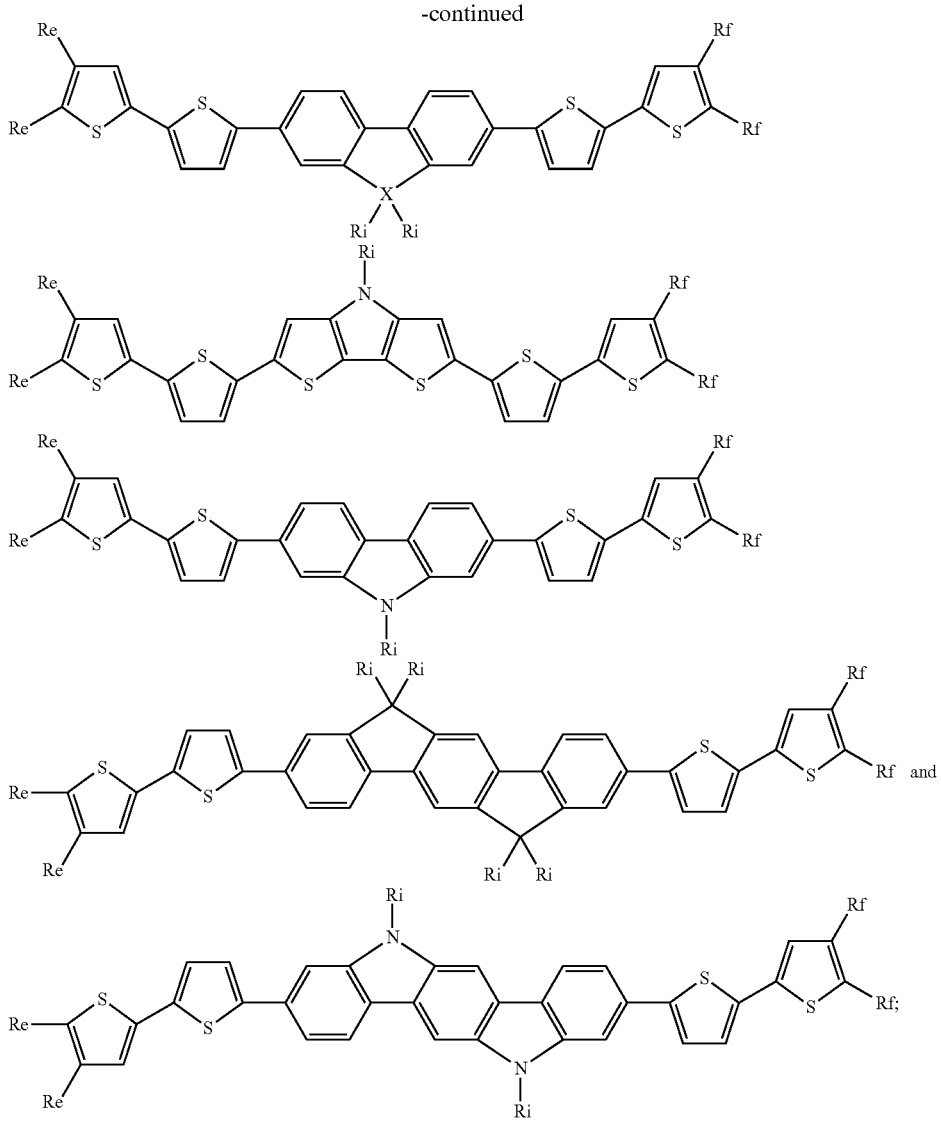

where each Ri is independently selected from the group consisting of —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aryl, F, Cl, Br, I, and —CN; and X is selected from O, S, or Se;

where at least one $R_e$ and at least one $R_f$ are each independently selected from the group consisting of -L-$R_h$ where each L is independently a linker group containing at least one carbon atom, and each $R_h$ is independently a hydrophilic group; and each remaining $R_e$ and each remaining $R_f$ is independently selected from the group consisting of —H, —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aryl, F, Cl, Br, I, and —CN.

7. The microbial fuel cell of claim 6, wherein each $R_h$ is independently a charged functional group or polar functional group.

8. The microbial fuel cell of claim 6, wherein each L is independently selected from branched or linear, saturated or unsaturated, substituted or unsubstituted alkyl or heteroalkyl chains containing at least one carbon atom, and optionally incorporating one or more aryl or heteroaryl groups within the chain.

9. The microbial fuel cell of claim 6, wherein each L is independently selected from $C_1$-$C_{12}$ alkyl, $C_2$-$C_{12}$ alkenyl, $C_2$-$C_{12}$ alkynyl, $C_2$-$C_{12}$ unsaturated hydrocarbyl, $C_1$-$C_{12}$ alkyl-$C_6$-$C_{10}$ aryl-$C_1$-$C_{12}$ alkyl, $C_1$-$C_{12}$ alkyl-$C_4$-$C_{10}$ heteroaryl-$C_1$-$C_{12}$ alkyl, and each L is independently optionally substituted with $C_1$-$C_{12}$ alkyl, $C_2$-$C_{12}$ alkenyl, $C_2$-$C_{12}$ alkynyl, $C_1$-$C_{12}$ alkyl-$C_6$-$C_{10}$ aryl-$C_1$-$C_{12}$ alkyl, $C_1$-$C_{12}$ alkyl-$C_4$-$C_{10}$ heteroaryl-$C_1$-$C_{12}$ alkyl, hydroxyl, —O—$C_1$-$C_{12}$ alkyl, —$C_1$-$C_{12}$-alkyl-OH, fluoro, chloro, bromo, iodo, cyano, oxo, thiol, thioalkyl, carboxylic acid, carboxylic ester, amine, or amide groups.

10. The microbial fuel cell of claim 6, where each $R_h$ is independently selected from the group consisting of: —$N^+$(R')(R'')(R'''),

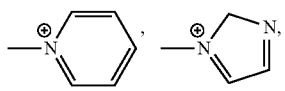

—SO$_3^-$, —CO$^{2-}$, PO$_3^{2-}$, —PO$_3$H$^-$, —PO$_3$H$_2$, —PO$_4^{2-}$, —PO$_4$H$^-$ and —PO$_4$H$_2$, where R', R", and R'" are independently selected from (C$_1$-C$_{12}$ alkyl), and where the groups optionally additionally comprise one or more counterions.

11. The microbial fuel cell of claim 4, wherein the at least one R$_e$ and at least one R$_f$ are independently selected from groups of the form:

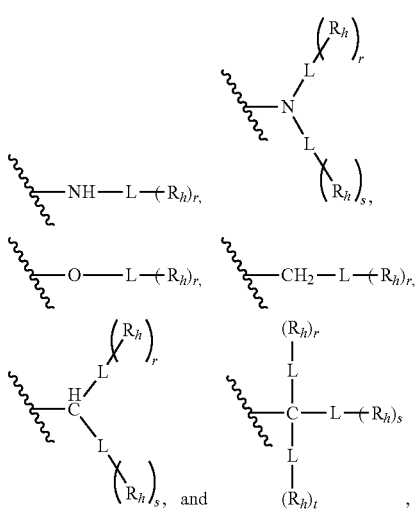

wherein each L is independently a linker group containing at least one carbon atom;
each R$_h$ is independently a hydrophilic group; and
r, s, and t are independently 0, 1, 2, or 3,
with the proviso that at least one R$_h$ is present in the R$_e$ or R$_f$ group.

12. The microbial fuel cell of claim 4, wherein the electron transfer agent is of the formula:

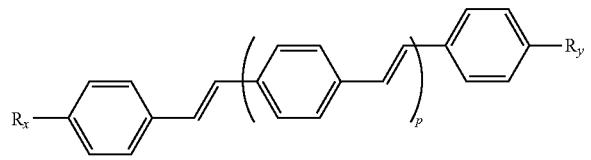

where p is an integer from 0 to 5, inclusive, and where R$_x$ and R$_y$ are groups containing a hydrophilic moiety.

13. The microbial fuel cell of claim 12, wherein R$_x$ is of the formula —N(R$_1$)(R$_2$) and R$_y$ is of the formula —N(R$_3$)(R$_4$), wherein each R$_1$, R$_2$, R$_3$ and R$_4$ is independently selected from the group consisting of -L-R$_h$ where each L is independently a linker group containing at least one carbon atom, and each R$_h$ is a independently hydrophilic group.

14. The microbial fuel cell of claim 13, wherein each R$_h$ is independently a charged functional group or polar functional group.

15. The microbial fuel cell of claim 13, wherein each L is independently selected from branched or linear, saturated or unsaturated, substituted or unsubstituted alkyl or heteroalkyl chains containing at least one carbon atom, and optionally incorporating one or more aryl or heteroaryl groups within the chain.

16. The microbial fuel cell of claim 13, wherein each L is independently selected from C$_1$-C$_{12}$ alkyl, C$_2$-C$_{12}$ alkenyl, C$_2$-C$_{12}$ alkynyl, C$_2$-C$_{12}$ unsaturated hydrocarbyl, C$_1$-C$_{12}$ alkyl-C$_6$-C$_{10}$ aryl-C$_1$-C$_{12}$ alkyl, C$_1$-C$_{12}$ alkyl-C$_4$-C$_{10}$ heteroaryl-C$_1$-C$_{12}$ alkyl, and each L is independently optionally substituted with C$_1$-C$_{12}$ alkyl, C$_2$-C$_{12}$ alkenyl, C$_2$-C$_{12}$ alkynyl, C$_1$-C$_{12}$ alkylene-C$_6$-C$_{10}$ aryl-C$_1$-C$_{12}$ alkylene, C$_1$-C$_{12}$ alkylene-C$_4$-C$_{10}$ heteroaryl-C$_1$-C$_{12}$ alkylene, hydroxyl, —O—C$_1$-C$_{12}$ alkyl, —C$_1$-C$_{12}$-alkyl-OH, fluoro, chloro, bromo, iodo, cyano, oxo, thiol, thioalkyl, carboxylic acid, carboxylic ester, amine, or amide groups.

17. The microbial fuel cell of claim 13, where each R$_h$ is independently selected from the group consisting of: —N$^+$(R')(R")(R'"),

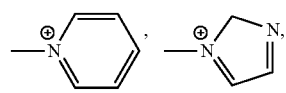

—SO$_3^-$, —CO$^{2-}$, —PO$_3^{2-}$, —PO$_3$H$^-$, —PO$_3$H$_2$, —PO$_4^{2-}$, —PO$_4$H$^-$ and —PO$_4$H$_2$, where R', R", and R'" are independently selected from (C$_1$-C$_{12}$ alkyl), and where the groups optionally additionally comprise one or more counterions.

18. The microbial fuel cell of claim 13, wherein the electron transfer agent is of the formula:

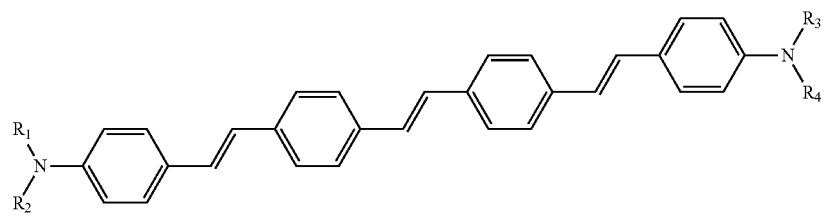

wherein $R_1$, $R_2$, $R_3$, and $R_4$ are independently selected from —($C_2$-$C_{12}$ alkylene)-$N^+$(R')(R'')(R'''),

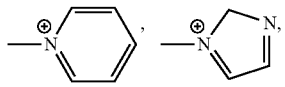

—$SO_3^-$, —$CO2^-$, and —$PO_3^{2-}$, where R', R", and R'" are independently selected from ($C_1$-$C_{12}$ alkyl).

19. The microbial fuel cell of claim 18, wherein $R_1$, $R_2$, $R_3$, and $R_4$ are —$C_6H_{12}$—$N^+$(R')(R'')(R''').

20. A method of increasing the rate of transmembrane charge transfer from a microorganism and/or increasing the electromotive force of transmembrane charge transfer from a microorganism having a cell membrane formed of a lipid bilayer, the method comprising:

adding an amount of transmembrane charge-transfer agent sufficient to increase the rate of transmembrane charge transfer from the microorganism and/or sufficient to increase the electromotive force of transmembrane charge transfer from the microorganism, wherein the transmembrane charge-transfer agent substantially resides within the lipid bilayer of the cell membrane so as to facilitate transmembrane electron transport; wherein the charge-transfer agent comprises: a first region which is hydrophilic, a second region of electronic delocalization, and a third region which is hydrophilic, wherein the charge-transfer agent is of sufficient length such that the first region contacts with the external environment of the microorganism and/or the hydrophilic portion of the cell membrane of the microorganism facing the external environment, the second region contacts with the hydrophobic portion of the cell membrane of the microorganism, and the third region contacts with the cytosol of the microorganism and/or the hydrophilic portion of the cell membrane of the microorganism facing the cytosol, respectively.

21. The method of claim 20, wherein the charge-transfer agent is not endogenous to the microorganism.

22. The method of claim 20, wherein the charge-transfer agent is a deficient endogenous charge-transfer agent.

23. The method of claim 20, wherein the lipid bilayer of the cell membrane includes a hydrophobic conjugated inner region within the cell membrane and polar pendant group terminals oriented outwardly on either side of the lipid bilayer which define a plane the membrane, and a longitudinal axis of the transmembrane charge-transfer agent orients substantially normal to the plane of the membrane lipid bilayer.

24. The method of claim 20, wherein the charge-transfer agent spans at least about 60% to at least about 150% of the width of the cell membrane when in extended conformation.

25. The method of claim 20, wherein the charge-transfer agent is an electron-transfer agent of the form:

where $R_e$ and $R_f$ can be the same or different and are groups containing a hydrophilic moiety, and Pi is a molecule with a delocalized π-electron system.

26. The method of claim 25, wherein the Pi component of the electron-transfer agent ranges from about 1 nm to about 10 nm.

27. The method of claim 25, wherein the electron transfer agent is of the formula:

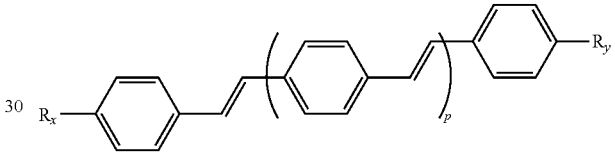

where p is an integer from 0 to 5, inclusive.

28. The method of claim 27, wherein $R_x$ is of the formula —$N(R_1)(R_2)$ and $R_y$ is of the formula —$N(R_3)(R_4)$, wherein $R_1$, $R_2$, $R_3$, and $R_4$ are independently selected from —($C_2$-$C_{12}$ alkylene)-$N^+$(R')(R'')(R'''),

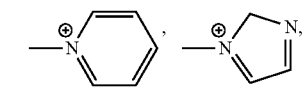

—$SO_3^-$, —$CO2^-$, and —$PO_3^{2-}$, where R', R", and R'" are independently selected from ($C_1$-$C_{12}$ alkyl).

29. The method of claim 25, wherein the electron transfer agent is selected from the group consisting of:

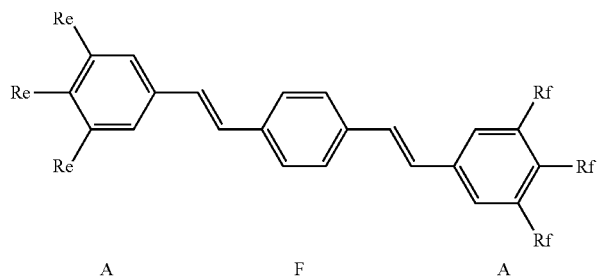

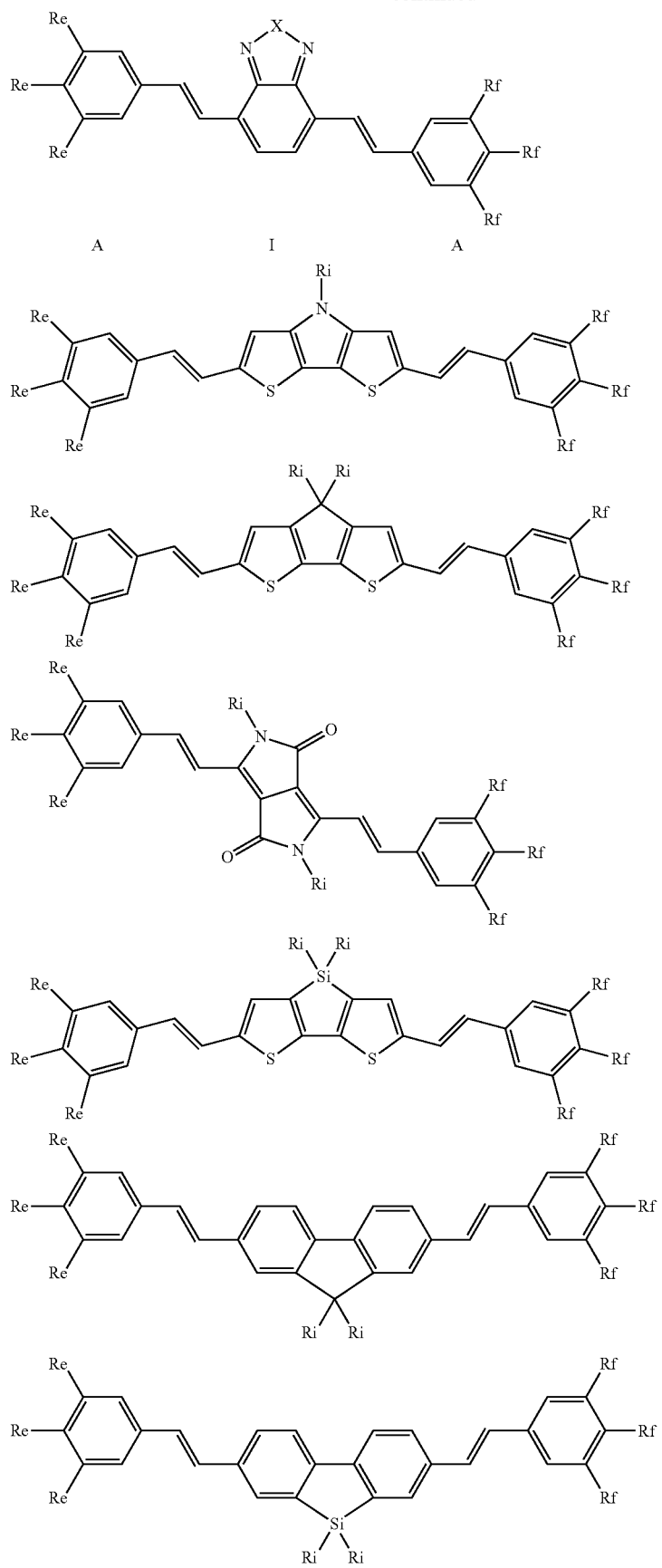

-continued
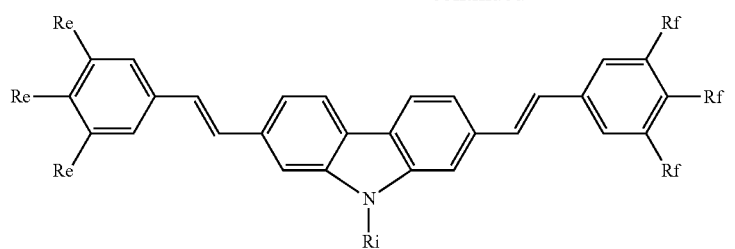
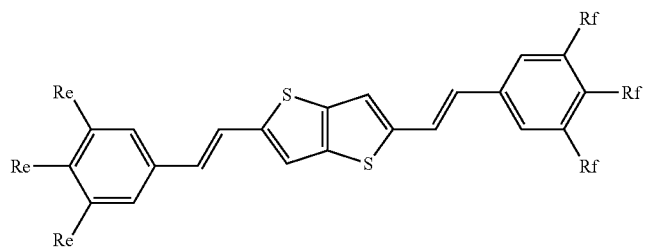
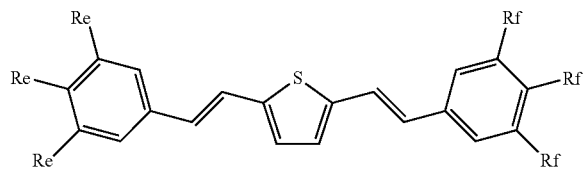
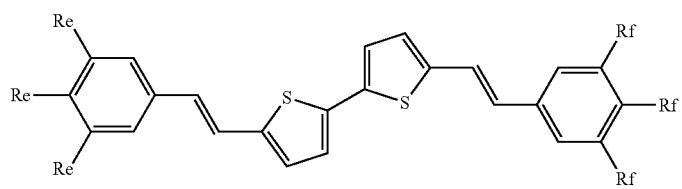
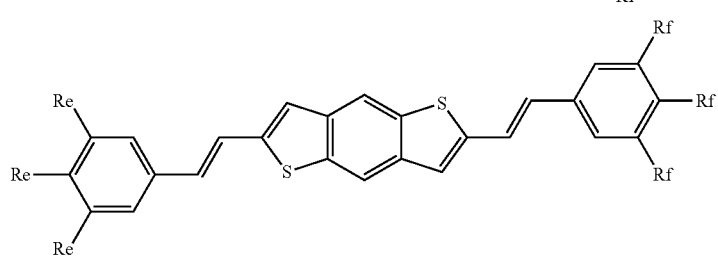
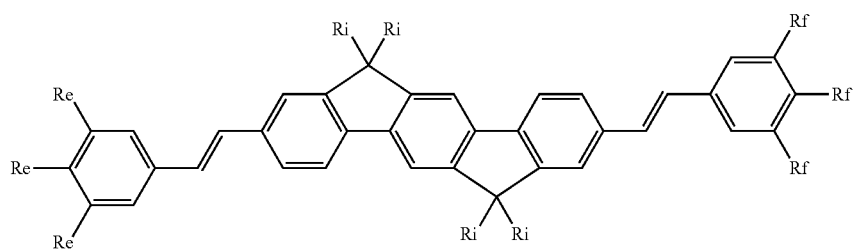
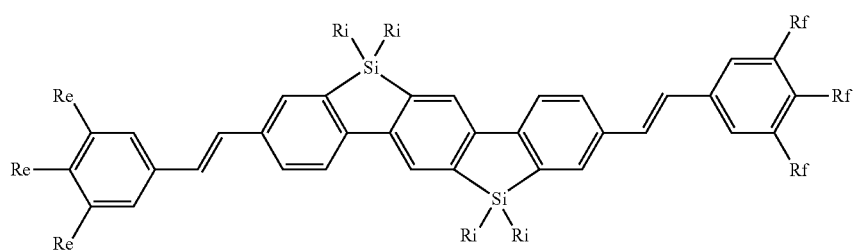

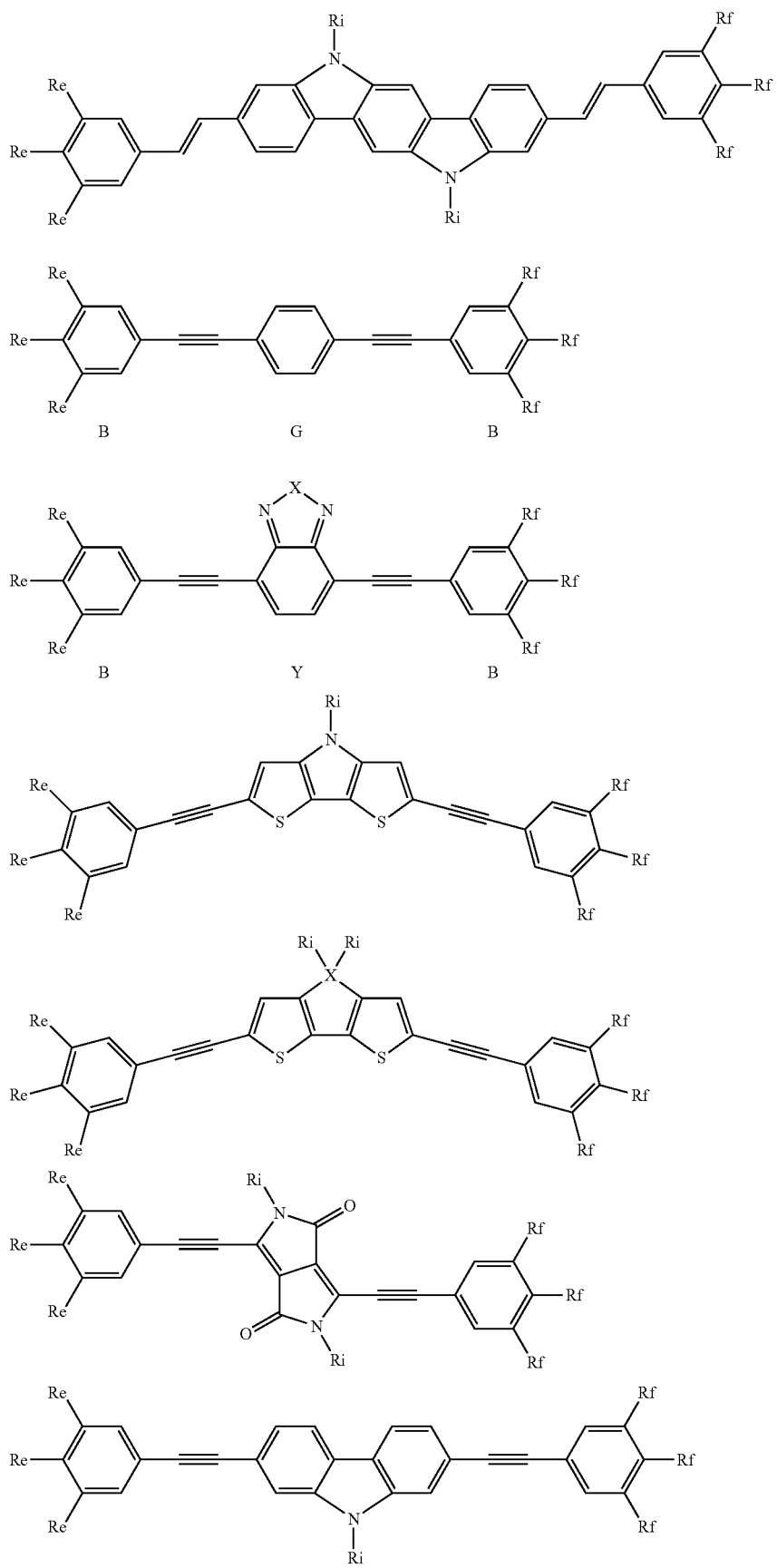

-continued
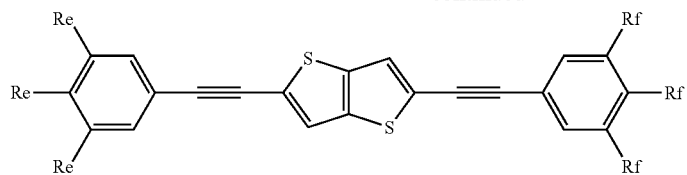
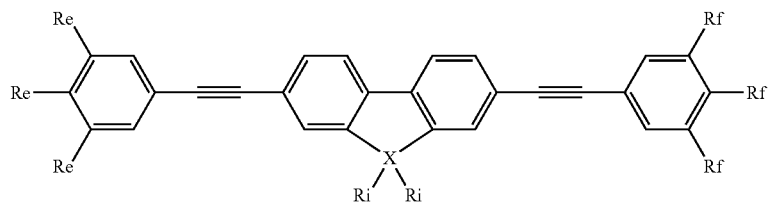
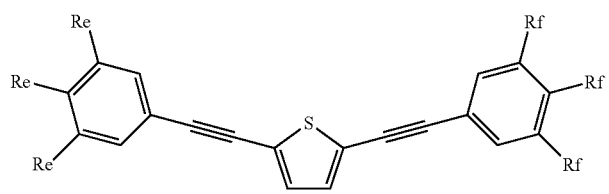
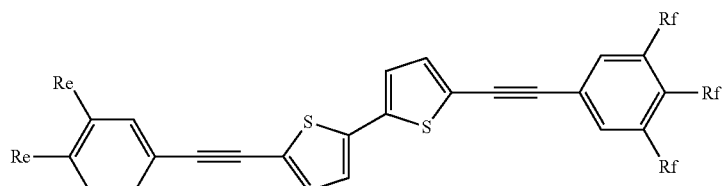
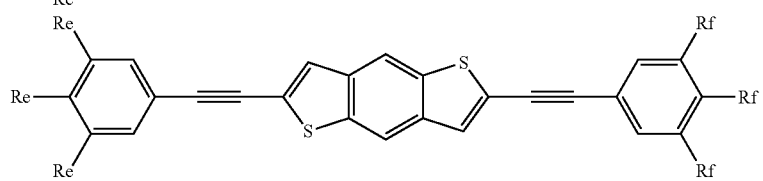
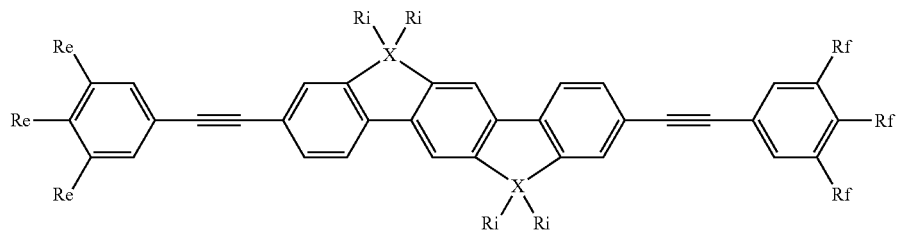
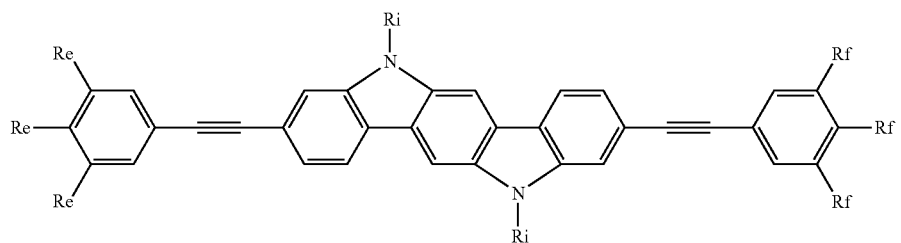
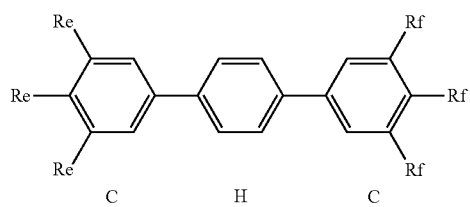

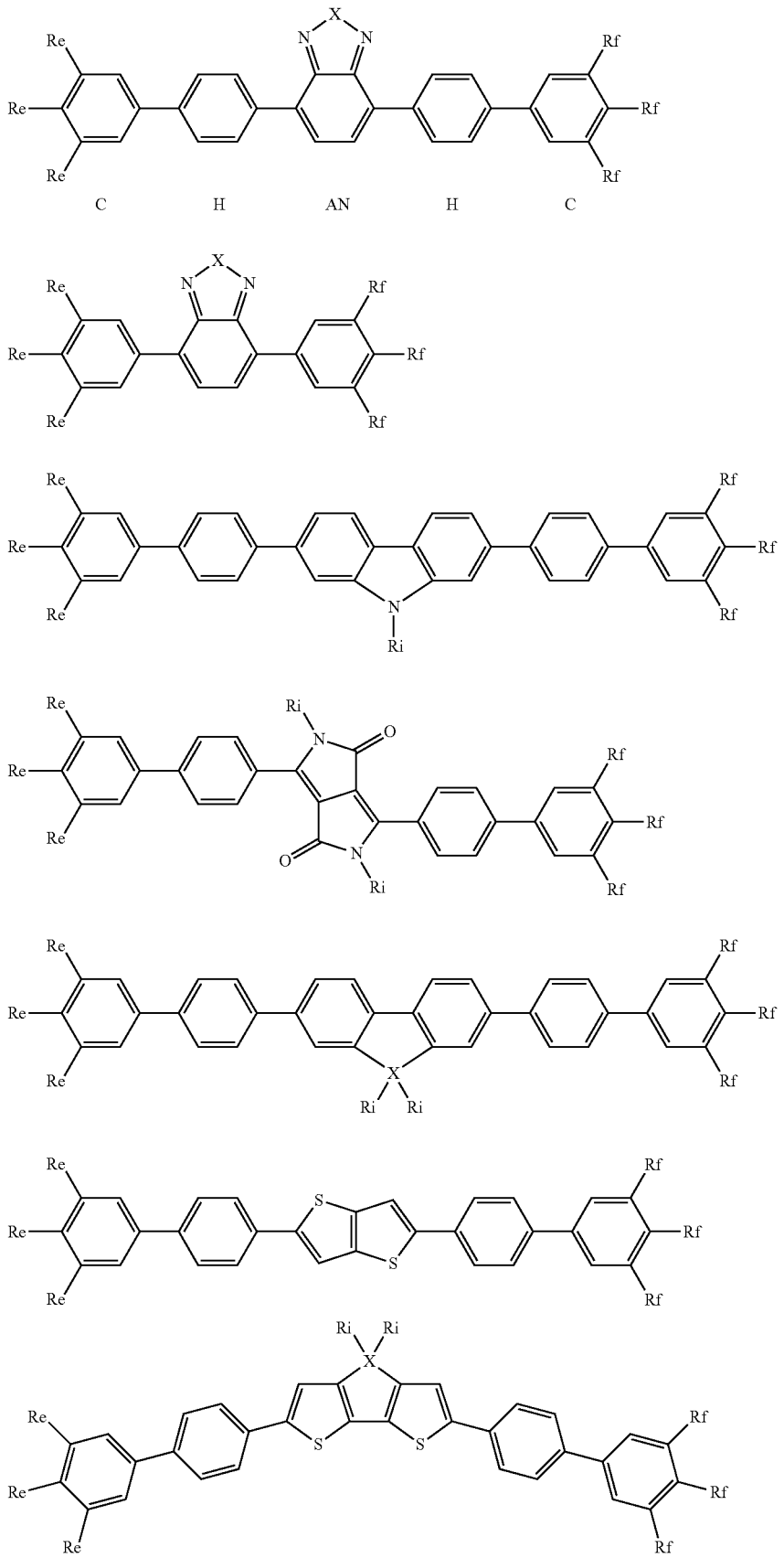

-continued
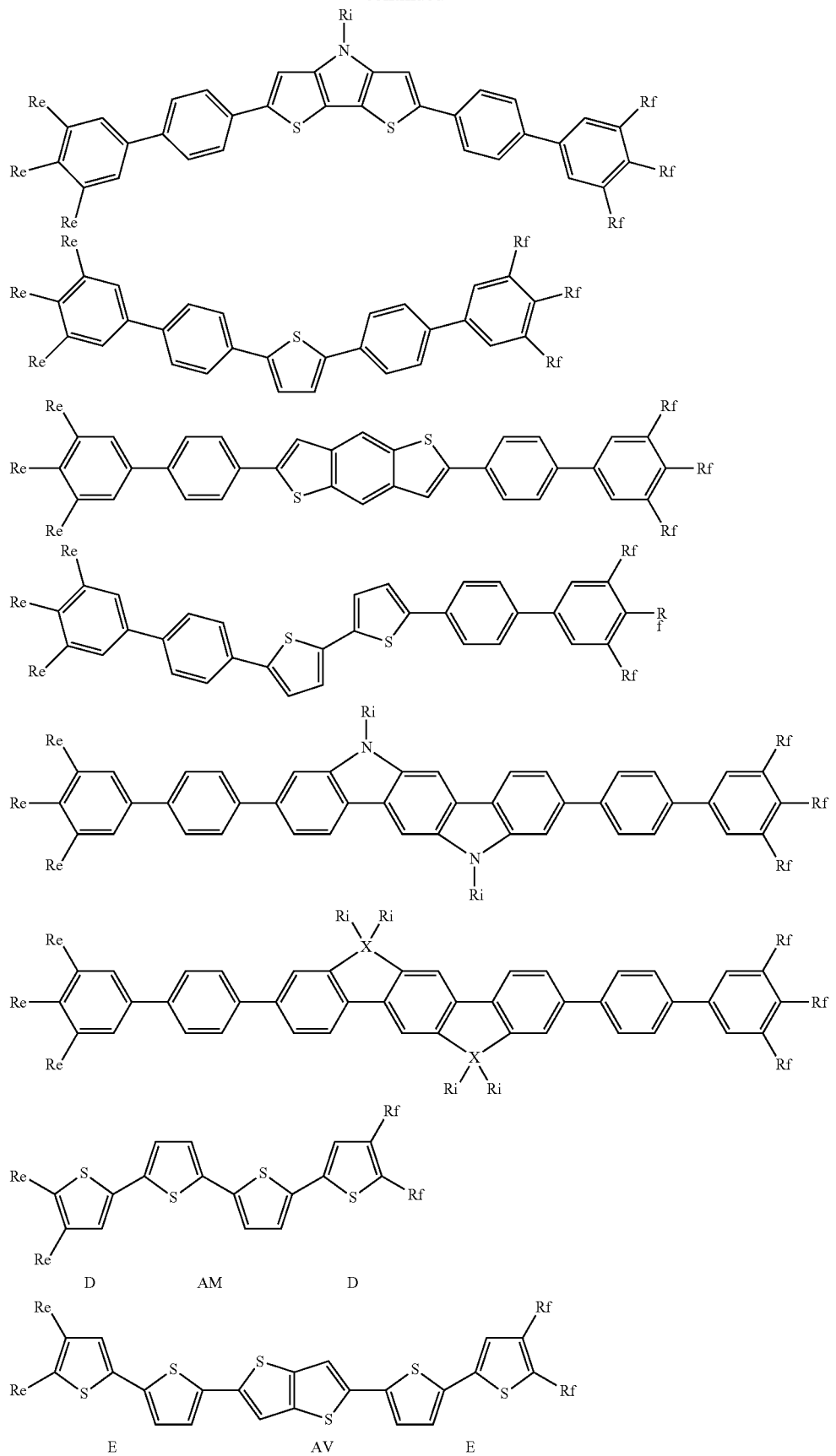

-continued
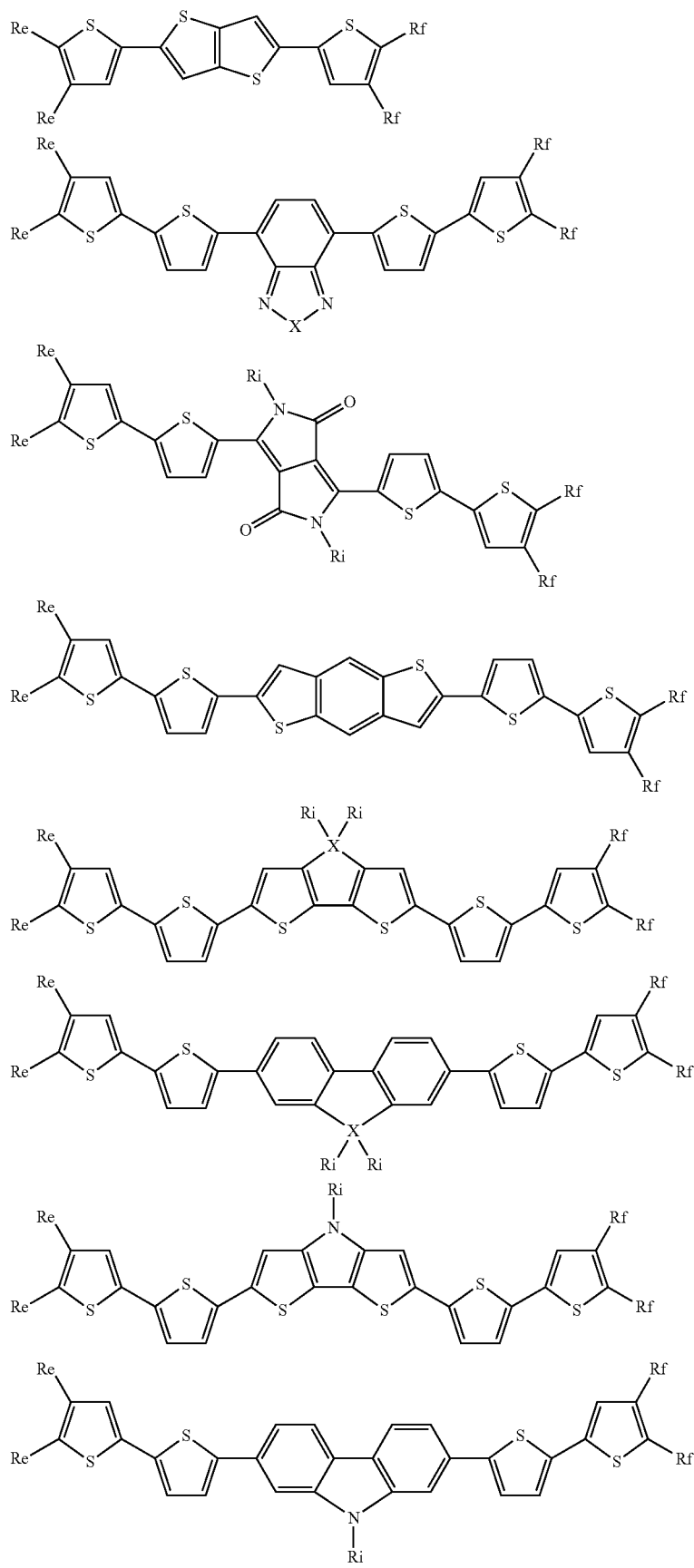

-continued

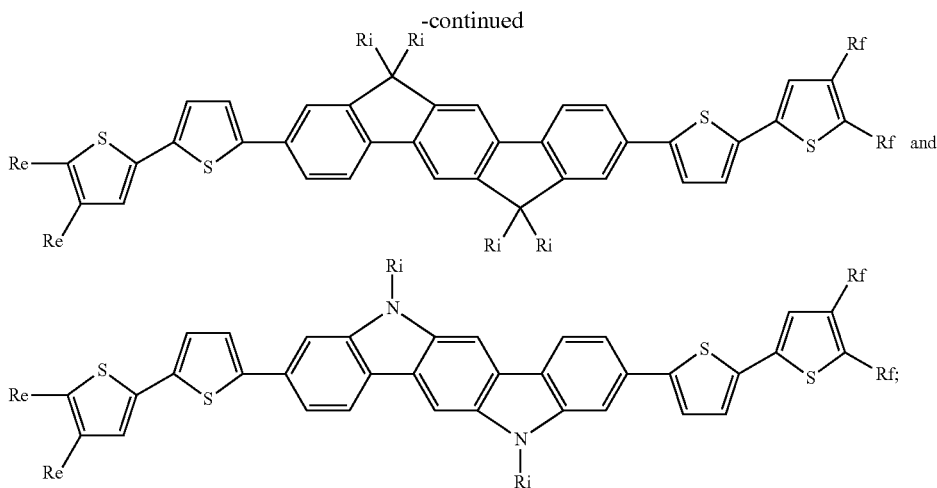

where each Ri is independently selected from the group consisting of —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aryl, F, Cl, Br, I, and —CN; and X is selected from O, S, or Se;

where at least one $R_e$ and at least one $R_f$ are each independently selected from the group consisting of -L-$R_h$ where each L is independently a linker group containing at least one carbon atom, and each $R_h$ is independently a hydrophilic group; and each remaining $R_e$ and each remaining $R_f$ is independently selected from the group consisting of —H, —$C_1$-$C_{12}$ alkyl, —$C_1$-$C_6$ alkyl, —$NH_2$, —NH—($C_1$-$C_{12}$ alkyl), —N($C_1$-$C_{12}$ alkyl)($C_1$-$C_{12}$ alkyl), —NH—($C_1$-$C_6$ alkyl), —N($C_1$-$C_6$ alkyl)($C_1$-$C_6$ alkyl), —O—$C_1$-$C_{12}$ alkyl, —O—$C_1$-$C_6$ alkyl, $C_6$-$C_{10}$ aryl, F, Cl, Br, I, and —CN.

30. The method of claim 29, wherein each $R_h$ is independently a charged functional group or polar functional group.

31. The method of claim 29, wherein each L is independently selected from branched or linear, saturated or unsaturated, substituted or unsubstituted alkyl or heteroalkyl chains containing at least one carbon atom, and optionally incorporating one or more aryl or heteroaryl groups within the chain.

32. The method of claim 29, wherein each L is independently selected from $C_1$-$C_{12}$ alkyl, $C_2$-$C_{12}$ alkenyl, $C_2$-$C_{12}$ alkynyl, $C_2$-$C_{12}$ unsaturated hydrocarbyl, $C_1$-$C_{12}$ alkyl-$C_6$-$C_{10}$ aryl-$C_1$-$C_{12}$ alkyl, $C_1$-$C_{12}$ alkyl-$C_4$-$C_{10}$ heteroaryl-$C_1$-$C_{12}$ alkyl, and each L is independently optionally substituted with $C_1$-$C_{12}$ alkyl, $C_2$-$C_{12}$ alkenyl, $C_2$-$C_{12}$ alkynyl, $C_1$-$C_{12}$ alkyl-$C_6$-$C_{10}$ aryl-$C_1$-$C_{12}$ alkyl, $C_1$-$C_{12}$ alkyl-$C_4$-$C_{10}$ heteroaryl-$C_1$-$C_{12}$ alkyl, hydroxyl, —O—$C_1$-$C_{12}$ alkyl, —$C_1$-$C_{12}$-alkyl-OH, fluoro, chloro, bromo, iodo, cyano, oxo, thiol, thioalkyl, carboxylic acid, carboxylic ester, amine, or amide groups.

33. The method of claim 29, where each $R_h$ is independently selected from the group consisting of: —$N^+$(R')(R'')(R''')

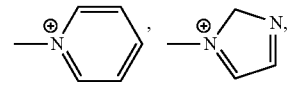

—$SO_3^-$, —$CO^{2-}$, —$PO_3^{2-}$, $PO_3H^-$, —$PO_3H_2$, —$PO_4^{2-}$, —$PO_4H^-$, and —$PO_4H_2$, where R', R'', and R''' are independently selected from ($C_1$-$C_{12}$ alkyl), and where the groups optionally additionally comprise one or more counterions.

34. The method of claim 25, wherein the at least one $R_e$ and at least one $R_f$ are independently selected from groups of the form:

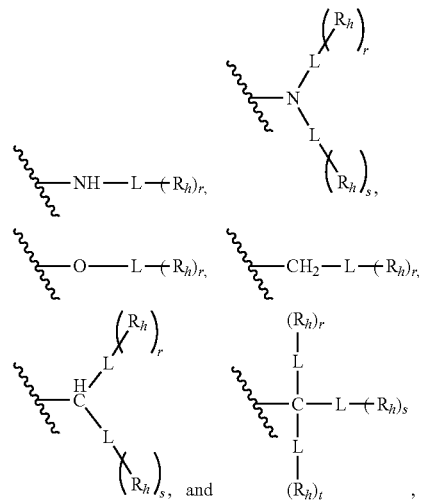

wherein each L is independently a linker group containing at least one carbon atom;
each $R_h$ is independently a hydrophilic group; and
r, s, and t are independently 0, 1, 2, or 3,
with the proviso that at least one $R_h$ is present in the $R_e$ or $R_f$ group.

* * * * *